(12) United States Patent
Shelton, IV et al.

(10) Patent No.: US 12,082,818 B2
(45) Date of Patent: Sep. 10, 2024

(54) METHOD FOR AUTHENTICATING THE COMPATIBILITY OF A STAPLE CARTRIDGE WITH A SURGICAL INSTRUMENT

(71) Applicant: Cilag GmbH International, Zug (CH)

(72) Inventors: Frederick E. Shelton, IV, Hillsboro, OH (US); Shane R. Adams, Lebanon, OH (US); Nicholas J. Ross, Franklin, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/342,338

(22) Filed: Jun. 27, 2023

(65) Prior Publication Data

US 2024/0065695 A1 Feb. 29, 2024

Related U.S. Application Data

(63) Continuation of application No. 17/551,810, filed on Dec. 15, 2021, now Pat. No. 11,744,593, which is a
(Continued)

(51) Int. Cl.
*A61B 17/064* (2006.01)
*A61B 17/072* (2006.01)
(Continued)

(52) U.S. Cl.
CPC ........ *A61B 17/1155* (2013.01); *A61B 17/072* (2013.01); *A61B 17/07207* (2013.01); *A61B 17/115* (2013.01); *A61B 90/96* (2016.02); *A61B 90/98* (2016.02); *G06K 7/10366* (2013.01); *G06K 19/07758* (2013.01); *A61B 2017/00039* (2013.01); *A61B 2017/00115* (2013.01);
(Continued)

(58) Field of Classification Search
CPC .................. A61B 17/1155; A61B 2017/0073
See application file for complete search history.

(56) References Cited

U.S. PATENT DOCUMENTS 5,403,312 A 4/1995 Yates et al.
6,978,921 B2 12/2005 Shelton, IV et al.
(Continued)

OTHER PUBLICATIONS

U.S. Appl. No. 62/665,128, entitled "Modular Surgical Instruments," filed May 1, 2018.
(Continued)

*Primary Examiner* — Eyamindae C Jallow
(74) *Attorney, Agent, or Firm* — Frost Brown Todd LLP

(57) ABSTRACT

A method for authenticating the compatibility of a staple cartridge with a surgical instrument is disclosed. The method can comprise inserting a staple cartridge into a surgical instrument, receiving a first signal from a first RFID tag on a first component of the staple cartridge with an RFID reader system, receiving a second signal from a second RFID tag on a second component of the staple cartridge with the RFID reader system, comparing the first signal and the second signal to stored data for a compatible staple cartridge, and locking a staple firing system of the surgical instrument if the first signal and the second signal do not match the stored data for a compatible staple cartridge.

20 Claims, 90 Drawing Sheets

Related U.S. Application Data continuation of application No. 16/458,104, filed on Jun. 30, 2019, now Pat. No. 11,229,437.

(60) Provisional application No. 62/868,457, filed on Jun. 28, 2019.

(51) Int. Cl.
| | | |
|---|---|---|
| *A61B 17/115* | (2006.01) | |
| *A61B 90/96* | (2016.01) | |
| *A61B 90/98* | (2016.01) | |
| *G06K 7/10* | (2006.01) | |
| *G06K 19/077* | (2006.01) | |
| *A61B 17/00* | (2006.01) | |

(52) U.S. Cl.
CPC ........... *A61B 2017/00119* (2013.01); *A61B 2017/00221* (2013.01); *A61B 2017/00367* (2013.01); *A61B 2017/00398* (2013.01); *A61B 2017/00477* (2013.01); *A61B 2017/00734* (2013.01); *A61B 2017/07228* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01)

(56) References Cited

U.S. PATENT DOCUMENTS

| | | | |
|---|---|---|---|
| 6,988,649 B2 | 1/2006 | Shelton, IV et al. | |
| 7,000,818 B2 | 2/2006 | Shelton, IV et al. | |
| 7,044,352 B2 | 5/2006 | Shelton, IV et al. | |
| 7,143,923 B2 | 12/2006 | Shelton, IV et al. | |
| 7,422,139 B2 | 9/2008 | Shelton, IV et al. | |
| 7,464,849 B2 | 12/2008 | Shelton, IV et al. | |
| 7,670,334 B2 | 3/2010 | Hueil et al. | |
| 7,753,245 B2 | 7/2010 | Boudreaux et al. | |
| 7,845,537 B2 | 12/2010 | Shelton, IV et al. | |
| 7,900,805 B2 * | 3/2011 | Shelton, IV | A61B 17/07207 227/176.1 |
| 7,959,050 B2 | 6/2011 | Smith et al. | |
| 7,980,443 B2 | 7/2011 | Scheib et al. | |
| 8,210,411 B2 | 7/2012 | Yates et al. | |
| 8,220,688 B2 | 7/2012 | Laurent et al. | |
| 8,308,040 B2 | 11/2012 | Huang et al. | |
| 8,393,514 B2 | 3/2013 | Shelton, IV et al. | |
| 8,561,870 B2 | 10/2013 | Baxter, III et al. | |
| 8,608,045 B2 | 12/2013 | Smith et al. | |
| 8,733,613 B2 | 5/2014 | Huitema et al. | |
| 9,050,083 B2 | 6/2015 | Yates et al. | |
| 9,072,535 B2 | 7/2015 | Shelton, IV et al. | |
| 9,101,358 B2 | 8/2015 | Kerr et al. | |
| 9,171,244 B2 | 10/2015 | Endou et al. | |
| 9,345,481 B2 | 5/2016 | Hall et al. | |
| 9,629,629 B2 | 4/2017 | Leimbach et al. | |
| 10,772,651 B2 | 9/2020 | Shelton, IV et al. | |
| 10,932,806 B2 | 3/2021 | Shelton, IV et al. | |
| 10,959,744 B2 | 3/2021 | Shelton, IV et al. | |
| 10,980,560 B2 | 4/2021 | Shelton, IV et al. | |
| 11,026,687 B2 | 6/2021 | Shelton, IV et al. | |
| 11,026,712 B2 | 6/2021 | Shelton, IV et al. | |
| 11,026,713 B2 | 6/2021 | Stokes et al. | |
| 11,045,197 B2 | 6/2021 | Shelton, IV et al. | |
| 11,051,836 B2 | 7/2021 | Shelton, IV et al. | |
| 11,071,560 B2 | 7/2021 | Deck et al. | |
| 11,103,268 B2 | 8/2021 | Shelton, IV et al. | |
| 11,109,866 B2 | 9/2021 | Shelton, IV et al. | |
| 11,109,878 B2 | 9/2021 | Shelton, IV et al. | |
| 11,123,070 B2 | 9/2021 | Shelton, IV et al. | |
| 11,129,636 B2 | 9/2021 | Shelton, IV et al. | |
| 11,141,160 B2 | 10/2021 | Shelton, IV et al. | |
| 11,207,090 B2 | 12/2021 | Shelton, IV et al. | |
| 11,229,436 B2 | 1/2022 | Shelton, IV et al. | |
| 11,229,437 B2 | 1/2022 | Shelton, IV et al. | |
| 11,291,465 B2 | 4/2022 | Parihar et al. | |
| 11,304,699 B2 | 4/2022 | Shelton, IV et al. | |
| 11,317,919 B2 | 5/2022 | Shelton, IV et al. | |
| 11,389,164 B2 | 7/2022 | Yates et al. | |
| 11,406,390 B2 | 8/2022 | Shelton, IV et al. | |
| 11,413,042 B2 | 8/2022 | Shelton, IV et al. | |
| 11,559,307 B2 | 1/2023 | Shelton, IV et al. | |
| 11,559,308 B2 | 1/2023 | Yates et al. | |
| 11,564,703 B2 | 1/2023 | Shelton, IV et al. | |
| 11,576,677 B2 | 2/2023 | Shelton, IV et al. | |
| 11,589,888 B2 | 2/2023 | Shelton, IV et al. | |
| 11,602,366 B2 | 3/2023 | Shelton, IV et al. | |
| 11,648,022 B2 | 5/2023 | Shelton, IV | |
| 11,659,023 B2 | 5/2023 | Shelton, IV et al. | |
| 2007/0175955 A1 | 8/2007 | Shelton et al. | |
| 2009/0057369 A1 | 3/2009 | Smith et al. | |
| 2009/0108048 A1 * | 4/2009 | Zemlok | A61B 17/105 227/176.1 |
| 2010/0075474 A1 | 3/2010 | Kudou et al. | |
| 2011/0288573 A1 * | 11/2011 | Yates | A61B 50/36 227/175.1 |
| 2012/0074198 A1 | 3/2012 | Huitema et al. | |
| 2013/0126581 A1 * | 5/2013 | Yates | A61B 17/1155 227/175.1 |
| 2014/0175150 A1 | 6/2014 | Shelton, IV et al. | |
| 2014/0246479 A1 * | 9/2014 | Baber | A61B 17/07207 227/180.1 |
| 2014/0263552 A1 | 9/2014 | Hall et al. | |
| 2015/0053737 A1 * | 2/2015 | Leimbach | H02J 7/00 227/175.1 |
| 2015/0053743 A1 | 2/2015 | Yates et al. | |
| 2015/0196347 A1 * | 7/2015 | Yates | A61B 17/068 227/180.1 |
| 2016/0249915 A1 | 9/2016 | Beckman et al. | |
| 2016/0249919 A1 | 9/2016 | Savage et al. | |
| 2016/0249927 A1 | 9/2016 | Beckman et al. | |
| 2019/0104919 A1 | 4/2019 | Shelton, IV et al. | |
| 2019/0125320 A1 | 5/2019 | Shelton, IV et al. | |
| 2019/0125336 A1 | 5/2019 | Deck et al. | |
| 2019/0125338 A1 | 5/2019 | Shelton, IV et al. | |
| 2019/0125361 A1 | 5/2019 | Shelton, IV et al. | |
| 2019/0125378 A1 | 5/2019 | Shelton, IV et al. | |
| 2019/0125388 A1 | 5/2019 | Shelton, IV et al. | |
| 2019/0125430 A1 | 5/2019 | Shelton, IV et al. | |
| 2019/0125432 A1 | 5/2019 | Shelton, IV et al. | |
| 2019/0125476 A1 | 5/2019 | Shelton, IV et al. | |
| 2019/0200844 A1 | 7/2019 | Shelton, IV et al. | |
| 2019/0200981 A1 * | 7/2019 | Harris | A61B 5/0022 |
| 2019/0201045 A1 | 7/2019 | Yates et al. | |
| 2019/0201594 A1 | 7/2019 | Shelton, IV et al. | |
| 2019/0206564 A1 | 7/2019 | Shelton, IV et al. | |
| 2019/0206569 A1 | 7/2019 | Shelton, IV et al. | |
| 2020/0405296 A1 | 12/2020 | Shelton, IV et al. | |
| 2020/0405297 A1 | 12/2020 | Shelton, IV et al. | |
| 2020/0405302 A1 | 12/2020 | Shelton, IV et al. | |
| 2020/0405303 A1 | 12/2020 | Shelton, IV | |
| 2020/0405311 A1 | 12/2020 | Shelton, IV et al. | |
| 2020/0405312 A1 | 12/2020 | Shelton, IV et al. | |
| 2020/0405313 A1 | 12/2020 | Shelton, IV | |
| 2020/0405314 A1 | 12/2020 | Shelton, IV et al. | |
| 2020/0405316 A1 | 12/2020 | Shelton, IV et al. | |
| 2020/0405409 A1 | 12/2020 | Shelton, IV et al. | |
| 2020/0405410 A1 | 12/2020 | Shelton, IV | |
| 2020/0405436 A1 | 12/2020 | Shelton, IV et al. | |
| 2020/0405437 A1 | 12/2020 | Shelton, IV et al. | |
| 2020/0405438 A1 | 12/2020 | Shelton, IV et al. | |
| 2020/0405439 A1 | 12/2020 | Shelton, IV et al. | |
| 2020/0405440 A1 | 12/2020 | Shelton, IV et al. | |
| 2020/0405441 A1 | 12/2020 | Shelton, IV et al. | |
| 2020/0410177 A1 | 12/2020 | Shelton, IV | |
| 2020/0410180 A1 | 12/2020 | Shelton, IV et al. | |
| 2022/0249095 A1 | 8/2022 | Shelton, IV et al. | |

OTHER PUBLICATIONS

U.S. Appl. No. 62/665,129, entitled "Surgical Suturing Systems," filed May 1, 2018.

(56) References Cited

OTHER PUBLICATIONS

U.S. Appl. No. 62/665,134, entitled "Surgical Clip Applier," filed May 1, 2018.
U.S. Appl. No. 62/665,139, entitled "Surgical Instruments Comprising Control Systems," filed May 1, 2018.
U.S. Appl. No. 62/665,177, entitled "Surgical Instruments Comprising Handle Arrangements," filed May 1, 2018.
U.S. Appl. No. 62/665,192, entitled "Surgical Dissectors," filed May 1, 2018.
U.S. Appl. No. 12/031,573, entitled "Surgical Cutting and Fastening Instrument Having RF Electrodes," filed Feb. 14, 2008.

* cited by examiner

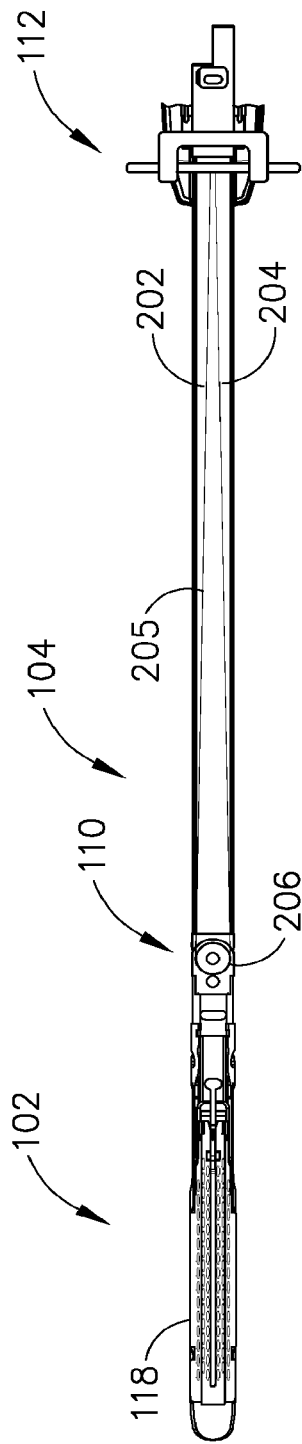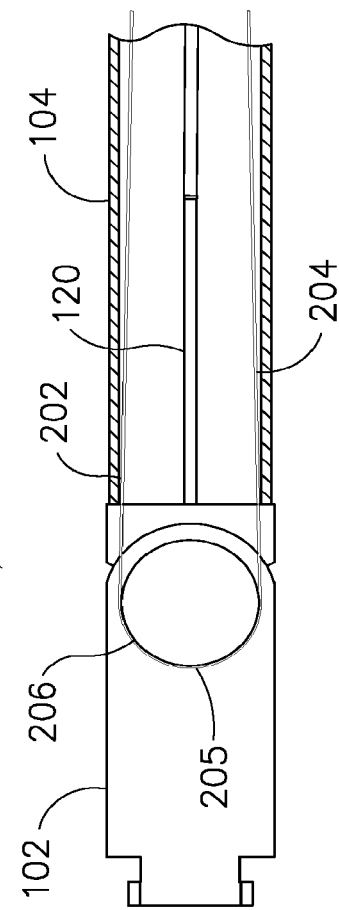

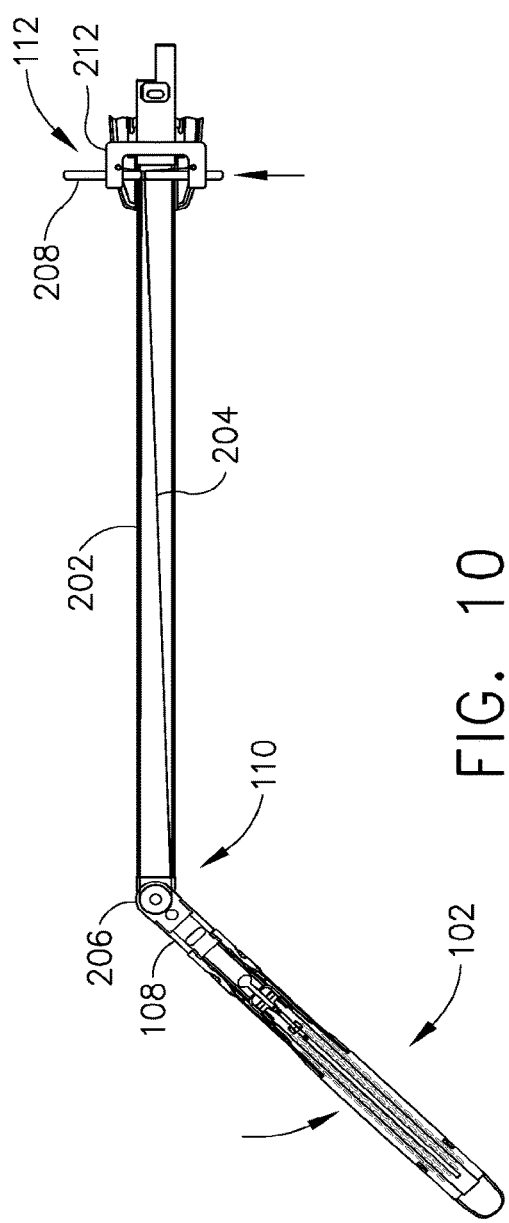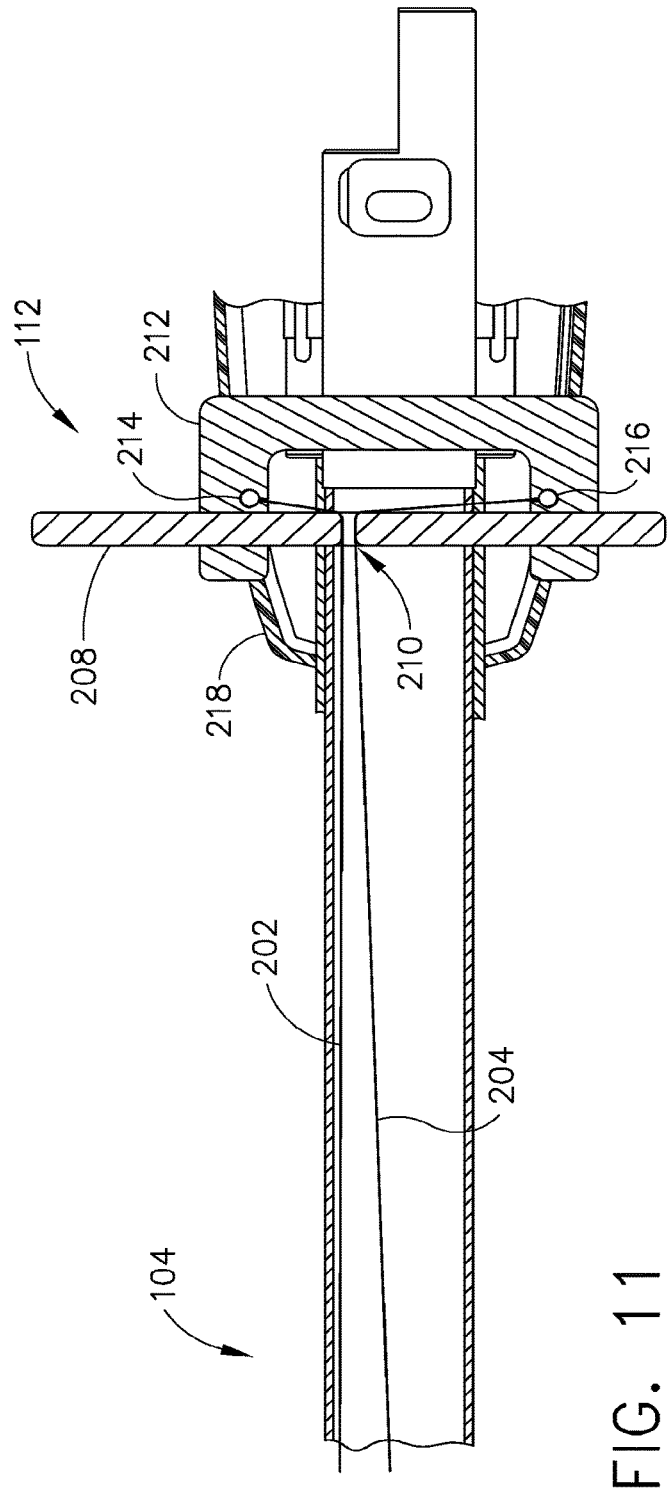

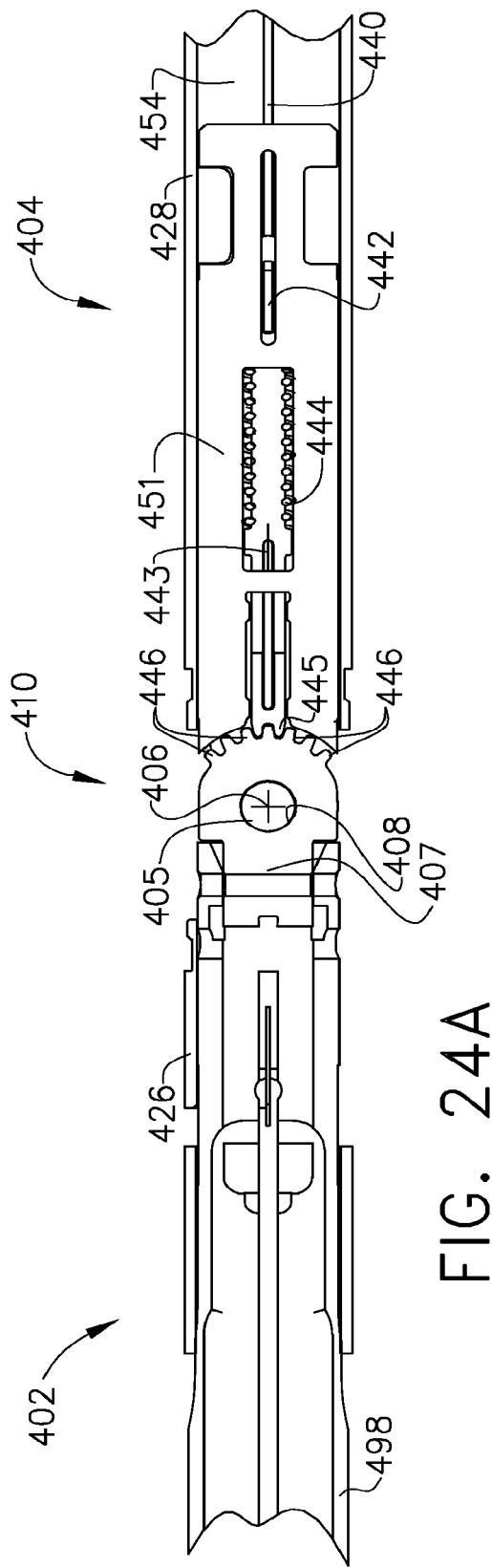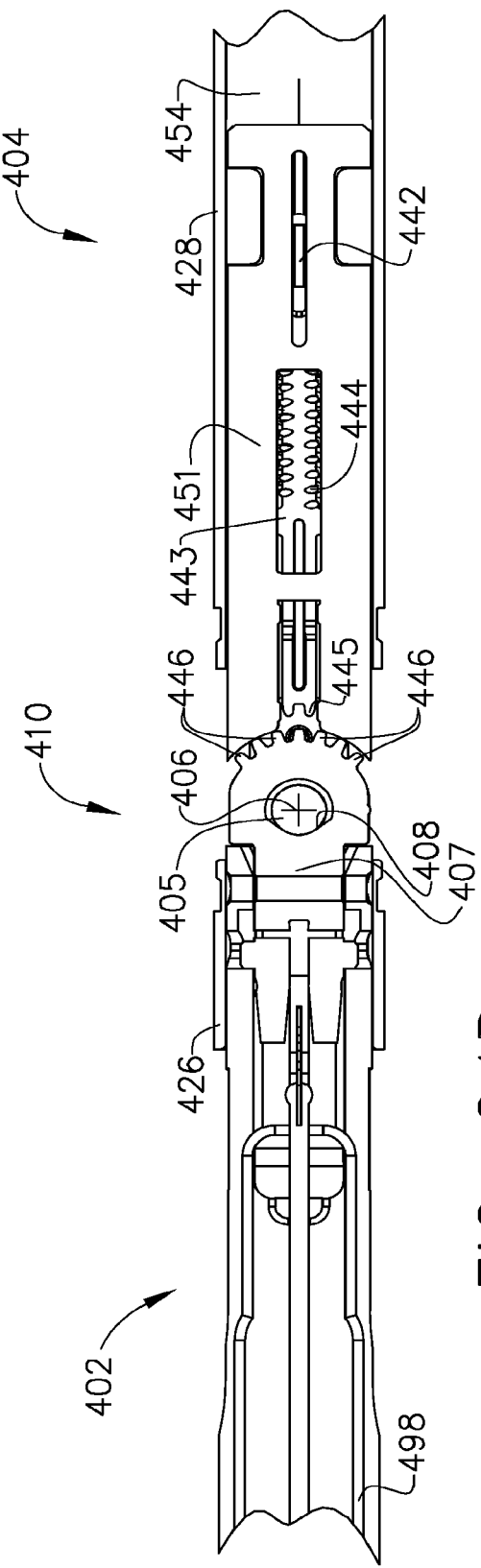

```
                         ┌──────────────────────────────────────────┐
                         │ Access characterization data stored in   │
                         │ memory, where the characterization data  │
          8001           │ represents the relationship between the  │
            ↘            │ articulation angle of the end effector   │
                         │ and the effective transection length     │
                         │ distal of an articulation joint    8102  │
                         └──────────────────────────────────────────┘
                                            │
                                            ▼
                         ┌──────────────────────────────────────────┐
                         │ Track the articulation angle of the end  │
                         │ effector during use of the surgical      │
                         │ instrument                         8104  │
                         └──────────────────────────────────────────┘
                                            │
                                            ▼
                         ┌──────────────────────────────────────────┐
                         │ Adjust the targeted transection length   │
                         │ set by surgical instrument based on the  │
                         │ known articulation angle and the         │
                         │ characterization data              8106  │
                         └──────────────────────────────────────────┘
```

FIG. 50

Key

| | SET PORT B TO | | | | | READ PORT B AS | | |
|---|---|---|---|---|---|---|---|---|
| | RB3 | RB2 | RB1 | RB0 | | RB3 | RB2 | RB1 |
| RB0 | | | | | | | | |
| SW1 | HiZ | HiZ | HiZ | 0 | | 0 | 0 | 1 | X |
| SW2 | HiZ | HiZ | HiZ | 0 | | 0 | 1 | 0 | X |
| SW3 | HiZ | HiZ | HiZ | 0 | | 0 | 1 | 1 | X |
| SW4 | HiZ | HiZ | HiZ | 0 | | 1 | 0 | 0 | X |
| SW5 | HiZ | HiZ | 0 | HiZ | | 0 | 0 | X | 1 |
| SW6 | HiZ | HiZ | 0 | HiZ | | 0 | 1 | X | 1 |
| SW7 | HiZ | HiZ | 0 | HiZ | | 0 | 1 | X | 0 |
| SW8 | HiZ | HiZ | 0 | HiZ | | 1 | 0 | X | 1 |
| SW9 | HiZ | 0 | HiZ | HiZ | | 0 | X | 1 | 1 |
| SW10 | HiZ | 0 | HiZ | HiZ | | 0 | X | 0 | 1 |
| SW11 | HiZ | 0 | HiZ | HiZ | | 0 | X | 1 | 0 |
| SW12 | HiZ | 0 | HiZ | HiZ | | 1 | X | 0 | 1 |
| SW13 | 0 | HiZ | HiZ | HiZ | | X | 0 | 1 | 1 |
| SW14 | 0 | HiZ | HiZ | HiZ | | X | 1 | 0 | 1 |
| SW15 | 0 | HiZ | HiZ | HiZ | | X | 1 | 1 | 0 |
| SW16 | 0 | HiZ | HiZ | HiZ | | X | 0 | 0 | 1 |

Enc.Sn=(RFiD#1, RFiD#2, RFiD#3) {Hash / Internal key #X}

(Internal key X, ENC.Sn) {Hash / Private key}

X=1, for package authentication
X=2, " cartridge "
X=3, " retainer "
X=4, " sled "
X=5
X=6

FIG. 63

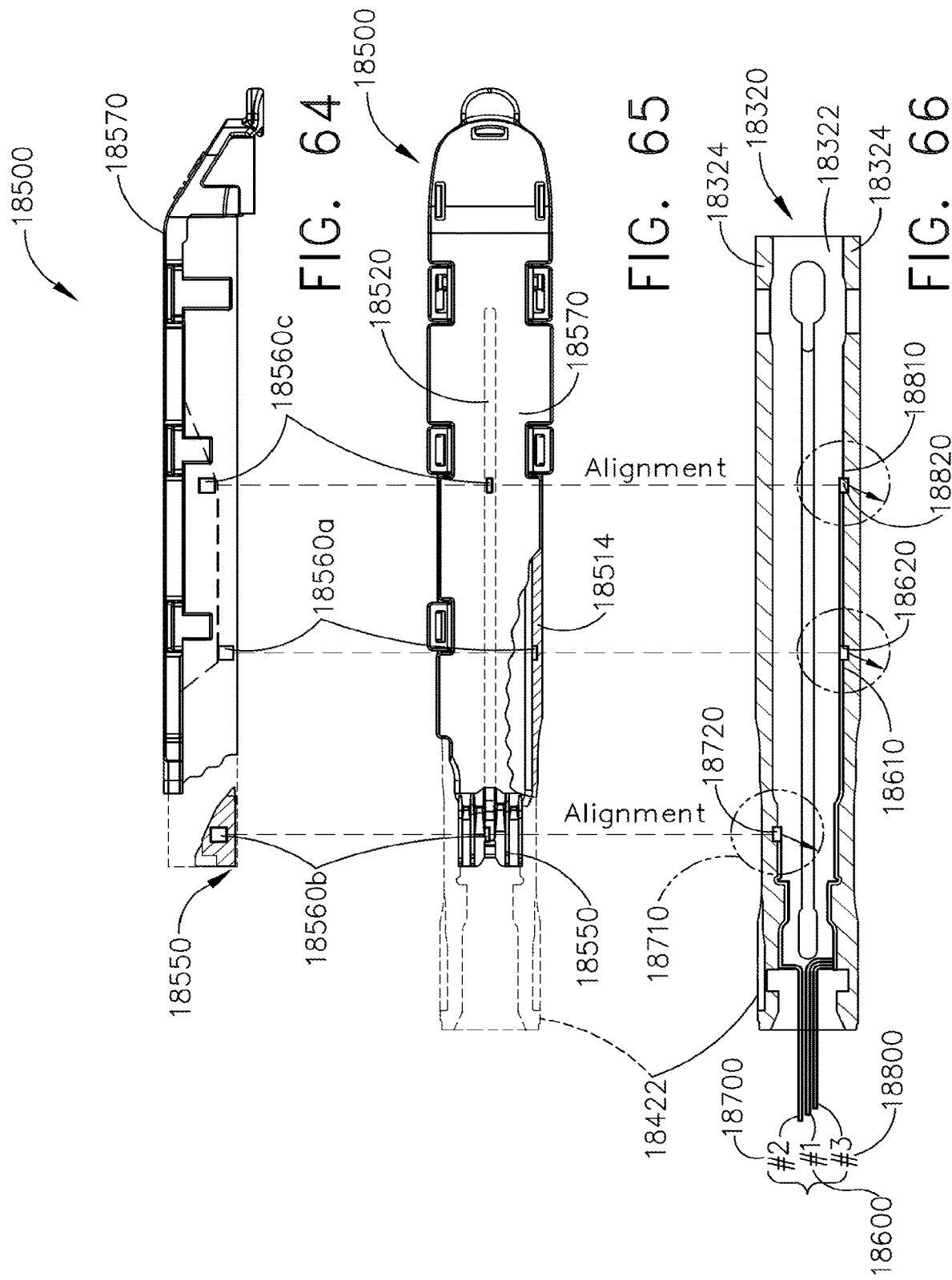

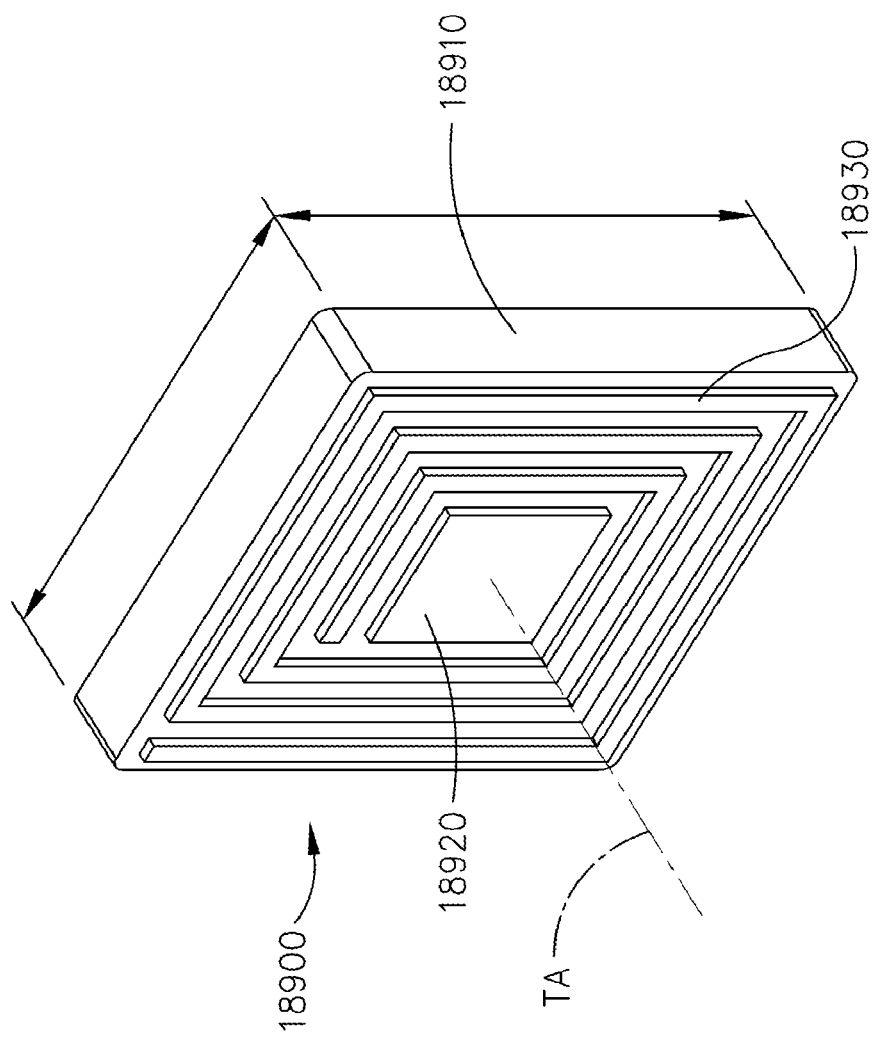

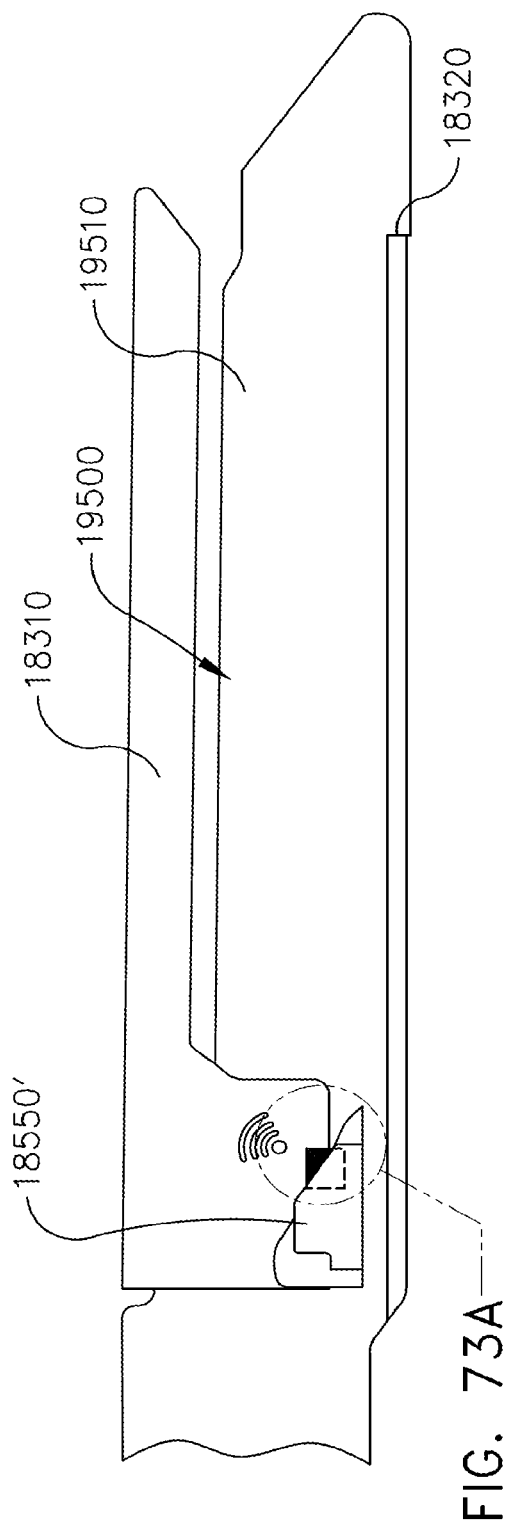

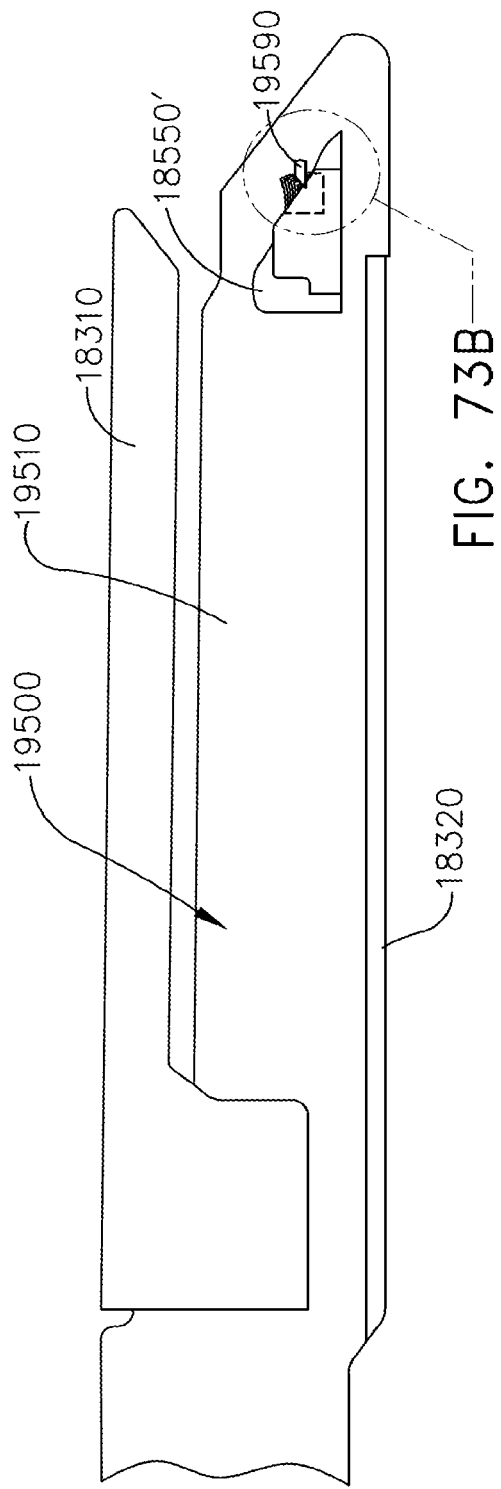

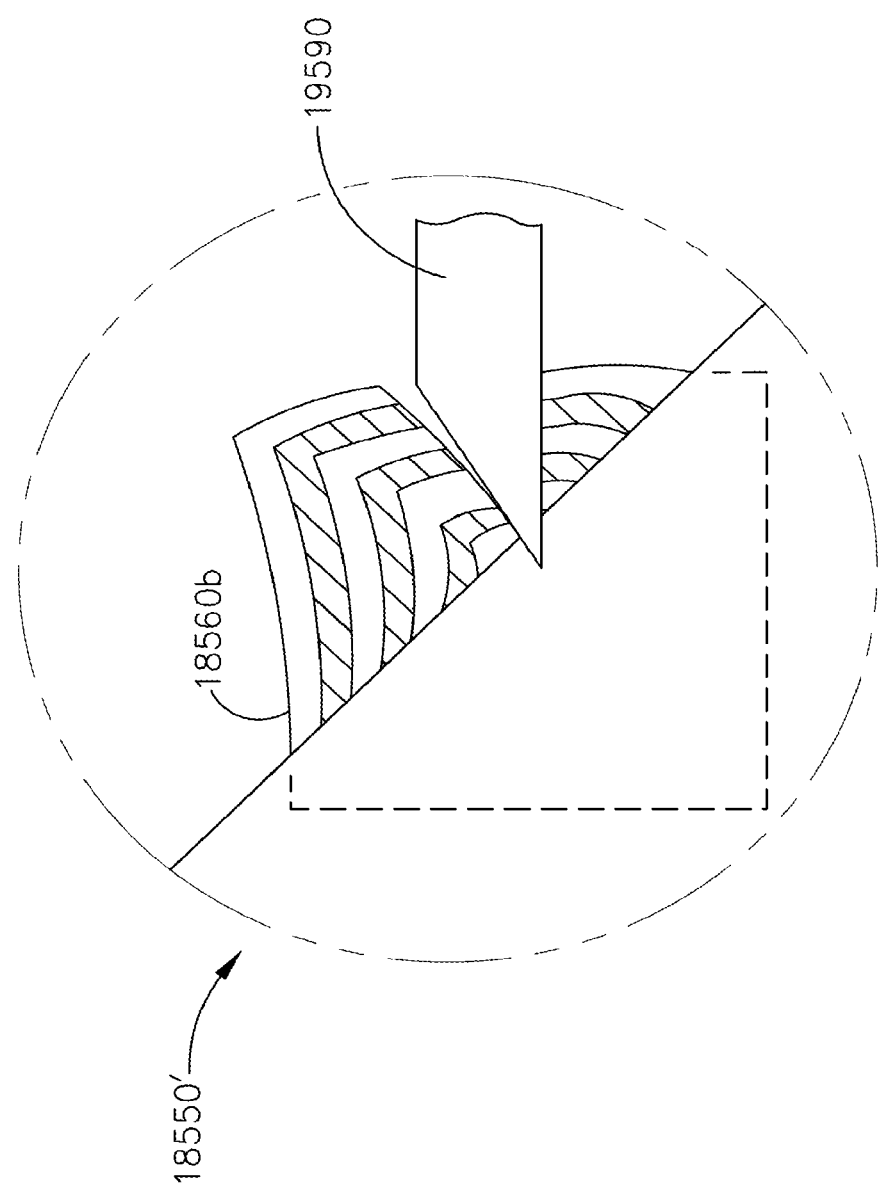

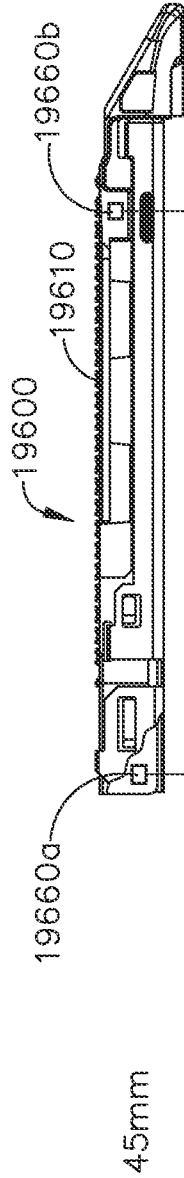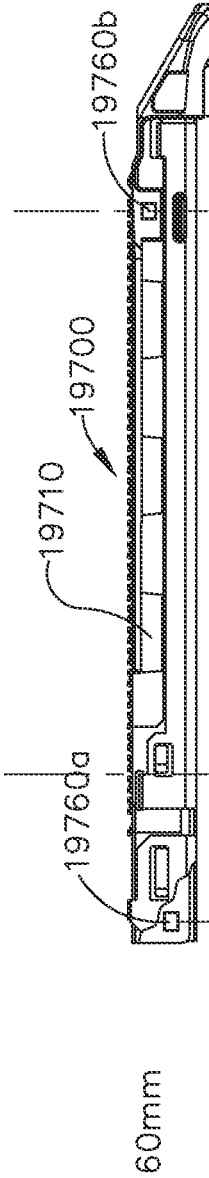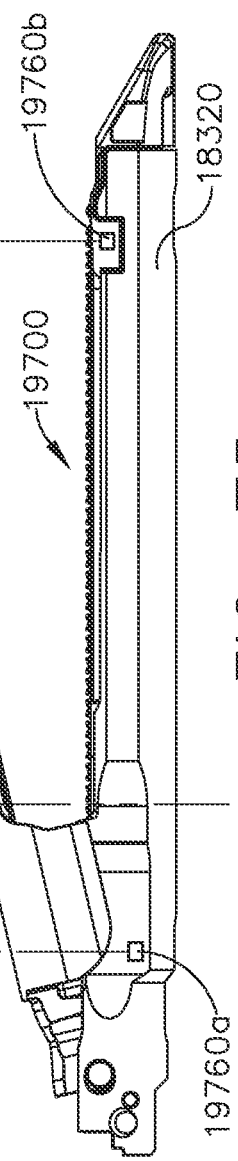

METHOD FOR AUTHENTICATING THE COMPATIBILITY OF A STAPLE CARTRIDGE WITH A SURGICAL INSTRUMENT

CROSS-REFERENCE TO RELATED APPLICATIONS

This application is a continuation application claiming priority under 35 U.S.C. § 120 to U.S. patent application Ser. No. 17/551,810, entitled METHOD FOR AUTHENTICATING THE COMPATIBILITY OF A STAPLE CARTRIDGE WITH A SURGICAL INSTRUMENT, filed on Dec. 15, 2021, issued on Sep. 5, 2023 as U.S. Pat. No. 11,744,593; which claims the benefit under 35 U.S.C. § 120 to U.S. patent application Ser. No. 16/458,104, entitled METHOD FOR AUTHENTICATING THE COMPATIBILITY OF A STAPLE CARTRIDGE WITH A SURGICAL INSTRUMENT, filed on Jun. 30, 2019, published as U.S. Patent Application Publication No. 2020/0405301, issued as U.S. Pat. No. 11,229,437 on Jan. 25, 2022, which claims the benefit under 35 U.S.C. § 119(e) to U.S. Provisional Patent Application Ser. No. 62/868,457, entitled SURGICAL SYSTEMS WITH MULTIPLE RFID TAGS, filed on Jun. 28, 2019, the entire disclosures of which are hereby incorporated by reference herein.

BACKGROUND

The present invention relates to surgical instruments and, in various embodiments, to surgical cutting and stapling instruments and staple cartridges therefor that are designed to cut and staple tissue. In various embodiments, RFID technology can be used to identify the components of a surgical instrument, such as staple cartridges, for example. Examples of surgical systems which use RFID technology can be found in the disclosures of U.S. Pat. No. 7,959,050, entitled ELECTRICALLY SELF-POWERED SURGICAL INSTRUMENT WITH MANUAL RELEASE, which issued on Jun. 14, 2011, and U.S. Patent Application No. 2015/0053743, entitled ERROR DETECTION ARRANGEMENTS FOR SURGICAL INSTRUMENT ASSEMBLIES, which published on Feb. 26, 2015, now abandoned, and both of which are incorporated by reference herein in their entireties.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 4 is a cross-sectional view of the end effector and the shaft of the surgical instrument of FIG. 1;

FIG. 5 is a detail view of an articulation joint which rotatable connects the shaft and the end effector of FIG. 1 which illustrates the end effector in a neutral, or centered, position;

FIG. 10 depicts the end effector of the surgical instrument of FIG. 1 articulated about the articulation joint;

FIG. 11 is a cross-sectional view of the articulation control of FIG. 6 actuated to move the end effector as shown in FIG. 10;

FIG. 24A is a plan view of the articulation joint of the surgical instrument of FIG. 17 illustrated in a locked configuration;

FIG. 24B is a plan view of the articulation joint of the surgical instrument of FIG. 17 illustrated in an unlocked configuration;

FIG. 50 illustrates one embodiment of a logic diagram for a method of compensating for the effect of splay in flexible knife bands on transection length;

FIG. 63 depicts the structure of a serial number that can be generated for a staple cartridge, such as the staple cartridge of FIG. 62, in accordance with at least one embodiment;

FIG. 64 is an elevation view of the staple cartridge of FIG. 62;

FIG. 65 is a plan view of the staple cartridge of FIG. 62;

FIG. 66 is a cross-sectional plan view of a jaw configured to receive the staple cartridge of FIG. 62;

FIG. 67 is a perspective view of an RFID tag in accordance with at least one embodiment;

FIG. 72 is an elevation view of an end effector including the sled of FIG. 70 in accordance with at least one embodiment;

FIG. 72B is an elevation view of the end effector of FIG. 72 illustrating the sled of FIG. 70 at the end of the staple firing stroke;

FIG. 73B is a detail view of the RFID tag being cut at the end of the staple firing stroke;

FIG. 74A illustrates a staple cartridge;

FIG. 74B illustrates a staple cartridge;

FIG. 75 illustrates an end effector, wherein the staple cartridge of FIG. 74B is compatible with the end effector and the staple cartridge of FIG. 74A is incompatible with the end effector;

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

Figure 1:
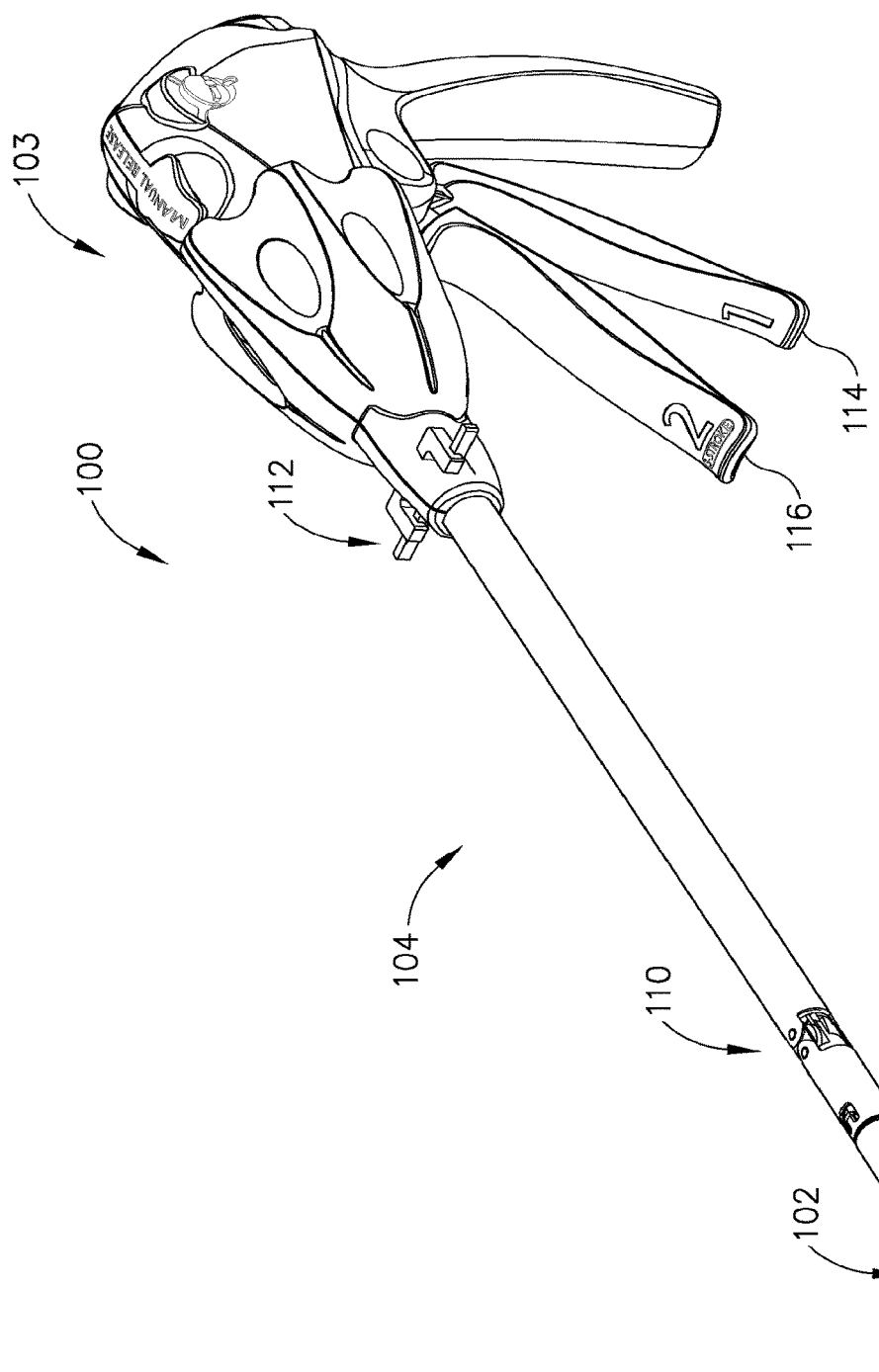
FIG. 1 is a perspective view of a surgical instrument comprising a handle, a shaft, and an articulatable end effector.

Applicant of the present application owns the following U.S. Patent Applications that were filed on Jun. 30, 2019 and which are each herein incorporated by reference in their respective entireties:

U.S. patent application Ser. No. 16/458,108, entitled SURGICAL INSTRUMENT SYSTEM COMPRISING AN RFID SYSTEM, now U.S. Patent Application Publication No. 2020/0405436;

U.S. patent application Ser. No. 16/458,111, entitled SURGICAL INSTRUMENT COMPRISING AN RFID SYSTEM FOR TRACKING A MOVABLE COMPONENT, now U.S. Patent Application Publication No. 2020/0405437;

U.S. patent application Ser. No. 16/458,114, entitled SURGICAL INSTRUMENT COMPRISING AN ALIGNED RFID SENSOR, now U.S. Patent Application Publication No. 2020/0405438;

U.S. patent application Ser. No. 16/458,105, entitled SURGICAL STAPLING SYSTEM HAVING AN INFORMATION DECRYPTION PROTOCOL, now U.S. Patent Application Publication No. 2020/0405302;

U.S. patent application Ser. No. 16/458,110, entitled SURGICAL STAPLING SYSTEM HAVING AN INFORMATION ENCRYPTION PROTOCOL, now U.S. Patent Application Publication No. 2020/0405297;

U.S. patent application Ser. No. 16/458,120, entitled SURGICAL STAPLING SYSTEM HAVING A LOCKOUT MECHANISM FOR AN INCOMPATIBLE CARTRIDGE, now U.S. Patent Application Publication No. 2020/0405303;

U.S. patent application Ser. No. 16/458,125, entitled SURGICAL STAPLING SYSTEM HAVING A FRANGIBLE RFID TAG, now U.S. Patent Application Publication No. 2020/0405441; and U.S. patent application Ser. No. 16/458,103, entitled PACKAGING FOR A REPLACEABLE COMPONENT OF A SURGICAL STAPLING SYSTEM, now U.S. Patent Application Publication No. 2020/0405296.

Applicant of the present application owns the following U.S. Patent Applications that were filed on Jun. 30, 2019 and which are each herein incorporated by reference in their respective entireties:

U.S. patent application Ser. No. 16/458,107, entitled METHOD OF USING MULTIPLE RFID CHIPS WITH A SURGICAL ASSEMBLY, now U.S. Patent Application Publication No. 2020/0405311;

U.S. patent application Ser. No. 16/458,109, entitled MECHANISMS FOR PROPER ANVIL ATTACHMENT SURGICAL STAPLING HEAD ASSEMBLY, now U.S. Patent Application Publication No. 2020/0405312;

U.S. patent application Ser. No. 16/458,119, entitled MECHANISMS FOR MOTOR CONTROL ADJUSTMENTS OF A MOTORIZED SURGICAL INSTRUMENT, now U.S. Patent Application Publication No. 2020/0405314;

U.S. patent application Ser. No. 16/458,115, entitled SURGICAL INSTRUMENT WITH BATTERY COMPATIBILITY VERIFICATION FUNCTIONALITY, now U.S. Patent Application Publication No. 2020/0405313;

U.S. patent application Ser. No. 16/458,117, entitled SURGICAL SYSTEM WITH RFID TAGS FOR UPDATING MOTOR ASSEMBLY PARAMETERS, now U.S. Patent Application Publication No. 2020/0405439;

U.S. patent application Ser. No. 16/458,121, entitled SURGICAL SYSTEMS WITH MULTIPLE RFID TAGS, now U.S. Patent Application Publication No. 2020/0405440;

U.S. patent application Ser. No. 16/458,122, entitled RFID IDENTIFICATION SYSTEMS FOR SURGICAL INSTRUMENTS, now U.S. Patent Application Publication No. 2020/0410177;

U.S. patent application Ser. No. 16/458,106, entitled RFID IDENTIFICATION SYSTEMS FOR SURGICAL INSTRUMENTS, now U.S. Patent Application Publication No. 2020/0405316;

U.S. patent application Ser. No. 16/458,112, entitled SURGICAL RFID ASSEMBLIES FOR DISPLAY AND COMMUNICATION, now U.S. Patent Application Publication No. 2020/0405409;

U.S. patent application Ser. No. 16/458,116, entitled SURGICAL RFID ASSEMBLIES FOR COMPATIBILITY DETECTION, now U.S. Patent Application Publication No. 2020/0410180; and U.S. patent application Ser. No. 16/458,118, entitled SURGICAL RFID ASSEMBLIES FOR INSTRUMENT OPERATIONAL SETTING CONTROL, now U.S. Patent Application Publication No. 2020/0405410.

Applicant of the present application owns the following U.S. Patent Applications that were filed on May 1, 2018 and which are each herein incorporated by reference in their respective entireties:

U.S. Provisional Patent Application Ser. No. 62/665,129, entitled SURGICAL SUTURING SYSTEMS;

U.S. Provisional Patent Application Ser. No. 62/665,139, entitled SURGICAL INSTRUMENTS COMPRISING CONTROL SYSTEMS;

U.S. Provisional Patent Application Ser. No. 62/665,177, entitled SURGICAL INSTRUMENTS COMPRISING HANDLE ARRANGEMENTS;

U.S. Provisional Patent Application Ser. No. 62/665,128, entitled MODULAR SURGICAL INSTRUMENTS;

U.S. Provisional Patent Application Ser. No. 62/665,192, entitled SURGICAL DISSECTORS; and U.S. Provisional Patent Application Ser. No. 62/665,134, entitled SURGICAL CLIP APPLIER.

Applicant of the present application owns the following U.S. Patent Applications that were filed on Aug. 24, 2018 which are each herein incorporated by reference in their respective entireties:

U.S. patent application Ser. No. 16/112,129, entitled SURGICAL SUTURING INSTRUMENT CONFIGURED TO MANIPULATE TISSUE USING MECHANICAL AND ELECTRICAL POWER;

U.S. patent application Ser. No. 16/112,155, entitled SURGICAL SUTURING INSTRUMENT COMPRISING A CAPTURE WIDTH WHICH IS LARGER THAN TROCAR DIAMETER;

U.S. patent application Ser. No. 16/112,168, entitled SURGICAL SUTURING INSTRUMENT COMPRISING A NON-CIRCULAR NEEDLE;

U.S. patent application Ser. No. 16/112,180, entitled ELECTRICAL POWER OUTPUT CONTROL BASED ON MECHANICAL FORCES;

U.S. patent application Ser. No. 16/112,193, entitled REACTIVE ALGORITHM FOR SURGICAL SYSTEM;

U.S. patent application Ser. No. 16/112,099, entitled SURGICAL INSTRUMENT COMPRISING AN ADAPTIVE ELECTRICAL SYSTEM;

U.S. patent application Ser. No. 16/112,112, entitled CONTROL SYSTEM ARRANGEMENTS FOR A MODULAR SURGICAL INSTRUMENT;

U.S. patent application Ser. No. 16/112,119, entitled ADAPTIVE CONTROL PROGRAMS FOR A SURGICAL SYSTEM COMPRISING MORE THAN ONE TYPE OF CARTRIDGE;

U.S. patent application Ser. No. 16/112,097, entitled SURGICAL INSTRUMENT SYSTEMS COMPRISING BATTERY ARRANGEMENTS;

U.S. patent application Ser. No. 16/112,109, entitled SURGICAL INSTRUMENT SYSTEMS COMPRISING HANDLE ARRANGEMENTS;

U.S. patent application Ser. No. 16/112,114, entitled SURGICAL INSTRUMENT SYSTEMS COMPRISING FEEDBACK MECHANISMS;

U.S. patent application Ser. No. 16/112,117, entitled SURGICAL INSTRUMENT SYSTEMS COMPRISING LOCKOUT MECHANISMS;

U.S. patent application Ser. No. 16/112,095, entitled SURGICAL INSTRUMENTS COMPRISING A LOCKABLE END EFFECTOR SOCKET;

U.S. patent application Ser. No. 16/112,121, entitled SURGICAL INSTRUMENTS COMPRISING A SHIFTING MECHANISM;

U.S. patent application Ser. No. 16/112,151, entitled SURGICAL INSTRUMENTS COMPRISING A SYSTEM FOR ARTICULATION AND ROTATION COMPENSATION;

U.S. patent application Ser. No. 16/112,154, entitled SURGICAL INSTRUMENTS COMPRISING A BIASED SHIFTING MECHANISM;

U.S. patent application Ser. No. 16/112,226, entitled SURGICAL INSTRUMENTS COMPRISING AN ARTICULATION DRIVE THAT PROVIDES FOR HIGH ARTICULATION ANGLES;

U.S. patent application Ser. No. 16/112,062, entitled SURGICAL DISSECTORS AND MANUFACTURING TECHNIQUES;

U.S. patent application Ser. No. 16/112,098, entitled SURGICAL DISSECTORS CONFIGURED TO APPLY MECHANICAL AND ELECTRICAL ENERGY;

U.S. patent application Ser. No. 16/112,237, entitled SURGICAL CLIP APPLIER CONFIGURED TO STORE CLIPS IN A STORED STATE;

U.S. patent application Ser. No. 16/112,245, entitled SURGICAL CLIP APPLIER COMPRISING AN EMPTY CLIP CARTRIDGE LOCKOUT;

U.S. patent application Ser. No. 16/112,249, entitled SURGICAL CLIP APPLIER COMPRISING AN AUTOMATIC CLIP FEEDING SYSTEM;

U.S. patent application Ser. No. 16/112,253, entitled SURGICAL CLIP APPLIER COMPRISING ADAPTIVE FIRING CONTROL; and U.S. patent application Ser. No. 16/112,257, entitled SURGICAL CLIP APPLIER COMPRISING ADAPTIVE CONTROL IN RESPONSE TO A STRAIN GAUGE CIRCUIT.

Applicant of the present application owns the following U.S. Patent Applications that were filed on Oct. 26, 2018 which are each herein incorporated by reference in their respective entireties:

U.S. patent application Ser. No. 16/172,130, entitled CLIP APPLIER COMPRISING INTERCHANGEABLE CLIP RELOADS;

U.S. patent application Ser. No. 16/172,066, entitled CLIP APPLIER COMPRISING A MOVABLE CLIP MAGAZINE;

U.S. patent application Ser. No. 16/172,078, entitled CLIP APPLIER COMPRISING A ROTATABLE CLIP MAGAZINE;

U.S. patent application Ser. No. 16/172,087, entitled CLIP APPLIER COMPRISING CLIP ADVANCING SYSTEMS;

U.S. patent application Ser. No. 16/172,094, entitled CLIP APPLIER COMPRISING A CLIP CRIMPING SYSTEM;

U.S. patent application Ser. No. 16/172,128, entitled CLIP APPLIER COMPRISING A RECIPROCATING CLIP ADVANCING MEMBER;

U.S. patent application Ser. No. 16/172,168, entitled CLIP APPLIER COMPRISING A MOTOR CONTROLLER;

U.S. patent application Ser. No. 16/172,164, entitled SURGICAL SYSTEM COMPRISING A SURGICAL TOOL AND A SURGICAL HUB; and U.S. patent application Ser. No. 16/172,303, entitled METHOD FOR OPERATING A POWERED ARTICULATING MULTI-CLIP APPLIER.

Applicant of the present application owns the following U.S. Patent Applications, filed on Dec. 4, 2018, the disclosure of each of which is herein incorporated by reference in its entirety:

U.S. patent application Ser. No. 16/209,385, entitled METHOD OF HUB COMMUNICATION, PROCESSING, STORAGE AND DISPLAY;

U.S. patent application Ser. No. 16/209,395, entitled METHOD OF HUB COMMUNICATION;

U.S. patent application Ser. No. 16/209,403, entitled METHOD OF CLOUD BASED DATA ANALYTICS FOR USE WITH THE HUB;

U.S. patent application Ser. No. 16/209,407, entitled METHOD OF ROBOTIC HUB COMMUNICATION, DETECTION, AND CONTROL;

U.S. patent application Ser. No. 16/209,416, entitled METHOD OF HUB COMMUNICATION, PROCESSING, DISPLAY, AND CLOUD ANALYTICS;

U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS;

U.S. patent application Ser. No. 16/209,427, entitled METHOD OF USING REINFORCED FLEXIBLE CIRCUITS WITH MULTIPLE SENSORS TO OPTIMIZE PERFORMANCE OF RADIO FREQUENCY DEVICES;

U.S. patent application Ser. No. 16/209,433, entitled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB;

U.S. patent application Ser. No. 16/209,447, entitled METHOD FOR SMOKE EVACUATION FOR SURGICAL HUB;

U.S. patent application Ser. No. 16/209,453, entitled METHOD FOR CONTROLLING SMART ENERGY DEVICES;

U.S. patent application Ser. No. 16/209,458, entitled METHOD FOR SMART ENERGY DEVICE INFRASTRUCTURE;

U.S. patent application Ser. No. 16/209,465, entitled METHOD FOR ADAPTIVE CONTROL SCHEMES FOR SURGICAL NETWORK CONTROL AND INTERACTION;

U.S. patent application Ser. No. 16/209,478, entitled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE;

U.S. patent application Ser. No. 16/209,490, entitled METHOD FOR FACILITY DATA COLLECTION AND INTERPRETATION; and U.S. patent application Ser. No. 16/209,491, entitled METHOD FOR CIRCULAR STAPLER CONTROL ALGORITHM ADJUSTMENT BASED ON SITUATIONAL AWARENESS.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 2:
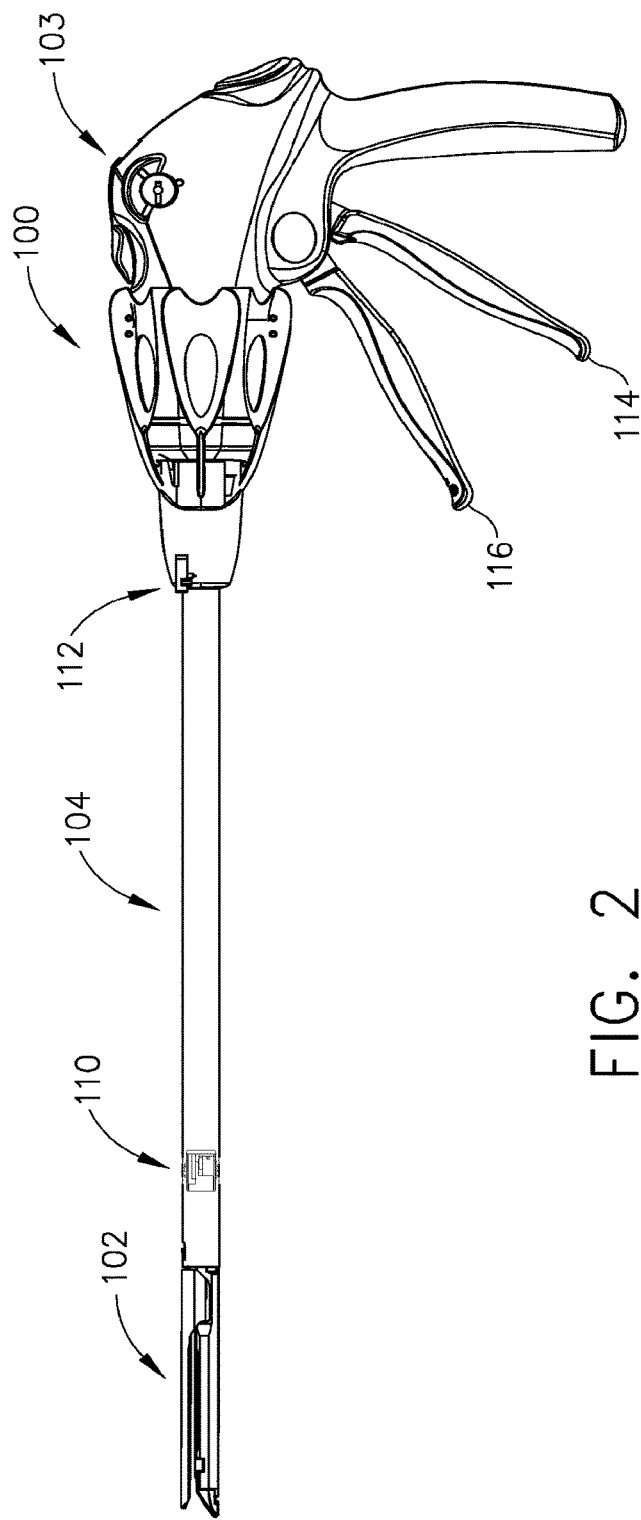
FIG. 2 is an elevational view of the surgical instrument of FIG. 1.
Figure 3:
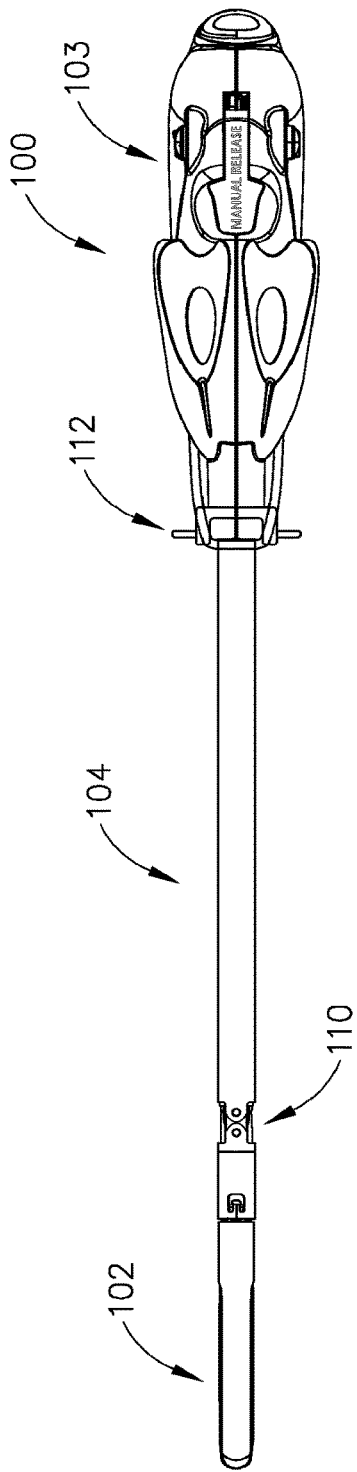
FIG. 3 is a plan view of the surgical instrument of FIG. 1.

FIGS. 1-3 illustrate an exemplary surgical instrument 100 which includes a handle 103, a shaft 104 and an articulating end effector 102 pivotally connected to the shaft 104 at articulation joint 110. An articulation control 112 is provided to effect rotation of the end effector 102 about articulation joint 110. The end effector 102 comprises an endocutter for clamping, severing and stapling tissue; however, it will be appreciated that various embodiments may include end effectors configured to act as other surgical devices including, for example, graspers, cutters, staplers, clip appliers, access devices, drug/gene therapy delivery devices, ultrasound, RF, and/or laser energy devices, etc. The handle 103 of the instrument 100 includes a closure trigger 114 and a firing trigger 116 for actuating the end effector 102. It will be appreciated that instruments having end effectors directed to different surgical tasks may have different numbers or types of triggers or other suitable controls for operating an end effector. The end effector 102 is connected to the handle 103 by a shaft 104. A clinician may articulate the end effector 102 relative to the shaft 104 by utilizing the articulation control 112, as described in greater detail further below.

It should be appreciated that spatial terms such as vertical, horizontal, right, left etc., are given herein with reference to the figures assuming that the longitudinal axis of the surgical instrument 100 is co-axial to the central axis of the shaft 104, with the triggers 114, 116 extending downwardly at an acute angle from the bottom of the handle 103. In actual practice, however, the surgical instrument 100 may be oriented at various angles and as such these spatial terms are used relative to the surgical instrument 100 itself. Further, proximal is used to denote a perspective of a clinician who is behind the handle 103 who places the end effector 102 distal, or away from him or herself. As used herein, the phrase, "substantially transverse to the longitudinal axis" where the "longitudinal axis" is the axis of the shaft, refers to a direction that is nearly perpendicular to the longitudinal axis. It will be appreciated, however, that directions that deviate some from perpendicular to the longitudinal axis are also substantially transverse to the longitudinal axis.

Various embodiments disclosed herein are directed to instruments having an articulation joint driven by bending cables or bands. FIGS. 4 and 5 show a cross-sectional top view of the elongate shaft 104 and the end effector 102 including a band 205 that is mechanically coupled to a boss 206 extending from the end effector 102. The band 205 may include band portions 202 and 204 extending proximally from the boss 206 along the elongate shaft 104 and through the articulation control 112. The band 205 and band portions 202, 204 can have a fixed length. The band 205 may be mechanically coupled to the boss 206 as shown using any suitable fastening method including, for example, glue, welding, etc. In various embodiments, each band portion 202, 204 may be provided as a separate band, with each separate band having one end mechanically coupled to the boss 206 and another end extending through the shaft 104 and articulation controller 112. The separate bands may be mechanically coupled to the boss 206 as described above.

Figure 6:
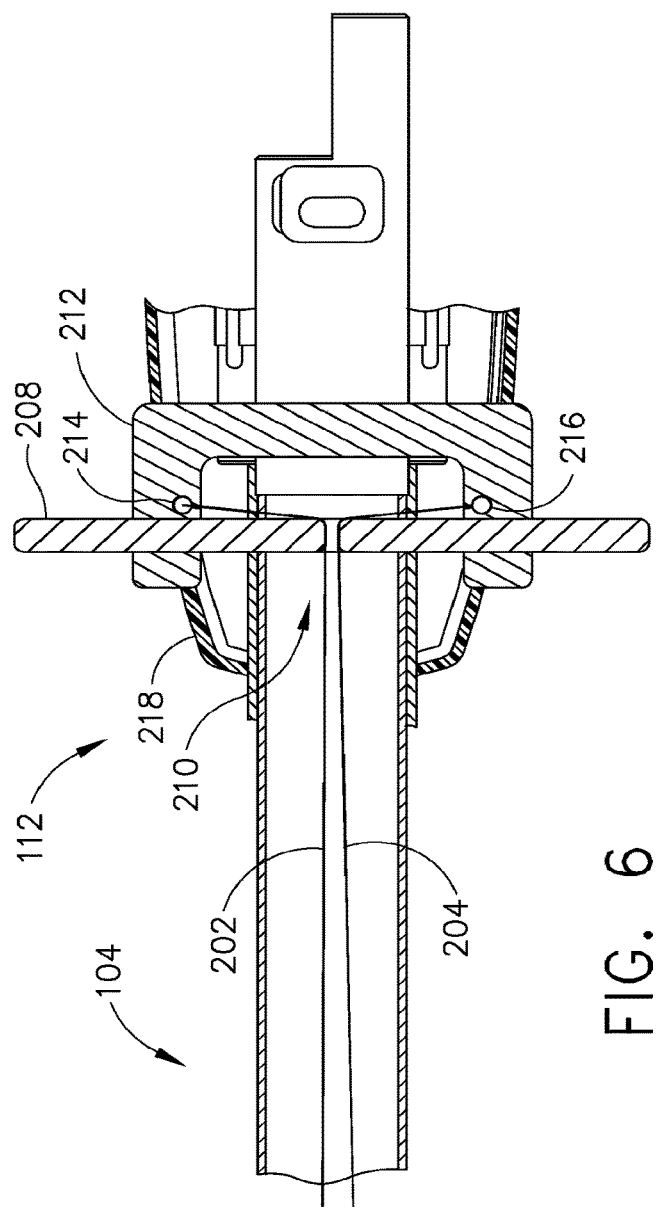
FIG. 6 is a cross-sectional view of an articulation control of the surgical instrument of FIG. 1 in a neutral, or centered, position.

Further to the above, band portions 202, 204 may extend from the boss 206, through the articulation joint 110 and along the shaft 104 to the articulation control 112, shown in FIG. 6. The articulation control 112 can include an articulation slide 208, a frame 212 and an enclosure 218. Band portions 202, 204 may pass through the articulation slide 208 by way of slot 210 or other aperture, although it will be appreciated that the band portions 202, 204 may be coupled to the slide 208 by any suitable means. The articulation slide 208 may be one piece, as shown in FIG. 6, or may include two pieces with an interface between the two pieces defining the slot 210. In one non-limiting embodiment, the articulation slide 208 may include multiple slots, for example, with each slot configured to receive one of the band portions 202, 204. Enclosure 218 may cover the various components of the articulation control 112 to prevent debris from entering the articulation control 112.

Referring again to FIG. 6, the band portions 202, 204 may be anchored to the frame 212 at connection points 214, 216, respectively, which are proximally located from the slot 210. It will be appreciated that band portions 202, 204 may be anchored anywhere in the instrument 10 located proximally from the slot 210, including the handle 103. The non-limiting embodiment of FIG. 6 shows that the band portions 202, 204 can comprise a bent configuration between the connection points 214, 216 and the slot 210 located near the longitudinal axis of the shaft 104. Other embodiments are envisioned in which the band portions 202, 204 are straight.

Figure 8:
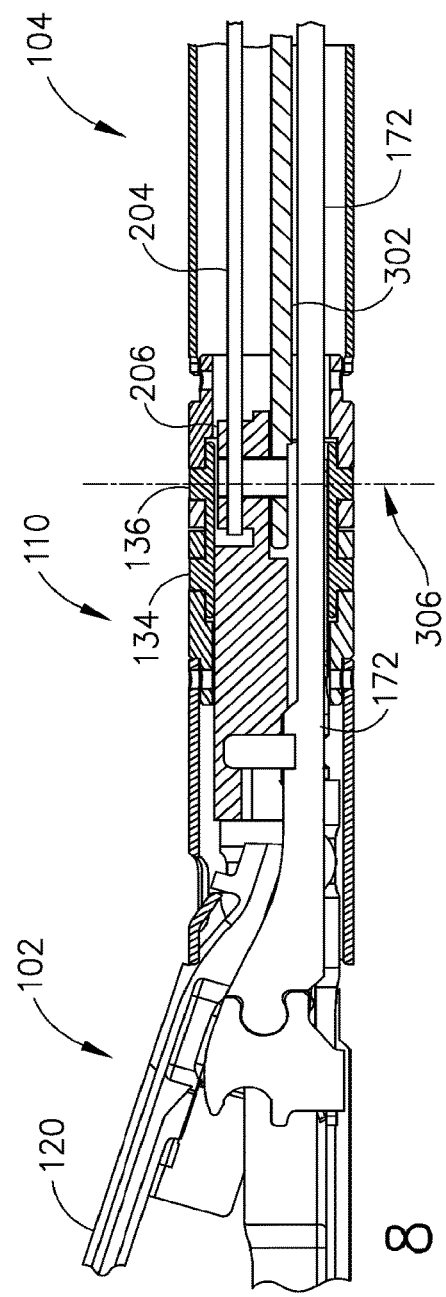
FIG. 8 is a cross-sectional view of the end effector, elongate shaft, and articulation joint of the surgical instrument of FIG. 1.
Figure 7:
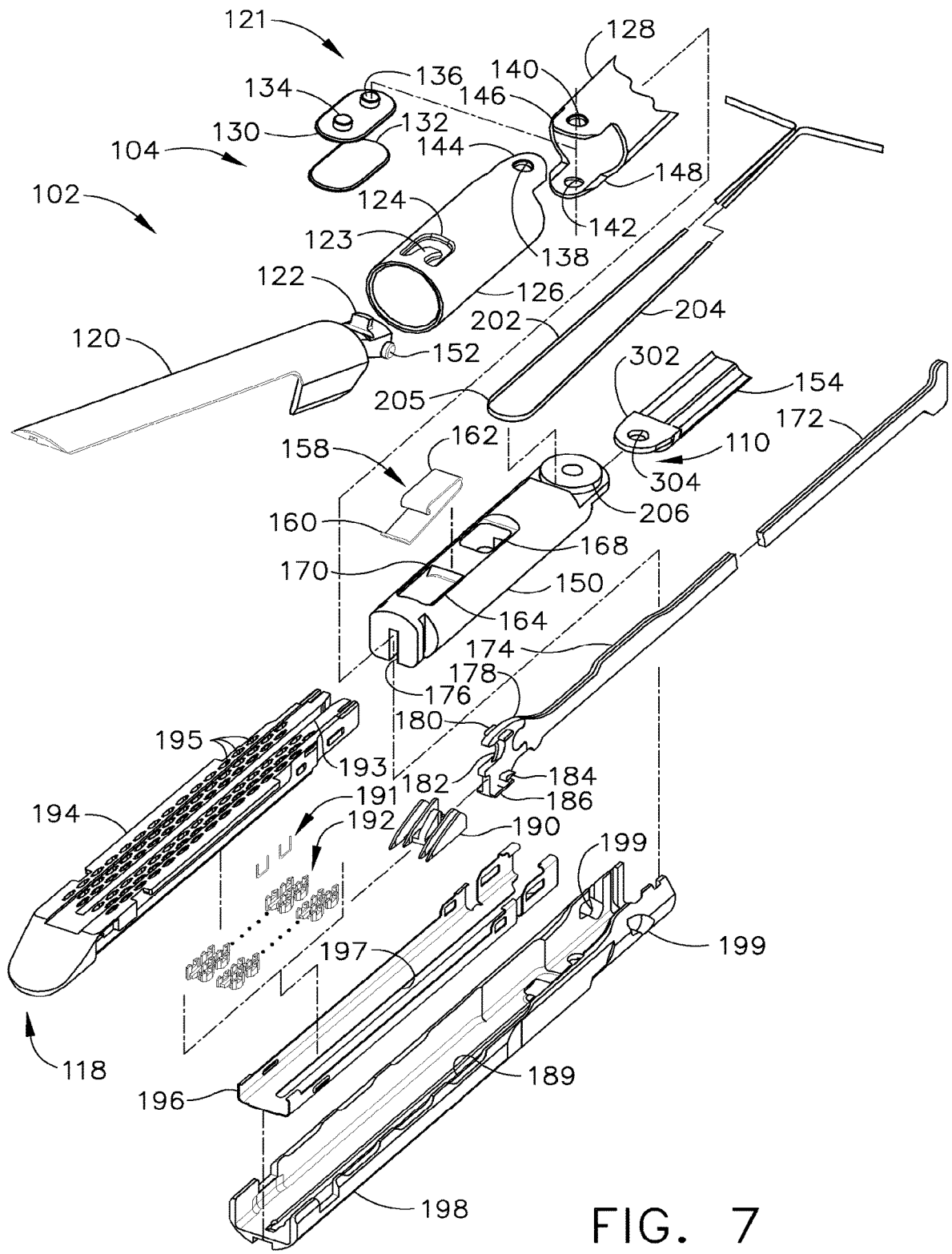
FIG. 7 is an exploded view of the end effector, elongate shaft, and articulation joint of the surgical instrument of FIG. 1.
Figure 9:
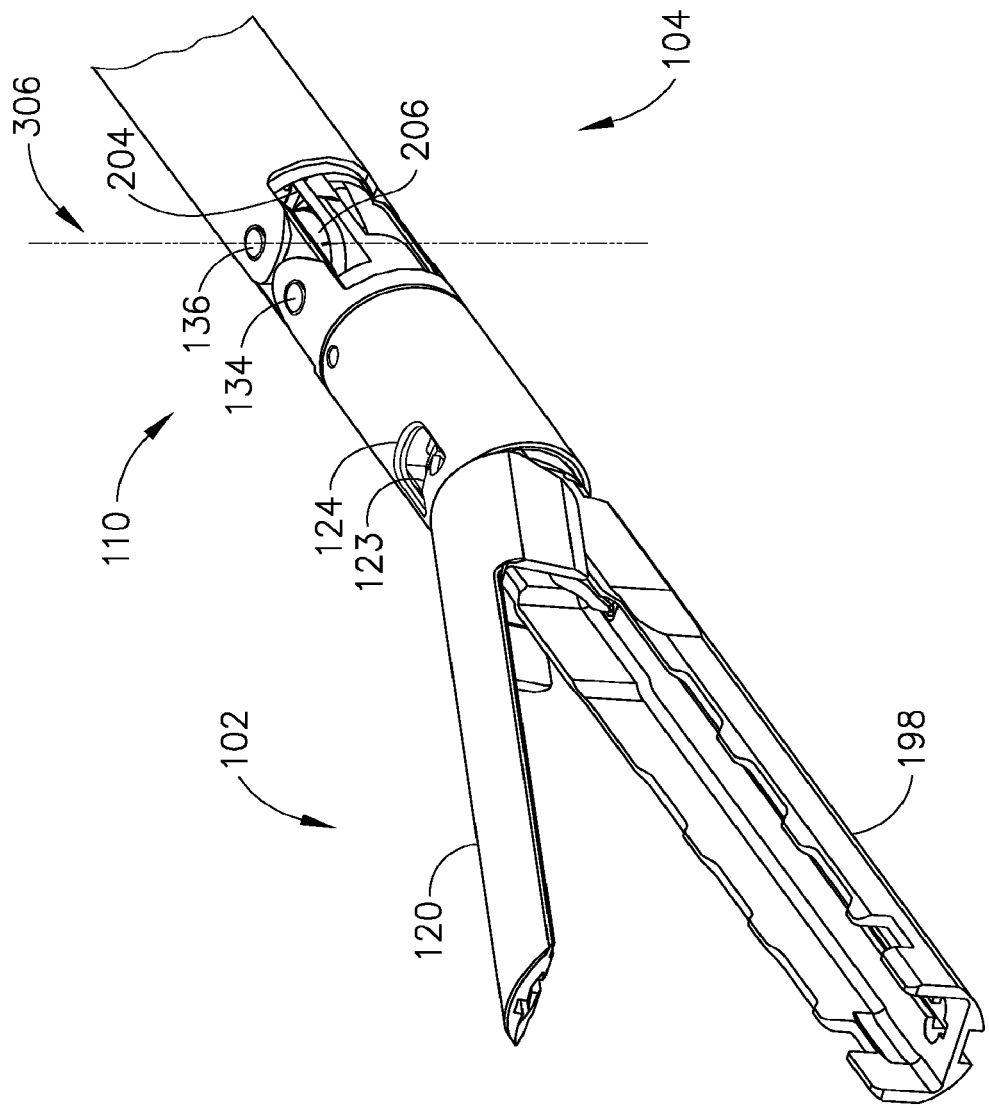
FIG. 9 is a perspective view of the end effector, elongate shaft, and articulation joint of the surgical instrument of FIG. 1.

FIGS. 7-9 show views of the end effector 102 and elongate shaft 104 of the instrument 100 including the articulation joint 110 shown in FIG. 5. FIG. 7 shows an exploded view of the end effector 102 and elongate shaft 104 including various internal components. In at least one embodiment, an end effector frame 150 and shaft frame 154 are configured to be joined at articulation joint 110. Boss 206 may be integral to the end effector frame 150 with band 205 interfacing the boss 206 as shown. The shaft frame 154 may include a distally directed tang 302 defining an aperture 304. The aperture 304 may be positioned to interface an articulation pin (not shown) included in end effector frame 150 allowing the end effector frame 150 to pivot relative to the shaft frame 154, and accordingly, the end effector 102 to pivot relative to the shaft 104. When assembled, the various components may pivot about articulation joint 110 at an articulation axis 306 shown in FIGS. 9 and 10.

FIG. 7 also shows an anvil 120. In this non-limiting embodiment, the anvil 120 is coupled to an elongate channel 198. For example, apertures 199 can be defined in the elongate channel 198 which can receive pins 152 extending from the anvil 120 and allow the anvil 120 to pivot from an open position to a closed position relative to the elongate channel 198 and staple cartridge 118. In addition, FIG. 7 shows a firing bar 172, configured to longitudinally translate through the shaft frame 154, through the flexible closure and pivoting frame articulation joint 110, and through a firing slot 176 in the distal frame 150 into the end effector 102. The firing bar 172 may be constructed from one solid section, or in various embodiments, may include a laminate material comprising, for example, a stack of steel plates. It will be appreciated that a firing bar 172 made from a laminate material may lower the force required to articulate the end effector 102. In various embodiments, a spring clip 158 can be mounted in the end effector frame 150 to bias the firing bar 172 downwardly. Distal and proximal square apertures 164, 168 formed on top of the end effector frame 150 may define a clip bar 170 therebetween that receives a top arm 162 of a clip spring 158 whose lower, distally extended arm 160 asserts a downward force on a raised portion 174 of the firing bar 172, as discussed below.

A distally projecting end of the firing bar 172 can be attached to an E-beam 178 that can, among other things, assist in spacing the anvil 120 from a staple cartridge 118 positioned in the elongate channel 198 when the anvil 120 is in a closed position. The E-beam 178 can also include a sharpened cutting edge 182 which can be used to sever tissue as the E-beam 178 is advanced distally by the firing bar 172. In operation, the E-beam 178 can also actuate, or fire, the staple cartridge 118. The staple cartridge 118 can include a molded cartridge body 194 that holds a plurality of staples 191 resting upon staple drivers 192 within respective upwardly open staple cavities 195. A wedge sled 190 is driven distally by the E-beam 178, sliding upon a cartridge tray 196 that holds together the various components of the replaceable staple cartridge 118. The wedge sled 190 upwardly cams the staple drivers 192 to force out the staples 191 into deforming contact with the anvil 120 while a cutting surface 182 of the E-beam 178 severs clamped tissue.

Further to the above, the E-beam 178 can include upper pins 180 which engage the anvil 120 during firing. The E-beam 178 can further include middle pins 184 and a bottom foot 186 which can engage various portions of the cartridge body 194, cartridge tray 196 and elongate channel 198. When a staple cartridge 118 is positioned within the elongate channel 198, a slot 193 defined in the cartridge body 194 can be aligned with a slot 197 defined in the cartridge tray 196 and a slot 189 defined in the elongate channel 198. In use, the E-beam 178 can slide through the aligned slots 193, 197, and 189 wherein, as indicated in FIG. 7, the bottom foot 186 of the E-beam 178 can engage a groove running along the bottom surface of channel 198 along the length of slot 189, the middle pins 184 can engage the top surfaces of cartridge tray 196 along the length of longitudinal slot 197, and the upper pins 180 can engage the anvil 120. In such circumstances, the E-beam 178 can space, or limit the relative movement between, the anvil 120 and the staple cartridge 118 as the firing bar 172 is moved distally to fire the staples from the staple cartridge 118 and/or incise the tissue captured between the anvil 120 and the staple cartridge 118. Thereafter, the firing bar 172 and the E-beam 178 can be retracted proximally allowing the anvil 120 to be opened to release the two stapled and severed tissue portions (not shown).

FIGS. 7-9 also show a double pivot closure sleeve assembly 121 according to various embodiments. With particular reference to FIG. 7, the double pivot closure sleeve assembly 121 includes a shaft closure tube section 128 having upper and lower distally projecting tangs 146, 148. An end effector closure tube section 126 includes a horseshoe aperture 124 and a tab 123 for engaging the opening tab 122 on the anvil 120. The horseshoe aperture 124 and tab 123 engage tab 122 when the anvil 120 is opened. The closure tube section 126 is shown having upper 144 and lower (not visible) proximally projecting tangs. An upper double pivot link 130 includes upwardly projecting distal and proximal pivot pins 134, 136 that engage respectively an upper distal pin hole 138 in the upper proximally projecting tang 144 and an upper proximal pin hole 140 in the upper distally projecting tang 146. A lower double pivot link 132 includes downwardly projecting distal and proximal pivot pins (not shown in FIG. 7, but see FIG. 8) that engage respectively a lower distal pin hole in the lower proximally projecting tang and a lower proximal pin hole 142 in the lower distally projecting tang 148.

In use, the closure sleeve assembly 121 is translated distally to close the anvil 120, for example, in response to the actuation of the closure trigger 114. The anvil 120 is closed by distally translating the closure tube section 126, and thus the sleeve assembly 121, causing it to strike a proximal surface on the anvil 120 located in FIG. 9A to the left of the tab 122. As shown more clearly in FIGS. 8 and 9, the anvil 120 is opened by proximally translating the tube section 126, and sleeve assembly 121, causing tab 123 and the horseshoe aperture 124 to contact and push against the tab 122 to lift the anvil 120. In the anvil-open position, the double pivot closure sleeve assembly 121 is moved to its proximal position.

Figure 12:
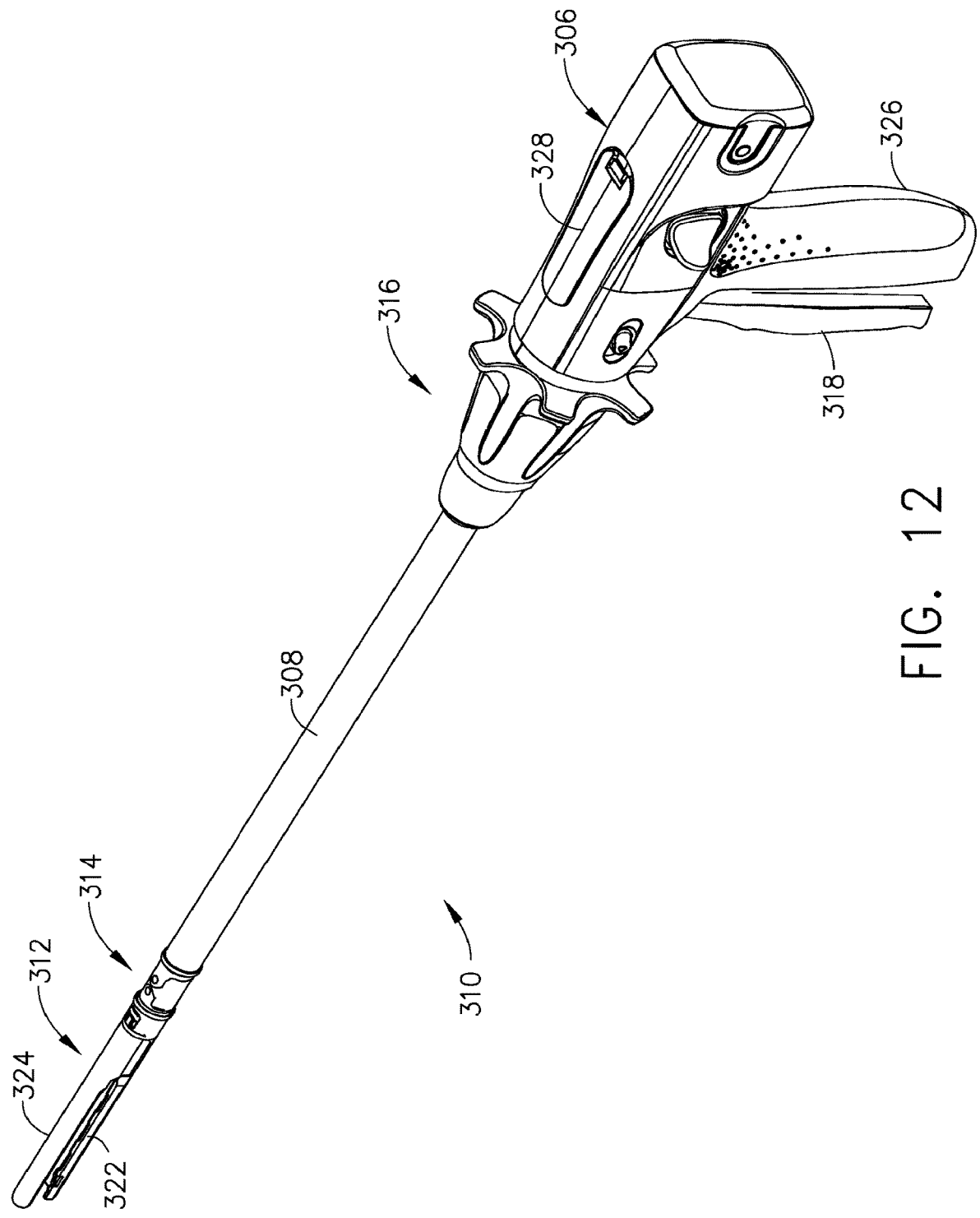
FIG. 12 is a perspective view of a surgical instrument comprising a handle, a shaft, and an articulatable end effector.

In operation, the clinician may articulate the end effector 102 of the instrument 100 relative to the shaft 104 about pivot 110 by pushing the control 112 laterally. From the neutral position, the clinician may articulate the end effector 102 to the left relative to the shaft 104 by providing a lateral force to the left side of the control 112. In response to force, the articulation slide 208 may be pushed at least partially into the frame 212. As the slide 208 is pushed into the frame 212, the slot 210 as well as band portion 204 may be translated across the elongate shaft 104 in a transverse direction, for example, a direction substantially transverse, or perpendicular, to the longitudinal axis of the shaft 104. Accordingly, a force is applied to band portion 204, causing it to resiliently bend and/or displace from its initial pre-bent position toward the opposite side of the shaft 104. Concurrently, band portion 202 is relaxed from its initial pre-bent position. Such movement of the band portion 204, coupled with the straightening of band portion 202, can apply a counter-clockwise rotational force at boss 206 which in turn causes the boss 206 and end effector 102 to pivot to the left about the articulation pivot 110 to a desired angle relative to the axis of the shaft 104 as shown in FIG. 12. The relaxation of the band portion 202 decreases the tension on that band portion, allowing the band portion 204 to articulate the end effector 102 without substantial interference from the band portion 202. It will be appreciated that the clinician may also articulate the end effector 102 to the right relative to the shaft 104 by providing a lateral force to the right side of the control 112. This bends cable portion 202, causing a clockwise rotational force at boss 206 which, in turn, causes the boss 206 and end effector to pivot to the right about articulation pivot 110. Similar to the above, band portion 204 can be concurrently relaxed to permit such movement.

Figure 13:
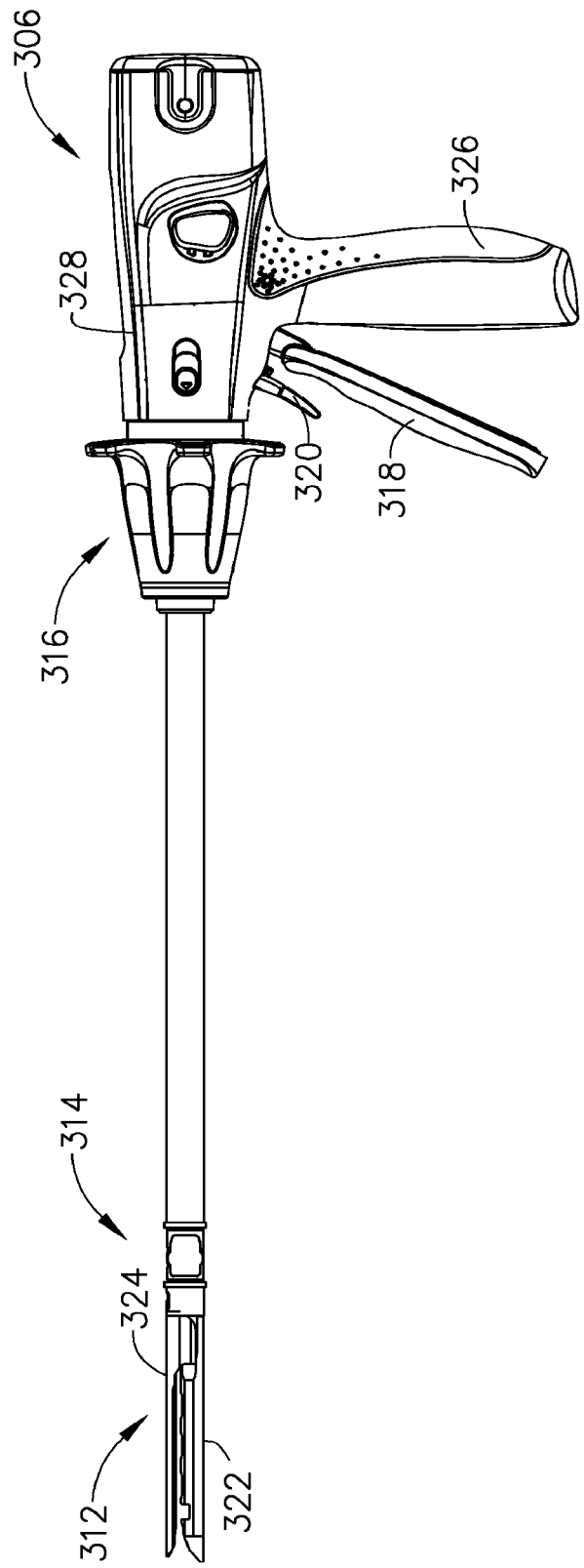
FIG. 13 is a side view of the surgical instrument of FIG. 12.

FIGS. 12 and 13 depict a motor-driven surgical cutting and fastening instrument 310. This illustrated embodiment depicts an endoscopic instrument and, in general, the instrument 310 is described herein as an endoscopic surgical cutting and fastening instrument; however, it should be noted that the invention is not so limited and that, according to other embodiments, any instrument disclosed herein may comprise a non-endoscopic surgical cutting and fastening instrument. The surgical instrument 310 depicted in FIGS. 12 and 13 comprises a handle 306, a shaft 308, and an end effector 312 connected to the shaft 308. In various embodiments, the end effector 312 can be articulated relative to the shaft 308 about an articulation joint 314. Various means for articulating the end effector 312 and/or means for permitting the end effector 312 to articulate relative to the shaft 308 are disclosed in U.S. Pat. No. 7,753,245, entitled SURGICAL STAPLING INSTRUMENTS, which issued on Jul. 13, 2010, and U.S. Pat. No. 7,670,334, entitled SURGICAL INSTRUMENT HAVING AN ARTICULATING END EFFECTOR, which issued on Mar. 2, 2010, the entire disclosures of which are incorporated by reference herein. Various other means for articulating the end effector 312 are discussed in greater detail below. Similar to the above, the end effector 312 is configured to act as an endocutter for clamping, severing, and/or stapling tissue, although, in other embodiments, different types of end effectors may be used, such as end effectors for other types of surgical devices, graspers, cutters, staplers, clip appliers, access devices, drug/gene therapy devices, ultrasound, RF and/or laser devices, etc. Several RF devices may be found in U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL CUTTING AND FASTENING INSTRUMENT HAVING RF ELECTRODES, filed Feb. 14, 2008, now abandoned, the entire disclosures of which are incorporated by reference in their entirety.

It will be appreciated that the terms "proximal" and "distal" are used herein with reference to a clinician gripping the handle 306 of the instrument 310. Thus, the end effector 312 is distal with respect to the more proximal handle 306. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The end effector 312 can include, among other things, a staple channel 322 and a pivotally translatable clamping member, such as an anvil 324, for example. The handle 306 of the instrument 310 may include a closure trigger 318 and a firing trigger 320 for actuating the end effector 312. It will be appreciated that instruments having end effectors directed to different surgical tasks may have different numbers or types of triggers or other suitable controls for operating the end effector 312. The handle 306 can include a downwardly extending pistol grip 326 toward which the closure trigger 318 is pivotally drawn by the clinician to cause clamping or closing of the anvil 324 toward the staple channel 322 of the end effector 312 to thereby clamp tissue positioned between the anvil 324 and channel 322. In other embodiments, different types of clamping members in addition to or lieu of the anvil 324 could be used. The handle 306 can further include a lock which can be configured to releasably hold the closure trigger 318 in its closed position. More details regarding embodiments of an exemplary closure system for closing (or clamping) the anvil 324 of the end effector 312 by retracting the closure trigger 318 are provided in U.S. Pat. No. 7,000,818, entitled SURGICAL STAPLING INSTRUMENT HAVING SEPARATE DISTINCT CLOSING AND FIRING SYSTEMS, which issued on Feb. 21, 2006, U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008, and U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008, the entire disclosures of which are incorporated by reference herein.

Once the clinician is satisfied with the positioning of the end effector 312, the clinician may draw back the closure trigger 318 to its fully closed, locked position proximate to the pistol grip 326. The firing trigger 320 may then be actuated, or fired. In at least one such embodiment, the firing trigger 320 can be farther outboard of the closure trigger 318 wherein the closure of the closure trigger 318 can move, or rotate, the firing trigger 320 toward the pistol grip 326 so that the firing trigger 320 can be reached by the operator using one hand. in various circumstances. Thereafter, the operator may pivotally draw the firing trigger 320 toward the pistol grip 312 to cause the stapling and severing of clamped tissue in the end effector 312. Thereafter, the firing trigger 320 can be returned to its unactuated, or unfired, position (shown in FIGS. 1 and 2) after the clinician relaxes or releases the force being applied to the firing trigger 320. A release button on the handle 306, when depressed, may release the locked closure trigger 318. The release button may be implemented in various forms such as, for example, those disclosed in published U.S. Patent Application Publication No. 2007/0175955, entitled SURGICAL CUTTING AND FASTENING INSTRUMENT WITH CLOSURE TRIGGER LOCKING MECHANISM, which was filed on Jan. 31, 2006, now abandoned, the entire disclosure of which is incorporated herein by reference in its entirety.

Further to the above, the end effector 312 may include a cutting instrument, such as knife, for example, for cutting tissue clamped in the end effector 312 when the firing trigger 320 is retracted by a user. Also further to the above, the end effector 312 may also comprise means for fastening the tissue severed by the cutting instrument, such as staples, RF electrodes, and/or adhesives, for example. A longitudinally movable drive shaft located within the shaft 308 of the instrument 310 may drive/actuate the cutting instrument and the fastening means in the end effector 312. An electric motor, located in the handle 306 of the instrument 310 may be used to drive the drive shaft, as described further herein. In various embodiments, the motor may be a DC brushed driving motor having a maximum rotation of, approximately, 25,000 RPM, for example. In other embodiments, the motor may include a brushless motor, a cordless motor, a synchronous motor, a stepper motor, or any other suitable electric motor. A battery (or "power source" or "power pack"), such as a Li ion battery, for example, may be provided in the pistol grip portion 26 of the handle 6 adjacent to the motor wherein the battery can supply electric power to the motor via a motor control circuit. According to various embodiments, a number of battery cells connected in series may be used as the power source to power the motor. In addition, the power source may be replaceable and/or rechargeable.

Figure 14:
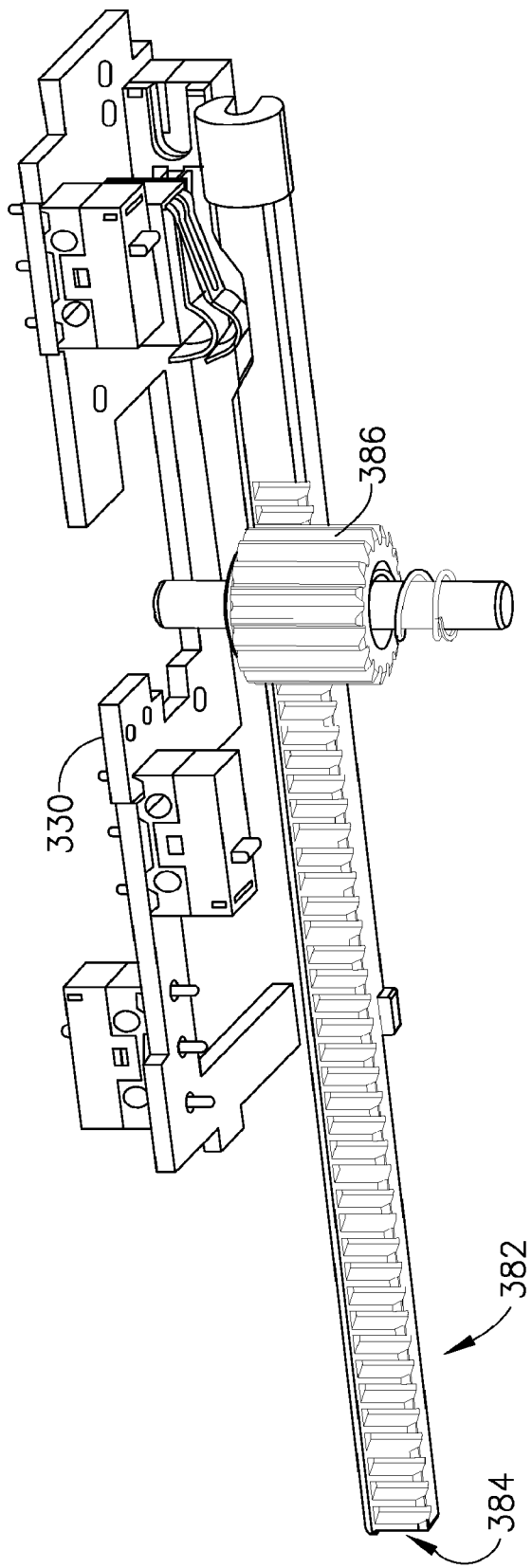
FIG. 14 is a perspective view of a firing member and a pinion gear positioned within the handle of FIG. 12.
Figure 15:
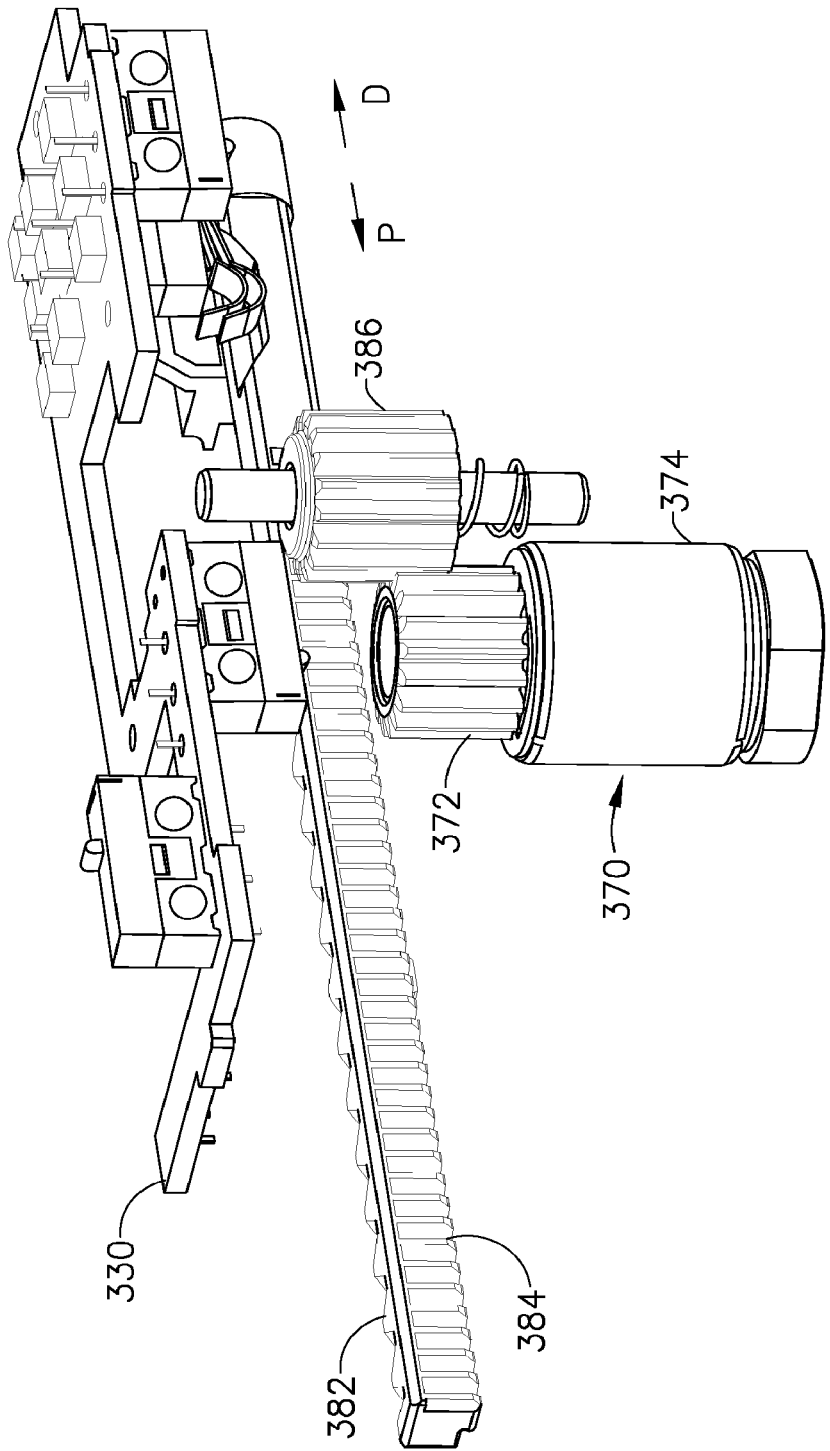
FIG. 15 is a perspective view of the firing member and the pinion gear of FIG. 14 and a gear reducer assembly operably engaged with the pinion gear.
Figure 16:
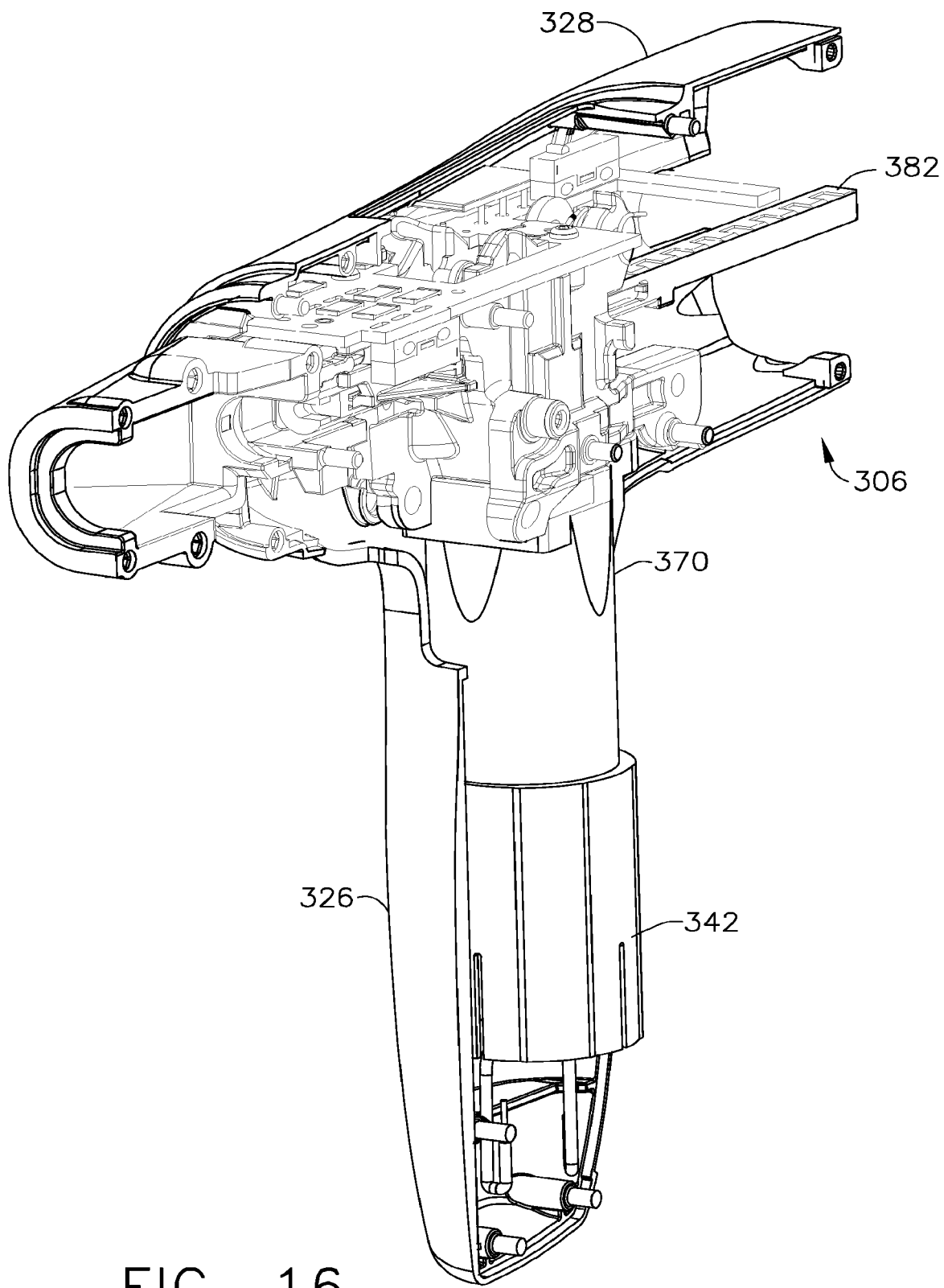
FIG. 16 is a perspective view of the handle of FIG. 12 with portions thereof removed to illustrate the firing member and the pinion gear of FIG. 14, the gear reducer assembly of FIG. 15, and an electric motor configured to drive the firing member distally and/or proximally depending on the direction in which the electric motor is turned.

As outlined above, the electric motor in the handle 306 of the instrument 310 can be operably engaged with the longitudinally-movable drive member positioned within the shaft 308. Referring now to FIGS. 14-16, an electric motor 342 can be mounted to and positioned within the pistol grip portion 326 of the handle 306. The electric motor 342 can include a rotatable shaft operably coupled with a gear reducer assembly 370 wherein the gear reducer assembly 370 can include, among other things, a housing 374 and an output pinion gear 372. In certain embodiments, the output pinion gear 372 can be directly operably engaged with a longitudinally-movable drive member 382 or, alternatively, operably engaged with the drive member 382 via one or more intermediate gears 386. The intermediate gear 386, in at least one such embodiment, can be meshingly engaged with a set, or rack, of drive teeth 384 defined in the drive member 382. In use, the electric motor 342 can be drive the drive member distally, indicated by an arrow D (FIG. 15), and/or proximally, indicated by an arrow D (FIG. 16), depending on the direction in which the electric motor 342 rotates the intermediate gear 386. In use, a voltage polarity provided by the battery can operate the electric motor 342 in a clockwise direction wherein the voltage polarity applied to the electric motor by the battery can be reversed in order to operate the electric motor 342 in a counter-clockwise direction. The handle 306 can include a switch which can be configured to reverse the polarity applied to the electric motor 342 by the battery. The handle 306 can also include a sensor 330 configured to detect the position of the drive member 382 and/or the direction in which the drive member 382 is being moved.

As indicated above, the surgical instrument 310 can include an articulation joint 314 about which the end effector 312 can be articulated. The instrument 310 can further include an articulation lock which can be configured and operated to selectively lock the end effector 312 in position. In at least one such embodiment, the articulation lock can extend from the proximal end of the shaft 308 to the distal end of the shaft 308 wherein a distal end of the articulation lock can engage the end effector 312 to lock the end effector 312 in position. Referring again to FIGS. 12 and 13, the instrument 310 can further include an articulation control 316 which can be engaged with a proximal end of the articulation lock and can be configured to operate the articulation lock between a locked state and an unlocked state. In use, the articulation control 316 can be pulled proximally to unlock the end effector 312 and permit the end effector 312 to rotate about the articulation joint 314. After the end effector 312 has been suitably articulated, the articulation control 316 can be moved distally to re-lock the end effector 312 in position. In at least one such embodiment, the handle 306 can further include a spring and/or other suitable biasing elements configured to bias the articulation control 316 distally and to bias the articulation lock into a locked configuration with the end effector 312. If the clinician desires, the clinician can once again pull the articulation control 316 back, or proximally, to unlock the end effector 312, articulate the end effector 312, and then move the articulation control 316 back into its locked state. In such a locked state, the end effector 312 may not articulate relative to the shaft 308.

As outlined above, the surgical instrument 310 can include an articulation lock configured to hold the end effector 312 in position relative to the shaft 308. As also outlined above, the end effector 312 can be rotated, or articulated, relative to the shaft 308 when the articulation lock is in its unlocked state. In such an unlocked state, the end effector 312 can be positioned and pushed against soft tissue and/or bone, for example, surrounding the surgical site within the patient in order to cause the end effector 312 to articulate relative to the shaft 308. In certain embodiments, the articulation control 316 can comprise an articulation switch or can be configured to operate an articulation switch which can selectively permit and/or prevent the firing trigger 320 from operating the electric motor 342. For instance, such an articulation switch can be placed in series with the electric motor 342 and a firing switch operably associated with the firing trigger 320 wherein the articulation switch can be in a closed state when the articulation control 316 is in a locked state. When the articulation control 316 is moved into an unlocked state, the articulation control 316 can open the articulation switch thereby electrically decoupling the operation of the firing trigger 320 and the operation of the electric motor 342. In such circumstances, the firing drive of the instrument 310 cannot be fired while the end effector 312 is in an unlocked state and is articulatable relative to the shaft 308. When the articulation control 316 is returned to its locked state, the articulation control 316 can re-close the articulation switch which can then electrically couple the operation of the firing trigger 320 with the electric motor 342. Various details of one or more surgical stapling instruments are disclosed in U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, which was filed on Dec. 24, 2009, and which published on Jun. 30, 2011 as U.S. Patent Application Publication No. 2011/0155785, now U.S. Pat. No. 8,220,688, the entire disclosure of which are incorporated by reference herein.

Turning now to FIGS. 17-29, a surgical instrument 400 can comprise a handle 403, a shaft 404 extending from the handle 403, and an end effector 402 extending from the shaft 404. As the reader will note, portions of the handle 403 have been removed for the purposes of illustration; however, the handle 403 can include a closure trigger and a firing trigger similar to the closure trigger 114 and the firing trigger 116 depicted in FIG. 1, for example. As will be described in greater detail below, the firing trigger 116 can be operably coupled with a firing drive including a firing member 470 extending through the shaft 404 wherein the operation of the firing trigger 116 can advance the firing member 470 distally toward the end effector 402. As will also be described in greater detail below, the surgical instrument 400 can further include an articulation drive which can be selectively coupled with the firing member 470 such that, when the firing member 470 is motivated by the firing trigger 116 and/or by a separate articulation trigger and/or button, for example, the articulation drive can be driven by the firing member 470 and the articulation drive can, in turn, articulate the end effector 402 about an articulation joint 410.

Figure 17:
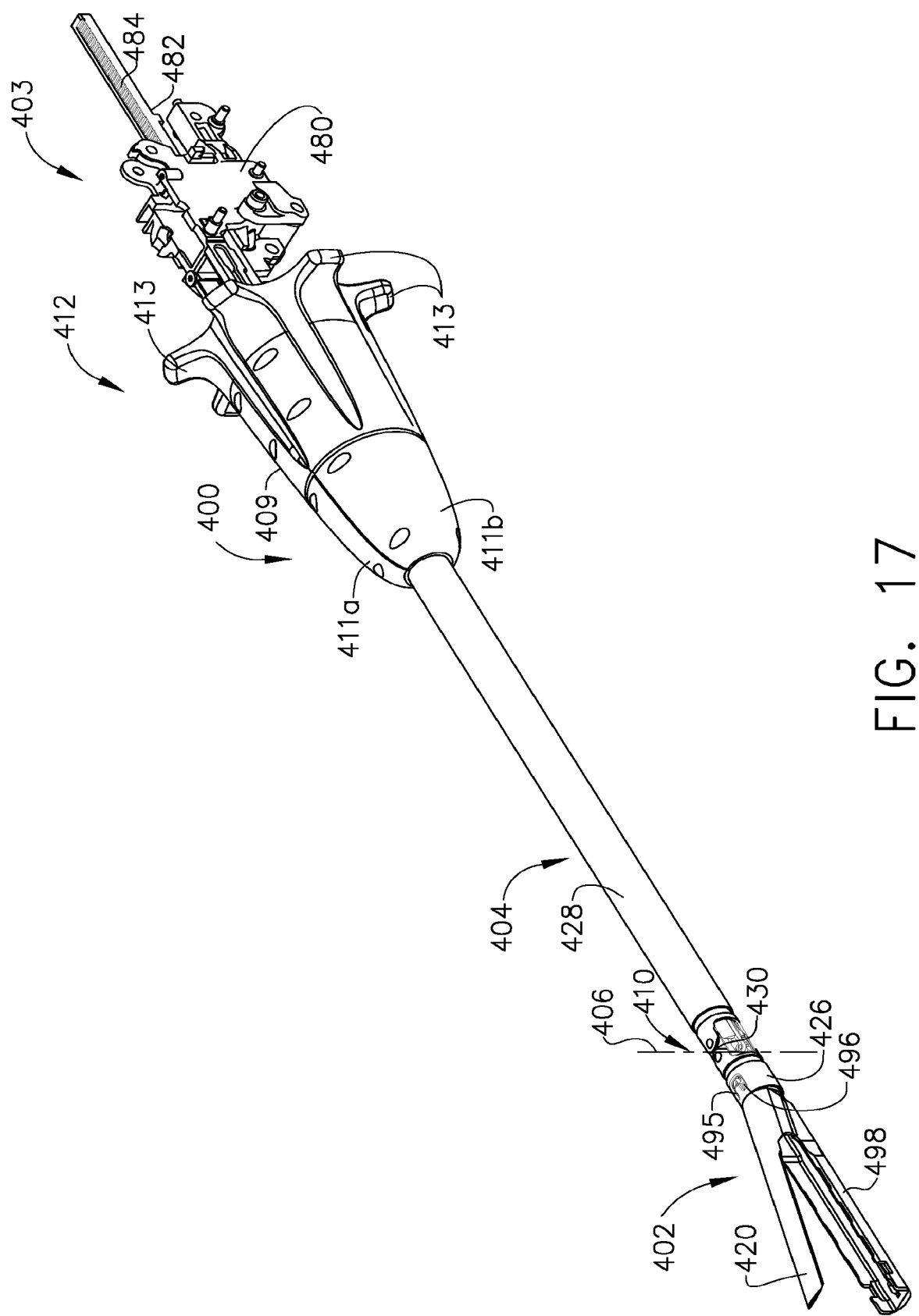
FIG. 17 is a perspective view of a surgical instrument comprising a handle, a shaft, an end effector, and an articulation joint connecting the end effector to the shaft illustrated with portions of the handle removed for the purposes of illustration.
Figure 19:
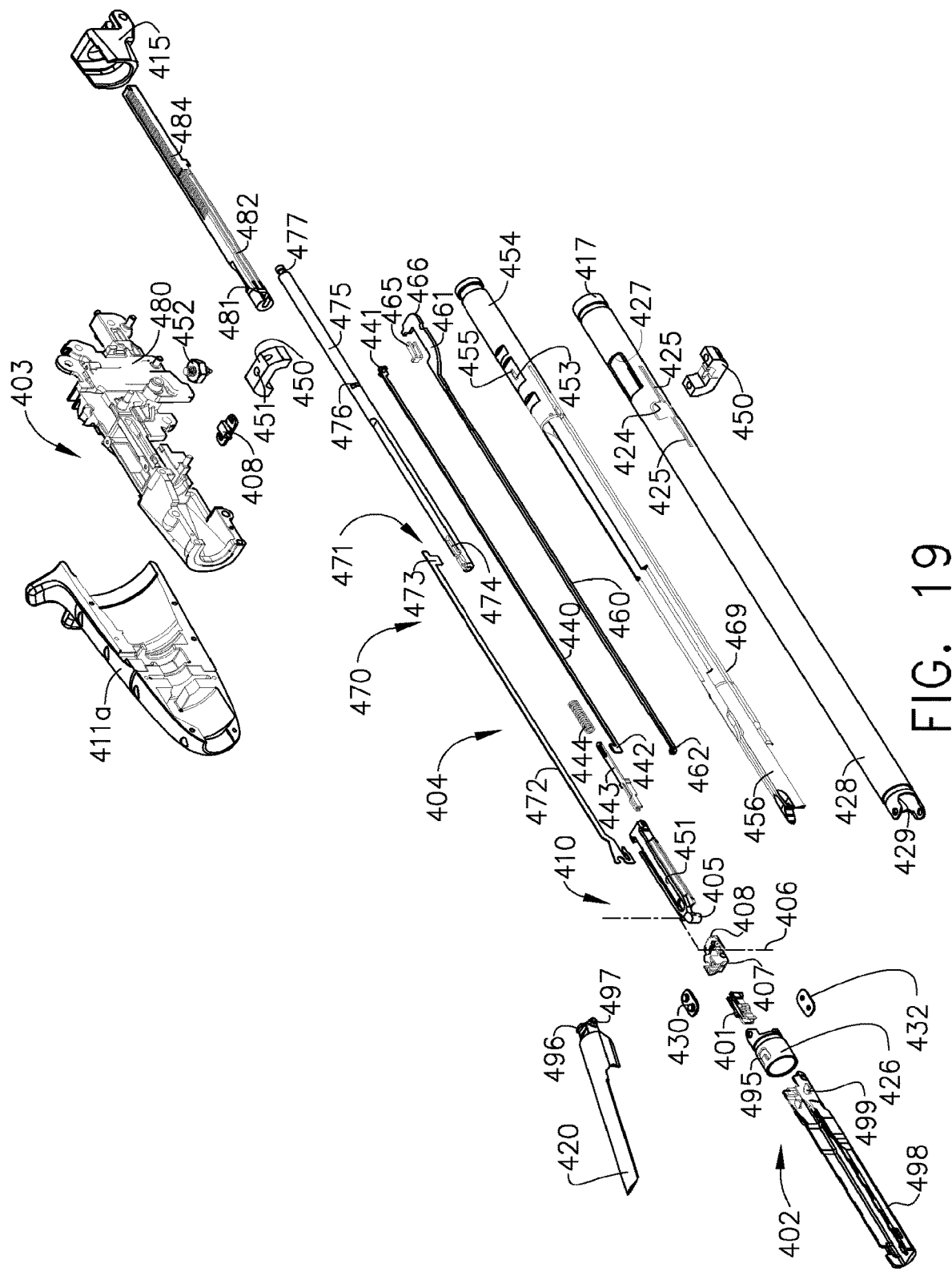
FIG. 19 is an exploded view of the surgical instrument of FIG. 17.
Figure 20:
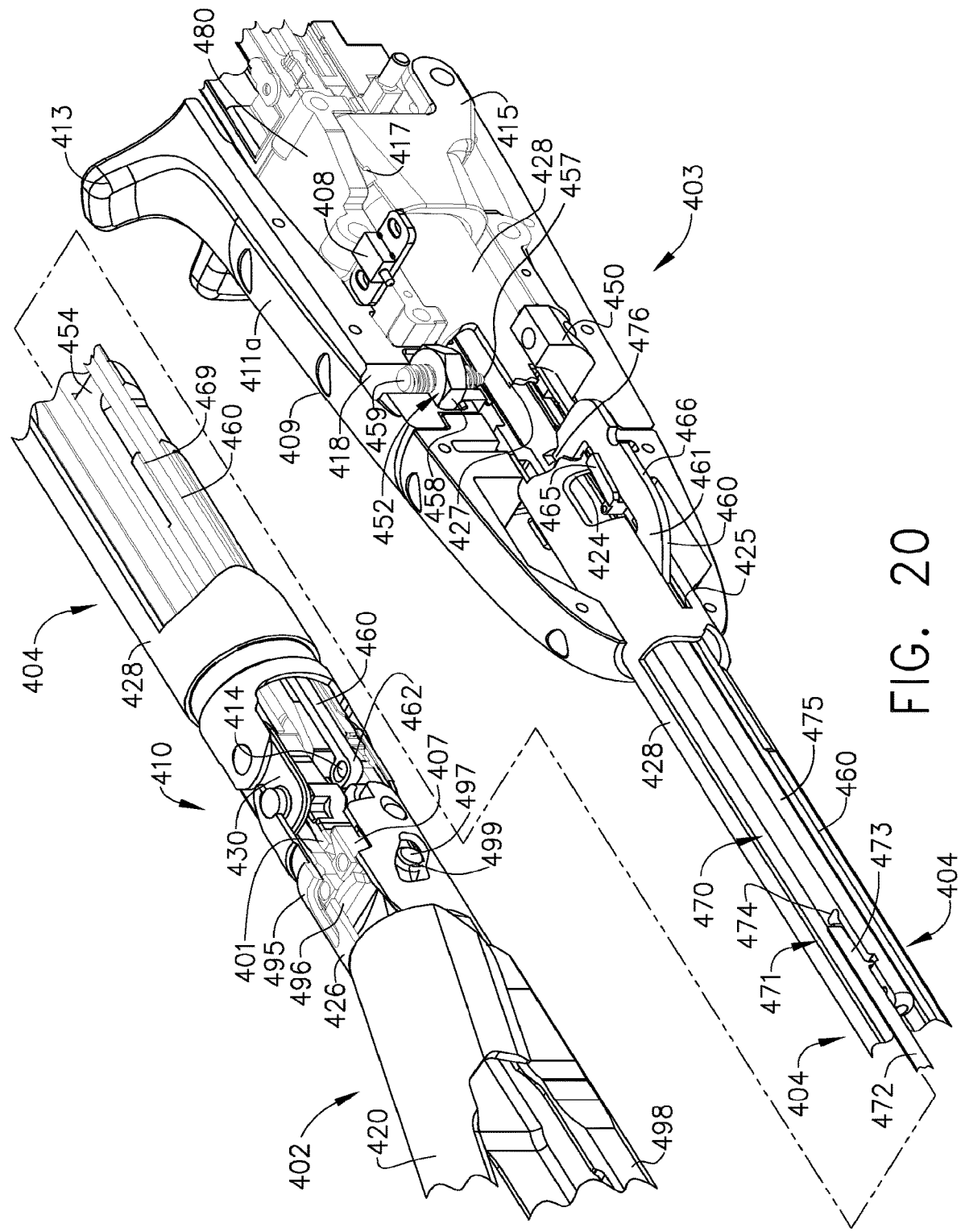
FIG. 20 is a cross-sectional detail view of the surgical instrument of FIG. 17 illustrated with the end effector in an open configuration, the articulation joint in an unlocked configuration, and an articulation lock actuator of the surgical instrument handle illustrated in an unlocked configuration.

Turning now to FIG. 17, the reader will note that the end effector 402 of the surgical instrument 400 is illustrated in an open configuration. More particularly, a first jaw of the end effector 402 comprising an anvil 420 is illustrated in an open position relative to a channel 498 of a second jaw of the end effector 402. Similar to the above, the channel 498 can be configured to receive and secure a staple cartridge therein. Turning now to FIG. 20 which also illustrates the end effector 420 in an open configuration, the handle 403 of the surgical instrument 400 can include an articulation lock actuator 409 which can be moved between a distal, or locked, position in which the end effector 402 is locked in position relative to the shaft 404 and a proximal, or unlocked, position in which the end effector 402 can be articulated relative to the shaft 404 about the articulation joint 410. Although the end effector 402 and the shaft 404 are illustrated in FIG. 20 as being aligned in a straight configuration, the articulation lock actuator 409 is illustrated in its retracted, unlocked position and, as a result, the end effector 402 can be articulated relative to the shaft 404. Referring to FIGS. 19, 24A and 24B, the articulation lock actuator 409 (FIG. 21) can be operably coupled with an articulation lock 443 wherein the articulation lock actuator 409 can move the articulation lock 443 between a distal position (FIG. 24A) in which the articulation lock 443 is engaged with a proximal lock member 407 of the end effector 402 and a proximal position (FIG. 24B) in which the articulation lock 443 is disengaged from the end effector 402. As the reader will appreciate, the distal, locked, position of the articulation lock actuator 409 corresponds with the distal position of the articulation lock 443 and the proximal, unlocked, position of the articulation lock actuator 409 corresponds with the proximal position of the articulation lock 443. Turning now to FIG. 19, the articulation lock 443 is coupled to the articulation lock actuator 409 by an articulation lock bar 440 which comprises a distal end 442 engaged with the articulation lock 443, as better seen in FIG. 24A, and a proximal end 441 engaged with the articulation lock actuator 409, as better seen in FIG. 22. As illustrated in FIGS. 24A and 24B, the articulation lock 443 can comprise one or more teeth 445 which can be configured to meshingly engage one or more teeth 446 defined around the perimeter of the proximal lock member 407, for example. Referring primarily to FIG. 19, the shaft 404 can further comprise a biasing member, such as a spring 444, for example, which can be configured to bias the teeth 445 of the articulation lock 443 into engagement with the teeth 446 of the proximal lock member 407 of the end effector 402. Similarly, the handle 403 can further comprise a biasing member positioned within the cavity 488 (FIG. 23) defined between the articulation lock actuator 409 and the frame 480 such that the biasing member can push the articulation lock actuator 409 towards its distal, locked, position.

As illustrated in FIG. 17, the articulation lock actuator 409 can be comprised of two nozzle halves, or portions, 411a and 411b wherein, as the reader will note, the nozzle portion 411b has been removed from FIGS. 18-27 for the purposes of illustration. As also illustrated in FIG. 17, the articulation lock actuator 409 can comprise a plurality of finger hooks 413 which can be grasped by the surgeon, or other clinician, in order to retract the articulation lock actuator 409 into its proximal, unlocked, configuration. The articulation lock actuator 409, referring again to FIG. 20, can further include a detent assembly 452 which can be configured to bias a detent member 457 against the frame of the shaft 404 or the frame of the handle 403. More particularly, the shaft 404 can comprise a shaft frame 454 extending from a handle frame 480 wherein the detent assembly 452 can be configured to bias the detent member 457 against the shaft frame 454. Referring to FIG. 19, the shaft frame 454 can include a detent channel 453 defined therein which can be aligned with the detent member 457 such that, as the articulation lock actuator 409 is slid between its locked and unlocked positions described above, the detent member 457 can slide within the detent channel 453. The detent assembly 452, referring again to FIG. 20, can include a stationary frame portion 458 which can define a threaded aperture configured to receive an adjustable threaded member 459. The adjustable threaded member 459 can include an internal aperture wherein at least a portion of the detent member 457 can be positioned within the internal aperture and wherein the detent member 457 can be biased to the end of the internal aperture by a spring, for example, positioned intermediate the detent member 457 and a closed end of the internal aperture, for example. As illustrated in FIG. 19, the proximal end of the detent channel 453 can comprise a detent seat 455 which can be configured to removably receive the detent member 457 when the articulation lock actuator 409 has reached its proximal, unlocked, position. In various circumstances, the detent member 457, the detent seat 455, and the biasing spring positioned in the adjustable threaded member 459 can be sized and configured such that the detent assembly 452 can releasably hold the articulation lock actuator 409 in its proximal, unlocked, position. As described in greater detail below, the articulation lock actuator 409 can be held in its proximal, unlocked, position until the end effector 402 has been suitably articulated. At such point, the articulation lock actuator 409 can be pushed forward to disengage the detent member 457 from the detent seat 455. As the reader will appreciate, referring primarily to FIG. 20, the adjustable threaded member 459 can be rotated downwardly toward the shaft frame 454 in order to increase the force needed to unseat the detent member 457 from the detent seat 455 while the adjustable threaded member 459 can be rotated upwardly away from the shaft frame 454 in order to decrease the force needed to unseat the detent member 457 from the detent seat 455. As also illustrated in FIG. 20, the articulation lock actuator 409 can comprise an access port 418 which can be utilized to access and rotate the threaded member 459.

Figure 18:
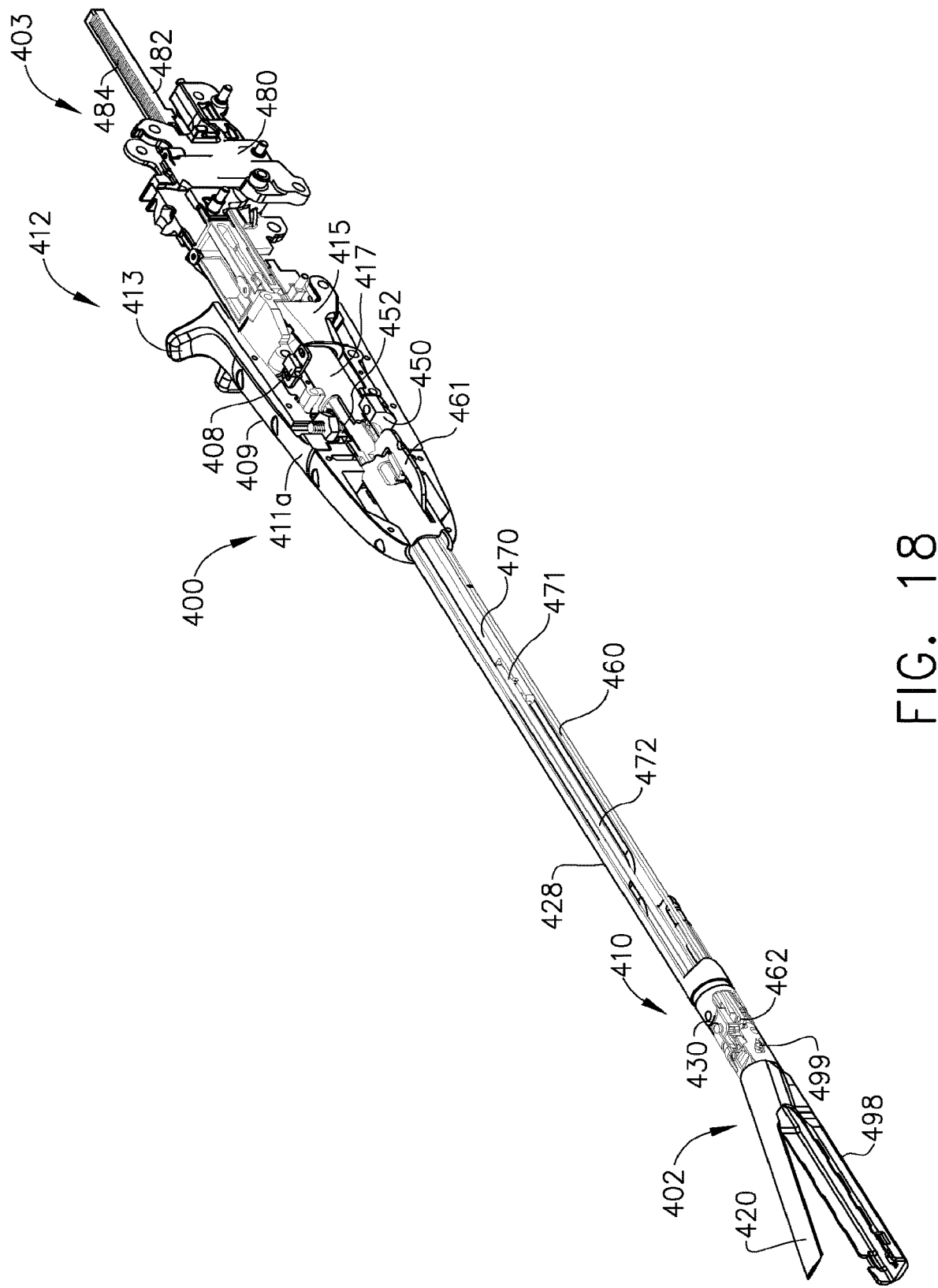
FIG. 18 is a cross-sectional view of the surgical instrument of FIG. 17.
Figure 21:
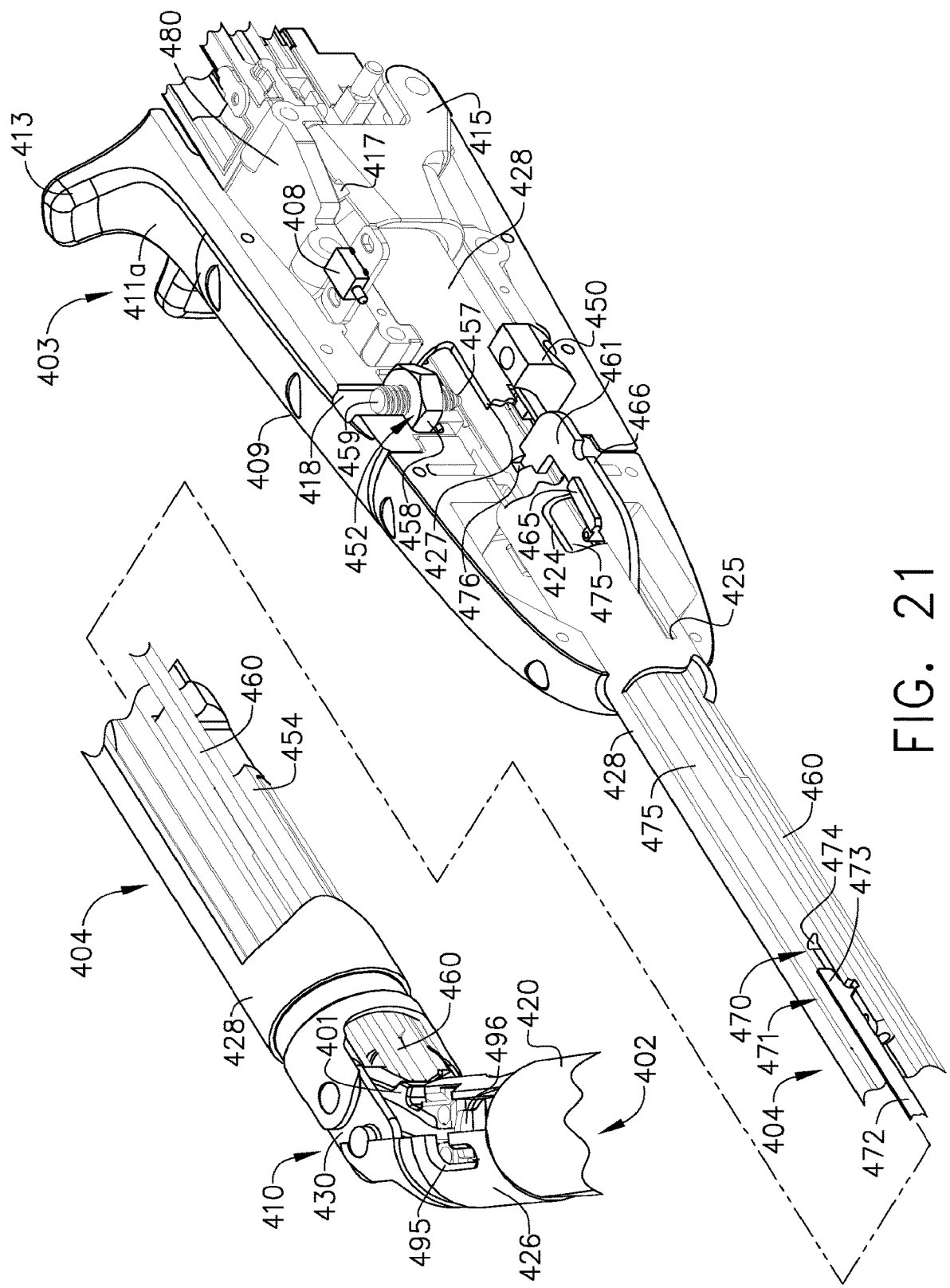
FIG. 21 is a cross-sectional detail view of the surgical instrument of FIG. 17 illustrating the end effector in an articulated, open configuration, the articulation joint in an unlocked configuration, and an articulation driver engaged with a firing member of the surgical instrument of FIG. 17, wherein the movement of the firing member can motivate the articulation driver and articulate the end effector.

As discussed above, the articulation lock actuator 409 is in a retracted, unlocked, position in FIG. 20 and the end effector 402 is in an unlocked configuration, as illustrated in FIG. 24B. Referring now to FIGS. 19 and 20, the surgical instrument 400 further comprises an articulation driver 460 which can be pushed distally to rotate the end effector 402 about the articulation joint 410 in a first direction and pulled proximally to rotate the end effector 402 about the articulation joint in a second, or opposite, direction, as illustrated in FIG. 21. Upon comparing FIGS. 20 and 21, the reader will note that the articulation driver 460 has been pulled proximally by the firing member 470. More specifically, an intermediate portion 475 of the firing member 470 can comprise a notch, or slot, 476 defined therein which can be configured to receive a proximal end 461 of the articulation driver 460 such that, when the firing member 470 is pulled proximally, the firing member 470 can pull the articulation driver 460 proximally as well. Similarly, when the firing member 470 is pushed distally, the firing member 470 can push the articulation driver 460 distally. As also illustrated in FIGS. 20 and 21, the articulation driver 460 can comprise a distal end 462 engaged with a projection 414 extending from the proximal lock member 407, for example, which can be configured to transmit the proximal and distal articulation motions of the articulation driver 460 to the end effector 102. Referring primarily to FIGS. 18-20, the handle 404 can further comprise a proximal firing member portion 482 of the firing member 470 including a distal end 481 engaged with a proximal end 477 of the intermediate portion 475 of the firing member 470. Similar to the above, the handle 403 can include an electric motor comprising an output shaft and a gear operably engaged with the output shaft wherein the gear can be operably engaged with a longitudinal set of teeth 484 defined in a surface of the firing member portion 482. In use, further to the above, the electric motor can be operated in a first direction to advance the firing member 470 distally and a second, or opposite, direction to retract the firing member 470 proximally. Although not illustrated, the handle 403 can further comprise a switch which can be positioned in a first condition to operate the electric motor in its first direction, a second condition to operate the electric motor in its second direction, and/or a neutral condition in which the electric motor is not operated in either direction. In at least one such embodiment, the switch can include at least one biasing member, such as a spring, for example, which can be configured to bias the switch into its neutral condition, for example. Also, in at least one such embodiment, the first condition of the articulation switch can comprise a first position of a switch toggle on a first side of a neutral position and the second condition of the articulation switch can comprise a second position of the switch toggle on a second, or opposite, side of the neutral position, for example.

In various circumstances, further to the above, the articulation switch can be used to make small adjustments in the position of the end effector 402. For instance, the surgeon can move the articulation switch in a first direction to rotate the end effector 402 about the articulation joint in a first direction and then reverse the movement of the end effector 402 by moving the articulation switch in the second direction, and/or any other suitable combinations of movements in the first and second directions, until the end effector 402 is positioned in a desired position. Referring primarily to FIGS. 19, 24A, and 24B, the articulation joint 410 can include a pivot pin 405 extending from a shaft frame member 451 and, in addition, an aperture 408 defined in the proximal lock member 407 which is configured to closely receive the pivot pin 405 therein such that the rotation of the end effector 402 is constrained to rotation about an articulation axis 406, for example. Referring primarily to FIG. 19, the distal end of the shaft frame 454 can include a recess 456 configured to receive the shaft frame member 451 therein. As will be described in greater detail below, the shaft 404 can include an outer sleeve which can be slid relative to the shaft frame 454 in order to close the anvil 420. Referring primarily to FIGS. 19-21, the outer sleeve of the shaft 410 can comprise a proximal portion 428 and a distal portion 426 which can be connected to one another by articulation links 430 and 432. When the outer sleeve is slid relative to the articulation joint 410, the articulation links 430 can accommodate the angled relative movement between the distal portion 426 and the proximal portion 428 of the outer sleeve when the end effector 402 has been articulated, as illustrated in FIG. 21. In various circumstances, the articulation links 430 and 432 can provide two or more degrees of freedom at the articulation joint 410 in order to accommodate the articulation of the end effector 402. The reader will also note that the articulation joint 410 can further include a guide 401 which can be configured to receive a distal cutting portion 472 of the firing member 470 therein and guide the distal cutting portion 472 as it is advanced distally and/or retracted proximally within and/or relative to the articulation joint 410.

As outlined above, the firing member 470 can be advanced distally in order to advance the articulation driver 460 distally and, as a result, rotate the end effector 402 in a first direction and, similarly, the firing member 470 can be retracted proximally in order to retract the articulation driver 460 proximally and, as a result, rotate the end effector 402 in an opposite direction. In some circumstances, however, it may be undesirable to move, or at least substantially move, the distal cutting portion 472 of the firing member 470 when the firing member 470 is being utilized to articulate the end effector 402. Turning now to FIGS. 19-21, the intermediate portion 475 of the firing member 470 can comprise a longitudinal slot 474 defined in the distal end thereof which can be configured to receive the proximal end 473 of the distal cutting portion 472. The longitudinal slot 474 and the proximal end 473 can be sized and configured to permit relative movement therebetween and can comprise a slip joint 471. The slip joint 471 can permit the intermediate portion 475 of the firing drive 470 to be moved to articulate the end effector 402 without moving, or at least substantially moving, the distal cutting portion 472. Once the end effector 402 has been suitably oriented, the intermediate portion 475 can be advanced distally until a proximal sidewall of the longitudinal slot 474 comes into contact with the proximal end 473 in order to advance the distal cutting portion 472 and fire the staple cartridge positioned within the channel 498, as described in greater detail further below. Referring primarily to FIG. 19, the shaft frame 454 can comprise a longitudinal slot 469 defined therein which can be configured to slidably receive the articulation driver 460 and, similarly, the proximal portion 428 of the outer shaft sleeve can comprise a longitudinal opening 425 configured to accommodate the relative movement between the articulation driver 460 and the outer sleeve of the shaft 404 described above.

Further to the above, the articulation lock actuator 409 can be configured to bias the proximal portion 461 of the articulation driver 460 toward the drive member 470 when the articulation lock actuator 409 is in its proximal, unlocked, position. More particularly, in at least one such embodiment, the inner surface of the articulation lock actuator 409 can comprise a cam which can engage a lateral side 466 of the proximal portion 461 and bias the proximal portion 461 into engagement with the slot 476 defined in the intermediate portion 475 of the drive member 470. When the articulation lock actuator 409 is moved back into its distal, locked, position, the articulation lock actuator 409 may no longer bias the proximal portion 461 inwardly toward the drive member 470. In at least one such embodiment, the handle 403 and/or the shaft 404 can comprise a resilient member, such as a spring, for example, which can be configured to bias the proximal portion 461 outwardly away from the firing member 470 such that the proximal portion 461 is not operably engaged with the slot 476 unless the biasing force of the resilient member is overcome by the articulation lock actuator 409 when the articulation lock actuator 409 is moved proximally into its unlocked position, as described above. In various circumstances, the proximal portion 461 and the slot 476 can comprise a force-limiting clutch.

Figure 22:
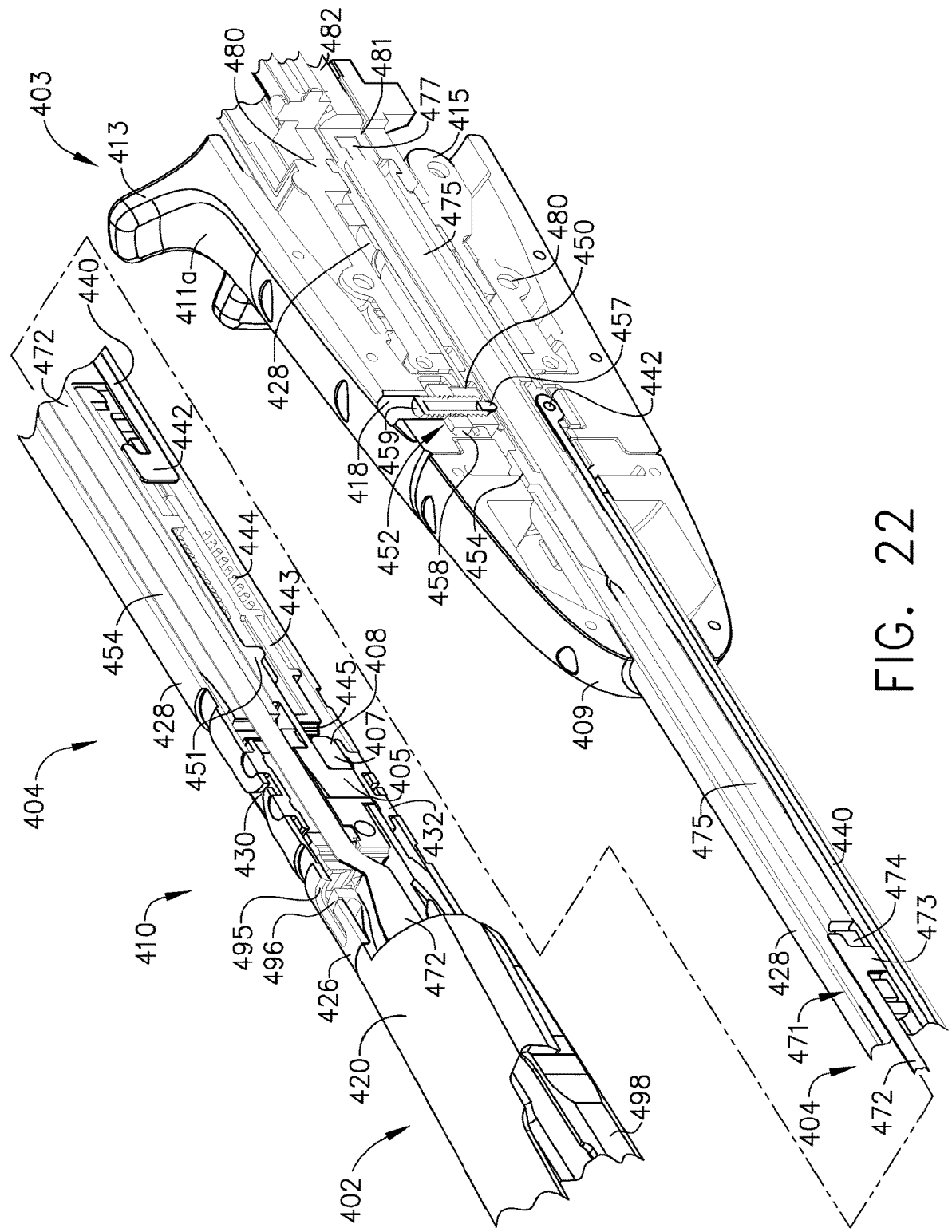
FIG. 22 is a cross-sectional detail view of the surgical instrument of FIG. 17 illustrating the end effector in a closed configuration, the articulation joint in an unlocked configuration, and an end effector closing drive being actuated to close the end effector and move the articulation lock actuator into a locked configuration.
Figure 22A:
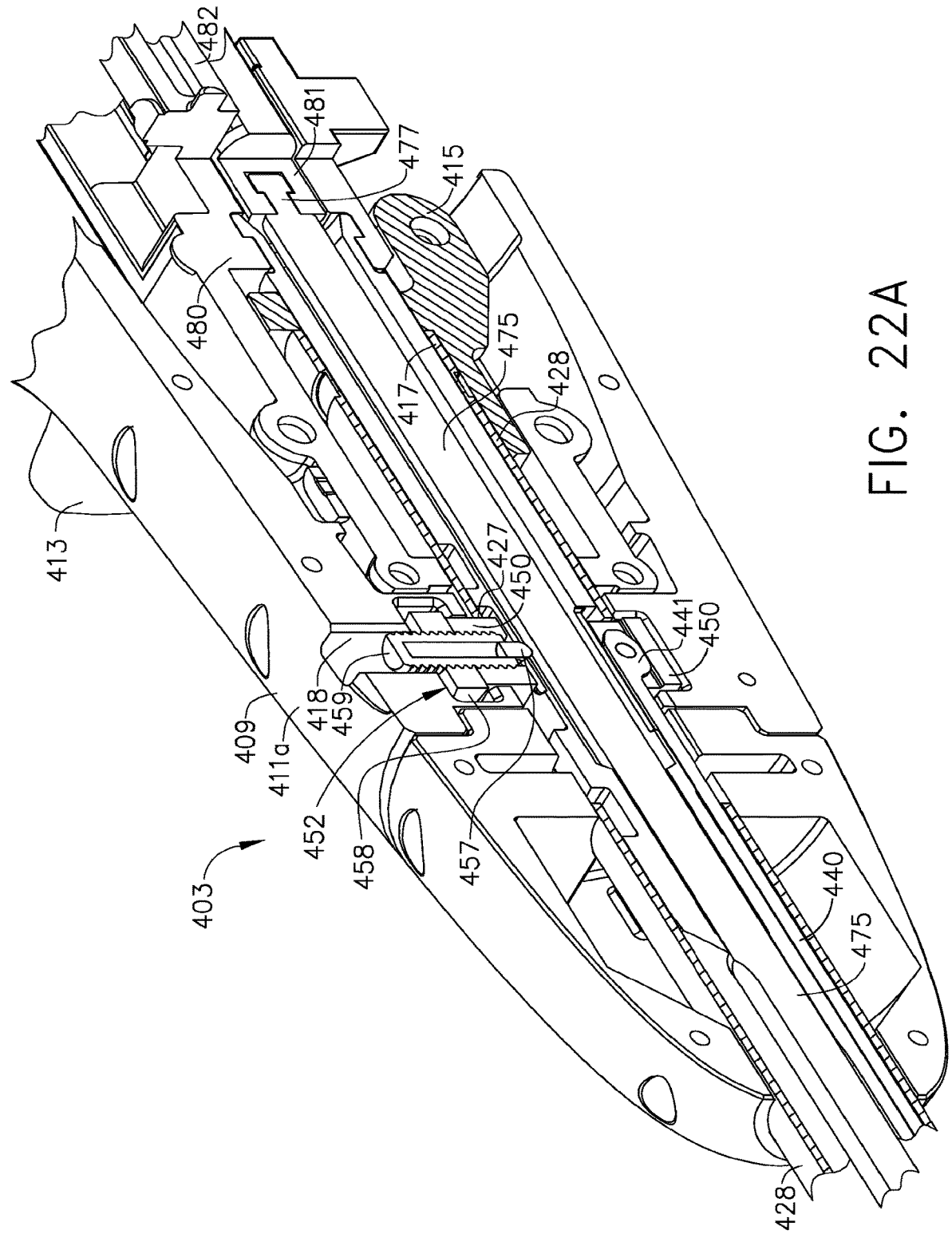
FIG. 22A is a cross-sectional detail view of the handle of the surgical instrument of FIG. 17 illustrated in the configuration described with regard to FIG. 22.
Figure 23:
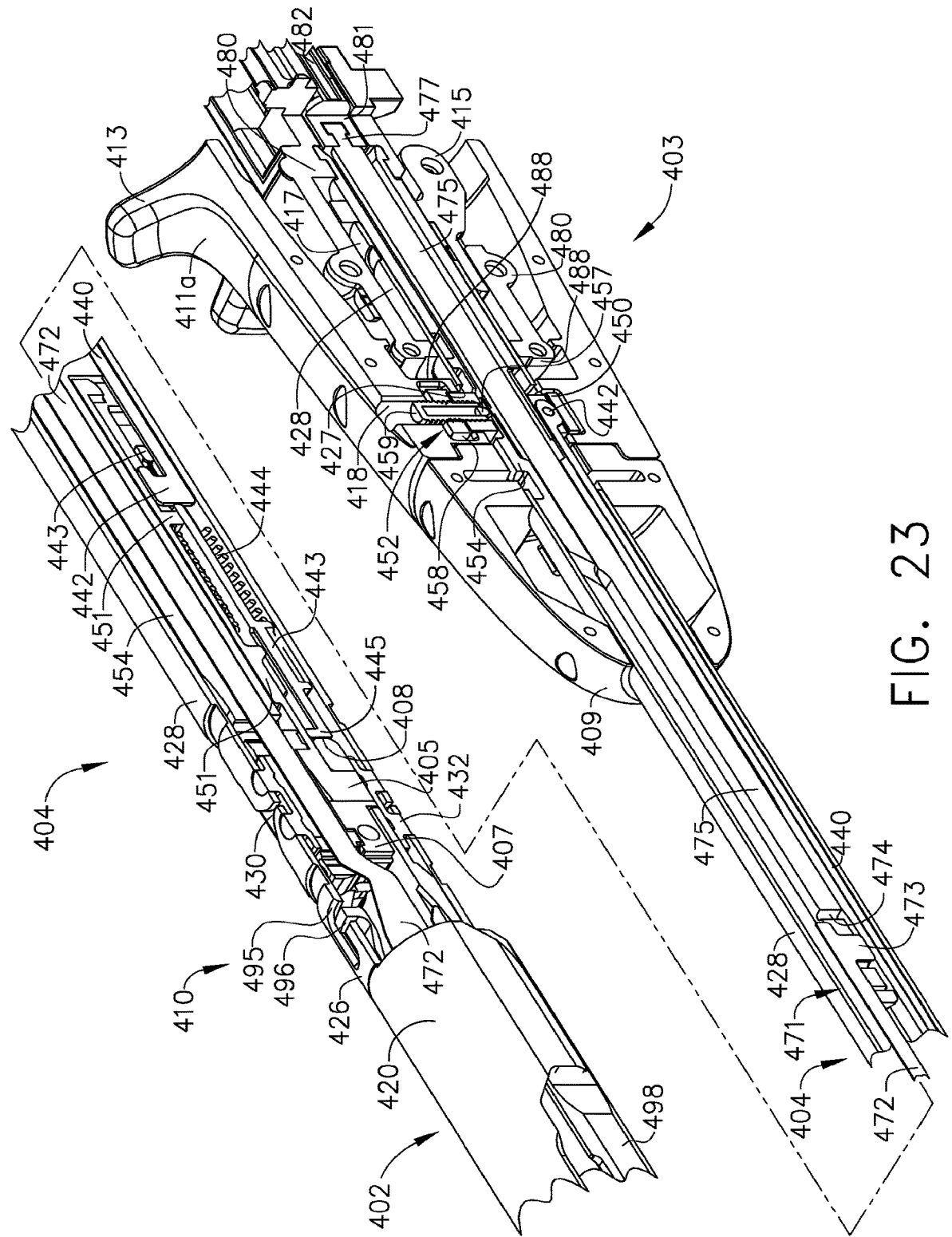
FIG. 23 is a cross-sectional detail view of the surgical instrument of FIG. 17 illustrating the end effector in a closed configuration and the articulation joint in a locked configuration, wherein the actuated closing drive prevents the articulation lock actuator from being moved into its unlocked configuration illustrated in FIGS. 20-22.

Once the end effector 402 has been articulated into the desired orientation, further to the above, the closure trigger 114 can be actuated to move the anvil 420 toward its closed position, as illustrated in FIG. 22. More particularly, the closure trigger 114 can advance the outer sleeve of the shaft 410 distally such that the distal portion 426 of the outer sleeve can push the anvil 420 distally and downwardly, for example. The anvil 420 can comprise projections 497 extending from opposite sides of the anvil 420 which can each be configured to slide and rotate within elongate slots 499 defined in the cartridge channel 498. The anvil 420 can further comprise a projection 496 extending upwardly therefrom which can be positioned within an aperture 495 defined in the distal portion 426 of the outer sleeve wherein a sidewall of the aperture 495 can contact the projection 496 as the distal portion 426 is advanced distally to move the anvil 420 toward the cartridge channel 498. The actuation of the closure drive, further to the above, can also move the articulation lock actuator 409 from its proximal, unlocked, position (FIGS. 20-22) into its distal, locked, position (FIG. 23). More specifically, the closure drive can be configured to advance a closure drive carriage 415 distally which can contact a collar 450 mounted within the articulation actuator 409, as illustrated in FIG. 22. As illustrated in FIGS. 19 and 22, the collar 450 can comprise opposing portions, or halves, which can be assembled together such that the opposing portions of the collar 450 can surround the shaft 404. The collar 450 can also support the detent assembly 452, which is discussed above, and can include a mounting portion engaged with the proximal end 441 of the articulation lock bar 440, which is also discussed above. In any event, the closure drive carriage 415 can contact the collar 450 and slide the articulation lock actuator 409 distally and, further to the above, displace the detent member 457 from the detent seat 455, referring to FIG. 19, into the detent channel 453 such that the articulation lock actuator 409 can be pushed into its locked position and the articulation lock 443 can be moved into engagement with the proximal lock portion 407 to lock the end effector 402 in position, as illustrated in FIG. 23. At such point, the closure drive carriage 415 can prevent the end effector 402 from being unlocked and articulated until the closure drive and the anvil 420 is reopened and the closure drive carriage 415 is moved proximally, as described in greater detail further below.

Figure 25:
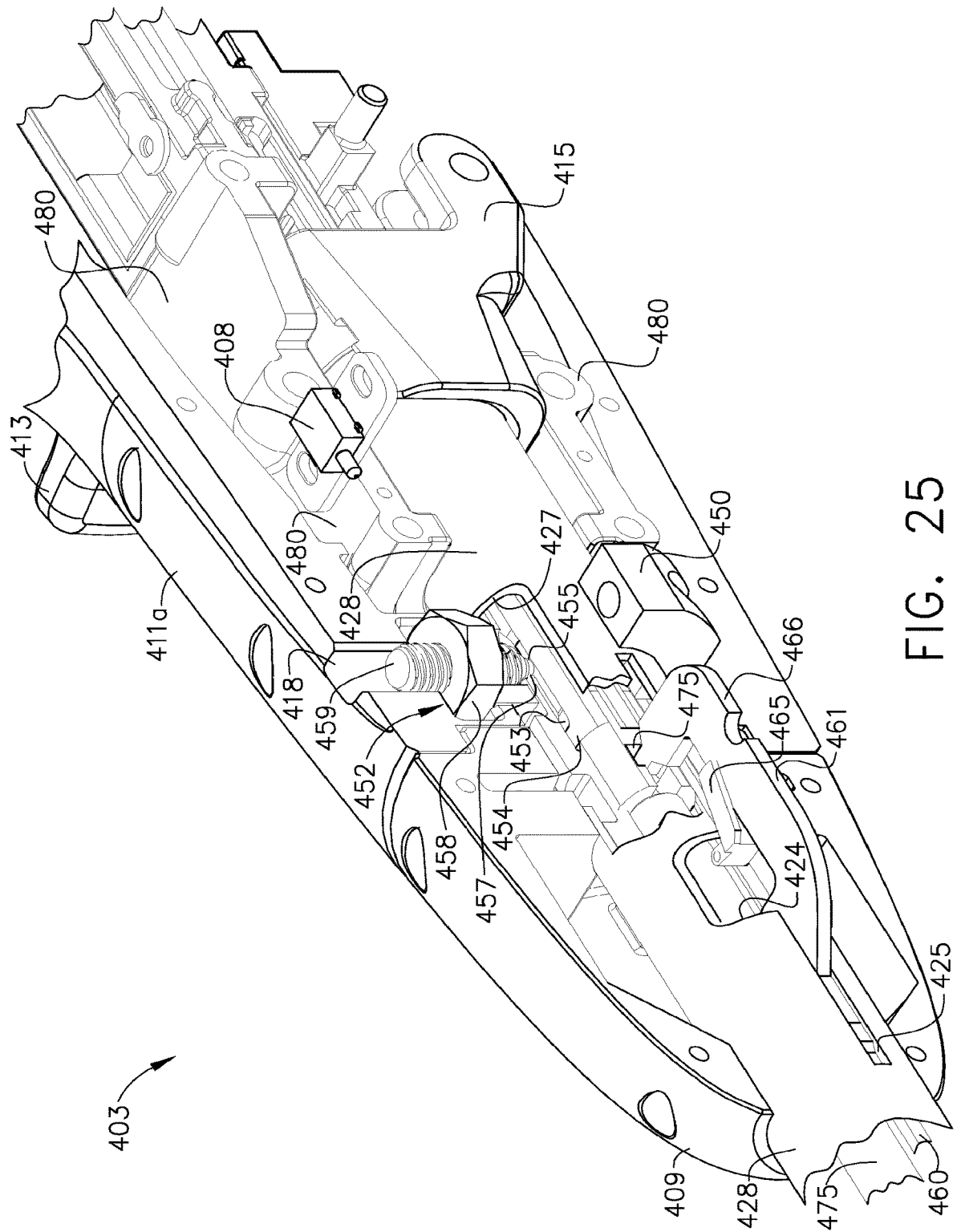
FIG. 25 is a cross-sectional detail view of the handle of the surgical instrument of FIG. 17 illustrating the articulation driver disconnected from the firing member by closure drive.

Referring now to FIG. 25, the actuation of the closure drive by the closure drive actuator 114 and the distal advancement of the outer sleeve 428 of the shaft 410 can also operably disengage the articulation driver 460 from the firing drive 470. Upon reviewing FIGS. 20 and 21 once again, the reader will note that the outer sleeve 428 includes a window 424 defined therein within which a rotatable cam member 465 can be positioned. The cam member 465 can comprise a first end rotatably pinned or coupled to the shaft frame 454 and a second end configured to rotate relative to the pinned end of the cam member 465 while, in other embodiments, the cam member 465 can comprise any suitable shape. When the outer sleeve 428 is in its proximal position and the anvil 420 is in its open configuration, the cam member 465 can be in a first position which permits the proximal end 461 of the articulation driver 460 to be engaged with the slot 476 defined in the firing member 470; however, when the outer sleeve 428 is advanced distally, a sidewall of the window 424 can engage the cam member 465 and lift the second end of the cam member 465 away from the shaft frame 454 into a second position. In this second position, the cam member 465 can move the proximal end 461 of the articulation driver 460 away from the firing drive 470 such that the proximal end 461 is no longer positioned within the slot 476 defined in the firing drive 470. Thus, when the closure drive has been actuated to close the anvil 420, the closure drive can push the articulation lock actuator 409 into its distal, locked, configuration, the articulation lock actuator 409 can push the articulation lock 445 into a locked configuration with the end effector 402, and, in addition, the closure drive can operably disconnect the articulation driver 460 from the firing drive 470. At such point in the operation of the surgical instrument 400, the actuation of the firing drive 470 will not articulate the end effector 402 and the firing drive 470 can move independently of the articulation driver 460.

Figure 26:
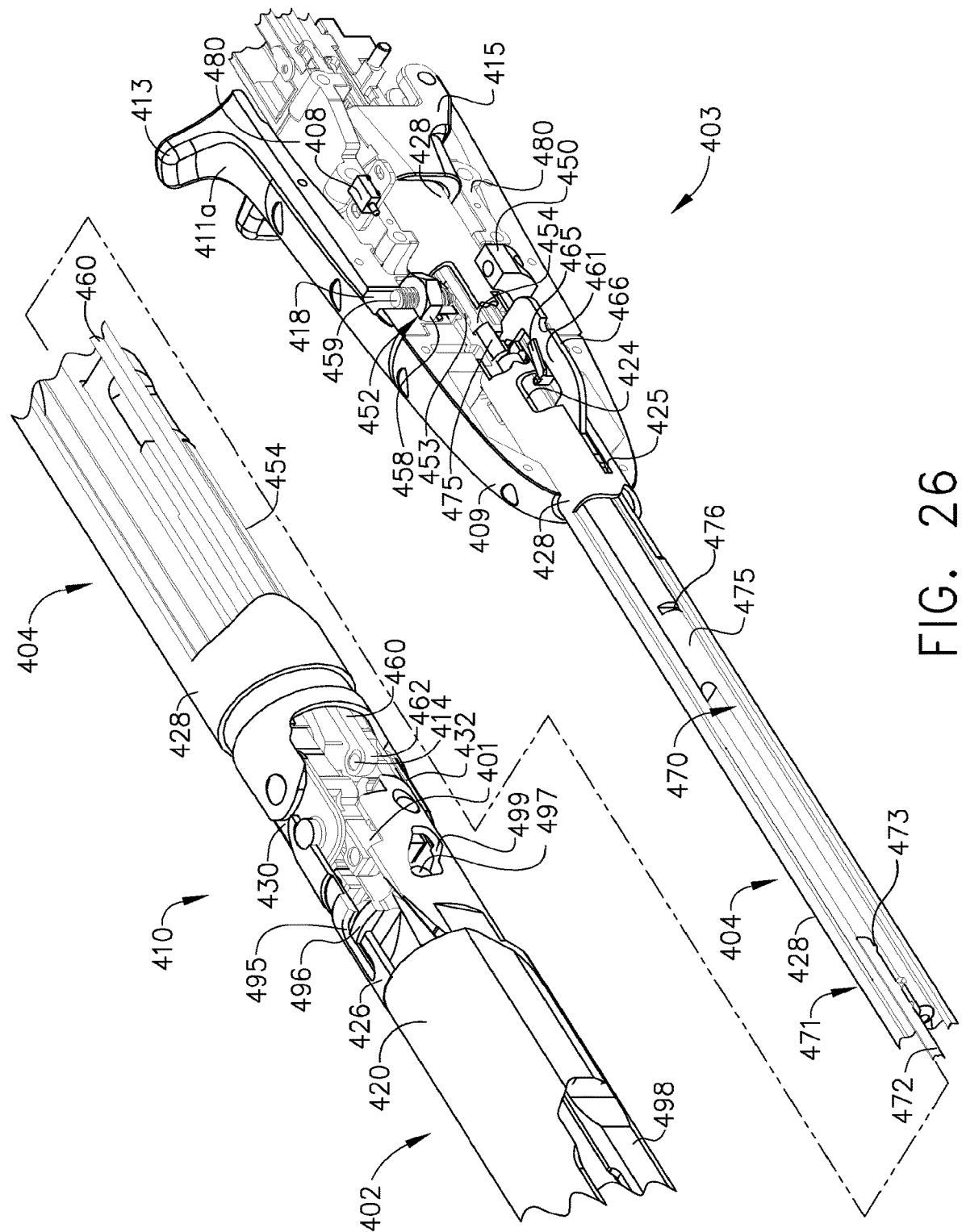
FIG. 26 is a cross-sectional detail view of the surgical instrument of FIG. 17 illustrating the firing member in an at least partially fired position and the articulation driver disconnected from the firing member by the closure drive.
Figure 27:
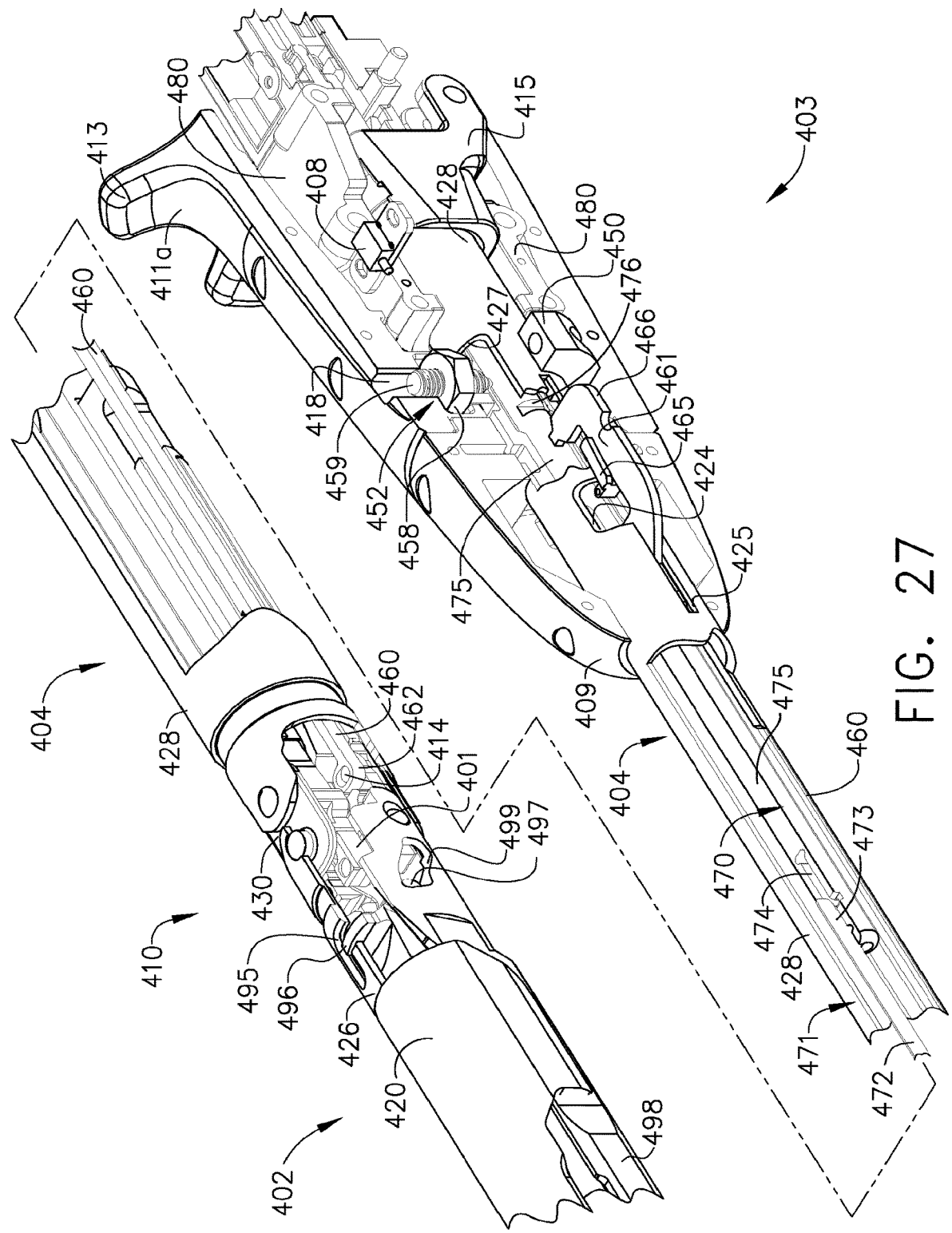
FIG. 27 is a cross-sectional detail view of the surgical instrument of FIG. 17 illustrating end effector in a closed configuration, the articulation joint and the articulation joint actuator in a locked configuration, and the firing member in a retracted position.
Figure 28:
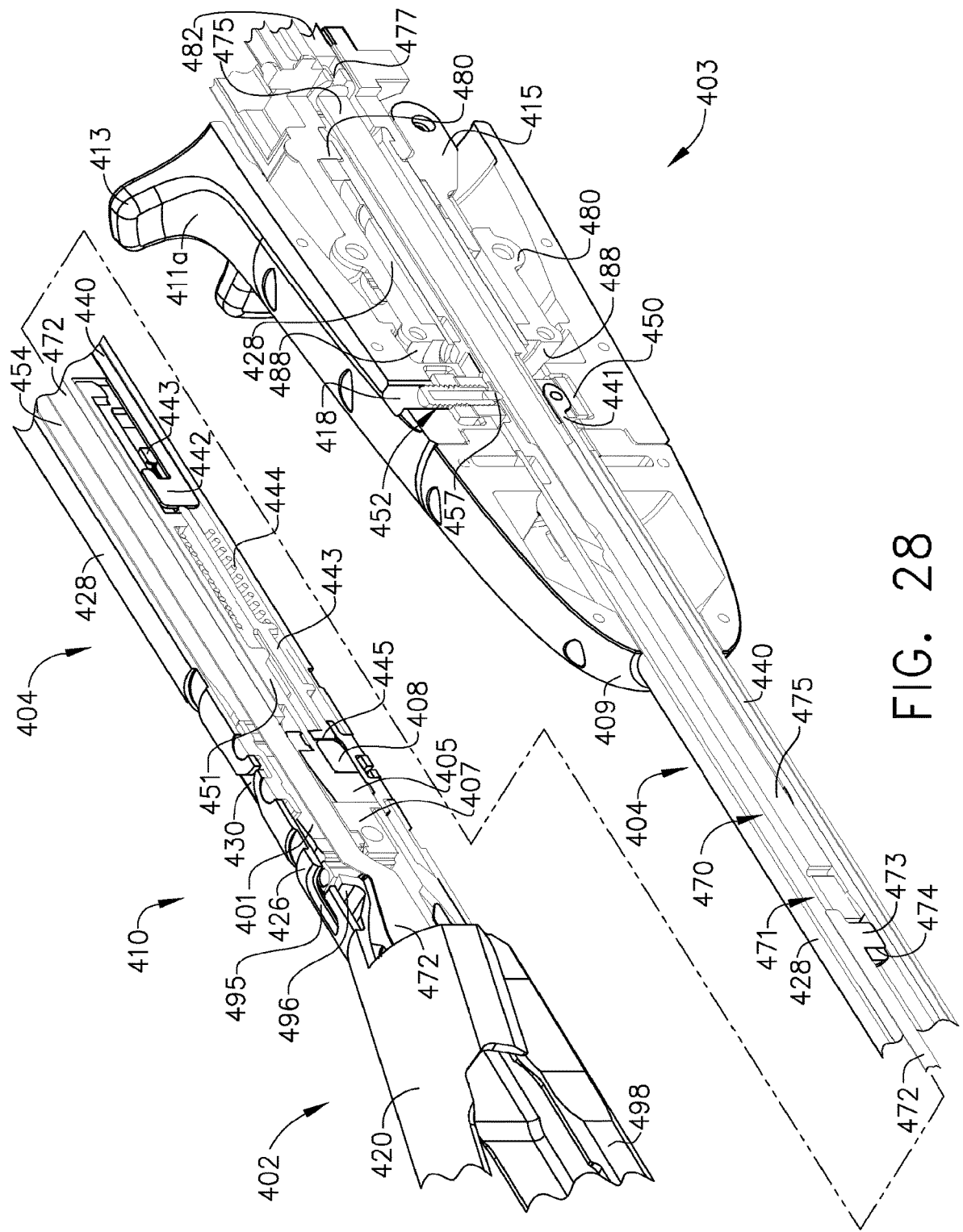
FIG. 28 is a cross-sectional detail view of the surgical instrument of FIG. 17 illustrating the end effector in an open configuration, the end effector closing drive in a retracted position, and the articulation joint in a locked configuration.

Turning now to FIG. 26, as mentioned above, the firing drive 470 can be advanced distally to eject staples from a staple cartridge positioned within the channel 498 of the end effector 402 and to deform the staples against the anvil 420. As outlined above, the firing drive 470 can further comprise a cutting member which can be configured to transect the tissue captured within the end effector 402. As also mentioned above, the electric motor within the handle 403 can be operated by the firing actuator 116 in order to advance the firing member 470 distally wherein, in various circumstances, the electric motor can be operated until the distal cutting portion 472 of the firing member 470 reaches the distal end of the staple cartridge and/or any other suitable position within the staple cartridge. In any event, the rotation of the electric motor can be reversed to retract the firing member 470 proximally, as illustrated in FIG. 27. In various circumstances, the electric motor can retract the proximal drive portion 482 and the intermediate portion 475 until the distal sidewall of the longitudinal slot 474 defined in the intermediate portion 475 comes into contact with the proximal end 473 of the distal cutting member 472. At such point, the further retraction of the proximal drive portion 482 and the intermediate portion 475 will retract the distal cutting member 472 proximally. In various circumstances, the electric motor can be operated until the slot 476 defined in the intermediate portion 475 of the firing member 470 is realigned with the proximal portion 461 of the articulation driver 460; however, as the closure sleeve 428 is still in a distally advanced position, the cam member 465 may still be biasing the articulation driver 460 out of engagement with the firing member 470. In order to permit the articulation driver 460 to be re-engaged with the firing member 470, in such circumstances, the closure drive would have to be re-opened to bring the window 424 defined in the outer sleeve portion 428 into alignment with the cam member 465 such that the cam member 465 can be pivoted inwardly toward the shaft frame 454 into its first position. In various circumstances, the articulation driver 460 can be resiliently flexed out of engagement with the firing member 470 such that, when the cam member 465 is permitted to move back into its first position, the articulation driver 460 can resiliently flex inwardly toward the shaft frame 454 to re-engage the proximal portion 461 of the articulation driver 460 with the slot 476 defined in the intermediate portion 475 of the drive member 470. In various embodiments, the surgical instrument 400 can further comprise a biasing member which can be configured to bias the proximal portion 461 back into engagement with the intermediate portion 475.

The reader will note that the intermediate portion 475 of the firing member 470 has been retracted proximally in FIG. 27 such that the slot 476 defined in the intermediate portion 475 is positioned proximally with respect to the proximal portion 461 of the articulation driver 460. In such circumstances, as a result, the proximal portion 461 may not be operably re-connected to the firing member 470 until the intermediate portion 475 is advanced distally to align the slot 476 with the proximal portion 461. Such circumstances may arise as a result of the relative slip between the intermediation portion 475 and the cutting member portion 472 of the firing member 470 created by the slip joint 471 which can be addressed by momentarily re-actuating the electric motor in the first direction, for example.

Figure 29:
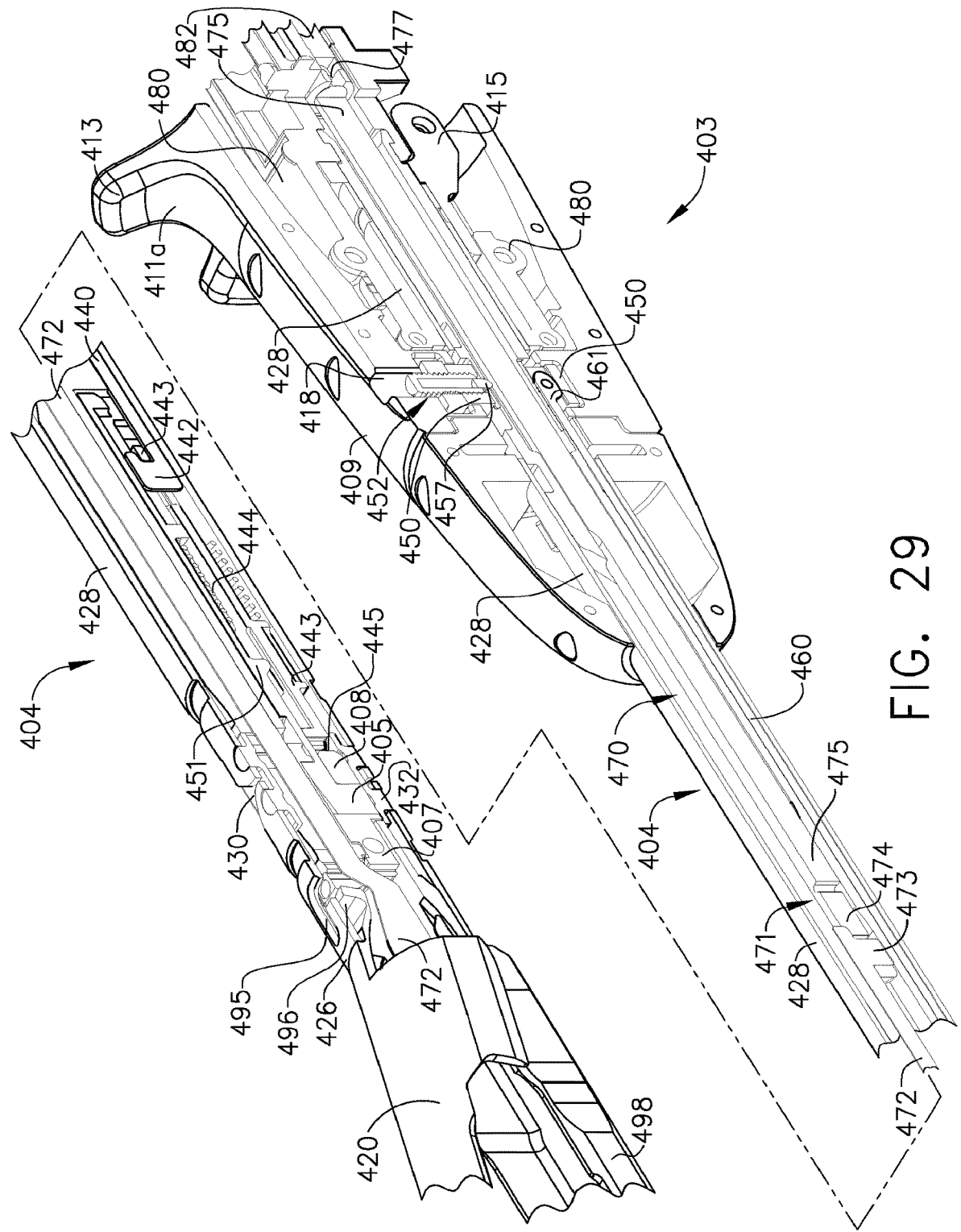
FIG. 29 is a cross-sectional detail view of the surgical instrument of FIG. 17 illustrating the end effector in an open configuration and the articulation joint and the articulation joint actuator in an unlocked configuration wherein the articulation driver can be reconnected to the firing drive and utilized to articulate the end effector once again.

Referring again to FIG. 27, the firing member 470 may be in a retracted or reset position, however, the closure drive is still in an actuated, or closed, configuration which can prevent the anvil 420 from being re-opened and the end effector 402 from being re-articulated. When the closure drive is released, referring now to FIG. 28, the closure drive carriage 415 can be retracted into a proximal position in which the closure sleeve including portions 426 and 428 are pulled proximally as well. Referring again to FIG. 19, the proximal sleeve portion 428 can include a proximal end 417 which can be engaged with the closure drive carriage 415 such that the proximal sleeve portion 428 and the closure drive carriage 415 move together in the distal direction and/or the proximal direction. In any event, further to the above, the proximal movement of the distal sleeve portion 426 can cause the distal sidewall of the aperture 495 to engage the projection 496 extending from the anvil 420 in order to pivot the anvil 420 into its open position, as illustrated in FIG. 29. Furthermore, the proximal movement of the closure drive carriage 415 can unlock the articulation lock actuator 409 such that the articulation lock actuator 409 can be moved into is proximal, unlocked, position which can, as a result, pull the articulation lock 443 proximally to compress the spring 444 and unlock the end effector 402. As described above, the end effector 402 can be then articulated about the articulation joint 410 and the operation of the surgical instrument 400 described above can be repeated. Referring primarily to FIGS. 18-20, the handle 404 can further comprise a switch 408 mounted to the handle frame 480 which can be configured to detect whether the articulation lock actuator 409 is in its proximal, unlocked, position. In some embodiments, the switch 408 can be operably coupled with an indicator in the handle 404, such as light, for example, which can indicate to the operator of the surgical instrument 400 that the end effector 402 is in an unlocked condition and that the operator may utilize the articulation switch to articulate the end effector 402, for example.

Figure 30:
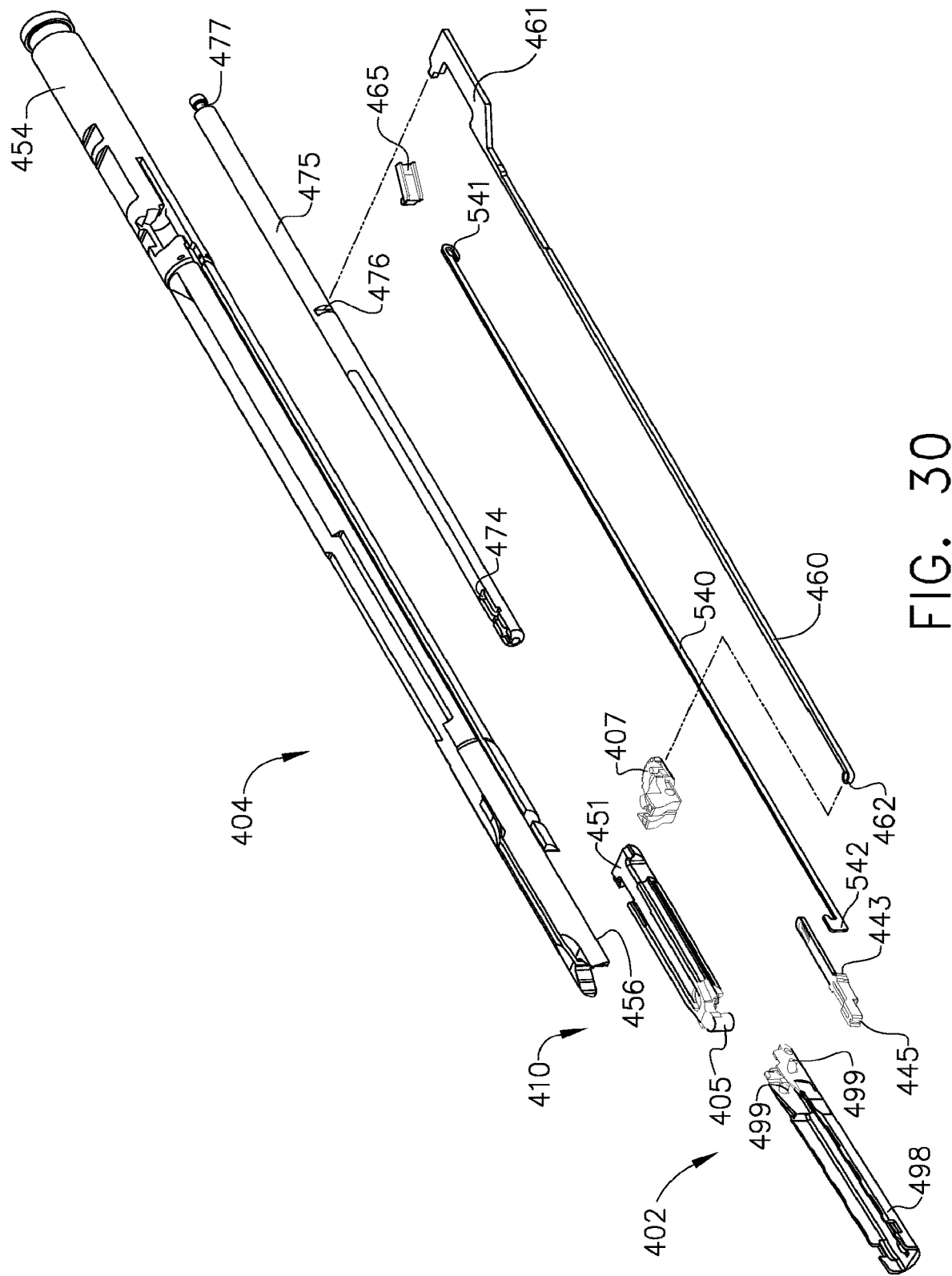
FIG. 30 is an exploded view of a shaft and an end effector of a surgical instrument including an alternative articulation lock arrangement.
Figure 31:
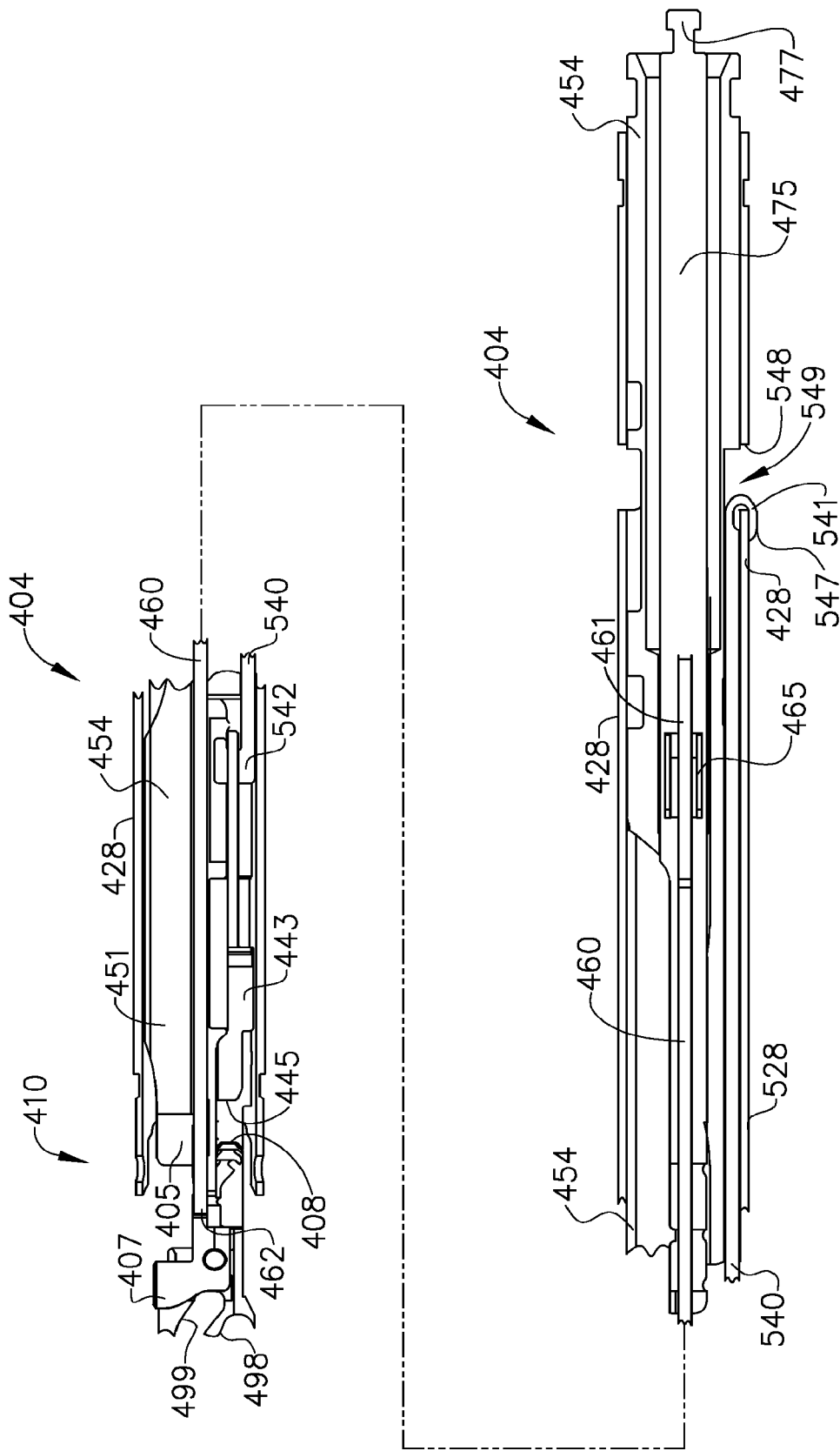
FIG. 31 is a cross-sectional elevational view of the end effector and the shaft of the surgical instrument of FIG. 30 illustrating the end effector in an unlocked configuration.
Figure 32:
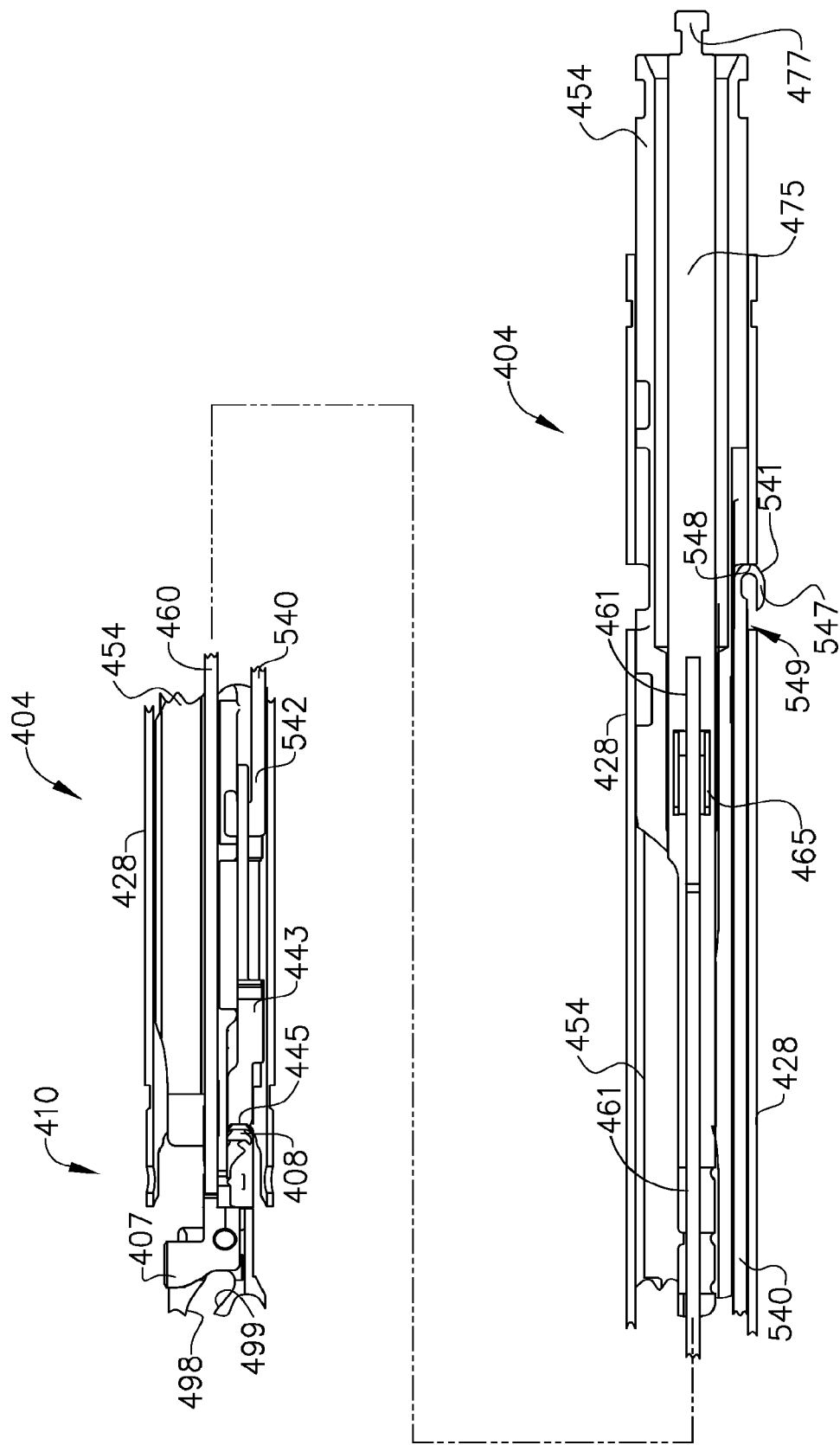
FIG. 32 is a cross-sectional elevational view of the end effector and the shaft of the surgical instrument of FIG. 30 illustrating the end effector in a locked configuration.

As described above in connection with the embodiment of FIG. 17, the surgical instrument 400 can comprise an articulation lock system configured to lock and unlock the end effector 402 and a closure drive configured to open and close the anvil 420 of the end effector 402. Although these two systems of the surgical instrument 400 interact in several respects, which are described above, the systems can be actuated independently of one another in other respects. For instance, the articulation lock actuator 409 and the end effector lock 443 can be actuated without closing the anvil 420. In this embodiment of the surgical instrument 400, the closure drive is operated independently to close the anvil 420. Turning now to FIGS. 30-32, the surgical instrument 400 can include an alternate arrangement in which the closure drive is actuated to, one, close the anvil 420 and, two, lock the end effector 402 in position. Referring primarily to FIGS. 31 and 32, the shaft 404 can comprise an articulation lock bar 540 which can be moved between a proximal, unlocked, position (FIG. 31) in which the end effector 402 can be articulated about the articulation joint 410 and a distal, locked, position (FIG. 32) in which the end effector 402 can be locked in position. Similar to the articulation lock bar 440, the articulation lock bar 540 can include a distal end 542 which is operably engaged with the articulation lock 443 such that, when the articulation lock bar 540 is pulled proximally, the articulation lock 443 can be pulled proximally. Similarly, when the articulation lock bar 540 is pushed distally, the articulation lock 443 can be pushed distally as well. In contrast to the articulation lock bar 440 which is pushed distally and pulled proximally by the articulation lock actuator 409, as described above, the articulation lock bar 540 can be pushed distally and pulled proximally by the closure sleeve 428. More particularly, the proximal end 541 of the articulation lock bar 540 can comprise a hook 547 which, when the closure sleeve 428 is pulled proximally, can catch a portion of the closure sleeve 428 and be pulled proximally with the closure sleeve 428. In such circumstances, the sleeve 428 can pull the articulation lock bar 540 into an unlocked condition. As the reader will note, the closure sleeve 428 can include a window 549 within which the proximal end 541 of the articulation lock bar 540 can be positioned. When the closure sleeve 428 is pushed distally, further to the above, a proximal sidewall 548 of the window 549 can contact the proximal end 541 and push the articulation lock bar 540 and the articulation lock 443 distally in order to lock the end effector 402 in position.

Figure 33:
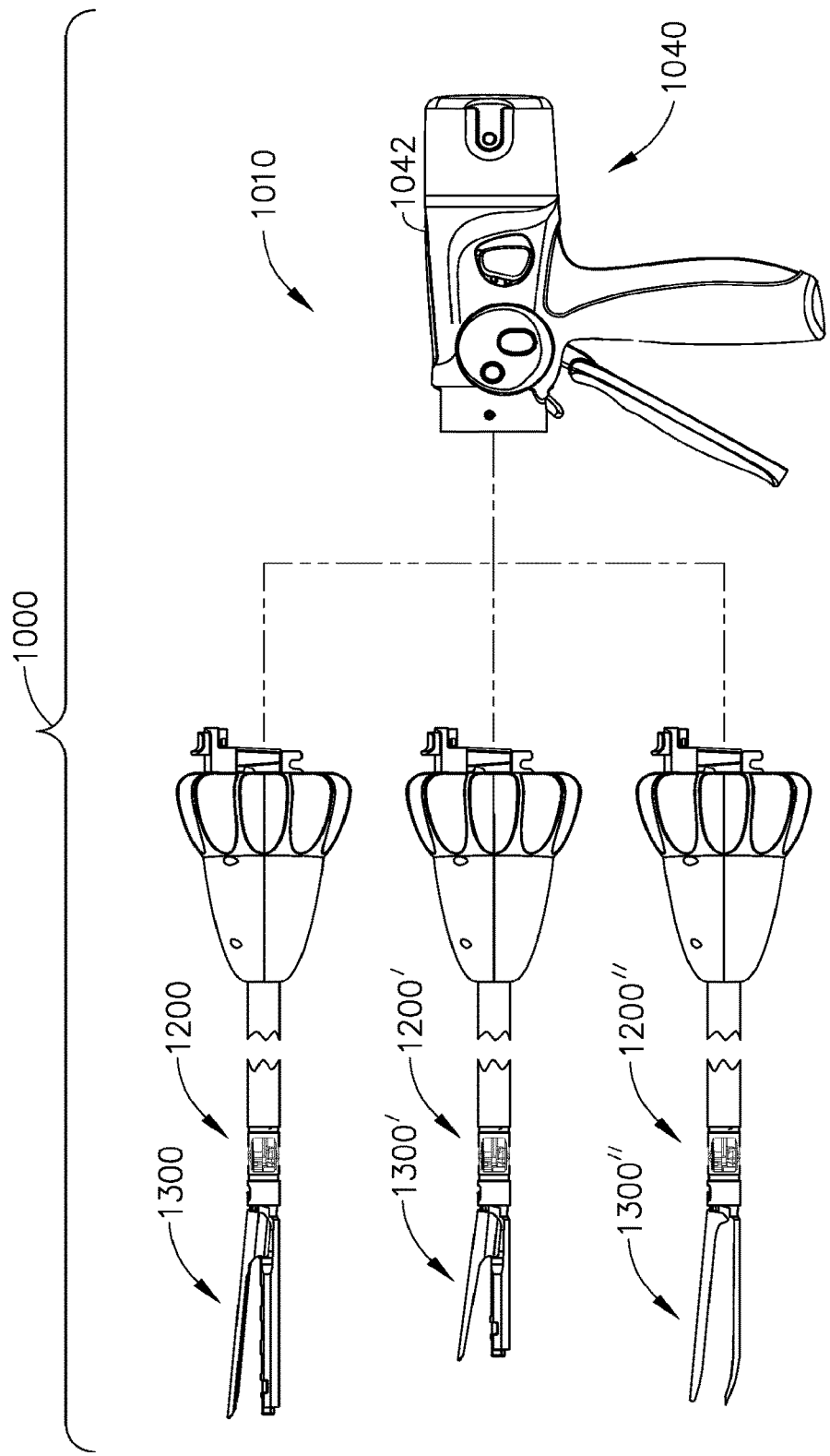
FIG. 33 is an assembly view of one form of surgical system including a surgical instrument and a plurality of interchangeable shaft assemblies.

As described herein, it may be desirable to employ surgical systems and devices that may include reusable portions that are configured to be used with interchangeable surgical components. Referring to FIG. 33, for example, there is shown a surgical system, generally designated as 1000, that, in at least one form, comprises a surgical instrument 1010 that may or may not be reused. The surgical instrument 1010 can be employed with a plurality of interchangeable shaft assemblies 1200, 1200', 1200". The interchangeable shaft assemblies 1200, 1200', 1200" may have a surgical end effector 1300, 1300', 1300" operably coupled thereto that is configured to perform one or more surgical tasks or procedures. For example, each of the surgical end effectors 1300, 1300', 1300" may comprise a surgical cutting and fastening device that is configured to operably support a surgical staple cartridge therein. Each of the shaft assemblies may employ end effectors that are adapted to support different sizes and types of staple cartridges, have different shaft lengths, sizes, and types, etc. While the present Figures illustrate end effectors that are configured to cut and staple tissue, various aspects of the surgical system 1000 may also be effectively employed with surgical instruments that are configured to apply other motions and forms of energy such as, for example, radio frequency (RF) energy, ultrasonic energy and/or motion, to interchangeable shaft-mounted end effector arrangements that are used in various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly. In various circumstances, a shaft assembly can be selected to be attached to a handle of a surgical instrument and a fastener cartridge can be selected to be attached to the shaft assembly.

The surgical instrument 1010 depicted in the FIG. 33 comprises a housing 1040 that consists of a handle 1042 that is configured to be grasped, manipulated and actuated by the clinician. As the present Detailed Description proceeds, however, it will be understood that the various unique and novel arrangements of the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. Patent Application Publication No. 2012/0298719, issued as U.S. Pat. No. 9,072,535 on Jul. 7, 2015. U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719, issued as U.S. Pat. No. 9,072,535 on Jul. 7, 2015, is incorporated by reference herein in its entirety.

Figure 34:
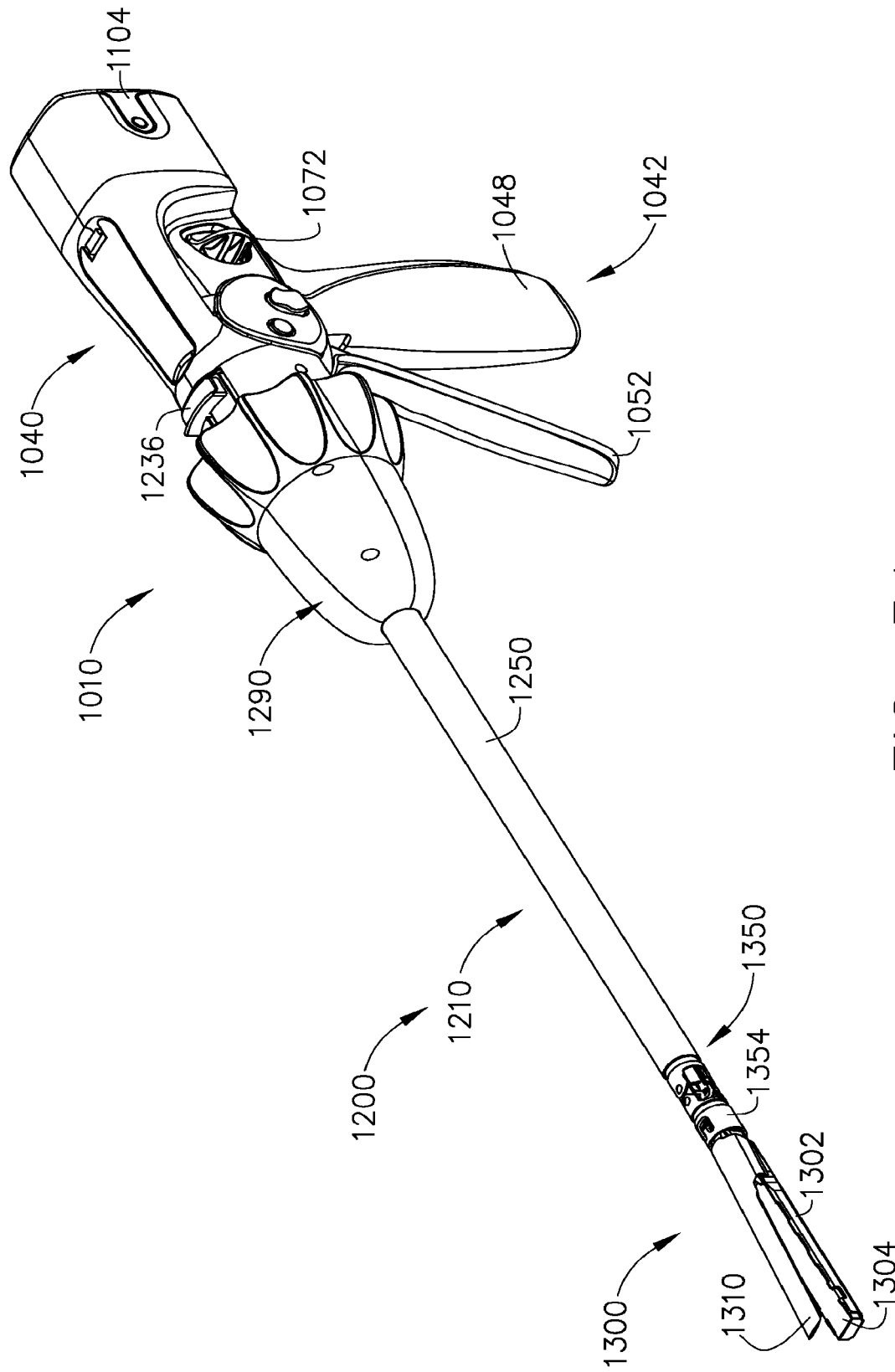
FIG. 34 is a perspective view of a surgical instrument handle coupled to an interchangeable shaft assembly.

FIG. 34 illustrates the surgical instrument 1010 with an interchangeable shaft assembly 1200 operably coupled thereto. In the illustrated form, the surgical instrument includes a handle 1042. In at least one form, the handle 1042 may comprise a pair of interconnectable housing segments 1044, 1046 that may be interconnected by screws, snap features, adhesive, etc. See FIG. 35. In the illustrated arrangement, the handle housing segments 1044, 1046 cooperate to form a pistol grip portion 1048 that can be gripped and manipulated by the clinician. As will be discussed in further detail below, the handle 1042 operably supports a plurality of drive systems therein that are configured to generate and apply various control motions to corresponding portions of the interchangeable shaft assembly that is operably attached thereto.

Figure 35:
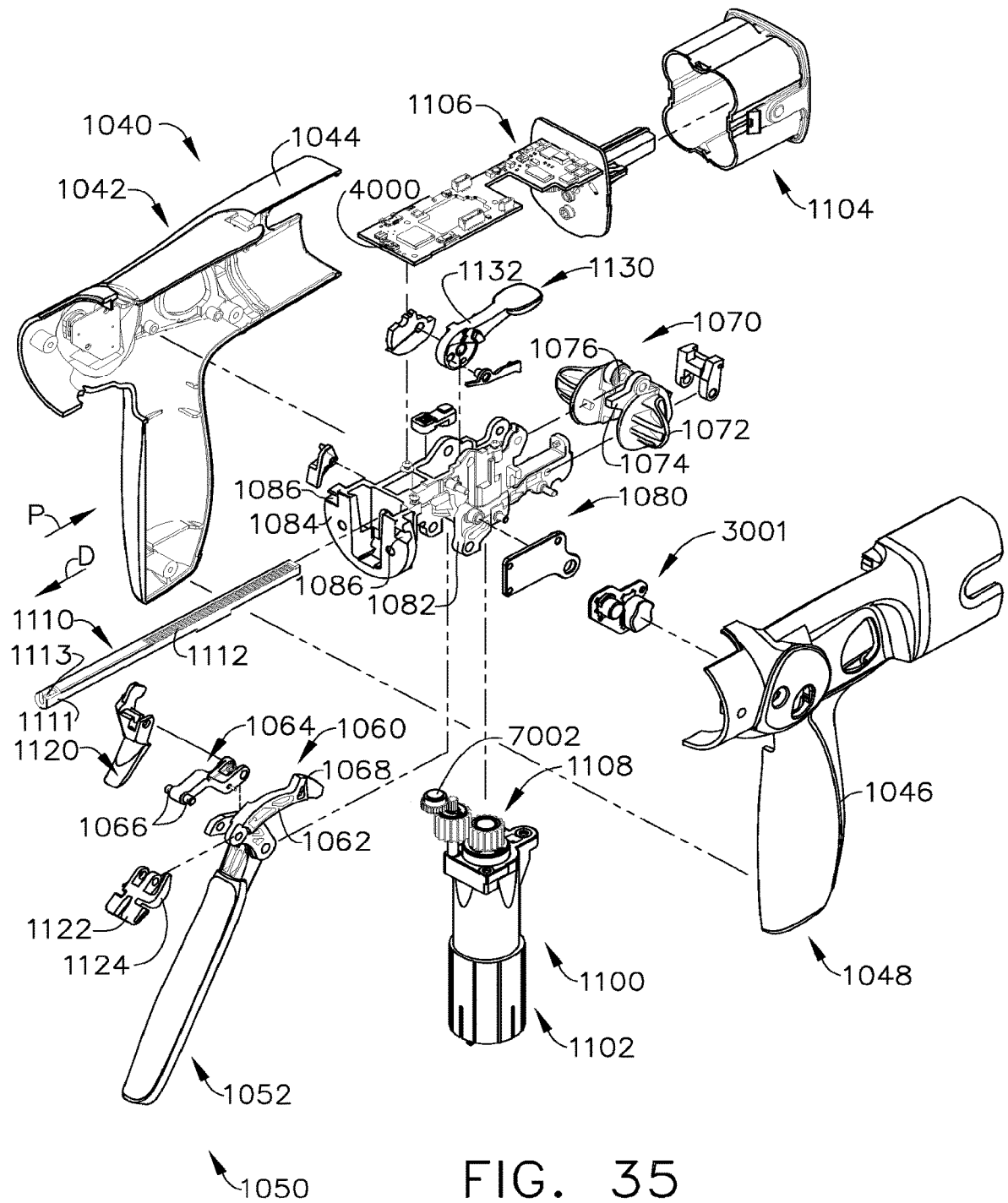
FIG. 35 is an exploded perspective view of the surgical instrument handle of FIG. 34.

The handle 1042 may further include a frame 1080 that operably supports a plurality of drive systems. For example, the frame 1080 can operably support a first or closure drive system, generally designated as 1050, which may be employed to apply a closing and opening motions to the interchangeable shaft assembly 1200 that is operably attached or coupled thereto. In at least one form, the closure drive system 1050 may include an actuator in the form of a closure trigger 1052 that is pivotally supported by the frame 1080. More specifically, as illustrated in FIG. 35, the closure trigger 1052 may be pivotally supported by frame 1080 such that when the clinician grips the pistol grip portion 1048 of the handle 1042, the closure trigger 1052 may be easily pivoted from a starting or unactuated position to an actuated position and more particularly to a fully compressed or fully actuated position. The closure trigger 1052 may be biased into the unactuated position by spring or other biasing arrangement (not shown). In various forms, the closure drive system 1050 further includes a closure linkage assembly 1060 that is pivotally coupled to the closure trigger 1052. As can be seen in FIG. 35, the closure linkage assembly 1060 may include a closure trigger 1052 that is pivotally coupled to a closure link 1064 that has a pair of laterally extending attachment lugs or portions 1066 protruding therefrom. The closure link 1064 may also be referred to herein as an "attachment member".

Still referring to FIG. 35, it can be observed that the closure trigger 1052 may have a locking wall 1068 thereon that is configured to cooperate with a closure release assembly 1070 that is pivotally coupled to the frame 1080. In at least one form, the closure release assembly 1070 may comprise a release button assembly 1072 that has a distally protruding cam follower arm 1074 formed thereon. The release button assembly 1072 may be pivoted in a counter-clockwise direction by a release spring 1076. As the clinician depresses the closure trigger 1052 from its unactuated position towards the pistol grip portion 1048 of the handle 1042, the closure link 1062 pivots upward to a point wherein the cam follower arm 1072 drops into retaining engagement with the locking wall 1068 on the closure link 1062 thereby preventing the closure trigger 1052 from returning to the unactuated position. Thus, the closure release assembly 1070 serves to lock the closure trigger 1052 in the fully actuated position. When the clinician desires to unlock the closure trigger 1052 to permit it to be biased to the unactuated position, the clinician simply pivots the closure release button assembly 1072 such that the cam follower arm 1074 is moved out of engagement with the locking wall 1068 on the closure trigger 1052. When the cam follower arm 1074 has been moved out of engagement with the closure trigger 1052, the closure trigger 1052 may pivot back to the unactuated position. Other closure trigger locking and release arrangements may also be employed.

In at least one form, the handle 1042 and the frame 1080 may operably support another drive system referred to herein as firing drive system 1100 that is configured to apply firing motions to corresponding portions of the interchangeable shaft assembly attached thereto. The firing drive system may also be referred to herein as a "second drive system". The firing drive system 1100 may employ an electric motor 1102, located in the pistol grip portion 1048 of the handle 1042. In various forms, the motor 1102 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. A battery 1104 (or "power source" or "power pack"), such as a Li ion battery, for example, may be coupled to the handle 1042 to supply power to a control circuit board assembly 1106 and ultimately to the motor 1102. FIG. 34 illustrates a battery pack housing 1104 that is configured to be releasably mounted to the handle 1042 for supplying control power to the surgical instrument 1010. A number of battery cells connected in series may be used as the power source to power the motor. In addition, the power source may be replaceable and/or rechargeable.

As outlined above with respect to other various forms, the electric motor 1102 can include a rotatable shaft (not shown) that operably interfaces with a gear reducer assembly 1108 that is mounted in meshing engagement with a with a set, or rack, of drive teeth 1112 on a longitudinally-movable drive member 1110. In use, a voltage polarity provided by the battery can operate the electric motor 1102 in a clockwise direction wherein the voltage polarity applied to the electric motor by the battery can be reversed in order to operate the electric motor 1102 in a counter-clockwise direction. When the electric motor 1102 is rotated in one direction, the drive member 1110 will be axially driven in the distal direction "D". When the motor 1102 is driven in the opposite rotary direction, the drive member 1110 will be axially driven in a proximal direction "P". See, for example, FIG. 35. The handle 1042 can include a switch which can be configured to reverse the polarity applied to the electric motor 1102 by the battery. As with the other forms described herein, the handle 1042 can also include a sensor that is configured to detect the position of the drive member 1110 and/or the direction in which the drive member 1110 is being moved.

Figure 36:
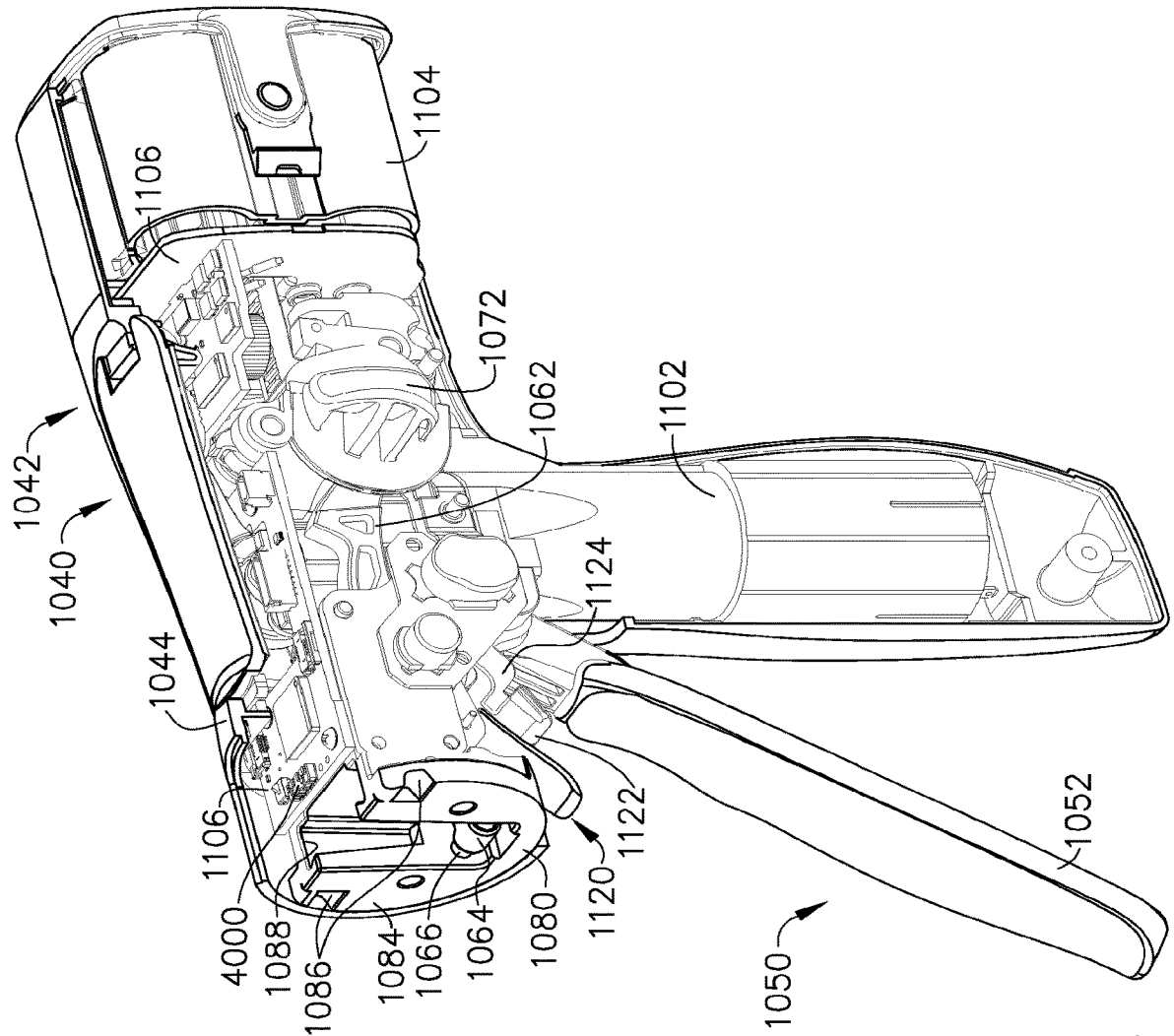
FIG. 36 is a side elevational view of the handle of FIG. 35 with a portion of the handle housing removed.
Figure 38:
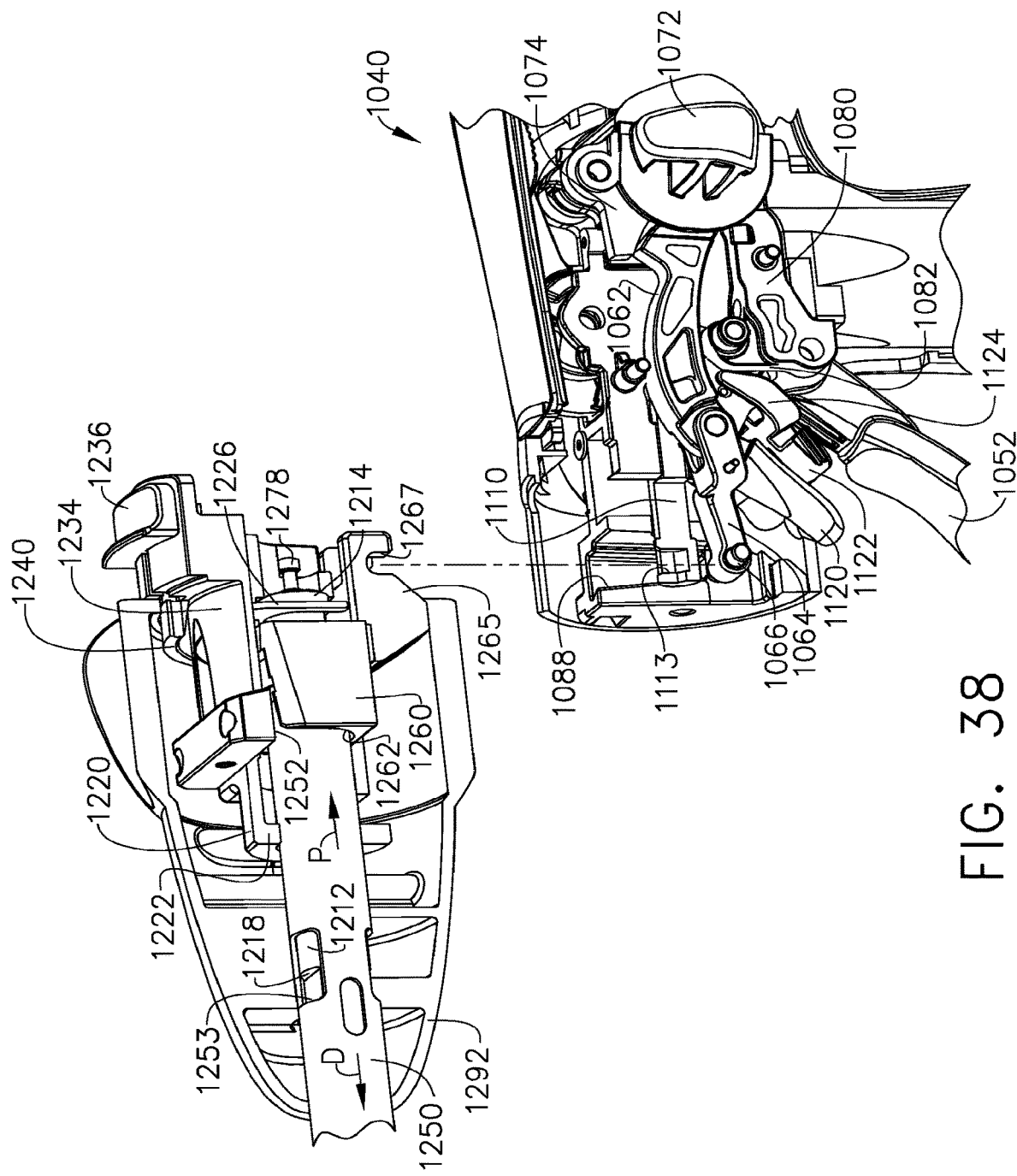
FIG. 38 is a side elevational assembly view of a portion of the handle and interchangeable shaft assembly of FIG. 34 illustrating the alignment of those components prior to being coupled together and with portions thereof omitted for clarity.

Actuation of the motor 1102 can be controlled by a firing trigger 1120 that is pivotally supported on the handle 1042. The firing trigger 1120 may be pivoted between an unactuated position and an actuated position. The firing trigger 1120 may be biased into the unactuated position by a spring (not shown) or other biasing arrangement such that when the clinician releases the firing trigger 1120, it may be pivoted or otherwise returned to the unactuated position by the spring or biasing arrangement. In at least one form, the firing trigger 1120 can be positioned "outboard" of the closure trigger 1052 as was discussed above. In at least one form, a firing trigger safety button 1122 may be pivotally mounted to the closure trigger 1052. As can be seen in FIGS. 35 and 36, for example, the safety button 1122 may be positioned between the firing trigger 1120 and the closure trigger 1052 and have a pivot arm 1124 protruding therefrom. As shown in FIG. 38, when the closure trigger 1052 is in the unactuated position, the safety button 1122 is contained in the handle housing where the clinician cannot readily access it and move it between a safety position preventing actuation of the firing trigger 1120 and a firing position wherein the firing trigger 1120 may be fired. As the clinician depresses the closure trigger 1052, the safety button 1122 and the firing trigger 1120 pivot down wherein they can then be manipulated by the clinician.

As indicated above, in at least one form, the longitudinally movable drive member 1110 has a rack of teeth 1112 formed thereon for meshing engagement with a corresponding drive gear 1114 of the gear reducer assembly 1108. At least one form may also include a manually-actuatable "bailout" assembly 1130 that is configured to enable the clinician to manually retract the longitudinally movable drive member 1110 should the motor become disabled. The bailout assembly 1130 may include a lever or bailout handle assembly 1132 that is configured to be manually pivoted into ratcheting engagement with the teeth 1112 in the drive member 1110. Thus, the clinician can manually retract the drive member 1110 by using the bailout handle assembly 1132 to ratchet the drive member in the proximal direction "P". U.S. Patent Application Publication No. U.S. 2010/0089970, now U.S. Pat. No. 8,608,045, discloses bailout arrangements and other components, arrangements and systems that may also be employed with the various instruments disclosed herein. U.S. patent application Ser. No. 12/249,117, entitled POWERED SURGICAL CUTTING AND STAPLING APPARATUS WITH MANUALLY RETRACTABLE FIRING SYSTEM, now U.S. Patent Application Publication No. 2010/0089970, now U.S. Pat. No. 8,608,045, is incorporated by reference in its entirety.

Figure 37:
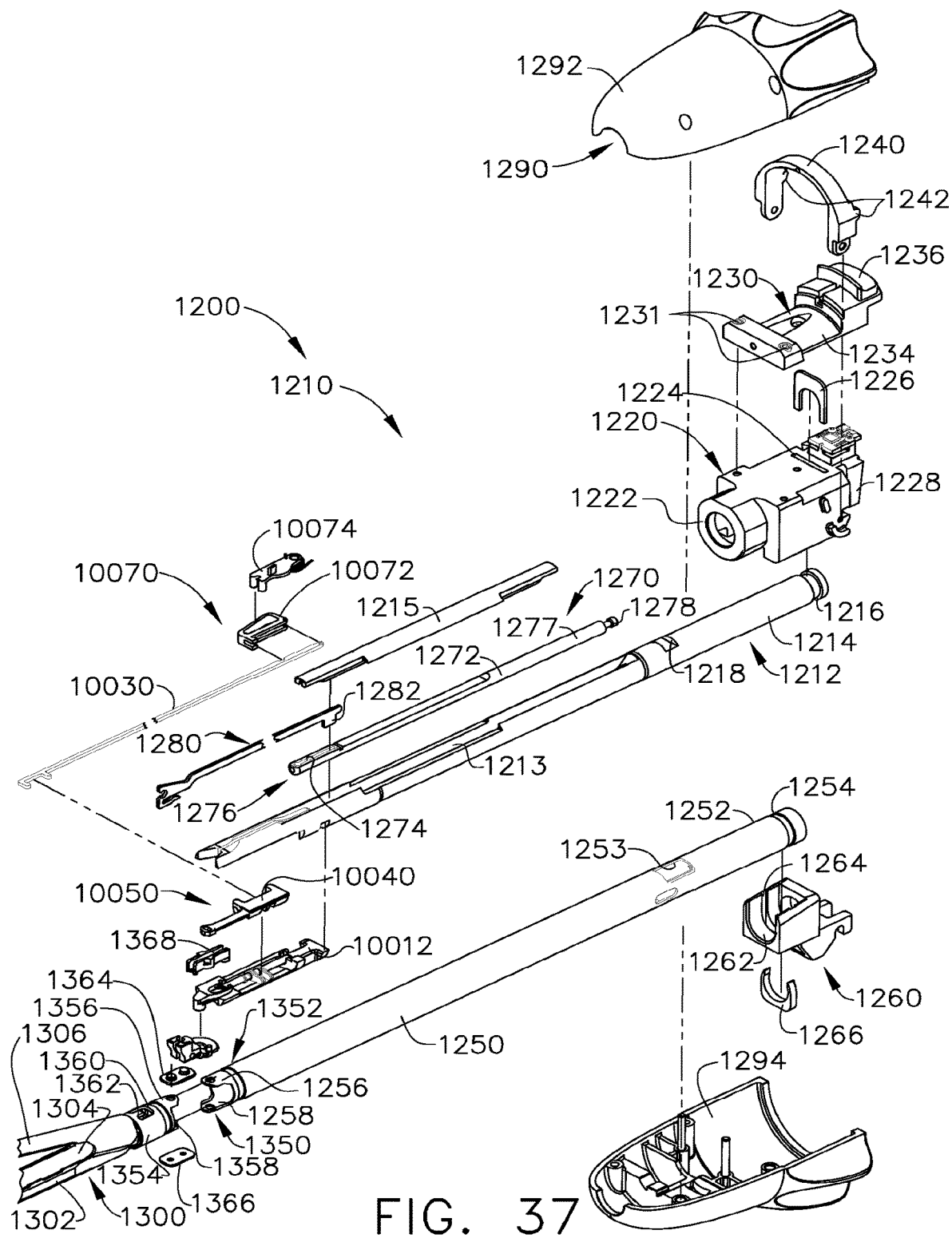
FIG. 37 is an exploded perspective view of an interchangeable shaft assembly.

FIGS. 34 and 37 illustrate one form of interchangeable shaft assembly 1200 that has, for example, a surgical end effector 1300 operably attached thereto. The end effector 1300 as illustrated in those Figures may be configured to cut and staple tissue in the various manners disclosed herein. For example, the end effector 1300 may include a channel 1302 that is configured to support a surgical staple cartridge 1304. The staple cartridge 1304 may comprise a removable staple cartridge 1304 such that it may be replaced when spent. However, the staple cartridge in other arrangements may be configured such that once installed within the channel 1302, it is not intended to be removed therefrom. The channel 1032 and staple cartridge 1304 may be collectively referred to as a "first jaw portion" of the end effector 1300. In various forms, the end effector 1300 may have a "second jaw portion", in the form of an anvil 1310, that is movably or pivotally supported on the channel 1302 in the various manners discussed herein.

The interchangeable shaft assembly 1200 may further include a shaft 1210 that includes a shaft frame 1212 that is coupled to a shaft attachment module or shaft attachment portion 1220. In at least one form, a proximal end 1214 of the shaft frame 1212 may extend through a hollow collar portion 1222 formed on the shaft attachment module 1220 and be rotatably attached thereto. For example, an annular groove 1216 may be provided in the proximal end 1214 of the shaft frame 1212 for engagement with a U-shaped retainer 1226 that extends through a slot 1224 in the shaft attachment module 1220. Such arrangement enables the shaft frame 1212 to be rotated relative to the shaft attachment module 1220.

The shaft assembly 1200 may further comprise a hollow outer sleeve or closure tube 1250 through which the shaft frame 1212 extends. The outer sleeve 1250 may also be referred to herein as a "first shaft" and/or a "first shaft assembly". The outer sleeve 1250 has a proximal end 1252 that is adapted to be rotatably coupled to a closure tube attachment yoke 1260. As can be seen in FIG. 37, the proximal end 1252 of the outer sleeve 1250 is configured to be received within a cradle 1262 in the closure tube attachment yoke 1260. A U-shaped connector 1266 extends through a slot 1264 in the closure tube attachment yoke 1260 to be received in an annular groove 1254 in the proximal end 1252 of the outer sleeve 1250. Such arrangement serves to rotatably couple the outer sleeve 1250 to the closure tube attachment yoke 1260 such that the outer sleeve 1250 may rotate relative thereto.

Figure 39:
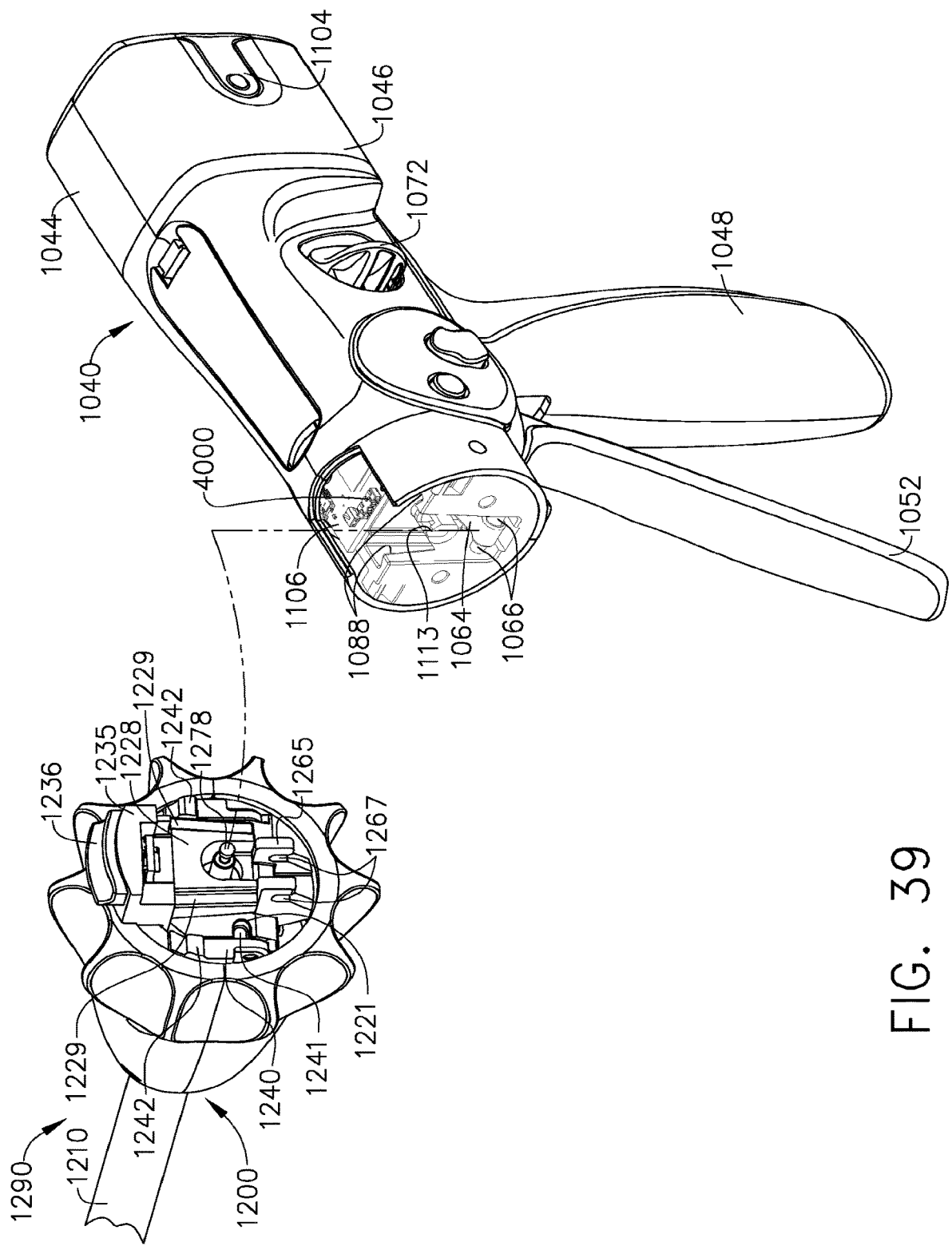
FIG. 39 is a perspective view of a portion of an interchangeable shaft assembly prior to attachment to a handle of a surgical instrument.

As can be seen in FIGS. 38 and 39, the proximal end 1214 of the shaft frame 1214 protrudes proximally out of the proximal end 1252 of the outer sleeve 1250 and is rotatably coupled to the shaft attachment module 1220 by the U-shaped retainer 1226 (shown in FIG. 38). The closure tube attachment yoke 1260 is configured to be slidably received within a passage 1268 in the shaft attachment module 1220. Such arrangement permits the outer sleeve 1250 to be axially moved in the proximal direction "P" and the distal direction "D" on the shaft frame 1212 relative to the shaft attachment module 1220 as will be discussed in further detail below.

In at least one form, the interchangeable shaft assembly 1200 may further include an articulation joint 1350. Other interchangeable shaft assemblies, however, may not be capable of articulation. As can be seen in FIG. 37, for example, the articulation joint 1350 includes a double pivot closure sleeve assembly 1352. According to various forms, the double pivot closure sleeve assembly 1352 includes a shaft closure sleeve assembly 1354 having upper and lower distally projecting tangs 1356, 1358. An end effector closure sleeve assembly 1354 includes a horseshoe aperture 1360 and a tab 1362 for engaging an opening tab on the anvil 1310 in the manner described above. As described above, the horseshoe aperture 1360 and tab 1362 engage the anvil tab when the anvil 1310 is opened. An upper double pivot link 1364 includes upwardly projecting distal and proximal pivot pins that engage respectively an upper distal pin hole in the upper proximally projecting tang 1356 and an upper proximal pin hole in an upper distally projecting tang 1256 on the outer sleeve 1250. A lower double pivot link 1366 includes downwardly projecting distal and proximal pivot pins that engage respectively a lower distal pin hole in the lower proximally projecting tang 1358 and a lower proximal pin hole in the lower distally projecting tang 1258.

In use, the closure sleeve assembly 1354 is translated distally (direction "D") to close the anvil 1310, for example, in response to the actuation of the closure trigger 1052. The anvil 1310 is closed by distally translating the outer sleeve 1250, and thus the shaft closure sleeve assembly 1354, causing it to strike a proximal surface on the anvil 1310 in the manner described above. As was also described above, the anvil 1310 is opened by proximally translating the outer sleeve 1250 and the shaft closure sleeve assembly 1354, causing tab 1362 and the horseshoe aperture 1360 to contact and push against the anvil tab to lift the anvil 1310. In the anvil-open position, the shaft closure sleeve assembly 1352 is moved to its proximal position.

In at least one form, the interchangeable shaft assembly 1200 further includes a firing member 1270 that is supported for axial travel within the shaft frame 1212. The firing member 1270 includes an intermediate firing shaft portion 1272 that is configured for attachment to a distal cutting portion 1280. The firing member 1270 may also be referred to herein as a "second shaft" and/or a "second shaft assembly". As can be seen in FIG. 37, the intermediate firing shaft portion 1272 may include a longitudinal slot 1274 in the distal end thereof which can be configured to receive the proximal end 1282 of the distal cutting portion 1280. The longitudinal slot 1274 and the proximal end 1282 can be sized and configured to permit relative movement therebetween and can comprise a slip joint 1276. The slip joint 1276 can permit the intermediate firing shaft portion 1272 of the firing drive 1270 to be moved to articulate the end effector 1300 without moving, or at least substantially moving, the distal cutting portion 1280. Once the end effector 1300 has been suitably oriented, the intermediate firing shaft portion 1272 can be advanced distally until a proximal sidewall of the longitudinal slot 1272 comes into contact with the proximal end 1282 in order to advance the distal cutting portion 1280 and fire the staple cartridge positioned within the channel 1302, as described herein. As can be further seen in FIG. 37, the shaft frame 1212 has an elongate opening or window 1213 therein to facilitate assembly and insertion of the intermediate firing shaft portion 1272 into the shaft frame 1212. Once the intermediate firing shaft portion 1272 has been inserted therein, a top frame segment 1215 may be engaged with the shaft frame 1212 to enclose the intermediate firing shaft portion 1272 and distal cutting portion 1280 therein. The reader will also note that the articulation joint 1350 can further include a guide 1368 which can be configured to receive the distal cutting portion 1280 of the firing member 1270 therein and guide the distal cutting portion 1280 as it is advanced distally and/or retracted proximally within and/or relative to the articulation joint 1350.

As can be seen in FIG. 37, the shaft attachment module 1220 may further include a latch actuator assembly 1230 that may be removably attached to the shaft attachment module by cap screws (not shown) or other suitable fasteners. The latch actuator assembly 1230 is configured to cooperate with a lock yoke 1240 that is pivotally coupled to the shaft attachment module 1220 for selective pivotal travel relative thereto. See FIG. 41. Referring to FIG. 39, the lock yoke 1240 may include two proximally protruding lock lugs 1242 (FIG. 37) that are configured for releasable engagement with corresponding lock detents or grooves 1086 formed in a frame attachment module portion 1084 of the frame 1080 as will be discussed in further detail below. The lock yoke 1240 is substantially U-shaped and is installed over the latch actuator assembly 1230 after the latch actuator assembly 1230 has been coupled to the shaft attachment module 1220. The latch actuator assembly 1230 may have an arcuate body portion 1234 that provides sufficient clearance for the lock yoke 1240 to pivot relative thereto between latched and unlatched positions.

In various forms, the lock yoke 1240 is biased in the proximal direction by spring or biasing member (not shown). Stated another way, the lock yoke 1240 is biased into the latched position (FIG. 40) and can be pivoted to an unlatched position (FIG. 41) by a latch button 1236 that is movably supported on the latch actuator assembly 1230. In at least one arrangement, for example, the latch button 1236 is slidably retained within a latch housing portion 1235 and is biased in the proximal direction "P" by a latch spring or biasing member (not shown). As will be discussed in further detail below, the latch button 1236 has a distally protruding release lug 1237 that is designed to engage the lock yoke 1240 and pivot it from the latched position to the unlatched position shown in FIG. 41 upon actuation of the latch button 1236.

The interchangeable shaft assembly 1200 may further include a nozzle assembly 1290 that is rotatably supported on the shaft attachment module 1220. In at least one form, for example, the nozzle assembly 1290 can be comprised of two nozzle halves, or portions, 1292, 1294 that may be interconnected by screws, snap features, adhesive, etc. When mounted on the shaft attachment module 1220, the nozzle assembly 1290 may interface with the outer sleeve 1250 and shaft frame 1212 to enable the clinician to selectively rotate the shaft 1210 relative to the shaft attachment module 1220 about a shaft axis SA-SA which may be defined for example, the axis of the firing member assembly 1270. In particular, a portion of the nozzle assembly 1290 may extend through a window 1253 in the outer sleeve to engage a notch 1218 in the shaft frame 1212. See FIG. 37. Thus, rotation of the nozzle assembly 1290 will result in rotation of the shaft frame 1212 and outer sleeve 1250 about axis A-A relative to the shaft attachment module 1220.

Figure 42:
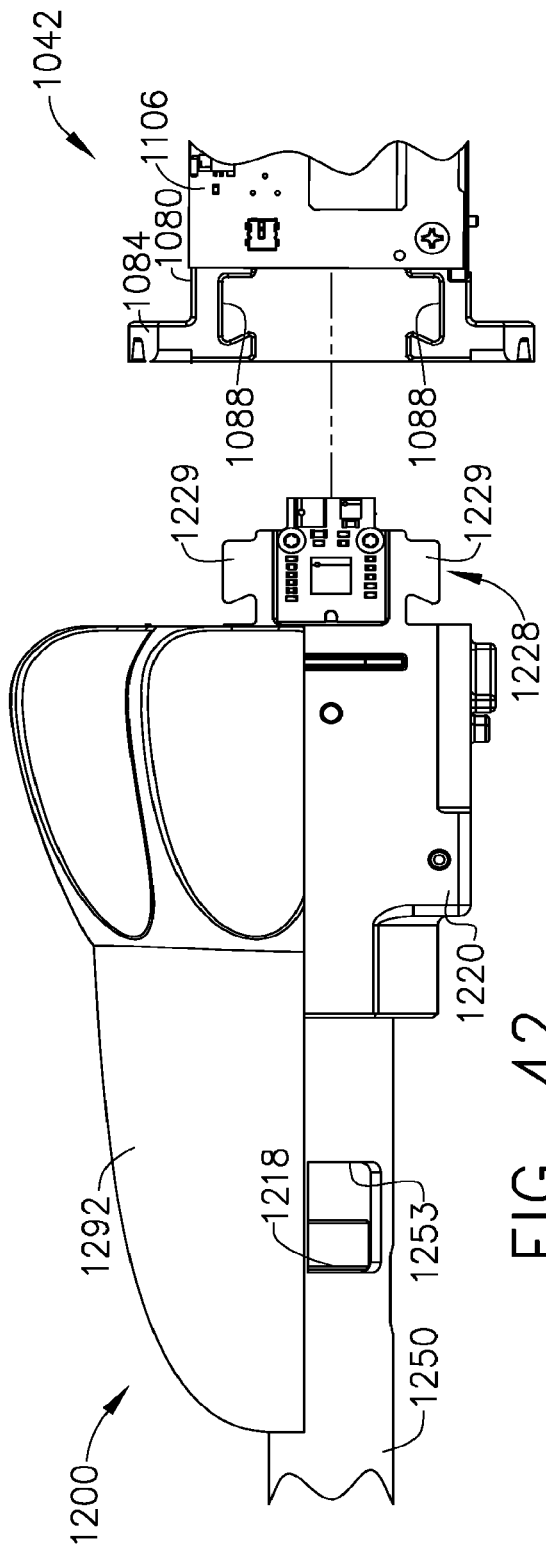
FIG. 42 is a top view of a portion of an interchangeable shaft assembly and handle prior to being coupled together.
Figure 43:
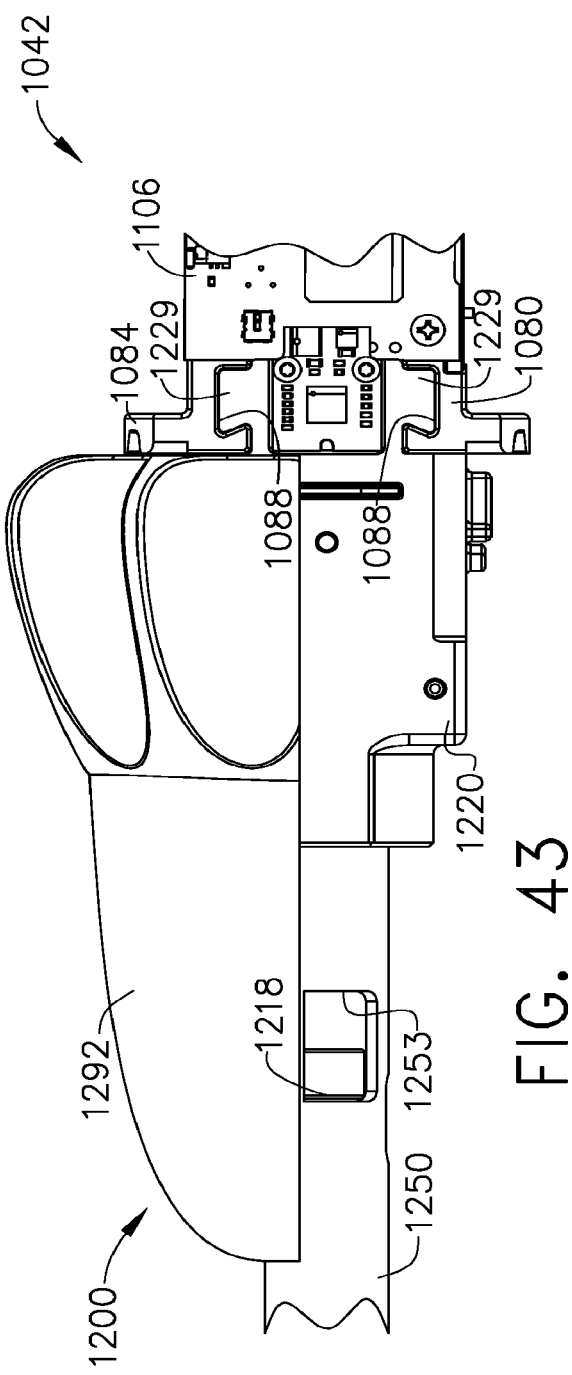
FIG. 43 is another top view of the interchangeable shaft assembly and handle of FIG. 42 coupled together.
Figure 44:
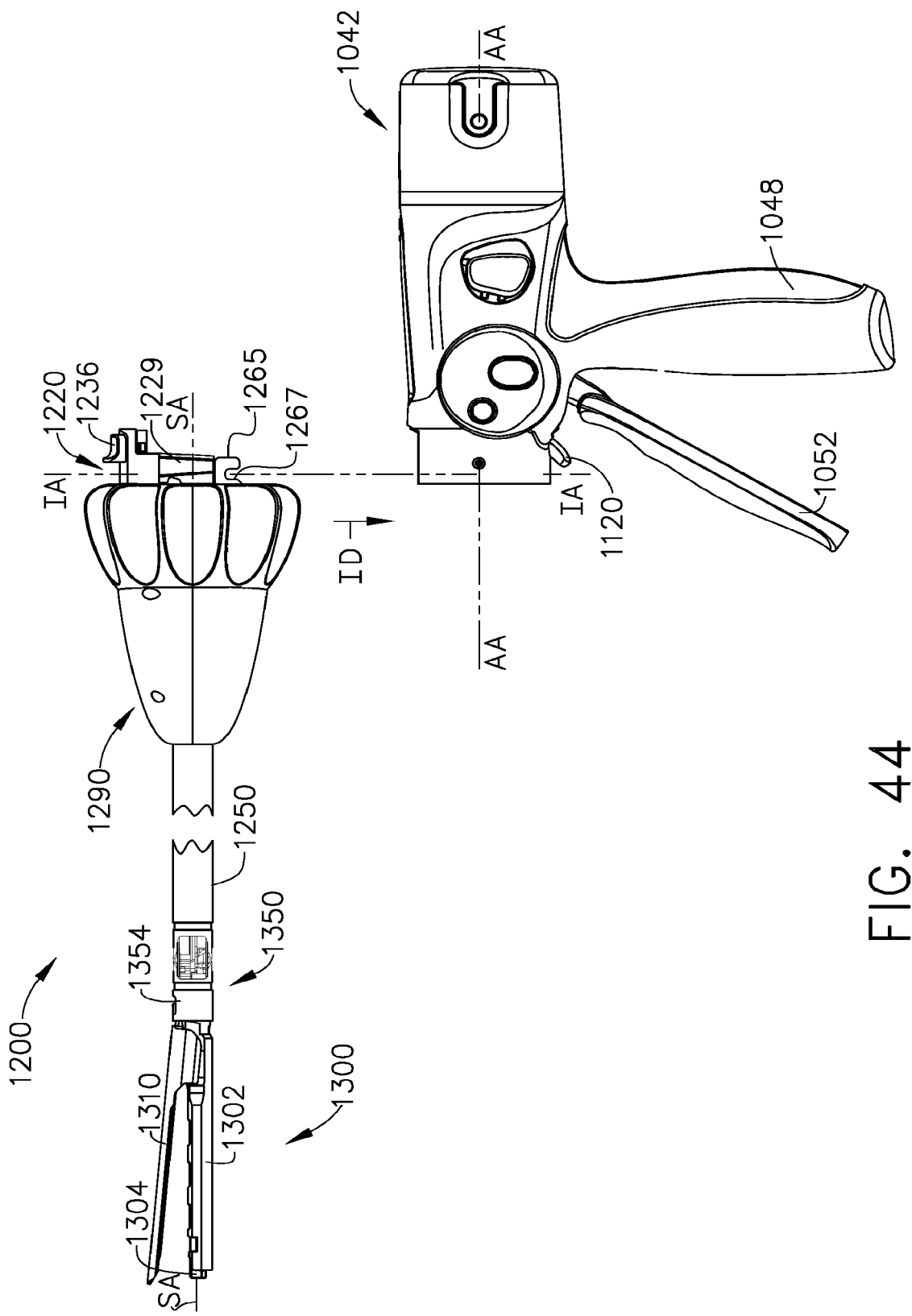
FIG. 44 is a side elevational view of an interchangeable shaft assembly aligned with a surgical instrument handle prior to being coupled together.

Referring now to FIGS. 42 and 43, the reader will observe that the frame attachment module portion 1084 of the frame 1080 is formed with two inwardly facing dovetail receiving slots 1088. Each dovetail receiving slot 1088 may be tapered or, stated another way, be somewhat V-shaped. See, for example, FIGS. 36 and 38 (only one of the slots 1088 is shown). The dovetail receiving slots 1088 are configured to releasably receive corresponding tapered attachment or lug portions 1229 of a proximally-extending connector portion 1228 of the shaft attachment module 1220. As can be further seen in FIGS. 37-39, a shaft attachment lug 1278 is formed on the proximal end 1277 of the intermediate firing shaft 1272. As will be discussed in further detail below, when the interchangeable shaft assembly 1200 is coupled to the handle 1042, the shaft attachment lug 1278 is received in a firing shaft attachment cradle 1113 formed in the distal end 1111 of the longitudinal drive member 1110. Also, the closure tube attachment yoke 1260 includes a proximally-extending yoke portion 1265 that includes two capture slots 1267 that open downwardly to capture the attachment lugs 1066 on the closure attachment bar 1064.

Figure 47:
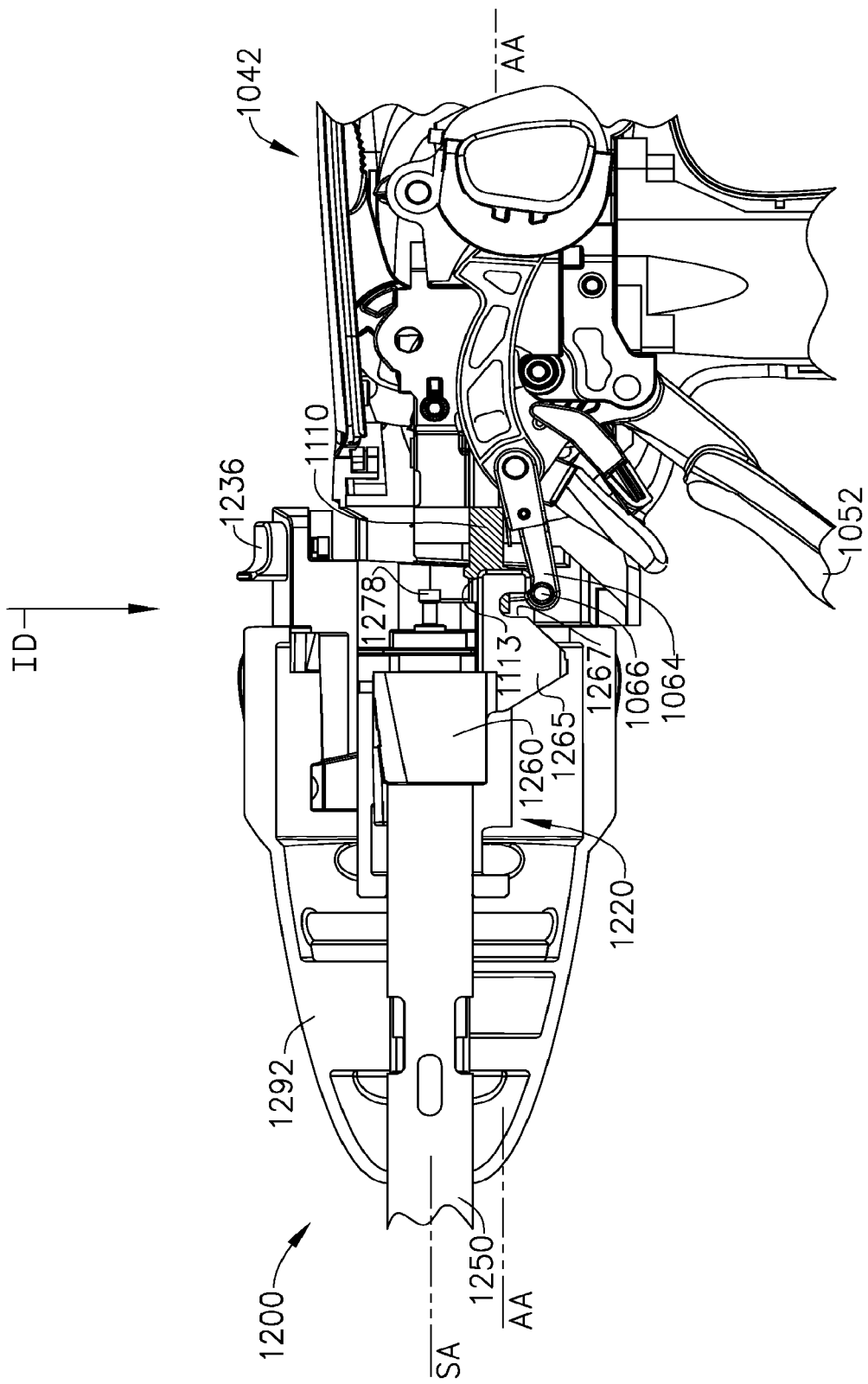
FIG. 47 is another side elevational view of the interchangeable shaft assembly and handle of FIG. 46 wherein the shaft assembly is in partial coupling engagement with the handle.
Figure 48:
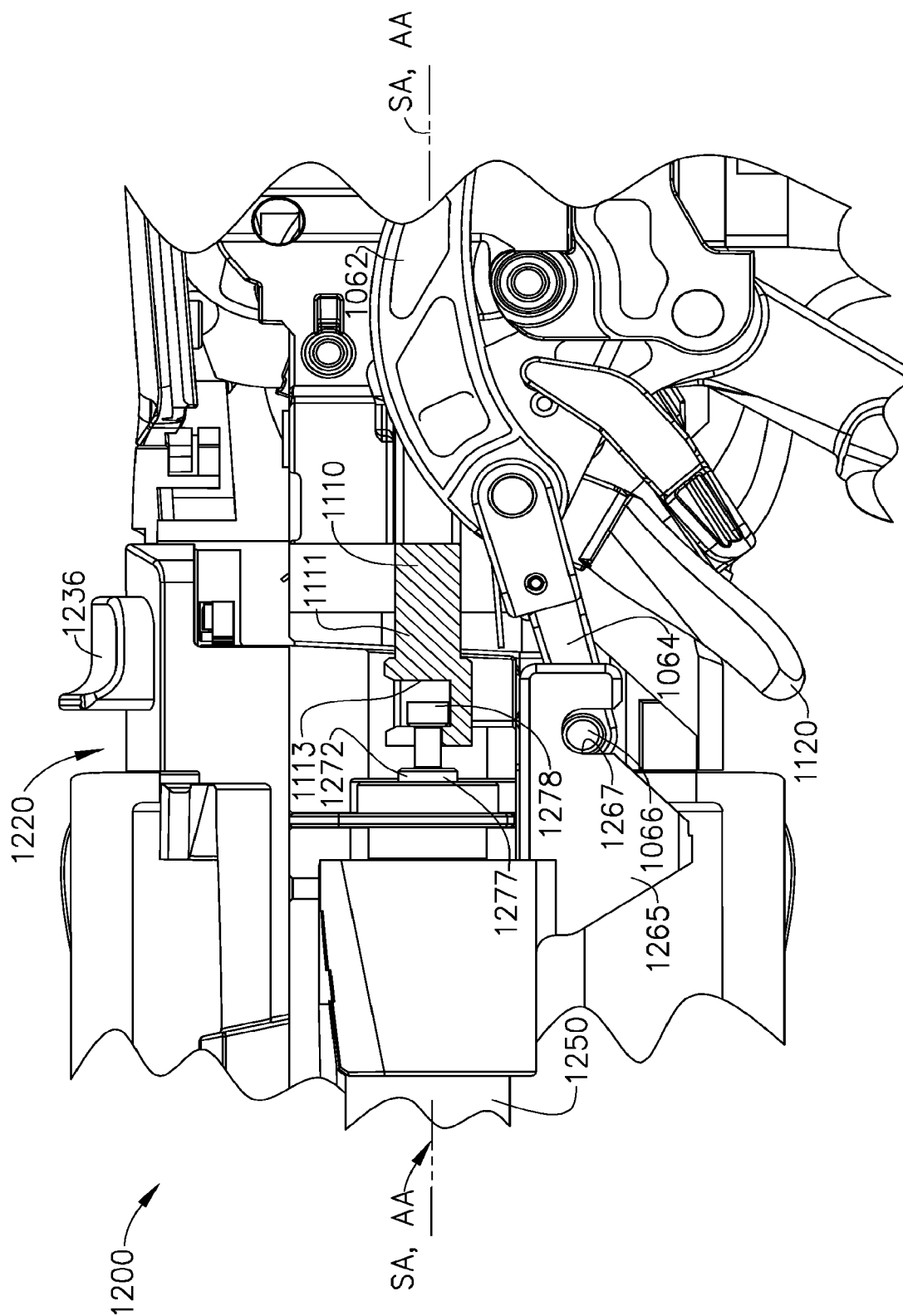
FIG. 48 is another side elevational view of the interchangeable shaft assembly and handle of FIGS. 46 and 47 after being coupled together.

Attachment of the interchangeable shaft assembly 1220 to the handle 1042 will now be described with reference to FIGS. 44-48. In various forms, the frame 1080 or at least one of the drive systems define an actuation axis AA-AA. For example, the actuation axis AA-AA may be defined by the axis of the longitudinally-movable drive member 1110. As such, when the intermediate firing shaft 1272 is operably coupled to the longitudinally movable drive member 1110, the actuation axis AA-AA is coaxial with the shaft axis SA-SA as shown in FIG. 48.

Figure 45:
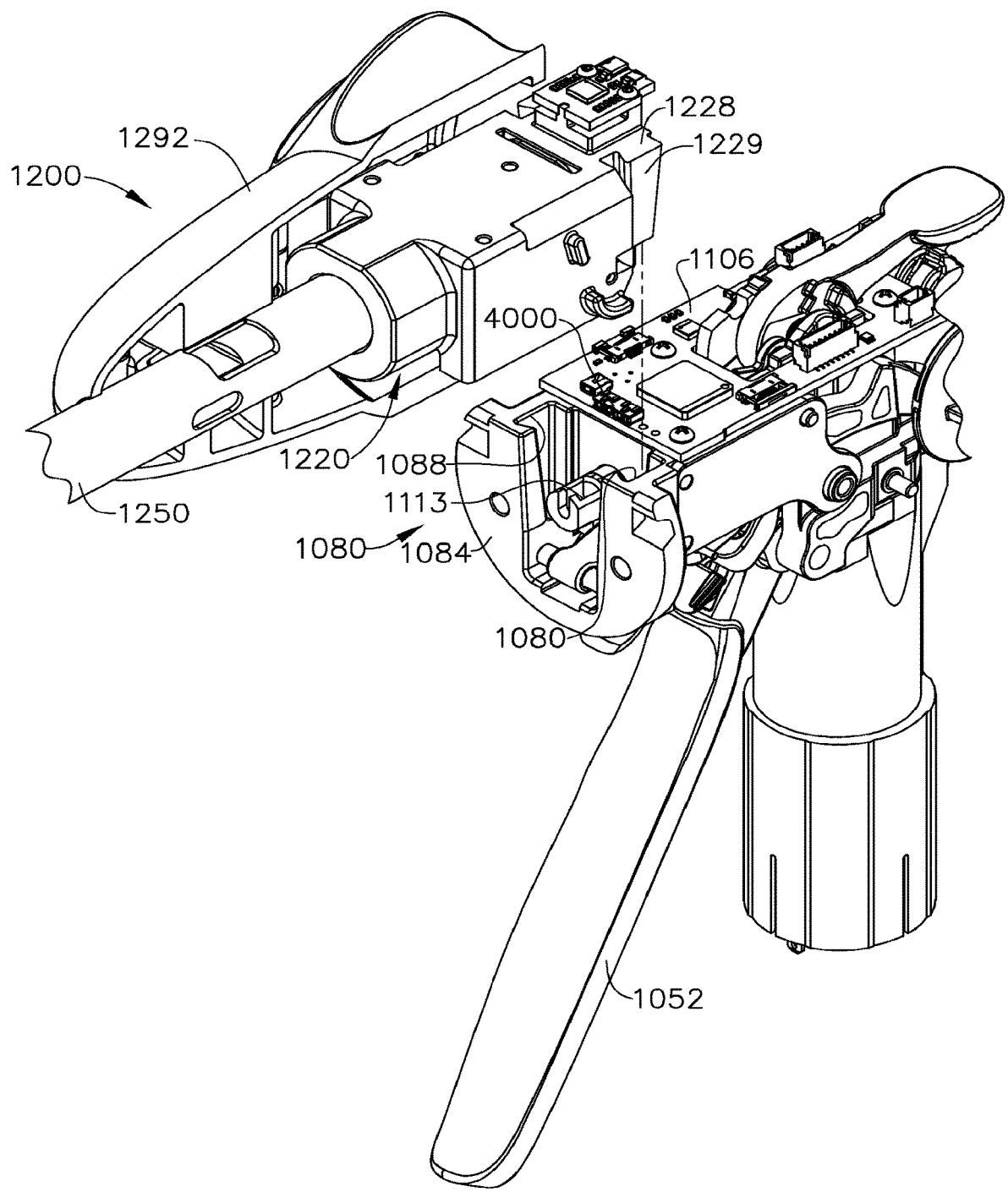
FIG. 45 is a front perspective view of the interchangeable shaft assembly and surgical instrument handle of FIG. 44 with portions thereof removed for clarity.
Figure 46:
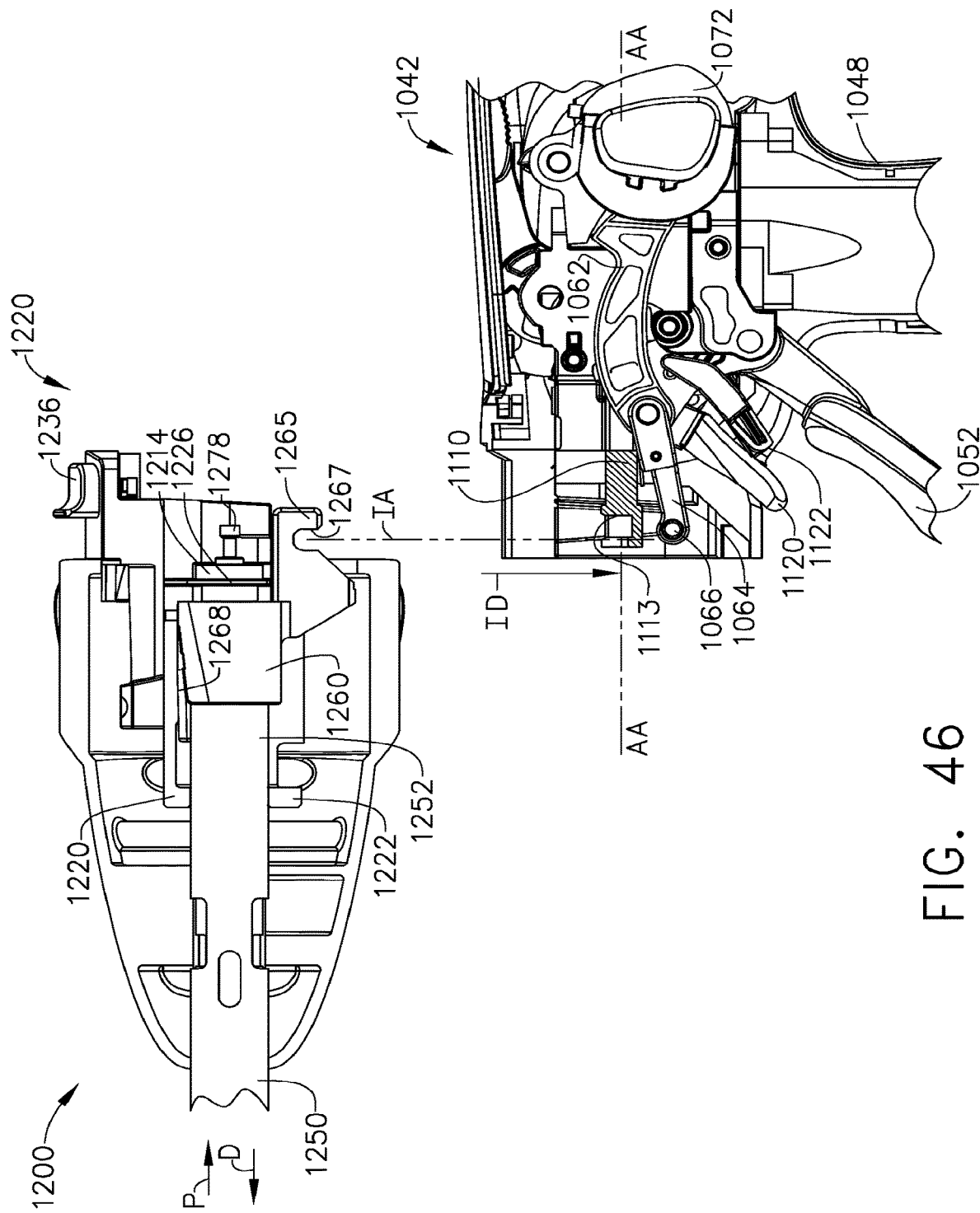
FIG. 46 is a side view of a portion of an interchangeable shaft assembly aligned with a portion of a surgical instrument handle prior to being coupled together and with portions thereof omitted for clarity.

To commence the coupling process, the clinician may position the shaft attachment module 1220 of the interchangeable shaft assembly 1200 above or adjacent to the frame attachment module portion 1084 of the frame 1080 such that the attachment lugs 1229 formed on the connector portion 1228 of the shaft attachment module 1220 are aligned with the dovetail slots 1088 in the attachment module portion 1084 as shown in FIG. 45. The clinician may then move the shaft attachment module 1220 along an installation axis IA-IA that is substantially transverse to the actuation axis AA-AA. Stated another way, the shaft attachment module 1220 is moved in an installation direction "ID" that is substantially transverse to the actuation axis AA-AA until the attachment lugs 1229 of the connector portion 1228 are seated in "operable engagement" with the corresponding dovetail receiving slots 1088. See FIGS. 44 and 46. FIG. 47 illustrates the position of the shaft attachment module 1220 prior to the shaft attachment lug 1278 on the intermediate firing shaft 1272 entering the cradle 1113 in the longitudinally movable drive member 1110 and the attachment lugs 1066 on the closure attachment bar 1064 entering the corresponding slots 1267 in the yoke portion 1265 of the closure tube attachment yoke 1260. FIG. 48 illustrates the position of the shaft attachment module 1220 after the attachment process has been completed. As can be seen in that Figure, the lugs 1066 (only one is shown) are seated in operable engagement in their respective slots 1267 in the yoke portion 1265 of the closure tube attachment yoke 1260. As used herein, the term "operable engagement" in the context of two components means that the two components are sufficiently engaged with each other so that upon application of an actuation motion thereto, the components may carry out their intended action, function and/or procedure.

As discussed above, referring again to FIGS. 44-49, at least five systems of the interchangeable shaft assembly 1200 can be operably coupled with at least five corresponding systems of the handle 1042. A first system can comprise a frame system which couples and/or aligns the frame of the shaft assembly 1200 with the frame of the handle 1042. As outlined above, the connector portion 1228 of the shaft assembly 1200 can be engaged with the attachment module portion 1084 of the handle frame 1080. A second system can comprise a closure drive system which can operably connect the closure trigger 1052 of the handle 1042 and the closure tube 1250 and the anvil 1310 of the shaft assembly 1200. As outlined above, the closure tube attachment yoke 1260 of the shaft assembly 1200 can be engaged with the attachment lugs 1066 of the handle 1042. A third system can comprise a firing drive system which can operably connect the firing trigger 1120 of the handle 1042 with the intermediate firing shaft 1272 of the shaft assembly 1200. As outlined above, the shaft attachment lug 1278 can be operably connected with the cradle 1113 of the longitudinal drive member 1110. A fourth system can comprise an electrical system which can, one, signal to a controller in the handle 1042, such as microcontroller 7004, for example, that a shaft assembly, such as shaft assembly 1200, for example, has been operably engaged with the handle 1042 and/or, two, conduct power and/or communication signals between the shaft assembly 1200 and the handle 1042. For instance, the shaft assembly 1200 can include six electrical contacts and the electrical connector 4000 can also include six electrical contacts wherein each electrical contact on the shaft assembly 1200 can be paired and mated with an electrical contact on the electrical connector 4000 when the shaft assembly 1200 is assembled to the handle 1042. The shaft assembly 1200 can also include a latch 1236 which can be part of a fifth system, such as a lock system, which can releasably lock the shaft assembly 1200 to the handle 1042. In various circumstances, the latch 1236 can close a circuit in the handle 1042, for example, when the latch 1236 is engaged with the handle 1042.

Further to the above, the frame system, the closure drive system, the firing drive system, and the electrical system of the shaft assembly 1200 can be assembled to the corresponding systems of the handle 1042 in a transverse direction, i.e., along axis IA-IA, for example. In various circumstances, the frame system, the closure drive system, and the firing drive system of the shaft assembly 1200 can be simultaneously coupled to the corresponding systems of the handle 1042. In certain circumstances, two of the frame system, the closure drive system, and the firing drive system of the shaft assembly 1200 can be simultaneously coupled to the corresponding systems of the handle 1042. In at least one circumstance, the frame system can be at least initially coupled before the closure drive system and the firing drive system are coupled. In such circumstances, the frame system can be configured to align the corresponding components of the closure drive system and the firing drive system before they are coupled as outlined above. In various circumstances, the electrical system portions of the housing assembly 1200 and the handle 1042 can be configured to be coupled at the same time that the frame system, the closure drive system, and/or the firing drive system are finally, or fully, seated. In certain circumstances, the electrical system portions of the housing assembly 1200 and the handle 1042 can be configured to be coupled before the frame system, the closure drive system, and/or the firing drive system are finally, or fully, seated. In some circumstances, the electrical system portions of the housing assembly 1200 and the handle 1042 can be configured to be coupled after the frame system has been at least partially coupled, but before the closure drive system and/or the firing drive system are have been coupled. In various circumstances, the locking system can be configured such that it is the last system to be engaged, i.e., after the frame system, the closure drive system, the firing drive system, and the electrical system have all been engaged.

Figure 51:
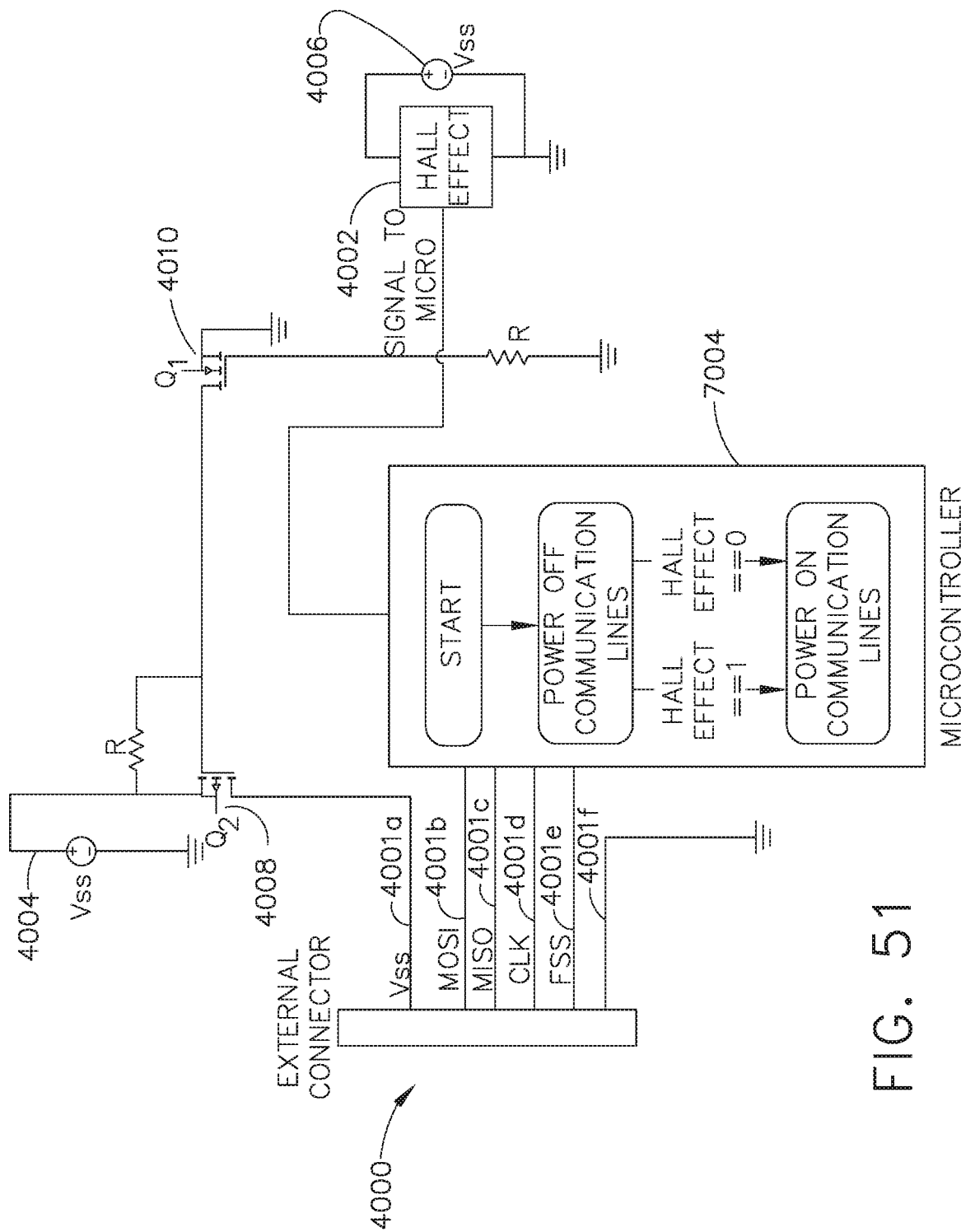
FIG. 51 is a schematic of a system for powering down an electrical connector of a surgical instrument handle when a shaft assembly is not coupled thereto.

As outlined above, referring again to FIGS. 44-49, the electrical connector 4000 of the handle 1042 can comprise a plurality of electrical contacts. Turning now to FIG. 51, the electrical connector 4000 can comprise a first contact 4001a, a second contact 4001b, a third contact 4001c, a fourth contact 4001d, a fifth contact 4001e, and a sixth contact 4001f, for example. While the illustrated embodiment utilizes six contacts, other embodiments are envisioned which may utilize more than six contacts or less than six contacts. As illustrated in FIG. 51, the first contact 4001a can be in electrical communication with a transistor 4008, contacts 4001b-4001e can be in electrical communication with a microcontroller 7004, and the sixth contact 4001f can be in electrical communication with a ground. Microcontroller 7004 is discussed in greater detail further below. In certain circumstances, one or more of the electrical contacts 4001b-4001e may be in electrical communication with one or more output channels of the microcontroller 7004 and can be energized, or have a voltage potential applied thereto, when the handle 1042 is in a powered state. In some circumstances, one or more of the electrical contacts 4001b-4001e may be in electrical communication with one or more input channels of the microcontroller 7004 and, when the handle 1042 is in a powered state, the microcontroller 7004 can be configured to detect when a voltage potential is applied to such electrical contacts. When a shaft assembly, such as shaft assembly 1200, for example, is assembled to the handle 1042, the electrical contacts 4001a-4001f may not communicate with each other. When a shaft assembly is not assembled to the handle 1042, however, the electrical contacts 4001a-4001f of the electrical connector 4000 may be exposed and, in some circumstances, one or more of the contacts 4001a-4001f may be accidentally placed in electrical communication with each other. Such circumstances can arise when one or more of the contacts 4001a-4001f come into contact with an electrically conductive material, for example. When this occurs, the microcontroller 7004 can receive an erroneous input and/or the shaft assembly 1200 can receive an erroneous output, for example. To address this issue, in various circumstances, the handle 1042 may be unpowered when a shaft assembly, such as shaft assembly 1200, for example, is not attached to the handle 1042. In other circumstances, the handle 1042 can be powered when a shaft assembly, such as shaft assembly 1200, for example, is not attached thereto. In such circumstances, the microcontroller 7004 can be configured to ignore inputs, or voltage potentials, applied to the contacts in electrical communication with the microcontroller 7004, i.e., contacts 4001b-4001e, for example, until a shaft assembly is attached to the handle 1042. Even though the microcontroller 7004 may be supplied with power to operate other functionalities of the handle 1042 in such circumstances, the handle 1042 may be in a powered-down state. In a way, the electrical connector 4000 may be in a powered-down state as voltage potentials applied to the electrical contacts 4001b-4001e may not affect the operation of the handle 1042. The reader will appreciate that, even though contacts 4001b-4001e may be in a powered-down state, the electrical contacts 4001a and 4001f, which are not in electrical communication with the microcontroller 7004, may or may not be in a powered-down state. For instance, sixth contact 4001f may remain in electrical communication with a ground regardless of whether the handle 1042 is in a powered-up or a powered-down state. Furthermore, the transistor 4008, and/or any other suitable arrangement of transistors, such as transistor 4010, for example, and/or switches may be configured to control the supply of power from a power source 4004, such as a battery 1104 within the handle 1042, for example, to the first electrical contact 4001a regardless of whether the handle 1042 is in a powered-up or a powered-down state as outlined above. In various circumstances, the latch 1236 of the shaft assembly 1200, for example, can be configured to change the state of the transistor 4008 when the latch 1236 is engaged with the handle 1042. In various circumstances, as described elsewhere herein, the latch 1236 can be configured to close a circuit when it engages the handle 1042 and, as a result, affect the state of the transistor 4008. In certain circumstances, further to the below, a Hall effect sensor 4002 can be configured to switch the state of transistor 4010 which, as a result, can switch the state of transistor 4008 and ultimately supply power from power source 4004 to first contact 4001a. In this way, further to the above, both the power circuits and the signal circuits to the connector 4000 can be powered down when a shaft assembly is not installed to the handle 1042 and powered up when a shaft assembly is installed to the handle 1042.

In various circumstances, referring again to FIG. 51, the handle 1042 can include the Hall effect sensor 4002, for example, which can be configured to detect a detectable element, such as a magnetic element, for example, on a shaft assembly, such as shaft assembly 1200, for example, when the shaft assembly is coupled to the handle 1042. The Hall effect sensor 4002 can be powered by a power source 4006, such as a battery, for example, which can, in effect, amplify the detection signal of the Hall effect sensor 4002 and communicate with an input channel of the microcontroller 7004 via the circuit illustrated in FIG. 51. Once the microcontroller 7004 has a received an input indicating that a shaft assembly has been at least partially coupled to the handle 1042, and that, as a result, the electrical contacts 4001a-4001f are no longer exposed, the microcontroller 7004 can enter into its normal, or powered-up, operating state. In such an operating state, the microcontroller 7004 will evaluate the signals transmitted to one or more of the contacts 4001b-4001e from the shaft assembly and/or transmit signals to the shaft assembly through one or more of the contacts 4001b-4001e in normal use thereof. In various circumstances, the shaft assembly 1200 may have to be fully seated before the Hall effect sensor 4002 can detect the magnetic element. While a Hall effect sensor 4002 can be utilized to detect the presence of the shaft assembly 1200, any suitable system of sensors and/or switches can be utilized to detect whether a shaft assembly has been assembled to the handle 1042, for example. In this way, further to the above, both the power circuits and the signal circuits to the connector 4000 can be powered down when a shaft assembly is not installed to the handle 1042 and powered up when a shaft assembly is installed to the handle 1042.

In various embodiments, any number of magnetic sensing elements may be employed to detect whether a shaft assembly has been assembled to the handle 1042, for example. For example, the technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

Figure 40:
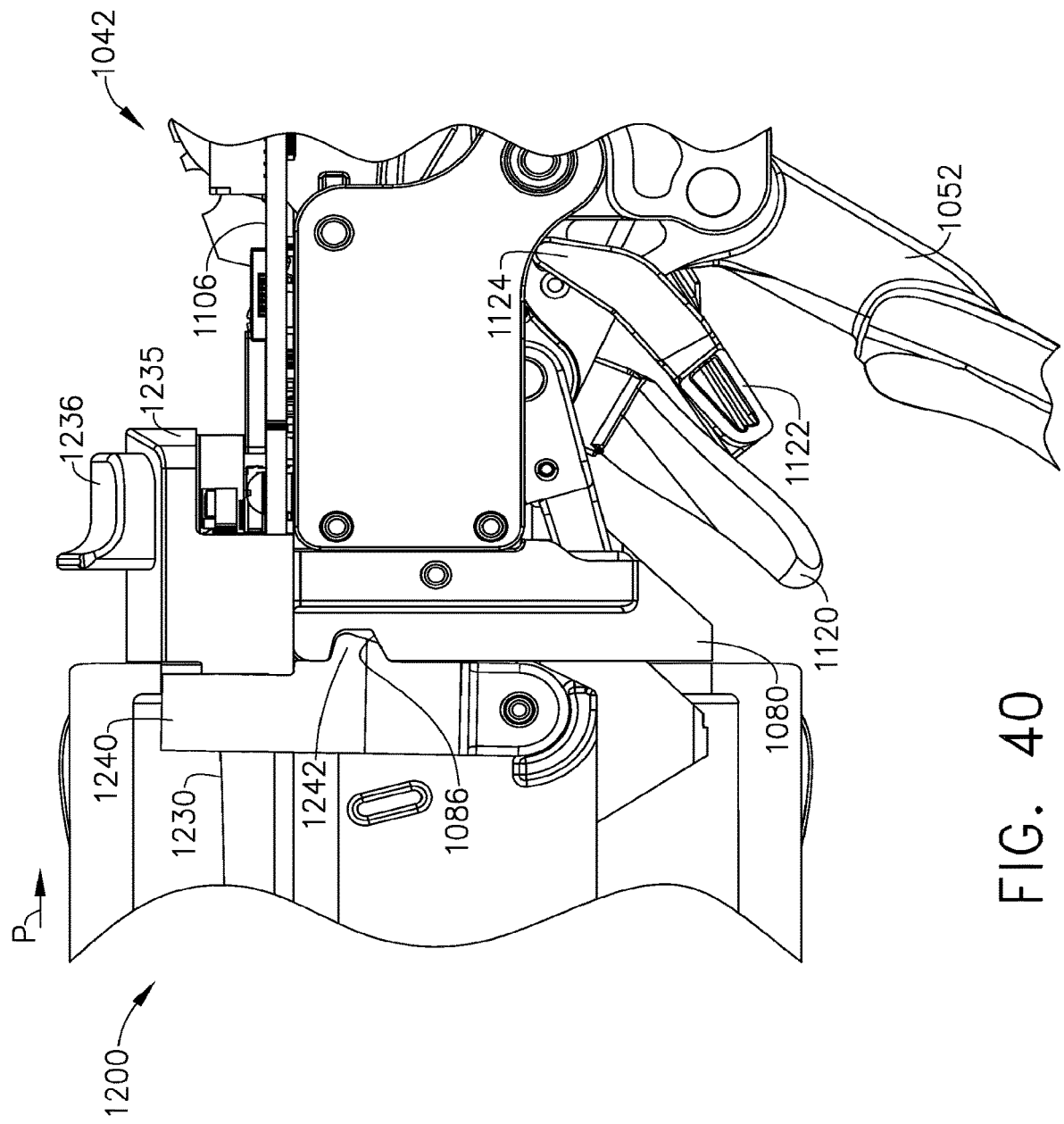
FIG. 40 is a side view of a portion of an interchangeable shaft assembly coupled to a handle with the lock yoke in a locked or engaged position with a portion of the frame attachment module of the handle.

After the interchangeable shaft assembly 1200 has been operably coupled to the handle 1042, actuation of the closure trigger 1052 will result in the distal axial advancement of the outer sleeve 1250 and the shaft closure sleeve assembly 1354 coupled thereto to actuate the anvil 1310 in the various manners disclosed herein. As can also be seen in FIG. 48, the firing member 1270 in the interchangeable shaft assembly 1200 is coupled to the longitudinally movable drive member 1110 in the handle 1042. More specifically, the shaft attachment lug 1278 formed on the proximal end 1277 of the intermediate firing shaft 1272 is receive within the firing shaft attachment cradle 1113 formed in the distal end 1111 of the longitudinally movable drive member 1110. Thus, actuation of the firing trigger 1120 which results in powering of the motor 1102 to axially advance the longitudinally movable drive member 1110 will also cause the firing member 1270 to axially move within the shaft frame 1212. Such action will cause the advancement of the distal cutting portion 1280 through the tissue clamped in the end effector 1300 in the various manners disclosed herein. Although not observable in FIG. 48, those of ordinary skill in the art will also understand that when in the coupled position depicted in that Figure, the attachment lug portions 1229 of the shaft attachment module 1220 are seated within their respective dovetail receiving slots 1088 in the attachment module portion 1084 of the frame 1080. Thus, the shaft attachment module 1220 is coupled to the frame 1080. In addition, although not shown in FIG. 48 (but which can be seen in FIG. 40), when the shaft attachment module 1220 has been coupled to the frame 1080, the lock lugs 1242 on the lock yoke 1240 are seated within their respective lock grooves 1086 (only one is shown in FIG. 40) in the attachment module portion 1084 of the frame 1080 to releasably retain the shaft attachment module 1220 in coupled operable engagement with the frame 1080.

Figure 41:
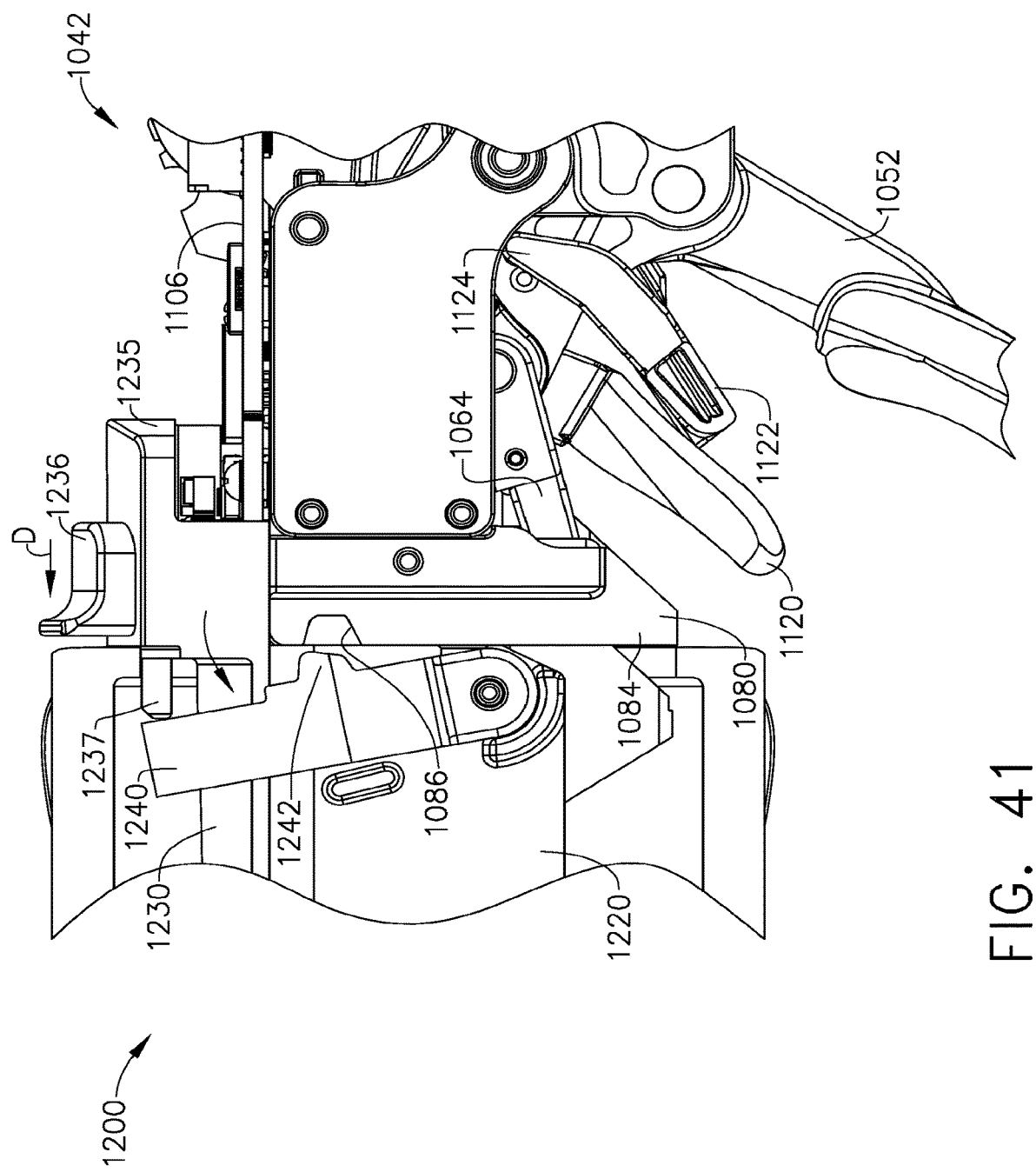
FIG. 41 is another side view of the interchangeable shaft assembly and handle of FIG. 40 with the lock yoke in the disengaged or unlocked position.
Figure 49:
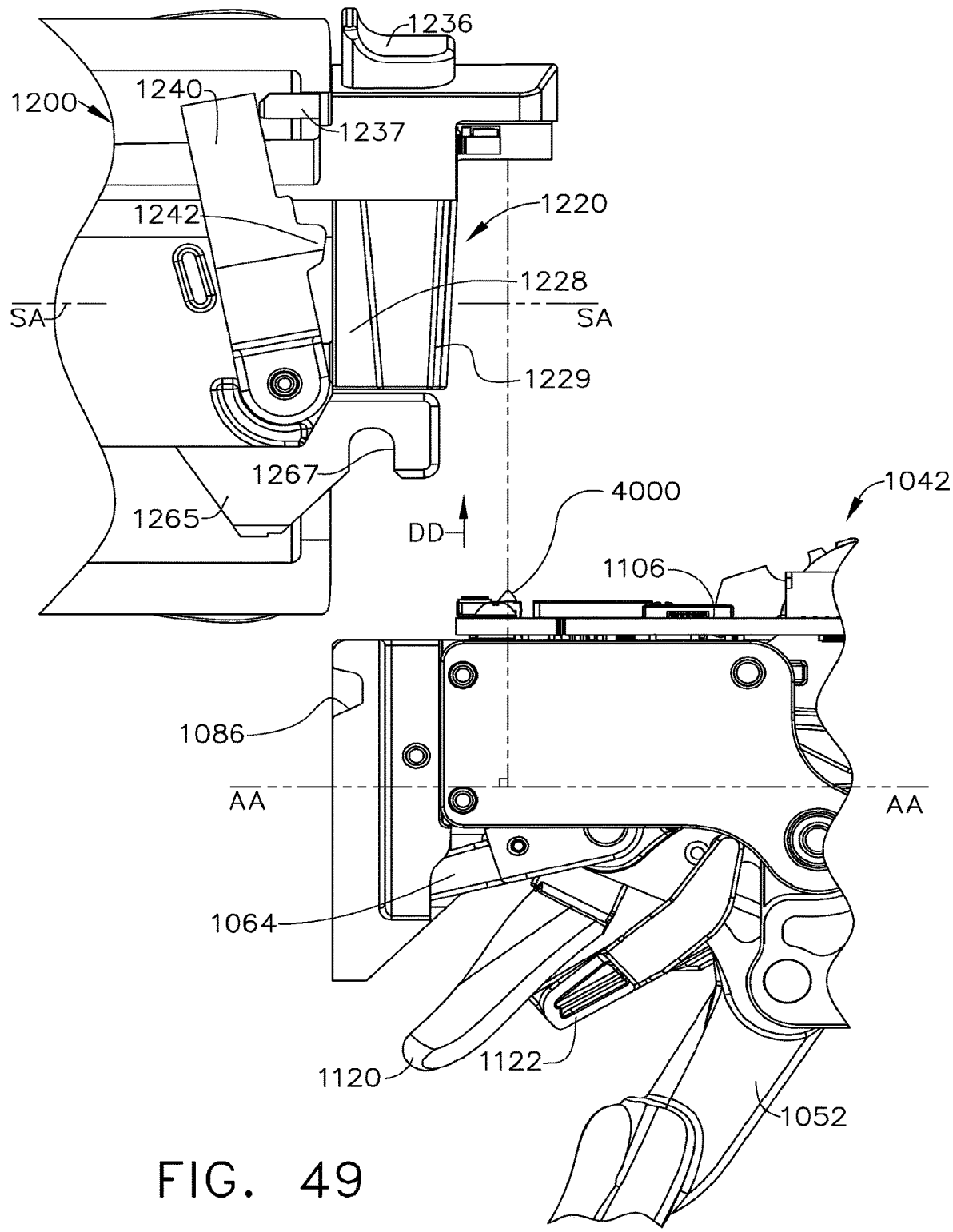
FIG. 49 is another side elevational view of a portion of an interchangeable shaft assembly aligned with a portion of handle prior to commencing the coupling process.

To detach the interchangeable shaft assembly 1220 from the frame 1080, the clinician pushes the latch button 1236 in the distal direction "D" to cause the lock yoke 1240 to pivot as shown in FIG. 41. Such pivotal movement of the lock yoke 1240 causes the lock lugs 1242 thereon to move out of retaining engagement with the lock grooves 1086. The clinician may then move the shaft attachment module 1220 away from the handle in a disconnecting direction "DD" as shown in FIG. 49.

Those of ordinary skill in the art will understand that the shaft attachment module 1220 may also be held stationary and the handle 1042 moved along the installation axis IA-IA that is substantially transverse to the shaft axis SA-SA to bring the lugs 1229 on the connector portion 1228 into seating engagement with the dovetail slots 1088. It will be further understood that the shaft attachment module 1220 and the handle 1042 may be simultaneously moved toward each other along the installation axis IA-IA that is substantially transverse to the shaft axis SA-SA and the actuation axis AA-AA.

As used herein, the phrase, "substantially transverse to the actuation axis and/or to the shaft axis" refers to a direction that is nearly perpendicular to the actuation axis and/or shaft axis. It will be appreciated, however, that directions that deviate some from perpendicular to the actuation axis and/or the shaft axis are also substantially transverse to those axes.

Figure 52:
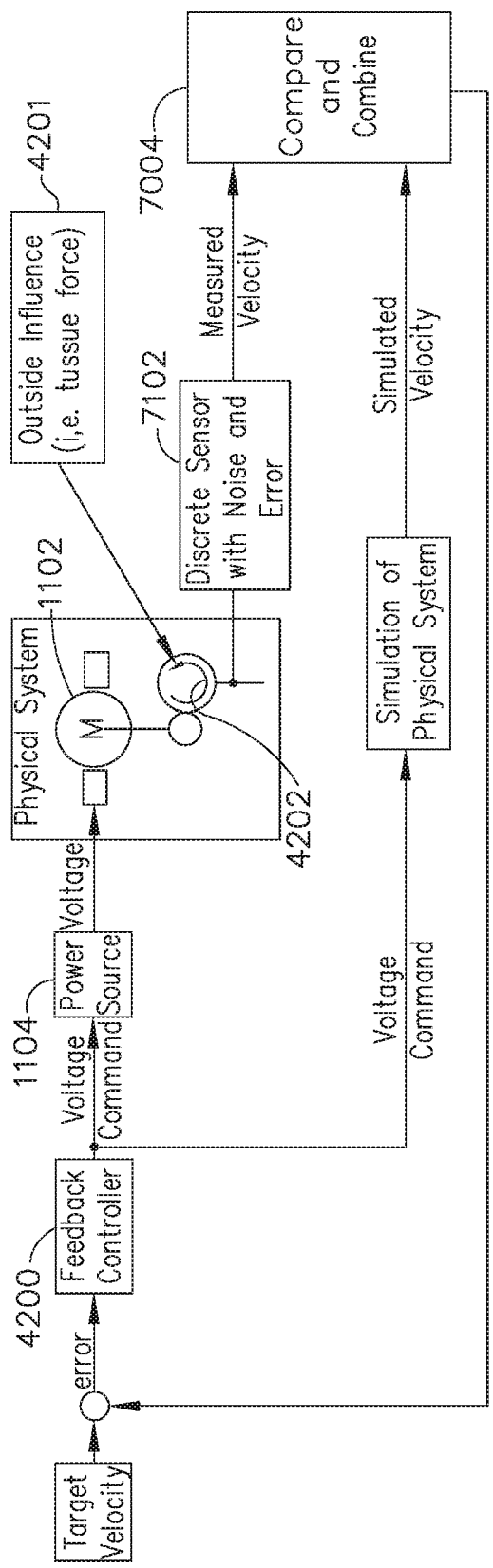
FIG. 52 is a schematic illustrating a system for controlling the speed of a motor and/or the speed of a driveable member of a surgical instrument disclosed herein.
Figure 53:
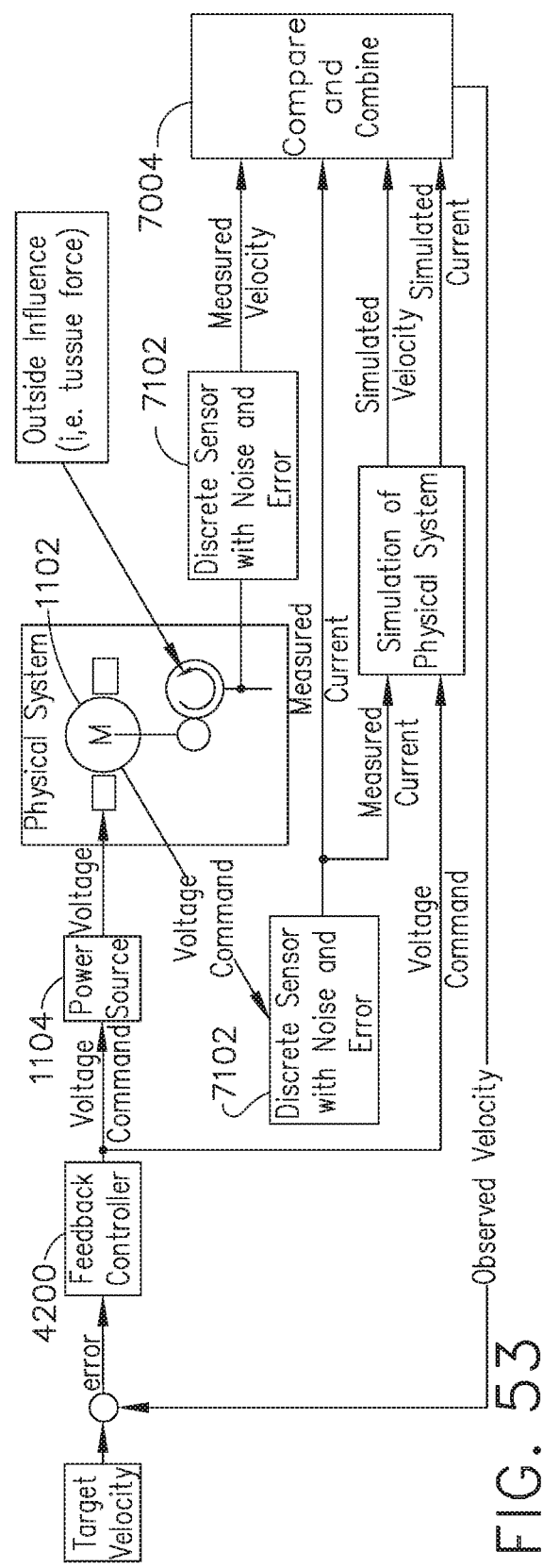
FIG. 53 is a schematic illustrating another system for controlling the speed of a motor and/or the speed of a driveable member of a surgical instrument disclosed herein.

Using the physical properties of the instruments disclosed herein, turning now to FIGS. 52 and 53, a controller, such as microcontroller 7004, for example, can be designed to simulate the response of the actual system of the instrument in the software of the controller. The simulated response is compared to a (noisy and discrete) measured response of the actual system to obtain an "observed" response, which is used for actual feedback decisions. The observed response is a favorable, tuned, value that balances the smooth, continuous nature of the simulated response with the measured response, which can detect outside influences on the system. With regard to FIGS. 52 and 53, a firing element, or cutting element, in the end effector 1300 of the shaft assembly 1200 can be moved at or near a target velocity, or speed. The systems disclosed in FIGS. 52 and 53 can be utilized to move the cutting element at a target velocity. The systems can include a feedback controller 4200, which can be one of any feedback controllers, including, but not limited to a PID, a State Feedback, LQR, and/or an Adaptive controller, for example. The systems can further include a power source. The power source can convert the signal from the feedback controller 4200 into a physical input to the system, in this case voltage, for example. Other examples include, but are not limited to, pulse width modulated (PWM) voltage, frequency modulated voltage, current, torque, and/or force, for example.

With continued reference to FIGS. 52 and 53, the physical system referred to therein is the actual drive system of the instrument configured to drive the firing member, or cutting member. One example is a brushed DC motor with gearbox and mechanical links to an articulation and/or knife system. Another example is the motor 1102 disclosed herein that operates the firing member 10060 and the articulation driver 10030, for example, of an interchangeable shaft assembly. The outside influence 4201 referred to in FIGS. 52 and 53 is the unmeasured, unpredictable influence of things like tissue, surrounding bodies and friction on the physical system, for example. Such outside influence can be referred to as drag and can be represented by a motor 4202 which acts in opposition to the motor 1102, for example. In various circumstances, outside influence, such as drag, is the primary cause for deviation of the simulation of the physical system from the actual physical system. The systems depicted in FIGS. 52 and 53 and further discussed below can address the differences between the predicted behavior of the firing member, or cutting member, and the actual behavior of the firing member, or cutting member.

With continued reference to FIGS. 52 and 53, the discrete sensor referred to therein measures physical parameters of the actual physical system. One embodiment of such a discrete sensor can include the absolute positioning sensor 7102 and system described herein. As the output of such a discrete sensor can be a digital signal (or connected to a digital data acquisition system) its output may have finite resolution and sampling frequency. The output of the discrete sensor can be supplied to a microcontroller, such as microcontroller 7004, for example. In various circumstances, the microcontroller can combine the simulated, or estimated, response with the measured response. In certain circumstances, it may be useful to use enough measured response to ensure that the outside influence is accounted for without making the observed response unusably noisy. Examples for algorithms that do so include a weighted average and/or a theoretical control loop that drives the simulated response towards the measured response, for example. Ultimately, further to the above, the simulation of the physical system takes in account of properties like mass, inertial, viscous friction, and/or inductance resistance, for example, to predict what the states and outputs of the physical system will be by knowing the input. FIG. 53 shows an addition of evaluating and measuring the current supplied to operate the actual system, which is yet another parameter that can be evaluated for controlling the speed of the cutting member, or firing member, of the shaft assembly 1200, for example. By measuring current in addition to or in lieu of measuring the voltage, in certain circumstances, the physical system can be made more accurate. Nonetheless, the ideas disclosed herein can be extended to the measurement of other state parameters of other physical systems.

Figure 54A:
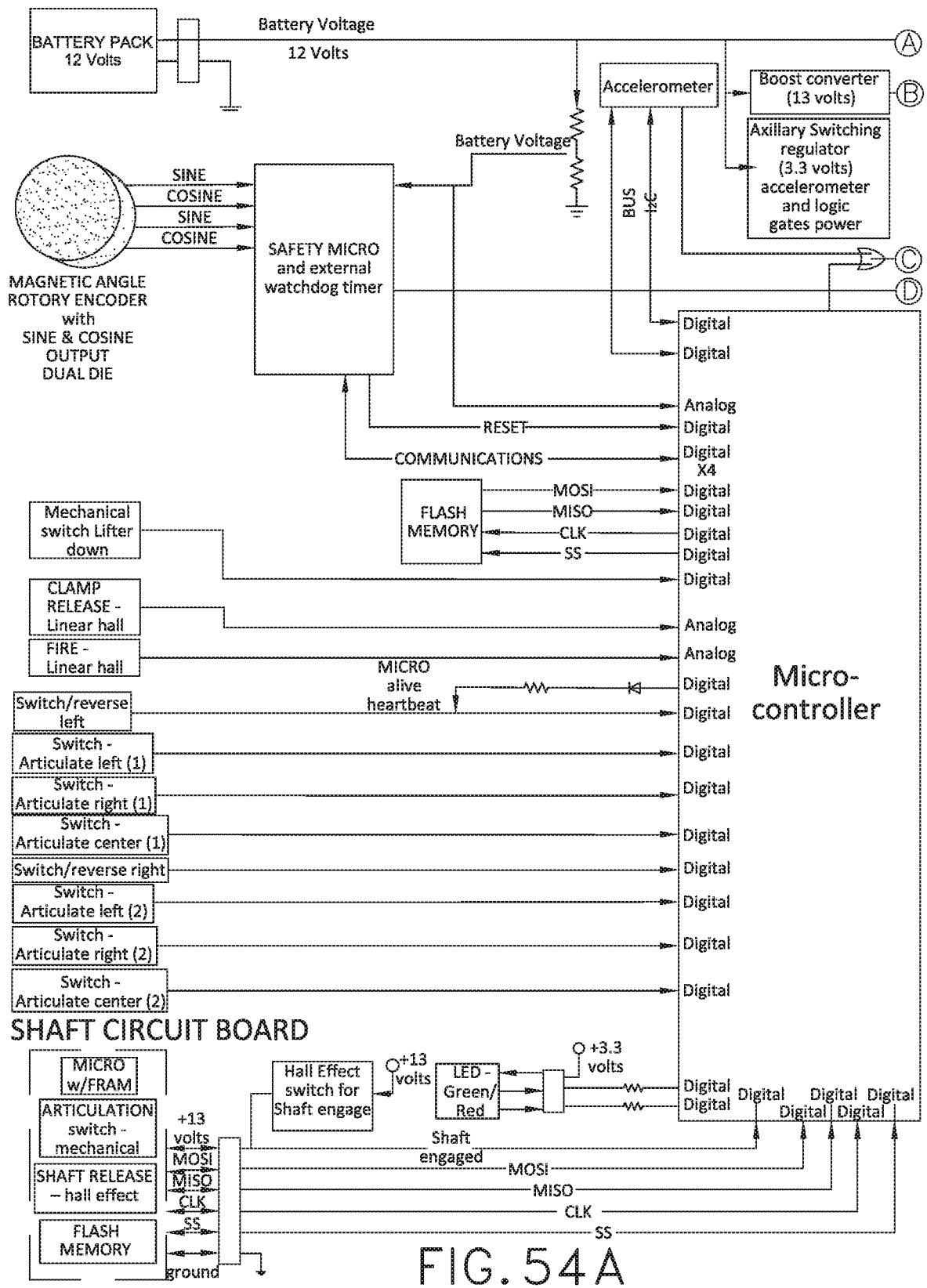
FIG. 54A is a first portion of a schematic illustrating a control system for controlling various operations of the various surgical instruments described herein according to various embodiments of the present disclosure.
Figure 54B:
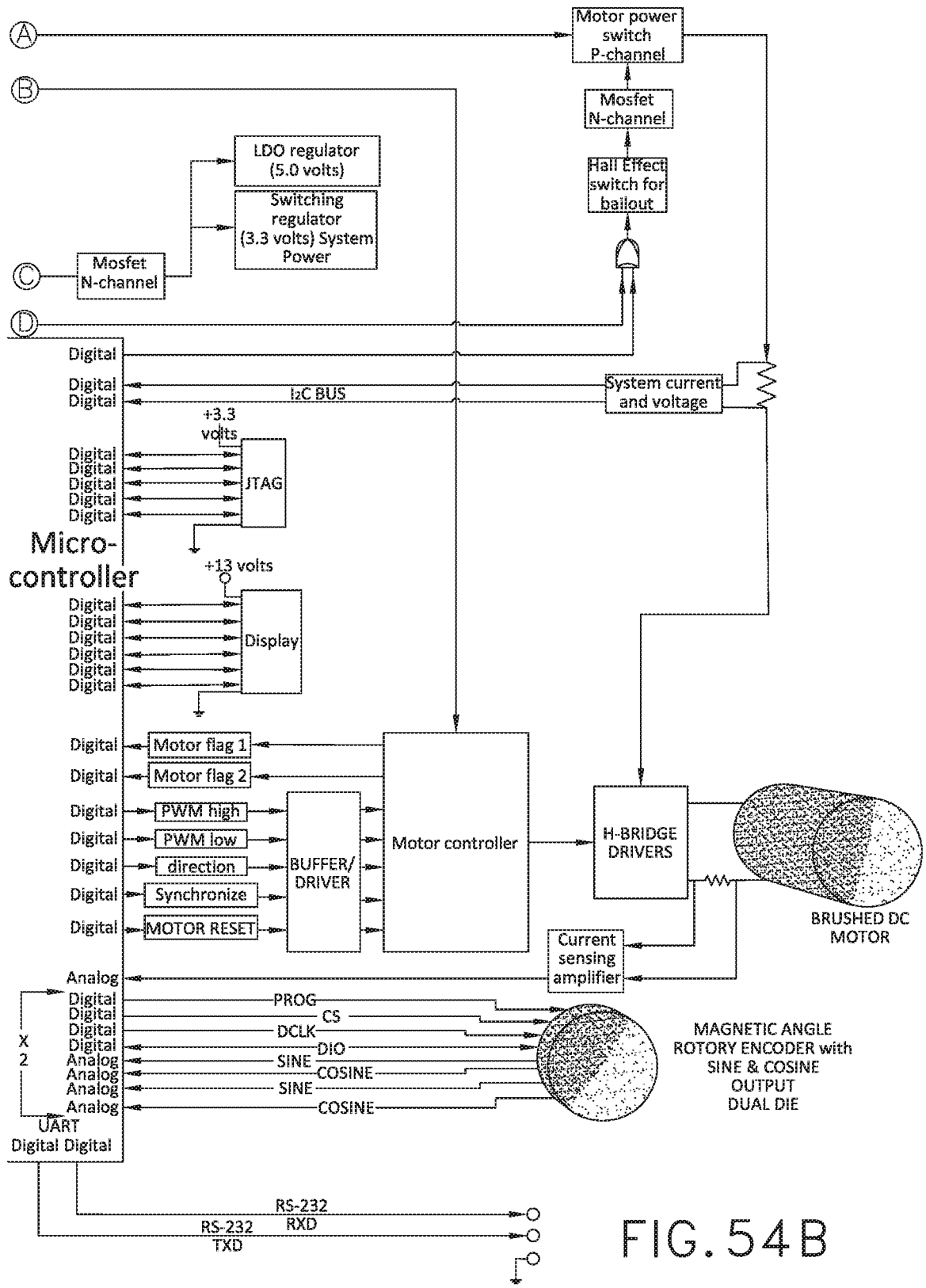
FIG. 54B is a second portion of a schematic that together with the first portion of FIG. 54A illustrate a control system for controlling various operations of the various surgical instruments described herein according to various embodiments of the present disclosure.
Figure 57A:
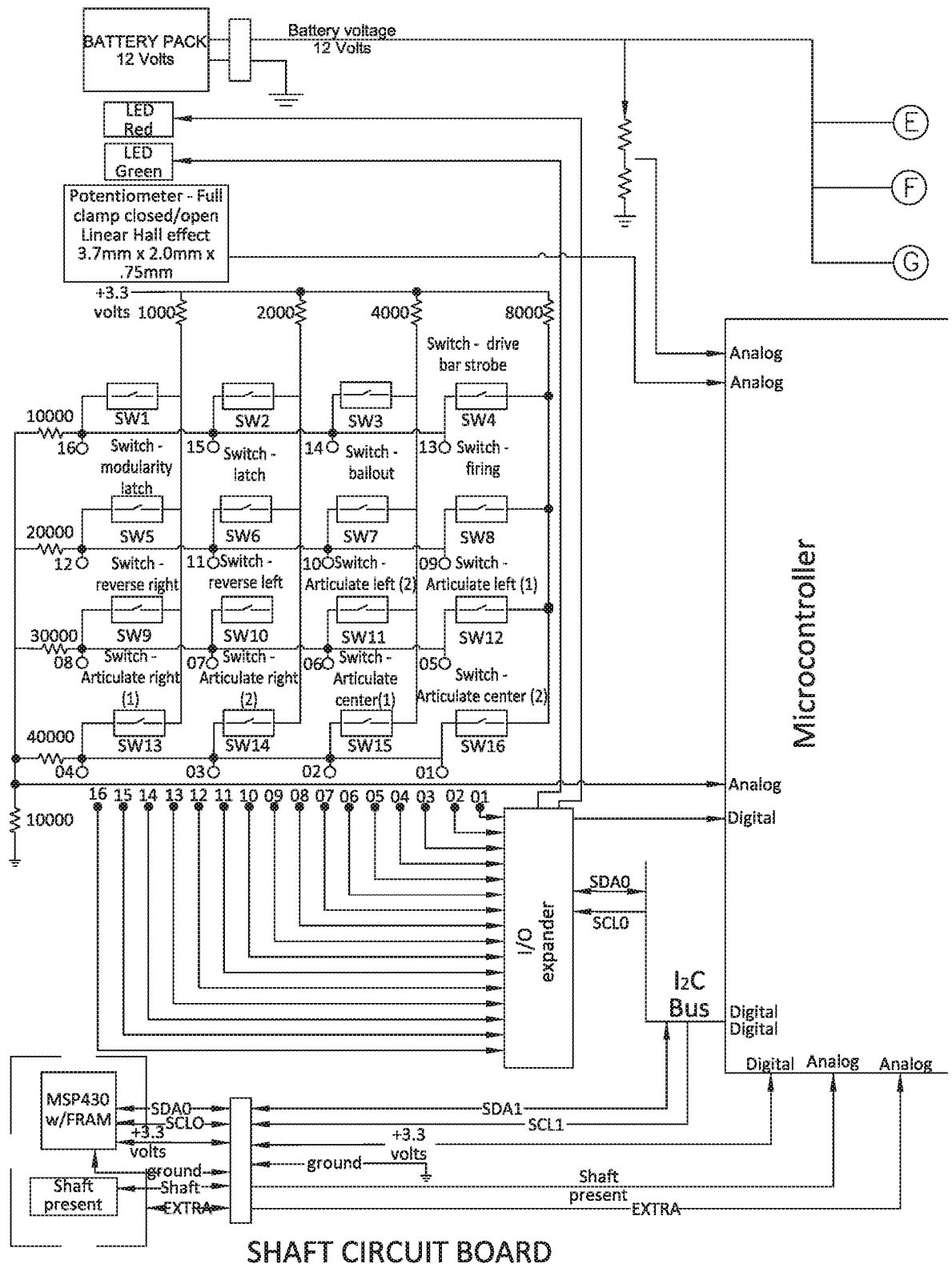
FIG. 57A is a first portion of a schematic illustrating a control system for controlling various operations of the various surgical instruments described herein according to various embodiments of the present disclosure.
Figure 57B:
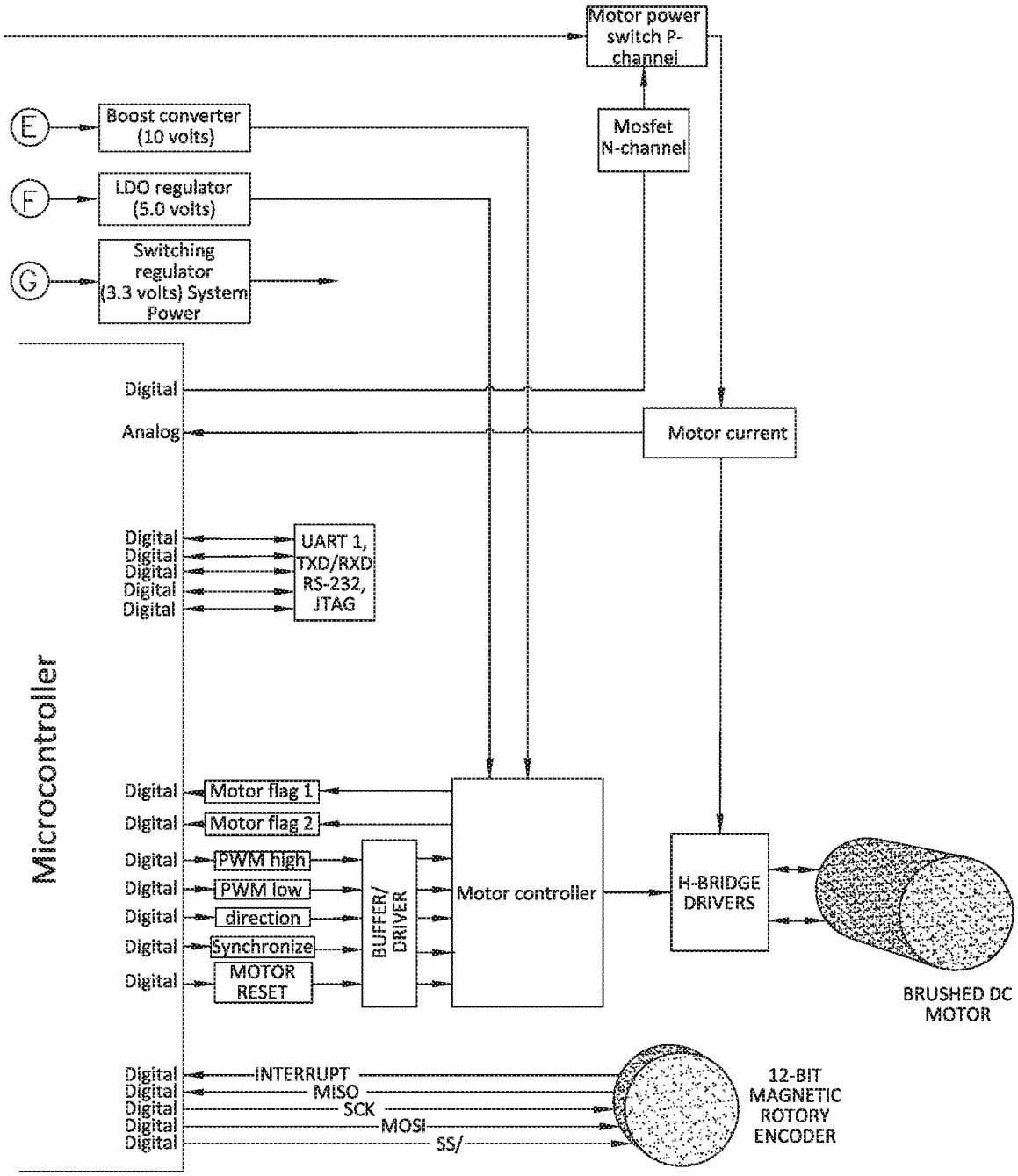
FIG. 57B is a second portion of a schematic that together with the first portion of FIG. 57A illustrate a control system for controlling various operations of the various surgical instruments described herein according to various embodiments of the present disclosure.

A control system, such as the control system illustrated in FIG. 54A-54B and/or FIG. 57A-57B, for example, can be utilized to control any of the surgical instruments disclosed herein. In various circumstances, the control system can comprise a microcontroller, such as microcontroller 7004, for example, which can be configured to operate the various systems of a surgical instrument. Further to the above, the control system can comprise assembly detection means for detecting whether a shaft assembly, such as shaft assembly 1200, for example, has been assembled, or at least partially assembled, to the handle 1042. Such assembly detection means can comprise the Hall effect sensor 4002 described above, for example, and means for maintaining the handle 1042 in a powered-down condition if the shaft assembly is not assembled to the handle 1042, and means for maintaining the handle 1042 in a powered-up condition if the shaft assembly is assembled to the handle 1042, further to the above. As outlined above, the microcontroller 7004, for example, can include such means. The control system can further comprise power communication means for communicating electrical power to and/or from the shaft assembly and/or signal communication means for communicating communication signals to and/or from the shaft assembly. Such power communication means and signal communication means can comprise the electrical connector 4000, a corresponding electrical connector on the shaft assembly, and/or the microcontroller 7004, for example.

Figure 58:
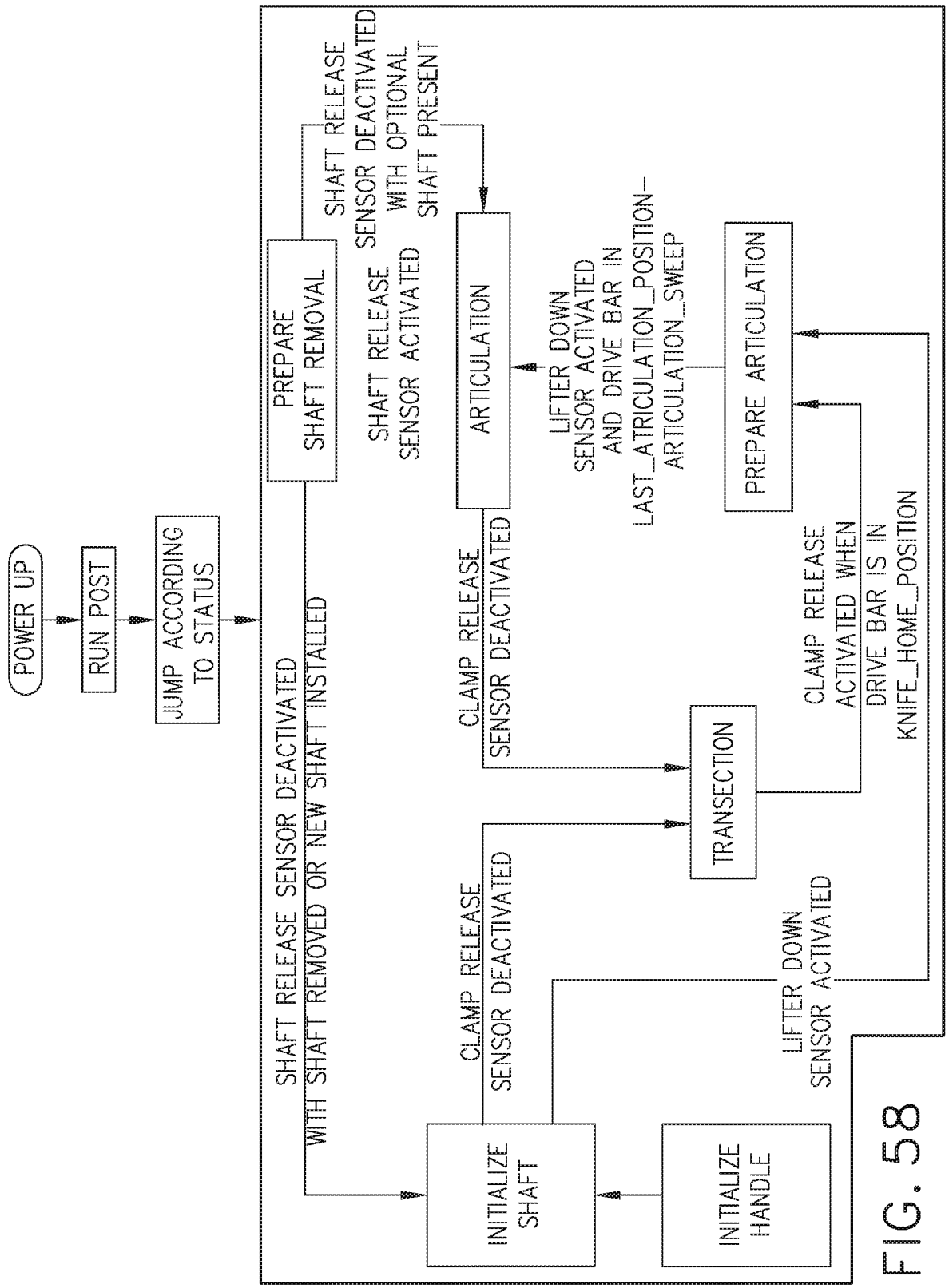
FIG. 58 is a schematic illustrating a control system for controlling various operations of the various surgical instruments described herein according to various embodiments of the present disclosure.
Figure 59:
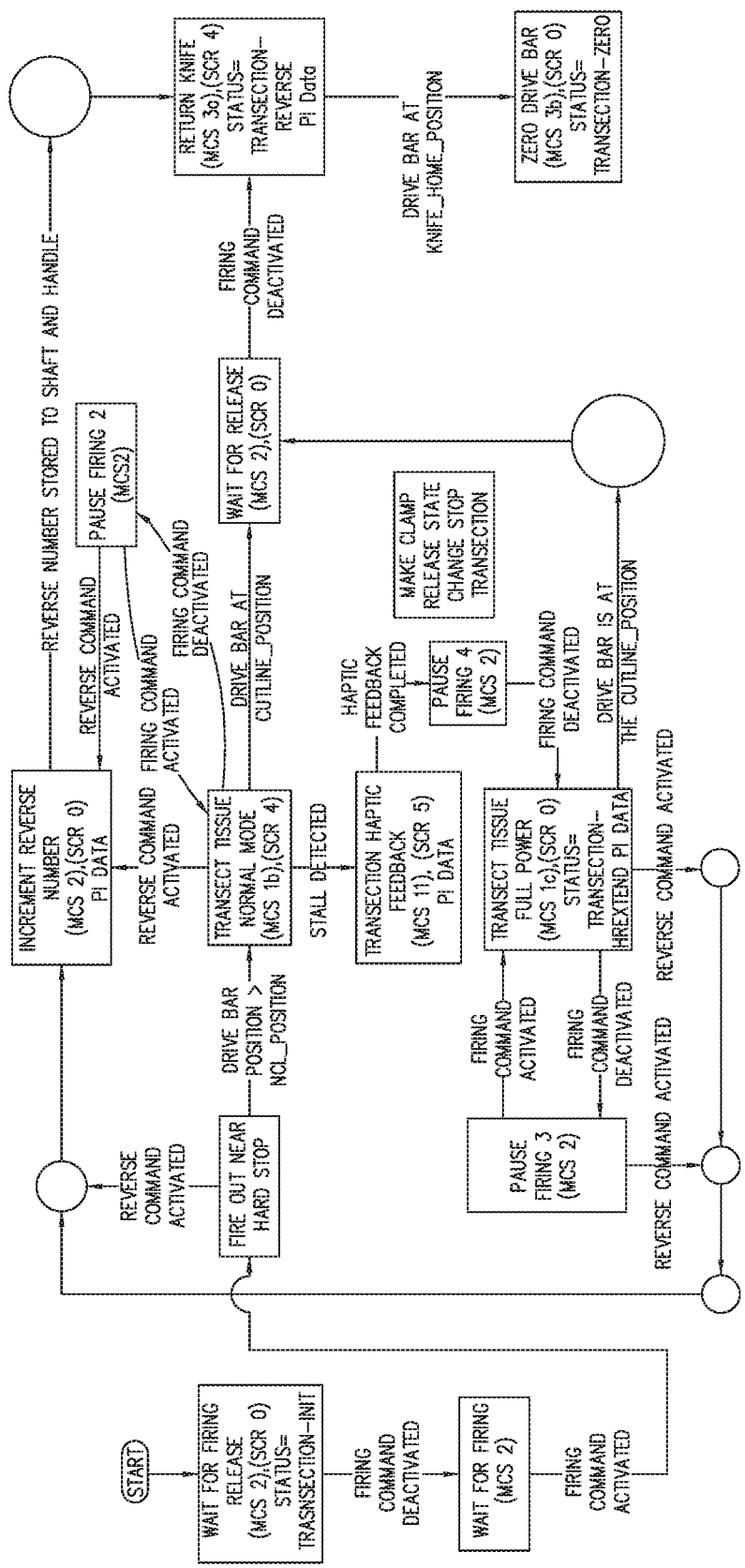
FIG. 59 is a schematic illustrating various sub-operations of the Transection Operation of FIG. 58 according to various embodiments of the present disclosure.
Figure 60:
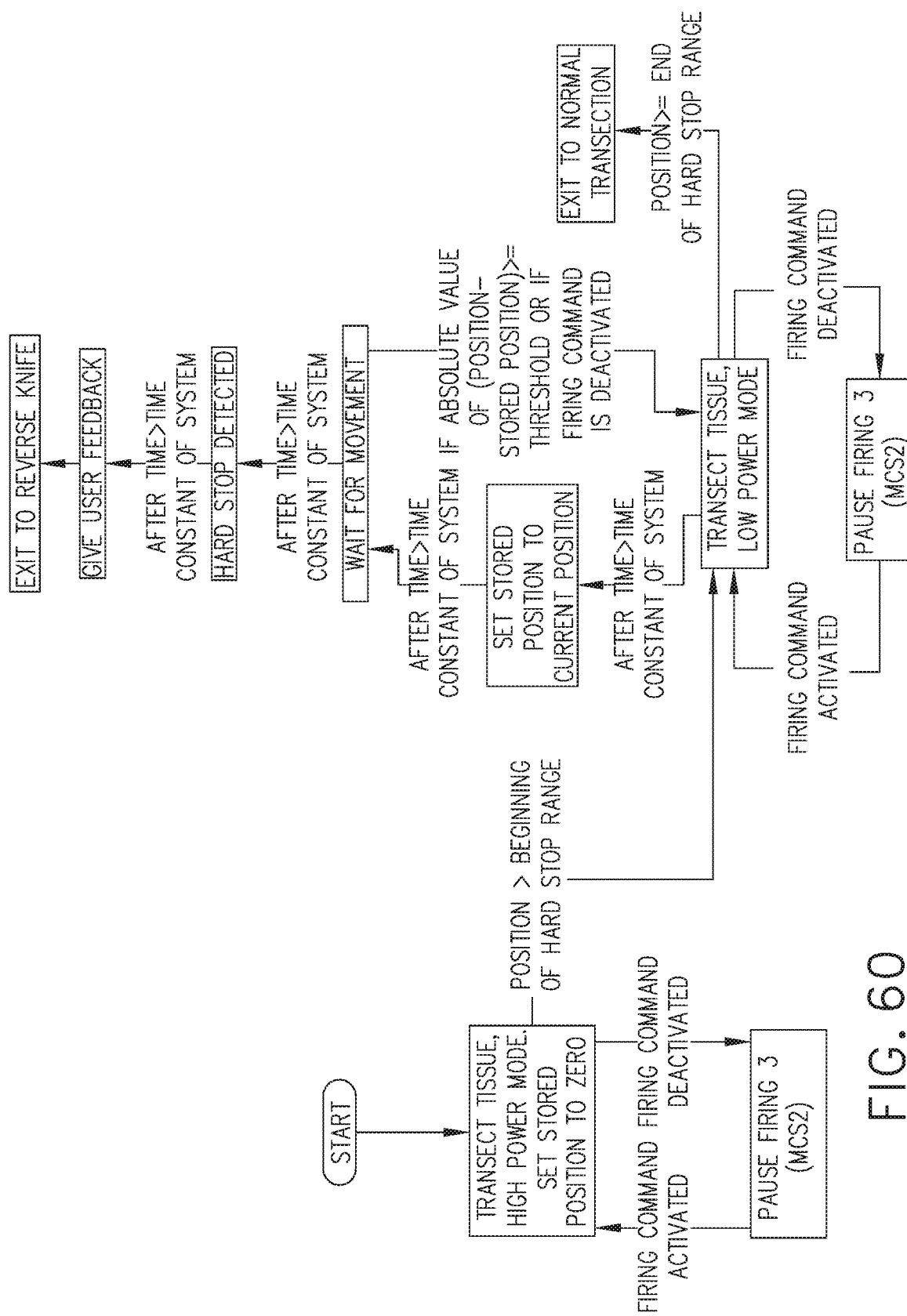
FIG. 60 is a schematic illustrating various sub-operations of the Fire Out Near Hard Stop Operation of FIG. 59 according to various embodiments of the present disclosure.

With further reference to FIGS. 54A-54B and 57A-57B, the control system can further comprise at least one closure trigger switch and at least one closure trigger circuit which can be configured to communicate to the microcontroller 7004, and/or be interpreted by the microcontroller 7004, that the closure trigger 1052, discussed above, has been closed. Various switches can include a potentiometer and/or a Hall effect sensor, for example. The control system can further comprise unclosed operating means for operating the surgical instrument in an unclosed operating condition when the closure trigger 1052 is in an unclosed position and closed operating means for operating the surgical instrument in a closed operating condition when the closure trigger 1052 is in a closed position. The control system can comprise a power supply, such as battery 1104, for example, and means for distributing power from the power supply throughout the control system. The control system can comprise a motor, such as motor 1102, for example, a motor power switch, such as firing trigger 1120, for example, and motor operating means for operating the motor 1102 in a desired way, as described elsewhere herein. Such motor operating means, in certain circumstances, can be configured to control the motor 1102 utilizing pulse width modulated (PWM) voltage control, for example. Moreover, PWM voltage control can be utilized to control the speed of the firing members 1272 and 1280, for example. In the unclosed operating condition of the surgical instrument, in some circumstances, the battery 1104 may be disconnected from the motor 1102 while, in certain circumstances, a motor controller can be configured to prevent the operation of the motor 1102 even though electrical power may be supplied to the motor 1102 until the microcontroller 7004 detects the closure of the closure trigger 1052. In such circumstances, the microcontroller 7004 can then operate the surgical instrument in its closed operating state. In the closed operating state, power can be supplied to the motor 1102 and the motor controller can be configured to operate the motor 1102 in response to the operation of the firing trigger 1120. FIGS. 58-60 illustrate various operations for operating the motor 1102 and the firing members 1272 and 1280, for example.

With further reference to FIGS. 54A-54B and 57A-57B, the control system can comprise a 12-bit magnetic rotary encoder, for example, and can be configured to monitor the position of the firing members 1272 and 1280. In various circumstances, the control system can include the absolute positioning sensor 7102 and the sensing system described above to monitor the position of the firing members 1272 and 1280. The control system can also comprise manual drive means for manually moving the firing members 1272 and 1280 and/or means for operating another system of the surgical instrument in light of the operation of the manual drive means. For instance, the manual drive means may comprise a manually-actuatable bailout assembly 1130, for example, which is described above. Also, for instance, the operation of the manual drive means may electrically deactivate the motor 1102. In some circumstances, the operation of the manual drive means can disconnect the battery 1104 from the motor 1102. In certain circumstances, the operation of the manual drive means can be detected by a motor controller which can be configured to prevent the operation of the motor 1102 even though electrical power may be supplied to the motor 1102. In various circumstances, the motor controller can comprise the microcontroller 7004, for example.

With further reference to FIGS. 54A-54B and 57A-57B, the control system can further comprise communication means for communicating with the operator of the instrument. In various circumstances, the communication means can comprise one or more light emitting diode (LED) lights, for example, on the handle 1042, for example, which can be configured to communicate to the operator of the surgical instrument that the surgical instrument is in a particular operating condition, for example. In at least one circumstance, the handle 1042 can include a green LED light, for example, which, when lit, can indicate that the surgical instrument is in an assembled, closed, and powered-up condition, for example. In such circumstances, the lit green LED light can indicate that the surgical instrument is ready for use. The handle 1042 can include a red LED light, for example, which, when lit, can indicate that the surgical instrument is in either an unassembled, unclosed, and/or powered-down condition. In such circumstances, the lit red LED light can indicate that the surgical instrument is not ready for use. Further to the above, the LED lights can be in electrical communication with output channels of the microcontroller 7004 wherein the microcontroller 7004 can be configured to determine and/or set the operating condition of the surgical instrument and communicate that condition through the LED lights, for example. In some circumstances, the communication means can include a display screen on the handle 1042, for example, which can be configured to communicate information to the operator of the surgical instrument. Further to the above, the microcontroller 7004 can be in electrical communication with the display screen to communicate the operating condition of the surgical instrument, for example.

Figure 55:
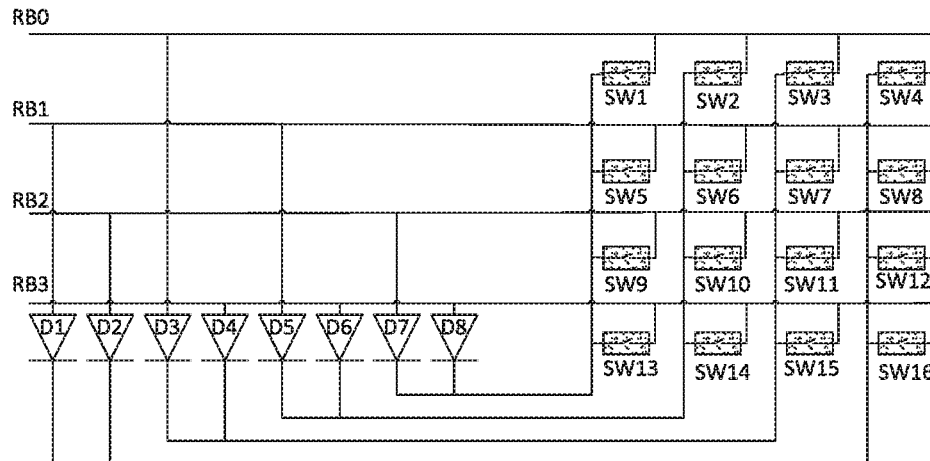
FIG. 55 is a schematic illustrating a switching circuit for a control system according to various embodiments of the present disclosure.
Figure 56:
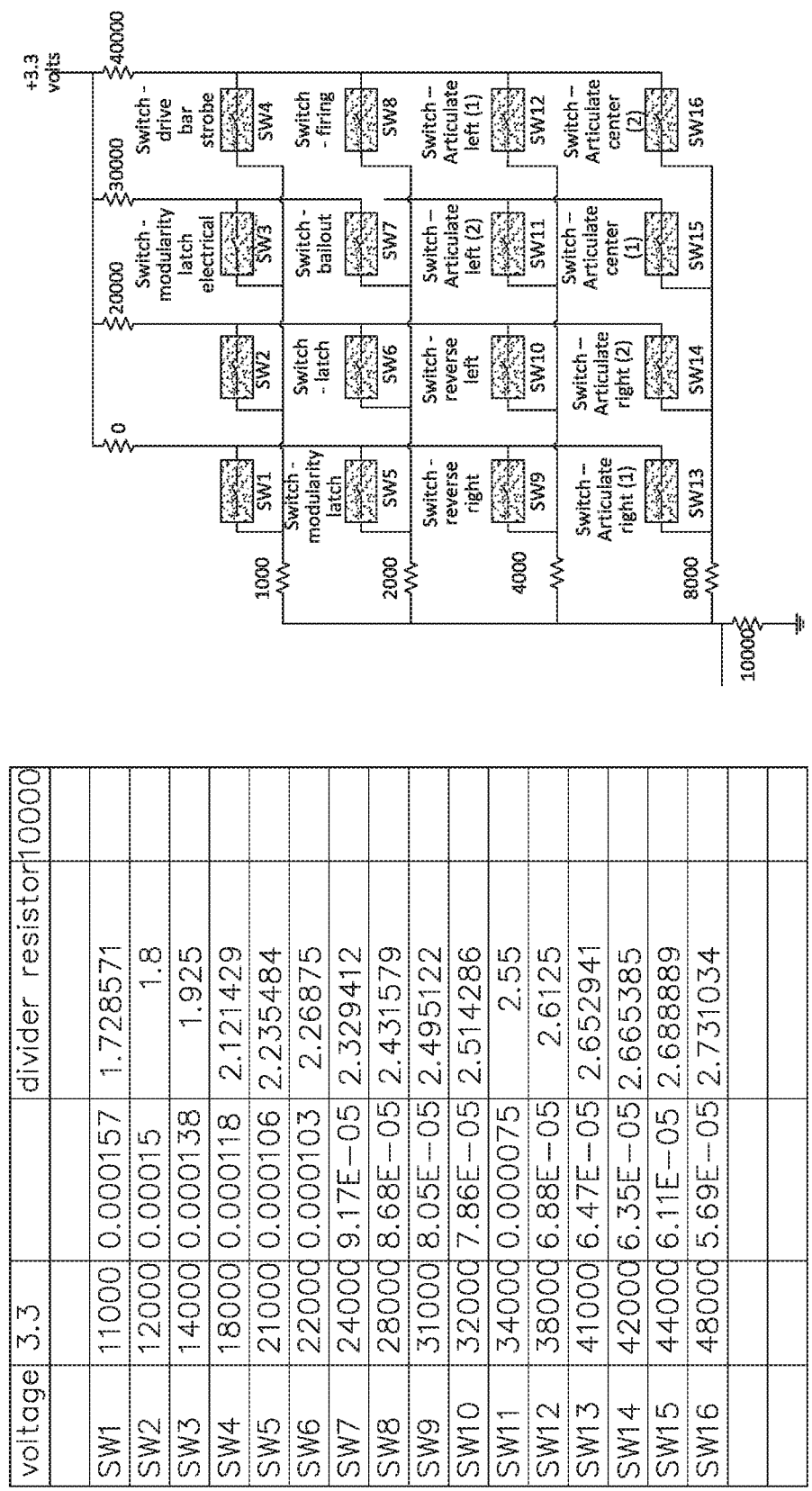
FIG. 56 is a schematic illustrating a switching circuit for a control system according to various embodiments of the present disclosure.

With further reference to 54A-54B and 57A-57B, and with additional reference to FIGS. 55 and 56, the control system can comprise a plurality of switches in electrical communication with the microcontroller 7004, for example. The switches can include the switches discussed above and/or in connection with any system and/or subsystem of the surgical instrument described herein. The switches can comprise a switch array which can be included in a switch circuit in electrical communication with the microcontroller 7004, for example. In certain circumstances, the switch circuit can include a 16-bit I/O encoder, for example, which can communicate with the microcontroller 7004. Moreover, the switch circuit can comprise a bus which is in electrical communication with the microcontroller 7004 and one or more contacts in the electrical connector 4000. Ultimately, then, the switch circuit and the switch array can span the handle 1042 and the shaft assembly 1200, for example. In various circumstances, the microcontroller 7004 can be configured to identify the shaft assembly attached to the handle 1042 and adjust the length of the firing stroke applied to the firing members 1272 and 1280, for example. The entire disclosure of U.S. Pat. No. 9,629,629, entitled CONTROL SYSTEMS FOR SURGICAL INSTRUMENTS, which issued on Apr. 25, 2017, is incorporated by reference herein.

Figure 61:
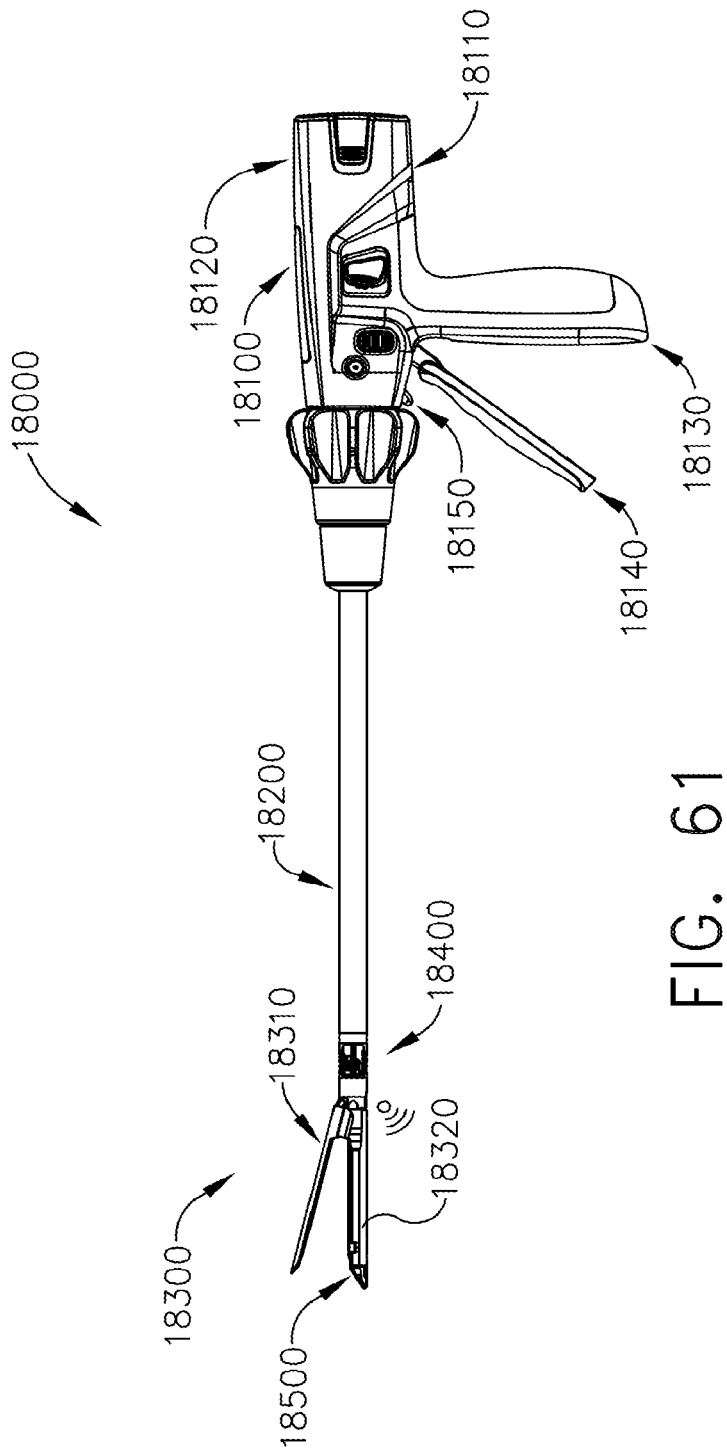
FIG. 61 is an elevation view of a surgical instrument comprising a handle, a shaft, and an articulatable end effector in accordance with at least one embodiment.

A surgical instrument 18000 is illustrated in FIG. 61. The surgical instrument 18000 is similar to the surgical instrument 400 in many respects. The surgical instrument 18000 comprises a handle 18100, a shaft 18200 extending from the handle 18100, and an end effector 18300 extending from the shaft 18200. The end effector 18300 comprises a first jaw 18310 and a second jaw 18320, where the first jaw 18310 is movable between an open, clamped position and a closed, clamped position to clamp tissue between the first jaw 18310 and the second jaw 18320. Moreover, the end effector 18300 is rotatably attached to the shaft 18200 about an articulation joint 18400. The handle 18100 comprises a frame 18110 and a housing 18120. The handle 18100 also comprises a grip 18130, a closing actuator 18140 operable to actuate an end effector closure system, and a firing actuator 18150 operable to actuate a staple firing system. The handle 18100 also comprises an articulation actuator operable to actuate an end effector articulation system. The second jaw 18320 comprises a replaceable staple cartridge 18500 including staples removably stored therein and the first jaw 18310 comprises an anvil configured to deform the staples. The surgical instrument 18000 also comprises an electric motor which is configured to drive the staple firing system of the surgical instrument 18000. Various staple firing systems are disclosed in U.S. Pat. No. 7,000,818, entitled SURGICAL STAPLING INSTRUMENT HAVING SEPARATE DISTINCT CLOSING AND FIRING SYSTEMS, which issued on Feb. 21, 2006, and is herein incorporated by reference.

Figure 62:
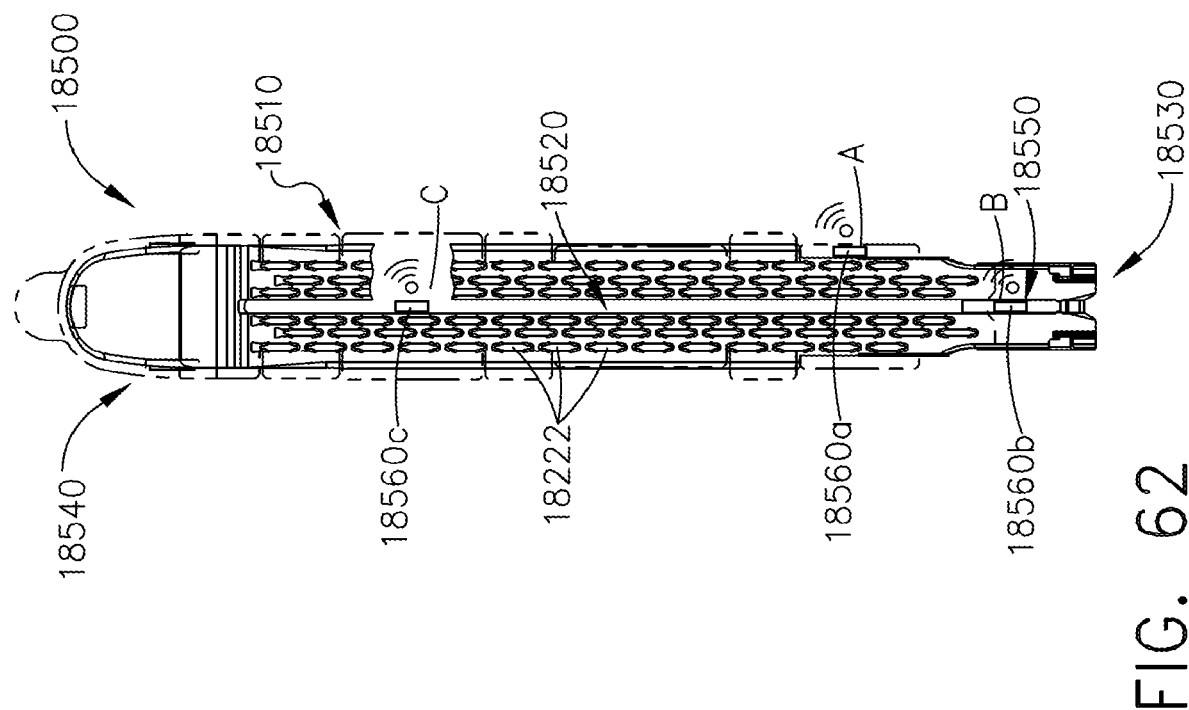
FIG. 62 is a top view of a staple cartridge in accordance with at least one embodiment.
Figure 69:
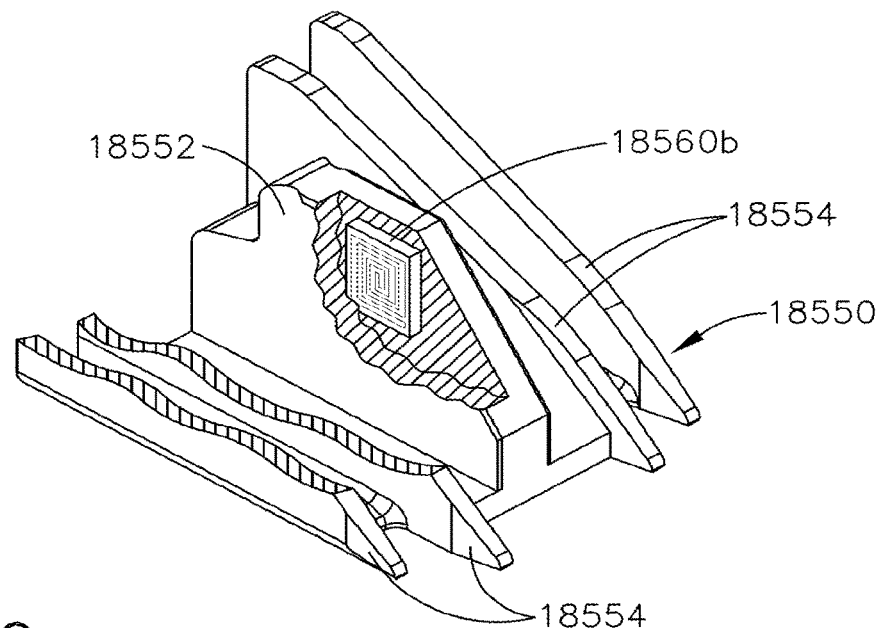
FIG. 69 is a cross-sectional view of a sled of the staple cartridge of FIG. 62.
Figure 68:
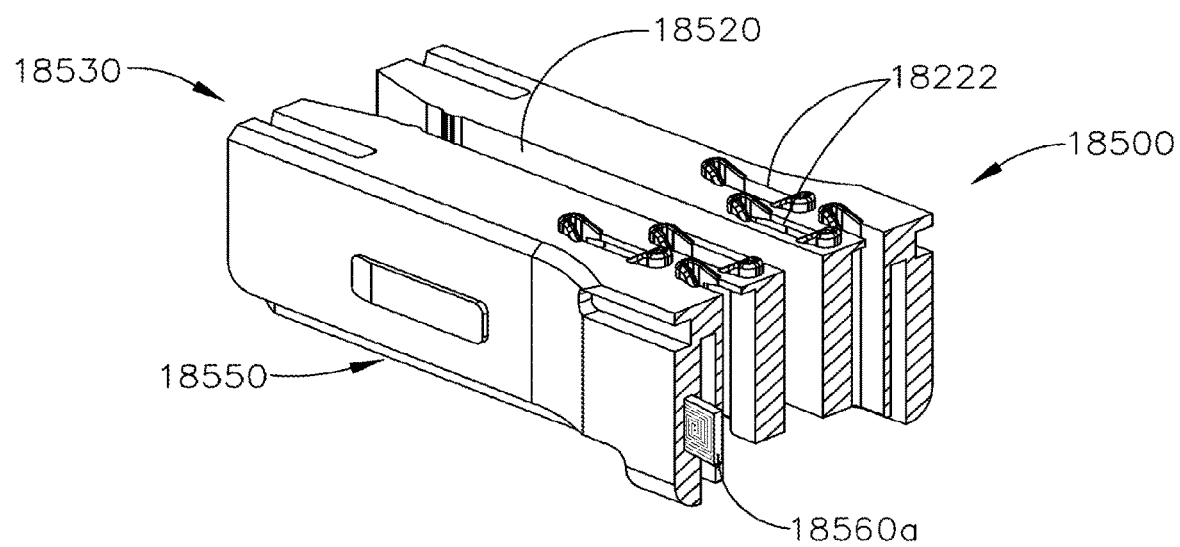
FIG. 68 is a partial cross-sectional view of a cartridge body of the staple cartridge of FIG. 62.
Figure 70:
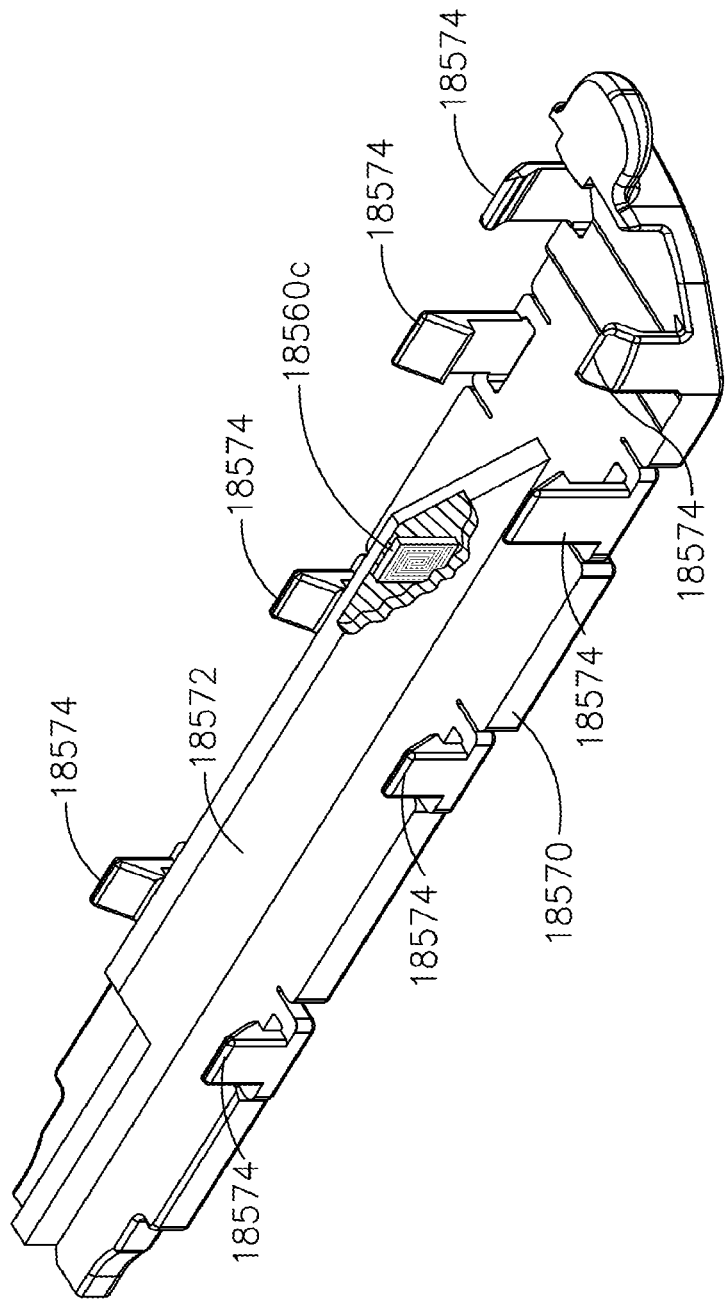
FIG. 70 is a perspective view of a removable cover of the staple cartridge of FIG. 62.

Referring now to FIG. 62, a staple cartridge 18500 comprises a cartridge body 18510 comprising a longitudinal slot 18520, a proximal end 18530, and a distal end 18540. The staple cartridge 18500 further comprises a plurality of staple cavities 18222 defined the cartridge body 18510 and staples removably stored in the staple cavities. The staple cartridge 18500 further comprises a sled 18550 (FIG. 69) movable distally by the staple firing system during a staple firing stroke to drive the staples upwardly out of the staple cavities 18222 and into the tissue of a patient. The staple cartridge 18500 further comprises a removable staple cartridge retainer, or cover, 18570 (FIG. 70) which extends over the staple cavities and protects the staples. Referring to FIG. 70, the cover comprises an elongate body, flexible latch arms 18574 extending from the body that releasably grip the cartridge body 18510, and a longitudinal fin 18572 extending into the longitudinal slot 18520. In many instances, the staple cartridge cover 18570 acts as a protective barrier between the clinician and the staples of the staple cartridge 18500. In various instances, the staple cartridge cover 18570 allows a clinician to place their thumb, for instance, on top of the staple cartridge 18500 to seat the staple cartridge 18500 in the second jaw 18320 without contacting the staples. Once the staple cartridge 18500 has been seated in the second jaw 18320, the cartridge cover 18570 is removed and the surgical instrument 18000 can then be inserted into a patient. If the cartridge cover 18570 is not removed after the staple cartridge 18500 has been installed, however, the cartridge cover 18570 will block the staples from properly contacting the anvil of the first jaw 18310.

The surgical instrument 18000 further comprises a controller including a microprocessor. The surgical instrument 18000 also further comprises an RFID system in communication with the controller. The RFID system comprises one or more RFID readers and one or more RFID tags, as will be discussed in greater detail below. In various embodiments, an RFID system is configured to determine whether a staple cartridge is positioned in the surgical instrument and/or whether the staple cartridge is an appropriate staple cartridge for use with the surgical instrument. Such an RFID system can also determine whether the staple cartridge includes the correct components intended for that staple cartridge. If the controller determines that the staple cartridge is appropriate and the components within the staple cartridge are correct, the surgical instrument 18000 can be used as intended. If the controller determines that the staple cartridge is not appropriate or that one or more of the components within the staple cartridge are incorrect, the controller can limit the operation of the surgical instrument in some way. In such instances, for example, the controller can permit the end effector to be opened and closed and/or permit the end effector to be articulated, but prevent the staple firing stroke from being performed. An RFID system can also be used to determine whether the staple cartridge has been properly positioned within a staple cartridge support. For example, the RFID system can indicate whether the proximal end of the staple cartridge and/or the distal end of the staple cartridge is properly seated within a staple cartridge channel and, if one of the ends of the staple cartridge has not been fully seated, the controller can prevent the staple firing stroke from being performed. Moreover, an RFID system can indicate whether the staple cartridge positioned in the surgical instrument is an unspent staple cartridge or if the staple cartridge has already been used, or otherwise spent. If the controller determines that the staple cartridge has been spent, the controller prevents the staple firing stroke from being performed until the spent staple cartridge has been replaced with an unspent staple cartridge. An RFID system can also be capable of tracking the motion a movable component of the staple cartridge, which will be discussed in greater detail below.

Radio-frequency identification (RFID) is used in a variety of industries to track and identify objects. RFID relies on radio waves to transfer digitally-stored information from a RFID tag to a RFID reader or receiver configured to receive the information. RFID technology uses RFID tags, sometimes referred to as chips, which contain electronically-stored information, and RFID readers, which serve to identify and communicate with the RFID tags. There are two different types of RFID systems—active RFID systems and passive RFID systems. Active RFID systems include RFID tags that comprise an on-board power source to broadcast their signals. Active RFID tags can include a battery within the RFID tag which allows the active RFID tag to function independently from the RFID reader. As such, RFID tags in an active RFID system do not need to wait to receive a signal from a RFID reader before sending out information. Instead, the active RFID tags are free to continuously send out a signal, or beacon. Many commercially available active RFID systems often operate at one of two main frequency ranges—433 MHz and 915 MHz, but any suitable frequency range can be used. Typically, a RFID tag must be within a specific distance or frequency range in order to be identified by its corresponding RFID reader.

Passive RFID systems include RFID tags which do not comprise an on-board power source but instead receive the energy needed to operate from an RFID reader. Contrary to active RFID tags, RFID tags in a passive RFID system do not actively send out a signal before receiving a prompt. Instead, passive RFID tags wait to receive information from a RFID reader before sending out a signal. Many commercially-available passive RFID systems often operate within three frequency ranges—Low Frequency ("LF"), High Frequency ("HF") & Near-Field Communication ("NFC"), and Ultra High Frequency ("UHF"). The LF bandwidth is 125-134 KHz and includes a longer wavelength with a short read range of approximately one to ten centimeters. The HF and NFC bandwidth is 13.56 MHz and includes a medium wavelength with a typical read range of one centimeter to one meter. The UHF bandwidth is 865-960 MHz and includes a short, high-energy wavelength of one meter which translates into a long read range. The above being said, any suitable frequency can be used.

A variety of RFID systems comprising differently-sized RFID tags exist. However, some are better suited for use in technology areas that require the tracking of very small objects. For example, Hitachi Chemical Co. Ltd. is a leading manufacturer in the RFID technology field. The Ultra Small size UHF RFID tag manufactured by Hitachi Chemical Co. Ltd. is typically no larger than 1.0 to 13 mm and enables communication between a RFID tag and a RFID reader at distances of several centimeters or more. Due to its compact nature, the Hitachi RFID tag is suitable for very small products which need to be identified. Each Hitachi RFID tag comprises an antenna, an IC chip connected to the antenna, and a sealing material that seals the IC chip and the antenna. Because the Hitachi RFID tag incorporates an antenna and an IC chip in a single unit, the Hitachi RFID tag is convenient enough to easily affix to any small object using an adhesive or tape, for example.

The Hitachi RFID tag comprises a square stainless steel plate and a metal antenna. The antenna comprises a LC resonant circuit or any other suitable circuit and is electrically connected to the plate. After the plate and the antenna are connected to one another, the antenna and plate are sealed together in a single unit with a sealing material. The sealing material is primarily composed of epoxy, carbon, and silica to enhance the heat resistance capabilities of the Hitachi RFID tag. That is, the heat resistance of the RFID tag substantially depends on the heat resistance capabilities of the sealing material. The sealing material has a high heat resistance withstanding temperatures of up to 250 to 300° C. for shorter time periods, such as a few seconds, and is resistant to heat for longer periods of time up to 150° C. Accordingly, the Hitachi RFID tag has a higher heat resistance than conventional RFID tags and can still operate normally even at high temperatures. Additional information regarding the Hitachi RFID tag can be found in the entire disclosure of U.S. Pat. No. 9,171,244, entitled RFID TAG, which issued on Oct. 27, 2015, and is incorporated by reference herein.

As mentioned above, the surgical instrument system 18000 comprises an RFID system which includes one or more RFID readers and one or more RFID tags. In various embodiments, referring to FIG. 62, the RFID system comprises a first RFID tag 18560a, a second RFID tag 18560b, and a third RFID tag 18560c. FIG. 67 illustrates a Hitachi Ultra Small Package UHF RFID tag 18900 which can be used for the RFID tags 18560a, 18560b, and 18560c, although any suitable RFID tag could be used. The tag 18900 comprises a size of 2.5 mm×2.5 mm×0.4 mm, for example. The tag 18900 comprises a substrate or base 18910, a microchip 18920 mounted to the substrate 18910, and an antenna 18930 mounted to the substrate 18910 in a circumferential pattern which is in communication with an output channel or pin of the microchip 18920. Additional details regarding the RFID tag 18900 are disclosed in U.S. Pat. No. 9,171,244, which is incorporated by reference herein in its entirety. That said, any suitable RFID tag could be used.

Referring to FIGS. 62, 64-66 and 68, the first RFID tag 18560a is affixed to the cartridge body 18510 at a first position A. The second RFID tag 18560b is affixed to the sled 18550 slidably positioned in the cartridge body 18510, as illustrated in FIG. 69, and the third RFID tag 18560c is affixed to the cover 18570, as illustrated in FIG. 70. Referring primarily to FIG. 66, the surgical instrument 18000 comprises a first RFID reader 18600, a second RFID reader 18700, and a third RFID reader 18800. The first RFID reader 18600 includes a flexible circuit extending between the controller in the surgical instrument handle 18100 and the second jaw 18320. The first RFID reader 18600 comprises a first inductive coil or sensor 18620 which is aligned with the first RFID tag 18560*a* when the staple cartridge 18500 is seated in the second jaw 18320. Similarly, the second RFID reader 18700 includes a flexible circuit extending between the controller in the surgical instrument handle 18100 and the second jaw 18320. The second RFID reader 18700 comprises a second inductive coil or sensor 18720 at position B (FIG. 62) which is aligned with the second RFID tag 18560*b* when the staple cartridge 18500 is seated in the second jaw 18320. Also, similarly, the third RFID reader 18600 includes a flexible circuit extending between the controller in the surgical instrument handle 18100 and the second jaw 18320. The third RFID reader 18800 comprises a third inductive coil or sensor 18820 at position C (FIG. 62) which is aligned with the third RFID tag 18560*c* when the staple cartridge 18500 is seated in the second jaw 18320.

The RFID tags 18560*a*, 18560*b*, and 18560*c* can be active and/or passive. When the RFID tags 18560*a*, 18560*b*, and 18560*c* are active RFID tags, they each emit a signal which is received by their respective RFID readers. For instance, the first RFID sensor 18620 receives a first beacon signal from the first RFID tag 18560*a*, the second RFID sensor 18720 receives a second beacon signal from the second RFID tag 18560*b*, and the third RFID sensor 18820 receives a third beacon signal from the third RFID tag 18560*c*. The first, second, and third beacon signals can all be emitted at the same frequency or at different frequencies. If the beacon signals are emitted at the same frequency, then the range of the beacon signals and/or the position of the RFID sensors must be controlled such that there isn't crosstalk between the RFID tags 18560*a*, 18560*b*, and 18560*c* and their respective RFID reader sensors 18620, 18720, and 18820. The ranges of the RFID beacon signals is determined by the power being used to transmit the beacon signals and the availability of that power from their respective power sources, or batteries. In general, the range of the beacon signal is proportional to the transmission power of the signal. If the beacon signals are emitted at different frequencies, then the range of the signals and the relative positioning of the RFID sensors 18620, 18720, and 18820 can be more flexible. In such embodiments, the controller comprises one or more signal filters, such as low-pass filters and/or high-pass filters, for example, which can be used to make sure that the signals, and data, received from the RFID tags 18560*a*, 18560*b*, and 18560*c* is being received on the correct input lines, or RFID readers. For instance, a low-pass filter can be used to filter out the second and third beacon signals on the first RFID reader 18600, a high-pass filter can be used to filter out the first and second beacon signals on the third RFID reader 18800, and both a low-pass filter and a high-pass filter can be used to filter out the first and third beacon signals on the second RFID reader 18700. In any event, the RFID readers 18600, 18700, and 18800 receive data from their respective RFID tags 18560*a*, 18560*b*, and 18560*c* as soon as the staple cartridge 18500 is seated in the second jaw 18320. Notably, the RFID tags 18560*a*, 18560*b*, and 18560*c* may begin to communicate with their respective RFID readers as the staple cartridge 18500 is being seated and/or when the staple cartridge 18500 is aligned with the second jaw 18320 and is about to be seated.

When the RFID tags 18560*a*, 18560*b*, and 18560*c* are passive RFID tags, the RFID tags 18560*a*, 18560*b*, and 18560*c* do not emit signals until they receive signals from their respective RFID scanners 18600, 18700, and 18800. For instance, the first RFID tag 18560*a* does not emit a signal until it is energized by a signal emitted from the first sensor 18620 of the RFID scanner 18600. In this way, the first sensor 18620 acts as a transmission antenna which broadcasts a first signal which, when received by the first RFID tag 18560*a*, causes the first RFID tag 18560*a* to emit a first return signal that is received by the first sensor 18620. As such, the first sensor 18620 acts as both a transmission antenna and a reception antenna. That said, the first RFID scanner 18600 can comprise a transmission antenna as part of a transmission circuit and a separate reception antenna as part of a reception circuit. Similarly, the second RFID tag 18560*b* does not emit a signal until it is energized by a signal emitted from the second sensor 18720 of the RFID scanner 18700. In this way, the first sensor 18720 acts as a transmission antenna which broadcasts a second signal which, when received by the second RFID tag 18560*b*, causes the second RFID tag 18560*b* to emit a second return signal that is received by the second sensor 18720. As such, the second sensor 18720 acts as both a transmission antenna and a reception antenna. That said, the second RFID scanner 18700 can comprise a transmission antenna as part of a transmission circuit and a separate reception antenna as part of a reception circuit. Also, similarly, the third RFID tag 18560*c* does not emit a signal until it is energized by a signal emitted from the third sensor 18820 of the RFID scanner 18800. In this way, the third sensor 18820 acts as a transmission antenna which broadcasts a third signal which, when received by the third RFID tag 18560*c*, causes the third RFID tag 18560*c* to emit a third return signal that is received by the third sensor 18820. As such, the third sensor 18820 acts as both a transmission antenna and a reception antenna. That said, the third RFID scanner 18800 can comprise a transmission antenna as part of a transmission circuit and a separate reception antenna as part of a reception circuit.

As described above, the first RFID tag 18560*a* is affixed to the cartridge body 18510 of the staple cartridge 18500. The first RFID tag 18560*a* is attached to the cartridge body 18510 using one or more adhesives. That said, the first RFID tag 18560*a* could be affixed to the cartridge body 18510 in any suitable manner. For instance, referring to FIG. 68, the first RFID tag 18560*a* can be integrally-molded with the cartridge body 18510 during an injection molding process. In such instances, at least part of the first RFID tag 18560*a* is embedded in the cartridge body 18510. That said, embodiments are envisioned in which the entirety of the first RFID tag 18560*a* is embedded in the cartridge body 18510. Moreover, embodiments are envisioned in which a wall of the cartridge body 18510 defines a recess, or pocket, and the first RFID tag 18560*a* is positioned in the recess. In various instances, the perimeter of the RFID tag 18560*a* matches the perimeter of the recess in the cartridge body 18510.

When the first RFID scanner 18600 receives the first signal from the first RFID tag 18560*a* and the first signal, or the data from the first signal, is communicated to the controller of the surgical instrument 18000, the controller determines that a staple cartridge is present in the second jaw 18520. In various embodiments, the controller performs an authentication evaluation to determine that the data received from the first RFID tag 18560*a* matches data from an acceptable staple cartridge. The data regarding an acceptable staple cartridge can be stored in a memory device of the controller and/or can be stored in an off-board controller and/or cloud environment, for example. If the controller determines that a staple cartridge is present in the second jaw 18320 and that the staple cartridge is compatible, the controller will perform additional checks with the second and third RFID tags 18560*b* and 18560*c* of the RFID system, as discussed in greater detail below. That said, embodiments are envisioned in which the first RFID tag 18560*a* is the only RFID tag in the RFID system and, once the presence of a compatible staple cartridge is verified via the first RFID tag 18560*a*, the controller can unlock the staple firing system.

As discussed above, the second RFID tag 18560*b* is affixed to the sled 18550 of the staple cartridge 18500. The second RFID tag 18560*b* is attached to the sled 18550 using one or more adhesives. That said, the second RFID tag 18560*b* could be affixed to the sled 18550 in any suitable manner. For instance, referring to FIG. 69, the second RFID tag 18560*b* can be integrally-molded with the sled 18550 during an injection molding process. In such instances, at least part of the second RFID tag 18560*b* can be embedded in the sled 18550. That said, embodiments are envisioned in which the entirety of the second RFID tag 18560*b* is embedded in the sled 18550. Moreover, embodiments are envisioned in which a wall of the sled 18550 defines a recess, or pocket, and the second RFID tag 18560*b* is positioned in the recess. In various instances, the perimeter of the RFID tag 18560*b* matches the perimeter of the recess in the sled 18550.

When the second RFID scanner 18700 receives the second signal from the second RFID tag 18560*b* and the second signal, or the data from the second signal, is communicated to the controller of the surgical instrument 18000, the controller determines that the sled is present in its proximal, unfired position within the staple cartridge. With this information, the controller can determine that the staple cartridge is in an unspent condition. If the sled 18550 is not in its proximal, unfired position, the second RFID tag 18560*b* will be out of range of the second RFID scanner 18700 and the controller will determine that the staple cartridge positioned in the second jaw 18320 has been at least partially spent. In such instances, the controller will not unlock the staple firing system until the staple cartridge has been replaced with a compatible unspent staple cartridge.

In various embodiments, the controller performs an authentication evaluation to determine that the data received from the second RFID tag 18560*b* matches data corresponding to the staple cartridge that was identified by the first RFID scanner 18600. If the controller determines that the sled 18550 is an appropriate component of the staple cartridge present in the second jaw 18320 via the data from the second RFID tag 18560*b*, the controller will perform an additional check with the third RFID tag 18560*c* of the RFID system, as discussed in greater detail below. That said, embodiments are envisioned that do not include a third RFID tag 18560*c* and, once the presence of a compatible unfired staple cartridge is verified via the first and second RFID tags 18560*a* and 18560*b*, as discussed above, the controller can unlock the staple firing system.

As discussed above, referring to FIG. 70, the third RFID tag 18560*c* is affixed to the removable cover 18570 of the staple cartridge 18500. The third RFID tag 18560*c* is attached to the cover 18570 using one or more adhesives. That said, the third RFID tag 18560*c* could be affixed to the cover 18570 in any suitable manner. For instance, referring to FIG. 70, the third RFID tag 18560*c* can be integrally-molded with the cover 18570 during an injection molding process. In such instances, at least part of the third RFID tag 18560*c* can be embedded in the cover 18570. That said, embodiments are envisioned in which the entirety of the third RFID tag 18560*c* is embedded in the cover 18570. Moreover, embodiments are envisioned in which a wall of the cover 18570 defines a recess, or pocket, and the third RFID tag 18560*c* is positioned in the recess. In various instances, the perimeter of the RFID tag 18560*c* matches the perimeter of the recess in the cover 18570.

When the third RFID scanner 18800 receives the third signal from the third RFID tag 18560*c* and the third signal, or the data from the third signal, is communicated to the controller of the surgical instrument 18000, the controller determines that the cover 18570 is attached to the staple cartridge. With this information, the controller can determine that the clinician inserted the staple cartridge into the surgical instrument 18000 with the cover 18570 on and, thus, did not disturb the staples stored in the cartridge body 18510. If the cover 18570 is not detected on the cartridge body 18510, the controller will determine that the staple cartridge may be damaged. In such instances, the controller will not unlock the staple firing system until the staple cartridge has been replaced with a compatible, unspent and undamaged staple cartridge.

In various embodiments, the controller performs an authentication evaluation to determine that the data received from the third RFID tag 18560*c* matches data corresponding to the staple cartridge that was identified by the third RFID scanner 18700. If the controller determines that the cover 18570 is an appropriate component of the staple cartridge present in the second jaw 18320 via the data from the third RFID tag 18560*c*, the controller unlocks the staple firing system. Additional RFID tags and RFID tag scanners can be used to evaluate the presence, condition, and/or compatibility of the staple cartridge positioned in the surgical instrument.

As discussed above, the second RFID scanner 18700 is used by the controller of the surgical instrument 18000 to assess whether or not the sled 18550 is in its proximal, unfired position. Absent more, the controller is unable to assess the position of the sled 18550 other than it is not within the communication range of the second RFID 18700 scanner. That said, a surgical instrument can comprise more than one RFID scanner which be used by the controller of the surgical instrument to assess the position of the sled 18500 and, thus, the progress of the staple firing stroke. Referring again to FIG. 66, the first RFID scanner 18600 and the third RFID scanner 18800 of the surgical instrument 18000 can be used to track the position of the sled 18500. As the sled 18500 is moved distally during the staple firing stroke, the second RFID tag 18560*b* passes through the transmission range 18610 of the first RFID scanner 18600 and the transmission range 18810 of the third RFID scanner. When the second signal of the second RFID tag 18560*b* is detected by the first RFID scanner 18600, the controller determines that the sled 18550 is adjacent position A. Likewise, the controller determines that the sled 18550 is adjacent position C when the second signal of the second RFID tag 18560*b* is detected by the third RFID scanner 18800. In various embodiments, the RFID system can comprise an RFID scanner adjacent the distal end of a staple cartridge in communication with the controller to detect when the sled 18550 has reached the end of the staple firing stroke.

Many commercially-available staple cartridges are sold in standard lengths. For instance, Ethicon, a subsidiary of Johnson & Johnson, sells staple cartridges configured to apply a 30 mm long staple pattern, staple cartridges configured to apply a 45 mm long staple pattern, and staple cartridges configured to apply a 60 mm long staple pattern, among others. The 30 mm, 45 mm, and 60 mm lengths do not represent the overall length of the staple cartridges; rather, these lengths represent the length of the staple patterns that these staple cartridges could apply. That said, Ethicon also sells surgical staplers configured to receive the 30 mm staple cartridges. Such surgical staplers comprise anvils that are configured to deform the staples in the 30 mm pattern. Ethicon also sells surgical staplers configured to receive 45 mm staples cartridges and surgical staplers configured to receive the 60 mm staple cartridges and have anvils configured to deform a 45 mm staple pattern and a 60 mm staple pattern, respectively. Absent other considerations, an anvil designed to create a 30 mm long staple pattern would not be able to deform all of the staples of a 60 mm staple pattern. In various embodiments, further to the above, a surgical instrument can include an RFID system configured to assess whether a staple cartridge that has been inserted into the surgical instrument has a staple pattern that matches the staple pattern that can be deformed by the anvil of the surgical instrument, as described in greater detail below.

Further to the above, referring to FIGS. 74A, 74B, and 75, an end effector 18300' of a surgical instrument comprises a first jaw 18310 and a second jaw 18320, where the second jaw 18320 is configured to receive a replaceable staple cartridge 19700 therein. The staple cartridge 19700 is similar to the staple cartridge 18500 in many respects and comprises a plurality of staples removably stored therein. The pattern of the staples stored in the staple cartridge 19700 matches a pattern of staple forming pockets defined in the anvil of the first jaw 18310. Another staple cartridge 19600 is illustrated in FIG. 74A. Similar to the staple cartridge 19700, the staple cartridge 19600 can be inserted into the second jaw 18320; however, the staple cartridge 19600 produces a staple pattern which is different than, or shorter in length than, the staple pattern produced by the staple cartridge 19700. As such, the staple cartridge 19600 is unsuitable for, or incorrect for use with, the surgical instrument while the staple cartridge 19700 is suitable for, or correct for use with, the surgical instrument. The surgical instrument comprises an RFID system in communication with the controller of the surgical instrument which is used to prevent the surgical instrument from performing a staple firing stroke when an incorrect staple cartridge, such as staple cartridge 19600, for example—or no staple cartridge—is positioned in the second jaw 18320. Correspondingly, the controller is configured to permit the stapling instrument to be used to perform a staple firing stroke when a correct staple cartridge, such as staple cartridge 19700, is positioned in the second jaw 18320 and recognized by the controller.

The end effector 18300' comprises a first RFID scanner comprising a first sensor at a proximal end of the second jaw 18320 and a second RFID scanner comprising a second sensor at a distal end of the second jaw 18320. The staple cartridge 19700 comprises a cartridge body 19710, a first RFID tag 19760*a* mounted to a proximal end of the cartridge body 19710, and a second RFID tag 19760*b* mounted to a distal end of the cartridge body 19710. When the staple cartridge 19700 is seated in the second jaw 18320, the first RFID tag 19760*a* is aligned with the sensor of the first RFID scanner and the second RFID tag 19760*b* is aligned with the sensor of the second RFID scanner. In such instances, the controller of the surgical instrument is able to verify the presence of a correct staple cartridge in the second jaw 18320 when both of the RFID scanners detect the presence of their respective RFID tags. As discussed herein, the controller can be configured to authenticate whether the signals and/or data received from the RFID tags match a set of signals and/or data that corresponds to a compatible staple cartridge. In any event, the controller is configured to unlock the staple firing system once the controller has determined the presence of a correct staple cartridge seated in the second jaw 18320.

Further to the above, the staple cartridge 19600 comprises a cartridge body 19610, a first RFID tag 19660*a* mounted to a proximal end of the cartridge body 19610, and a second RFID tag 19660*b* mounted to a distal end of the cartridge body 19610. When the staple cartridge 19600 is seated in the second jaw 18320, the second RFID tag 19660*b* is aligned with the sensor of the second RFID scanner; however, referring to FIG. 75, the first RFID tag 19660*a* is not aligned with the first RFID scanner. In fact, the first RFID tag 19660*a* is not positioned within the transmission, or communication, range of the first RFID scanner. As a result, the controller can receive a signal from the second RFID tag 19660*b*, but it cannot receive a signal from the first RFID tag 19660*a*. In such instances, the controller is configured to determine that a staple cartridge having an incorrect length has been seated in the second jaw 18320. Stated another way, the controller can determine that a staple cartridge is present in the second jaw 18320 owing to the detection of the second RFID tag 19660*b* by the second RFID scanner but that the staple cartridge is the wrong length owing to the lack of signal detected by the first RFID scanner. The controller is configured to maintain the staple firing system in a locked out state until the controller has determined that a correct staple cartridge is seated in the second jaw 18320. In at least one such embodiment, the controller is not responsive to a firing actuator input and does not power the electric motor of the staple firing system until the presence of a correct staple cartridge has been detected in the second jaw 18320.

Figure 76:
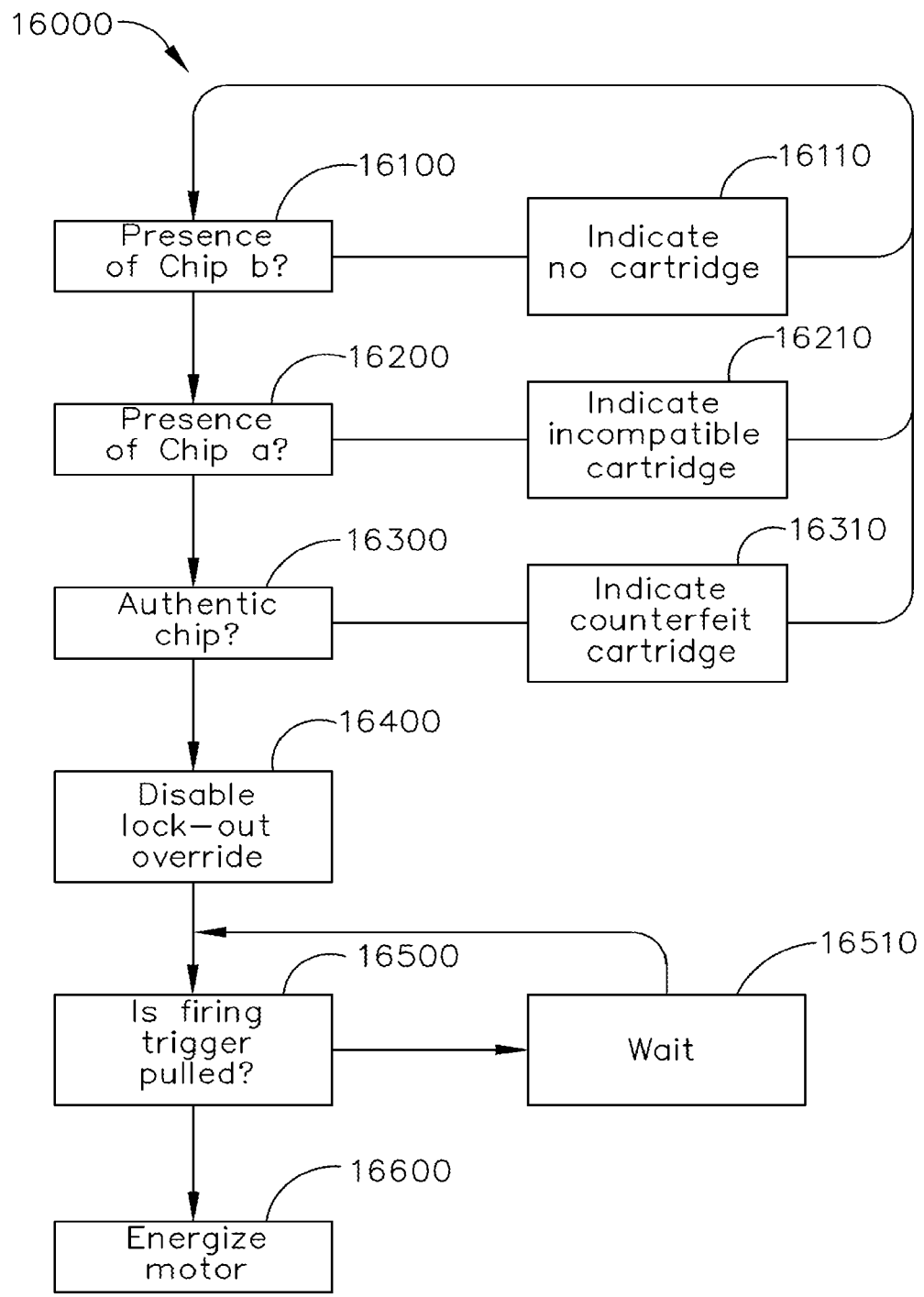
FIG. 76 illustrates an algorithm for a control system in accordance with at least one embodiment.

An algorithm 16000 of the controller of the embodiment of FIGS. 74 and 75 is illustrated in FIG. 76. At step 16100 the controller evaluates the presence of the second RFID tag 19660*b* using the second RFID scanner. If the controller does not receive a signal from the second RFID scanner, the controller determines that a staple cartridge is absent from the second jaw 18320 and the absence of a staple cartridge is indicated to the clinician at step 16110. In various instances, the surgical instrument comprises a display screen in communication with the controller which is used to convey the absence of a staple cartridge to the clinician. In such instances, the algorithm 16000 returns to step 16100 and waits for a staple cartridge to be inserted into the second jaw 18320 that can communicate with the second RFID scanner. If the controller receives a signal from the second RFID scanner at step 16100, the controller evaluates the presence of the first tag 19660*a* using the first RFID scanner at step 16200. If the controller does not receive a signal from the first RFID scanner, the controller determines that an incompatible staple cartridge is present in the second jaw 18320 which is indicated to the clinician at step 16210. This indication can be provided to the clinician via the display screen, for example. In such instances, the algorithm 16000 returns to step 16100 and waits for a compatible staple cartridge to be inserted into the second jaw 18320 that can communicate with the first and second RFID scanners. If the controller receives a signal from the first RFID scanner at step 16200, the controller verifies the authenticity of the first and/or second RFID tags at step 16300. In various instances, the controller comprises sets of data stored in a memory chip, or memory device, that can be used to authenticate the data received from the first and second RFID tags 19660*a* and 19660*b*. For instance, if the data from the first RFID signal and the second RFID signal match the set of data stored in the memory chip for the first and second RFID signals, the controller can determine that the staple cartridge positioned in the second jaw 18320 is authentic at step 16300. If the received data does not match the stored data at step 16300, then the controller indicates to the clinician at step 16310 that an inauthentic staple cartridge is present in the second jaw 18320 via the display screen, for example. In such instances, the algorithm 16000 returns to step 16100 and waits for a compatible authentic staple cartridge to be inserted into the second jaw 18320.

Once the controller determines that an authentic staple cartridge is position in the second jaw 18320, the controller enables the staple firing system at step 16400. At such point, the controller is responsive to an input from a staple firing actuator at step 16500 and applies a voltage potential to the electric motor of the staple firing system at step 16600 when the input is received, assuming that all other conditions for performing a staple firing stroke have been met. For instance, the controller is configured to not be responsive to an input from the staple firing actuator while the first jaw 18310 is in an open position. When the first jaw 18310 is closed, however, the controller can be responsive to the input from the staple firing actuator at steps 16500 and 16600. If an input is not received from the staple firing actuator, then the controller waits for such an input at step 16510.

In various embodiments, further to the above, the staple cartridge 19700 and/or the second jaw 18320 comprise features that create a snap-fit between the staple cartridge 19700 and the second jaw 18320 when the staple cartridge 19700 is seated in the second jaw 18320. Such a snap-fit arrangement securely holds the staple cartridge 19700 in the second jaw 18320, but still permits the staple cartridge 19700 to be removed from the second jaw 18320. In some instances, seating the distal end of the staple cartridge 19700 into the second jaw 18320 is relatively easy while seating the proximal end of the staple cartridge 19700 may be somewhat difficult owing to the proximity of the first jaw 18310. In various embodiments, the RFID system can be used to determine if a staple cartridge is fully seated in the second jaw 18320. For instance, if the proximal end of the staple cartridge 19700 is fully seated in the second jaw 18320 and the distal end of the staple cartridge 19700 is not seated in the second jaw 18320, the controller will detect the presence of the staple cartridge 19700 owing to the signal received from the first RFID reader but will determine that the distal end of the staple cartridge 19700 is not fully seated due to the absence of a signal from the second RFID reader. In such instances, the controller can communicate this condition to the clinician via the display, for example, and provide the clinician with instructions as to how to fix the problem. The controller can also be configured to determine that the proximal end of the staple cartridge is not fully seated in the second jaw 18320 when the second RF ID reader receives a signal from the second RFID tag 19760*b* and the first RFID reader does not receive a signal from the first RFID tag 19760*a*. In such instances, the controller can identify that the staple cartridge 19700 is an unseated, but nonetheless correct staple cartridge, or at least assume that the staple cartridge 19700 is a correct staple cartridge, by authenticating the partial set of data from the second RFID tag 19760*b*. In any event, if the controller determines that an end of the staple cartridge 19700 has not been fully seated, the controller will prevent the staple firing stroke from being actuated. Once both ends of the staple cartridge 19700 have been fully seated, the controller is responsive to an input from the firing system actuator assuming all of the conditions for performing a staple firing stroke have been met.

Figure 71:
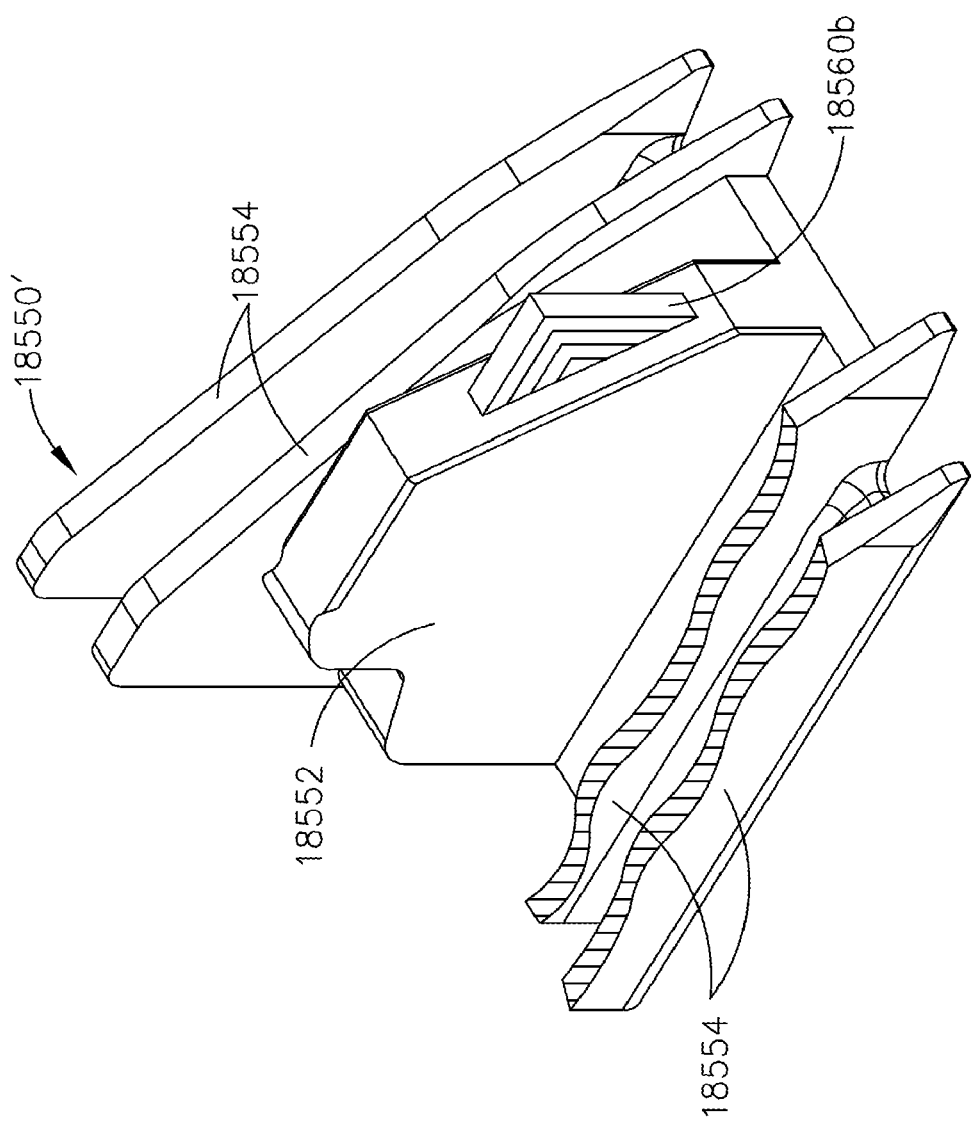
FIG. 71 is a cross-sectional view of a sled in accordance with at least one embodiment.
Figure 72A:
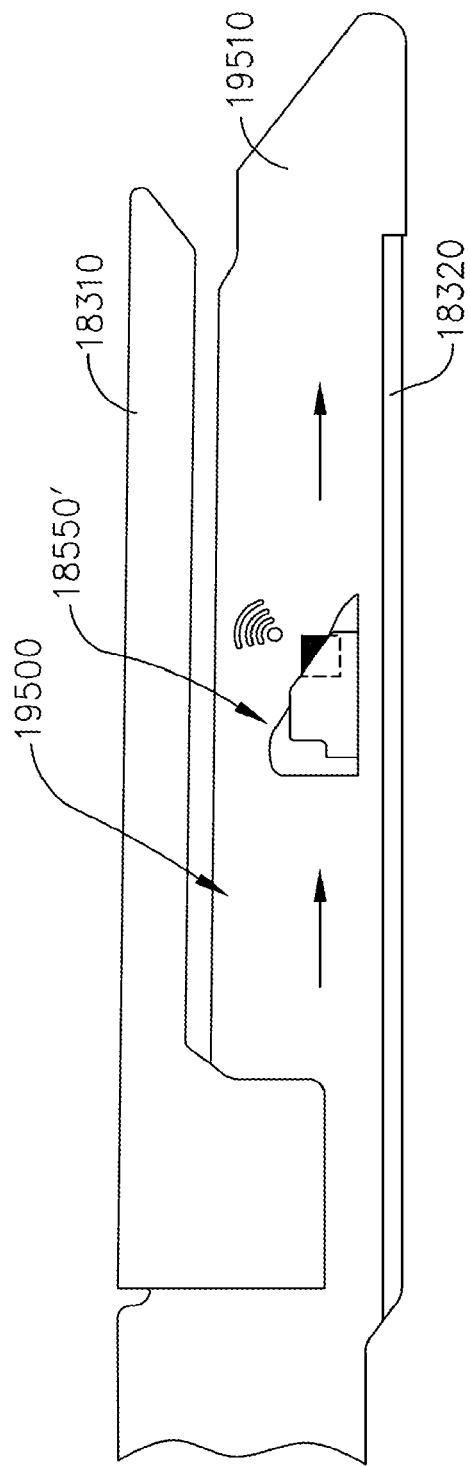
FIG. 72A is an elevation view of the end effector of FIG. 72 illustrating the sled of FIG. 70 being advanced distally during a staple firing stroke.
Figure 73A:
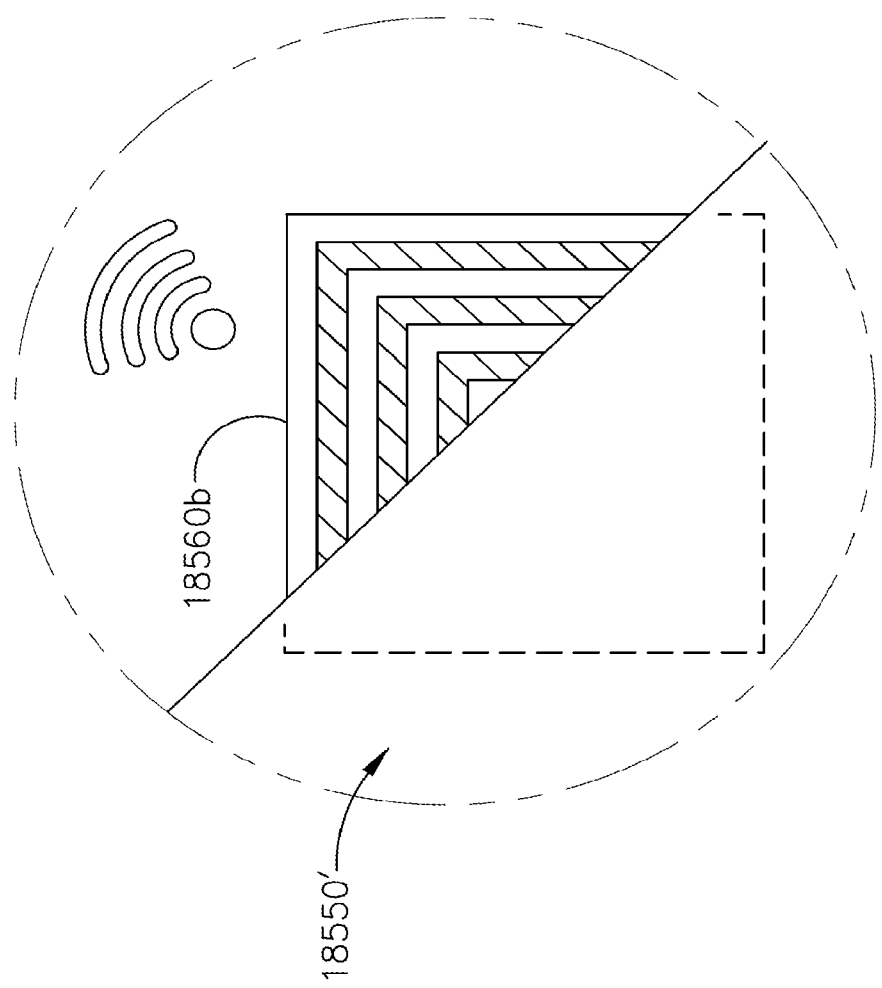
FIG. 73A is a detail view of an RFID tag embedded in the sled of FIG. 70.

As described above, a staple cartridge comprises staples removably stored therein which are ejected from the staple cartridge by a sled and/or firing member that is moved through the staple cartridge during a staple firing stroke. In various embodiments, the sled contacts the staples directly while, in other embodiments, the sled contacts staple drivers which support and drive the staples out of the staple cartridge during the staple firing stroke. The cartridge body, sled, and/or staple drivers of the staple cartridge often undergo significant stresses and strains during the staple firing stroke and, in such instances, re-using, or re-loading, the spent staple cartridge with new staples may not be desirable. With this in mind, various embodiments are envisioned in which one or more features of the staple cartridge are intentionally destroyed during and/or after the staple firing stroke to prevent the staple cartridge from being re-used. Referring to FIG. 72, a staple cartridge 19500 comprises a cartridge body 19510, staples removably stored in the cartridge body 19510, staple drivers movably stored within the cartridge body 19510, and a sled 18550' (FIG. 71) configured to move between a proximal position (FIG. 72) and a distal position (FIG. 72B) during a staple firing stroke. Similar to the sled 18550, the sled 18550' comprises an RFID tag 18560*b* mounted thereto and, similar to the above, the RFID system of the surgical instrument 18000 is configured to verify that the sled 18550' in its present in its proximal, unfired position (FIG. 72) when the staple cartridge 19500 is loaded into the surgical instrument 18000. When the staple cartridge 19500 has not been fired previously, referring to FIG. 73A, the RFID system can communicate with the RFID tag 18560*b* and permit the staple firing stroke to be performed. At the end of the staple firing stroke, however, the RFID tag 18560*b* of the sled 18550' contacts and is cut by a knife 19590 positioned at the distal end of the cartridge body 19510 as illustrated in FIG. 73B. When the RFID tag 18560*b* is cut in this manner, the RFID tag 18560*b* is no longer able to emit a signal and, even if the sled 18550' were to be pushed back, or reset, into its proximal, unfired position to reload the staple cartridge 19500, the re-loaded staple cartridge 19500 could not pass the authentication test performed by the RFID system of the surgical instrument 18000 owing to the damaged RFID tag 18560*b*. As a result, the surgical instrument 18000 would be unable to perform a staple firing stroke with the re-loaded staple cartridge 19500 positioned in the surgical instrument 18000.

Referring again to FIG. 71, the RFID tag 18560*b* is mounted to the central or longitudinal portion 18552 of the sled 18550' which slides within the longitudinal slot of the staple cartridge 19500. The RFID tag 18560*b* is partially embedded in the central portion 18552 and a portion of the RFID tag 18560*b* is exposed. More specifically, a portion of the RFID antenna is exposed. That said, the RFID tag 18560*b* could be mounted to the sled 18550' at any suitable location, such as on the rails 18554 of the sled 18550', for example. The exposed portion of the RFID tag 18560*b* faces the distal end of the sled 18550' such that the RFID tag 18560*b* comes into contact with the cartridge knife 19590 at the end of the staple firing stroke. That said, embodiments are envisioned in which the RFID tag 18560*b* on the sled 18550' is destroyed at the outset of the staple firing stroke. Moreover, embodiments are envisioned in which the RFID tag of other staple cartridge components is intentionally destroyed and/or disabled during use. One such embodiment is discussed further below in which the RFID tag of the staple cartridge cover is destroyed and/or disabled when it is removed from the staple cartridge. In such instances, a used staple cartridge cover could not be attached to a staple cartridge to pass the authentication test performed by the RFID system.

Figure 77:
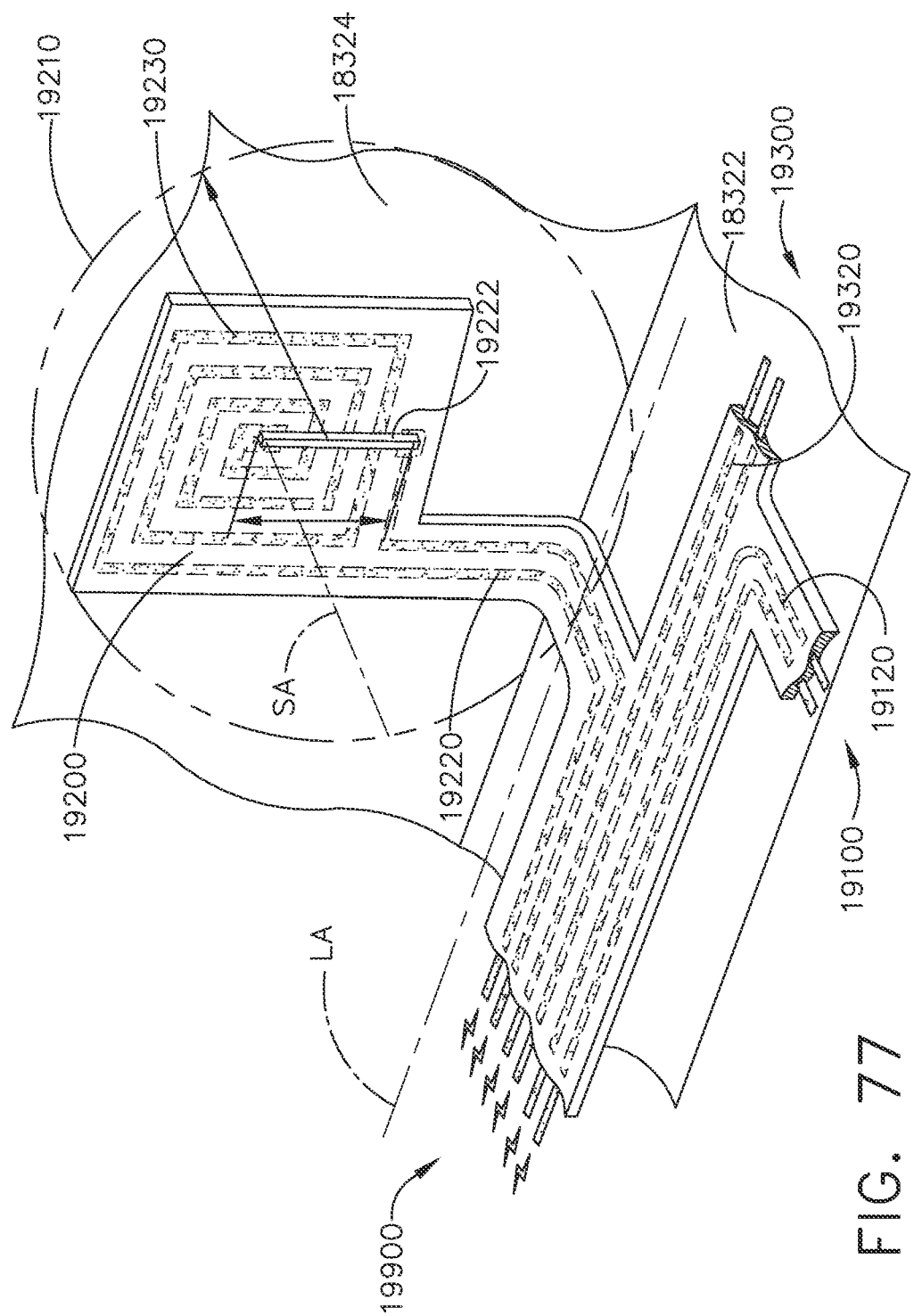
FIG. 77 illustrates a flex circuit including RFID scanners in accordance with at least one embodiment.

As discussed above, the RFID system of the surgical instrument 18000 comprises three RFID readers—each of which being able to communicate with and/or receive signals from a respective RFID tag. As also discussed above, the RFID readers can comprise flex circuits, for example, which extend into the end effector 18300 of the surgical instrument 18000. In such instances, referring to FIG. 66, the flex circuits can be mounted to the walls of the second jaw 18320 and can be sized and configured to accommodate a staple cartridge seated in the second jaw 18320. Among other things, referring again to FIG. 66, the second jaw 18320 comprises a bottom wall, or support, 18322 and two lateral sidewalls 18324 extending upwardly from the bottom wall 18322 which are configured to receive a staple cartridge therebetween. Two of the RFID flex circuits are mounted to one of the sidewalls and the other RFID flex circuit is mounted to the other sidewall. In various instances, the RFID flex circuits are mounted to the sidewalls using one or more adhesives, for example. In addition to or in lieu of the above, fasteners could be used to mount the RFID flex circuits to the walls of the second jaw 18320. In various alternative embodiments, referring to FIG. 77, the RFID scanners can be part of one flex circuit. In at least one such embodiment, the RFID scanners comprise sub-circuits of the flex circuit.

Referring again to FIG. 77, a flex circuit 19900 comprises a flexible substrate and conductors embedded in the flexible substrate. The flexible substrate is comprised of an insulative, or non-conductive, material, such as plastic, for example, and the conductors are comprised of copper, for example. The flex circuit 19900 is mounted to the bottom wall 18322 of the second jaw 18320 and comprises a first RFID scanner 19100, a second RFID scanner 19200, and a third RFID scanner 19300. The first RFID scanner 19100 comprises a sensor circuit including two conductors and a first sensor coil or array 19120. One of the conductors comprises a coil portion defined in the first sensor 19120 and a conductive connector which connects an end of the coil portion to the other conductor to complete the circuit of the first RFID scanner 19100. The first sensor 19120 is mounted to a first sidewall 18324 of the second jaw 18320. Similarly, the second RFID scanner 19200 comprises a sensor circuit including two conductors and a second sensor coil or array 19220. One of the conductors comprises a coil portion defined in the second sensor 19220 and a conductive connector 19222 which connects an end of the coil portion to the other conductor to complete the circuit of the second RFID scanner 19200. The second sensor 19220 is mounted to the second sidewall 18324 of the second jaw 18320. Also, similarly, the third RFID scanner 19300 comprises a sensor circuit including two conductors and a third sensor coil or array 19320. One of the conductors comprises a coil portion defined in the third sensor 19320 and a conductive connector which connects an end of the coil portion to the other conductor to complete the circuit of the third RFID scanner 19300. The third sensor 19320 is mounted to the base wall 18322 of the second jaw 18320.

When a staple cartridge, such as the staple cartridge 18500, for example, is seated in the second jaw 18320, referring again to FIG. 66, the first RFID tag 18560*a* is aligned with the sensor 18620 of the first RFID scanner 18600. In various embodiments, the first RFID tag 18560*a* comprises a substantially planar configuration. More specifically, the base, microchip, and tag antenna of the first RFID tag 18560*a* are arranged in a manner which appears to be visibly flat. The sensor 18620 of the first RFID scanner 18600, similar to sensor 19220 of the RFID scanner 19200, also comprises a substantially planar configuration which appears to be visibly flat. When the staple cartridge 18500 is seated in the second jaw 18320, the first RFID tag 18560*a* is parallel to, or at least substantially parallel to, the first sensor 18620. The first RFID tag 18560*a* and the first sensor 18620 are substantially parallel to one another when there is an approximately 10 degree, or less, angle between their two planes.

Moreover, further to the above, the tag antenna of the first RFID tag 18560*a* extends circumferentially about a tag antenna axis TA (FIG. 67) which is orthogonal, or at least substantially orthogonal, to the plane defined by the first RFID tag 18560*a*. The tag antenna axis TA is orthogonal to the first RFID tag 18560*a* when there is an approximately 80-100 degree angle between the tag antenna axis TA and the plane defined by the first RFID tag 18560*a*. Similarly, the reader antenna of the first sensor 18620 extends circumferentially about a reader antenna axis SA (FIG. 77) which is orthogonal, or at least substantially orthogonal, to the plane defined by the first sensor 18620. The reader antenna axis SA is orthogonal to the first reader antenna 18620 when there is an approximately 80-100 degree angle between the reader antenna axis SA and the plane defined by the first reader antenna 18620. When the staple cartridge 18500 is seated in the second jaw 18320, the tag antenna axis TA is aligned with the reader antenna axis SA. In various instances, the tag antenna axis TA is collinear with the reader antenna axis SA. Similar arrangements can be achieved between the second RFID tag 18560*b* and the antenna 18720 of the second RFID reader 18700. Also, similar arrangements can be achieved between the third RFID tag 18560*c* and the antenna 18820 of the third RFID reader 18800

Referring again to FIG. 66, the first RFID tag 18560*a*, the second RFID tag 18560*b*, and the third RFID tag 18560*c* are not aligned longitudinally in the second jaw 18320. More specifically, the second RFID tag 18560*b* is positioned proximally with respect to the first RFID tag 18560*a* and, also, the third RFID tag 18560*c* is positioned distally with respect to the first RFID tag 18560*a*. If the first RFID tag 18560*a*, the second RFID tag 18560*b*, and the third RFID tag 18560*c* are active RFID tags, the transmission ranges of the RFID tags 18560*a*, 18560*b*, and 18560*c* can be established such that they do not overlap. Moreover, the second sensor 18720 of the second RFID reader 18700 is positioned proximally with respect to the first sensor 18620 of the first RFID reader 18600 and, also, the third sensor 18820 of the third RFID reader 18800 is positioned distally with respect to the first sensor 18620. As also illustrated in FIG. 66, the second transmission range 18710 of the second sensor 18720 is proximal to and does not overlap lap with the first transmission range 18610 of the first sensor 18620 and, also, the third transmission range 18810 of the third sensor 18820 is distal to and does not overlap with the first transmission range 18610 of the first sensor 18620.

Further to the above, referring to FIGS. 64-66, the first RFID tag 18560*a* and the second RFID tag 18560*b* are not aligned laterally in the second jaw 18320. More specifically, the first RFID tag 18560*a* is positioned in a lateral sidewall 18514 of the cartridge body 18510 and the second RFID tag 18560*b* is positioned in the longitudinal slot 18520. Moreover, the first RFID tag 18560*a* and the third RFID tag

18560*c* are not aligned laterally in the second jaw 18320. More specifically, the first RFID tag 18560*a* is positioned in the lateral sidewall 18514 of the cartridge body 18510 and the third RFID tag 18560*c* is positioned in the longitudinal slot 18520.

As discussed herein, the controller of a surgical instrument, such as the surgical instrument 18000, for example, is configured to prevent a staple firing stroke from being performed or permit the staple firing stroke to be performed based on feedback from an RFID system. That said, the controller can be configured to alter the operation of the surgical instrument in one or more other ways based on feedback from the RFID system. For instance, the controller can be configured to change the speed of the staple firing stroke based on feedback from the RFID system. In at least one such embodiment, the controller can use data obtained from the RFID tags and/or data stored in a memory device to run the electric motor of the staple firing system at a desired speed for the staple cartridge seated in the surgical instrument. In at least one instance, the data instructs the electric motor to run at a slower speed during the staple firing stroke. Such an arrangement could be useful when the staple cartridge comprises an implantable adjunct releasably attached to the deck of the staple cartridge. Such an arrangement could also be useful when the staple cartridge comprises tall staples, or staples between approximately 2.5 mm and approximately 5.0 mm in height before being deformed against the anvil, for example. In other instances, the data instructs the electric motor to run at a faster speed during the staple firing stroke. Such an arrangement could be useful when the staple cartridge does not comprise an implantable adjunct releasably attached to the deck of the staple cartridge. Such an arrangement could also be useful when the staple cartridge comprises short staples, or staples less than approximately 2.5 mm in height before being deformed against the anvil, for example.

During various surgical procedures, surgical instruments comprising at least one replaceable component are used. It is important that such replaceable components be replaced with functional and/or compatible components. Various identification systems described in greater detail herein verify, among other things, a component's compatibility with the surgical instrument and/or verify an operating status of the component. For instance, the identification system can serve to, for example, ensure that the packaging containing the replaceable component has not been destroyed and/or tampered with, alert a clinician if a component is compatible or incompatible with the surgical instrument prior to opening the product packaging, and/or alert the clinician if a recall exists for a particular manufacturing batch or type of the replaceable component.

The identification systems described herein can either be active systems or passive systems. In various embodiments, a combination of active and passive identification systems are used. Passive systems can include, for example, a barcode, a quick response (QR) code, and/or a radio frequency identification (RFID) tag. Passive systems do not comprise an internal power source, and the passive systems described herein require a reader to send a first signal, such as, for example an interrogation signal.

The implementation of a barcode requires the use of an optical barcode reader and/or scanner. A barcode needs to be oriented properly relative to the scanner and the scanner needs to have an unobstructed view of the barcode in order for the barcode be properly scanned. For at least these reasons, the barcode is typically printed onto paper or plastic. The scanner decodes bars of the barcode which generally represent a series of numbers. The decoded information is sent to a computer, or a controller, which interprets what has been read. This information can contain data regarding, for example, the manufacturer of the replaceable component, a type or model of the replaceable component, and/or compatibility information of the replaceable component for use with a surgical instrument.

Another passive identification system comprises a quick response (QR) code. The QR code is a type of matrix barcode. QR codes often comprise data for a locator, identifier, or tracker that points to a website or an application for use on a mobile device. QR codes use four standardized encoding modes to efficiently store data. The four standardized encoding modes include numeric, alphanumeric, byte/binary, and kanji. A QR code consists of black squares arranged in a square grid on a white background, which is able to be read by an imaging device, such as a camera, for example. The captured image is processed using Reed-Solomon error correction until the captured image can be appropriately interpreted. The desired data is then extracted from patterns that are present in both horizontal and vertical components of the image. The desired data can comprise, for example, the manufacturer of the replaceable component, a type or model of the replaceable component, and/or compatibility information of the replaceable component and a surgical instrument.

Passive radio frequency identification (RFID) systems read information by using radio frequencies. Such passive RFID systems comprise an RFID scanner and an RFID tag with no internal power source. The RFID tag is powered by electromagnetic energy transmitted from the RFID scanner. Each RFID tag comprises a chip, such as a microchip, for example, that stores information about the replaceable component and/or a surgical instrument with which the replaceable component is compatible. While the chip may only contain a basic identification number, in various instances, the chip can store additional information such as, for example, the manufacturing data, shipping data, and/or maintenance history. Each RFID tag comprises a radio antenna that allows the RFID tag to communicate with the RFID scanner. The radio antenna extends the range in which the RFID tag can receive signals from the RFID scanner and transmit response signals back to the RFID scanner. In a passive RFID system, the RFID scanner, which also comprises its own antenna, transmits radio signals that activate RFID tags that are positioned within a pre-determined range. The RFID scanner is configured to receive the response signals that are "bounced back" from RFID tags, allowing the RFID scanner is to capture the identification information representative of the replaceable component. In various instances, the one or more response signals comprise the same signal as the interrogation signal. In various instances, the one or more response signals comprise a modified signal from the interrogation signal. In various instances, the RFID scanner is also able to write, or encode, information directly onto the RFID tag. In any event, software on the RFID scanner is able to pass information about the replaceable component to a controller, such as the control system of a surgical instrument, a surgical hub, and/or a remote surgical system. Various surgical hubs are described in described in U.S. patent application Ser. No. 16/209,395, titled METHOD OF HUB COMMUNICATION, and filed Dec. 4, 2018, issued as U.S. Pat. No. 11,659,023 on May 23, 2023, which is hereby incorporated by reference in its entirety. The RFID scanner is configured to read multiple RFID tags at once, as the RFID tags are activated by radio signals.

Active radio frequency identification (RFID) systems also comprise an RFID tag and an RFID scanner. However, the RFID tag in an active RFID system comprises an internal power source. Active RFID systems utilize battery-powered RFID tags that are configured to continuously broadcast their own signal. One type of active RFID tags is commonly referred to as a "beacon." Such beacon RFID tags do not wait to receive a first signal from an RFID scanner. Instead, the beacon RFID tag continuously transmits its stored information. For example, the beacon can send out its information at an interval of every 3-5 seconds. Another type of active RFID tag comprises a transponder. In such systems, the RFID scanner transmits a signal first. The RFID transponder tag then sends a signal back to the RFID scanner with the relevant information. Such RFID transponder tag systems are efficient, as they conserve battery life when, for example, the RFID tag is out of range of the RFID scanner. In various instances, the active RFID tag comprises an on-board sensor to track an environmental parameter. For example, the on-board sensor can track moisture levels, temperature, and/or other data that might be relevant.

Figure 78:
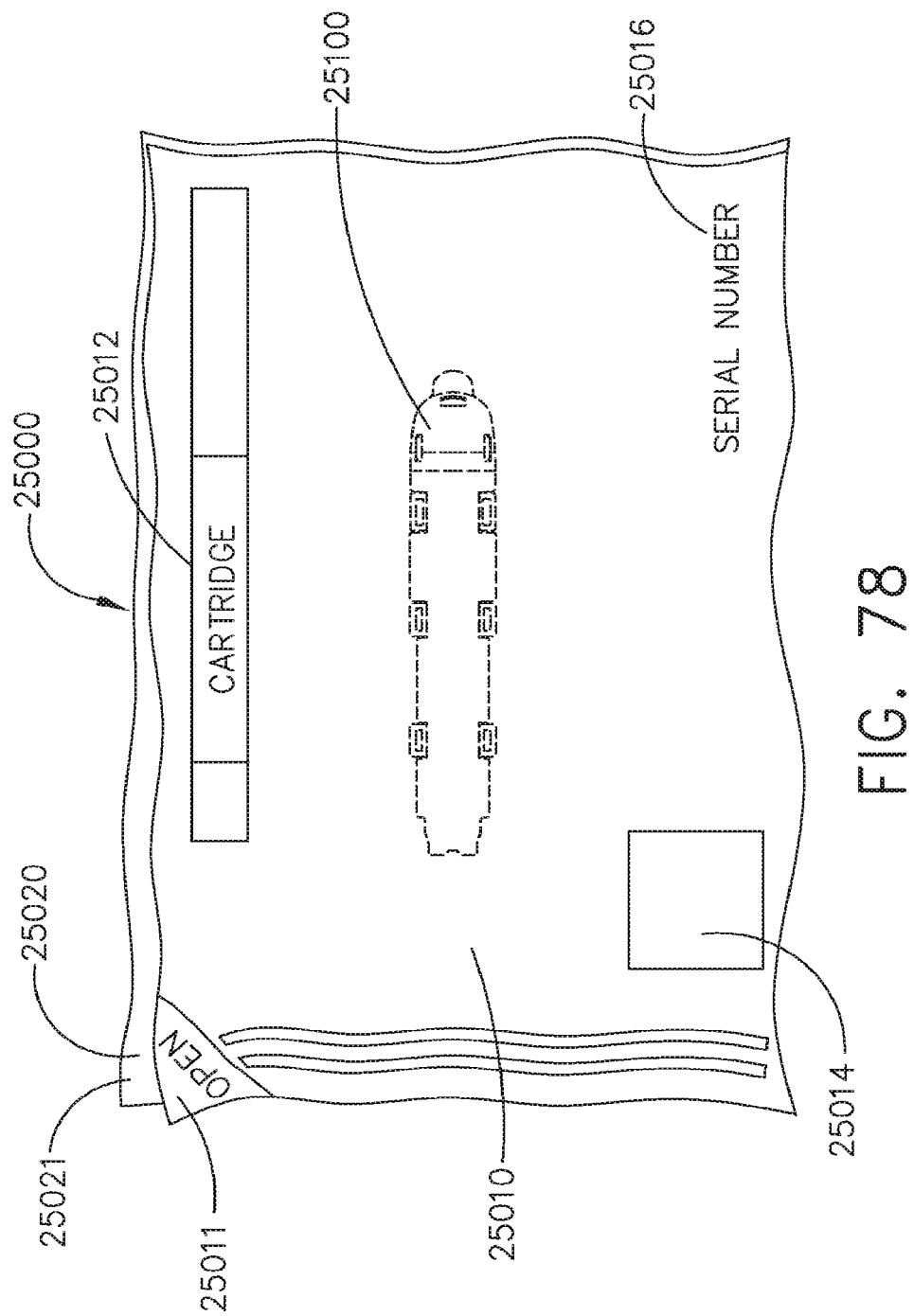
FIG. 78 is a perspective view of a surgical staple cartridge packaging, wherein the packaging comprises an identifying characteristic of the surgical staple cartridge contained therein.

Replacement staple cartridges are contained in a sealed packaging after being manufactured until the packaging is opened in the operating room. Various forms of packaging include, for example, peel-pouches, woven and/or non-woven material wrappers, and rigid containers. FIG. 78 depicts an example of a sealed packaging 25000. The depicted packaging 25000 is a peel-pouch. The packaging 25000 comprises a first layer 25010 and a second layer 25020. The first layer 25010 and the second layer 25020 form a protective barrier around a staple cartridge 25100, which is usable with a surgical instrument. An adhesive bonds the first layer 25010 and the second layer 25020 together to form an airtight and/or fluid-tight seal and/or pouch around an item. The adhesive forms a seal without creases, wrinkles, and/or gaps. The seal created by the adhesive prevents contaminants from coming into contact with the staple cartridge 25100 and/or prevents components of the staple cartridge 25100 from being misplaced, for example. In various instances, the staple cartridge 25100 is hermetically sealed within the packaging 25000. In various instances, the packaging 25000 provides a completely fluid-tight seal. In various instances, the packaging provides a completely fluid-tight and airtight seal.

The first layer 25010 comprises a first corner 25011 positioned outside of the seal, and the second layer 25020 comprises a second corner 25021 positioned outside of the seal. The clinician can expose the sealed staple cartridge 25100 by peeling the first layer 25010 apart from the second layer 25020. In various instances, the clinician can expose the sealed staple cartridge 25100 by holding the first corner 25011 and the second corner 25021 in separate hands and pulling the first corner 25011 in a direction away from the second layer 25021, although any suitable opening method could be used.

The first layer 25010 and the second layer 25020 are comprised of a material such as, for example, paper with a laminated inner surface. The laminated inner surface provides a barrier to prevent contaminants from entering the sealed portion of the packaging 25000. In various instances, the first layer 25010 and the second layer 25020 are comprised of plastic. The first layer 25010 and the second layer 25020 can be comprised of a material with a particular degree of transparency to allow a clinician, for example, to observe the contents of the packaging 25000. The above being said, any suitable material or combinations of materials can be used for the first layer 25010 and/or the second layer 25020.

The packaging 25000 comprises various identification systems that facilitate a surgical instrument and/or a clinician in selecting a staple cartridge 25100 that is compatible with a particular surgical instrument and/or a particular surgical procedure. The first layer 25010 of the packaging 25000 comprises various visual indicators that represent the contents of the packaging 25000 in some manner. For instance, as shown in FIG. 78, the name 25012 of the product contained within the packaging 25000 is printed, or otherwise displayed, on the first layer 25010.

The packaging 25000 further comprises one or more passive identification systems displayed on the first layer 25010. For example, the packaging 25000 comprises a QR code 25014. The QR code 25014 can assist, for example, in sorting and/or tracking a status of the packaging 25000. The QR code 25014 can also be scanned prior to breaking the seal of the packaging 25000 to ensure that the contents are appropriate for use with the particular instrument and/or during the particular surgical procedure.

In addition to the name 25012 of the contents of the packaging 25000 being displayed on the first layer 25010, the packaging 25000 comprises a serial number 25016 that can, for example, provide more detailed information that a clinician can utilize before deciding whether to open the packaging 25000. For example, the serial number 25016 may comprise alphanumeric symbols that are specific and/or unique to a surgical system. Each alphanumeric symbol can represent a component of a compatible assembled surgical system. For example, the alphanumeric symbols can represent a staple cartridge, an end effector, a shaft assembly, a surgical instrument, etc. The serial number 25016 can represent additional factors such as, manufacturing lot, date of manufacture, etc. In various instances, the serial number 25016 can comprise encrypted information as described in greater detail herein.

It is envisioned that the packaging 25000 can comprise some or all of the various forms of identification systems discussed herein.

Figure 79:
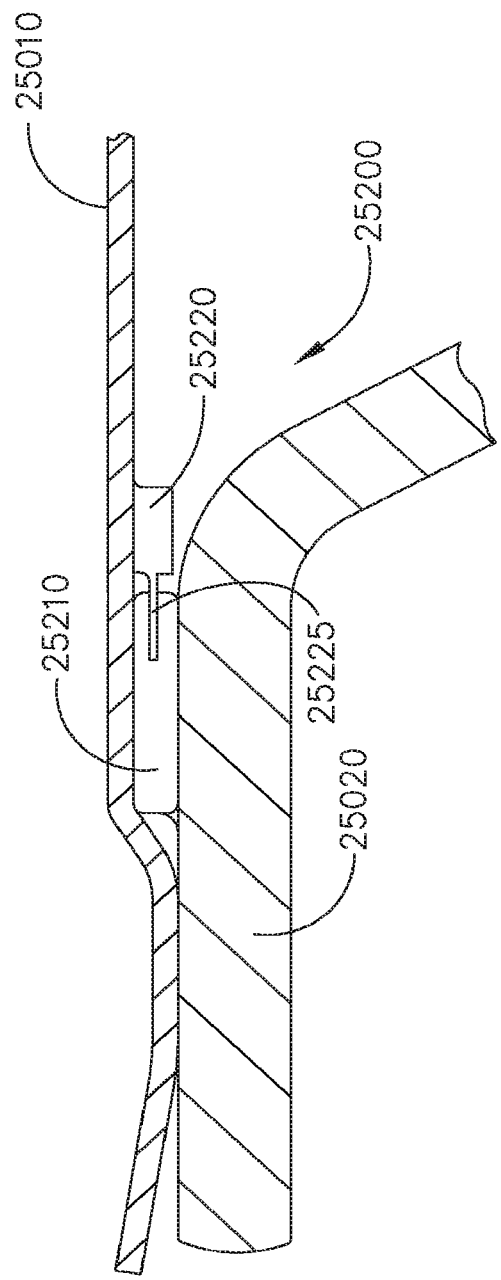
FIG. 79 is a partial cross-sectional view of an RFID system integrated with the packaging of FIG. 78 when the packaging is in a sealed configuration.
Figure 80:
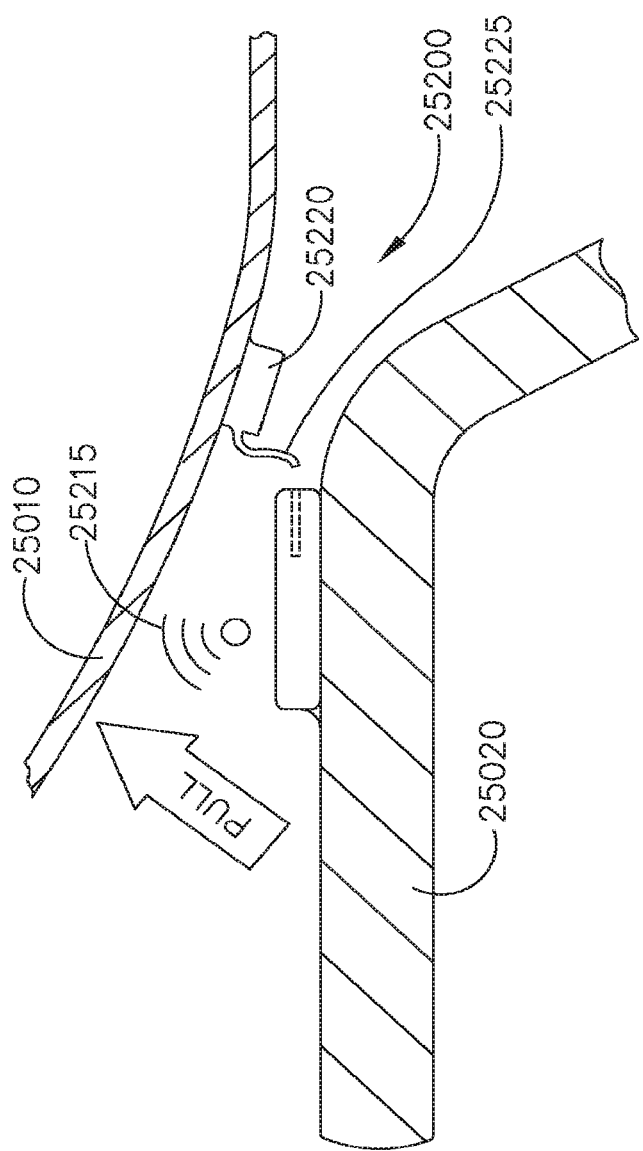
FIG. 80 is a partial cross-sectional view of the RFID system of FIG. 79 when the packaging is in an unsealed configuration.

FIGS. 79 and 80 depict an RFID system 25200 integrated with the packaging 25000. The RFID system 25200 comprises an RFID tag 25210 and an insulator 25220. The RFID tag 25210 comprises a chip, such as a microchip, for example, that stores information about the packaging 25000 and/or the contents of the packaging 25000. In various instances, the chip comprises a basic identification number. Such a basic identification can be assigned to the chip that can communicate the chip's existence to an RFID scanner. In various instances, the chip comprises additional information such as, for example, manufacturing data, shipping data, and/or compatibility data. The RFID tag 25210 further comprises a radio antenna configured to facilitate communication between the RFID tag 25210 and an RFID scanner.

The insulator 25220 is attached to the first layer 25010 of the packaging 25000, while the RFID tag 25210 is attached to the second layer 25020 of the packaging 25000. When the packaging is in a sealed configuration, the insulator 25220 is affixed to, or otherwise connected to, the RFID tag 25210. The RFID tag 25210 is part of an active RFID system 25200 that comprises an internal power source that is activated when the packaging 25000 is opened. Prior to the packaging 25000 being opened, the interface between the insulator 25220 and the RFID tag 25210 prevents the power source from providing power to the RFID tag 25210. In such instances, the RFID tag 25210 is unable to emit a signal.

When a clinician breaks the seal of the packaging 25000 by peeling the first layer 25010 away from the second layer 25020, the insulator 25220 is disconnected, or otherwise disassociated, from the RFID tag 25210. Upon disassociation of the insulator 25220 from the RFID tag 25210, the circuit between the power source and the RFID tag 25210 is closed, and the RFID tag 25210 is energized. As shown in FIG. 80, the RFID tag 25210 begins emitting a signal 25215 upon being energized. The RFID tag 25210 is configured to emit the signal 25215 at any appropriate frequency and/or for any appropriate duration. For example, the RFID tag 25210 can continuously emit the signal 25215 or the RFID tag 25210 can emit the signal 25215 every 3-5 seconds. The signal 25215 comprises some, or all, of the information stored on the chip. In various instances, the signal 25215 may serve to alert a surgical instrument that the packaging 25000 has been tampered with during shipping and/or storage or simply that the packaging 25000 has been unsealed, for example.

The RFID tag 25210 is configured to communicate with an RFID scanner. Once the insulator 25220 has been removed, the internal power source of the RFID tag 25210 allows the RFID tag 25210 to emit the signal 25215 prior to receiving a first signal, such as an interrogation signal, from the RFID scanner. The RFID scanner comprises a scanner antenna configured to transmit and/or receive radio signals 25215 from the RFID tag 25210. In various instances, the RFID scanner comprises reading and writing capabilities. Software on the RFID scanner is then able to pass the collected information from the RFID tag 25210 to a controller of the surgical instrument for further interpretation. The RFID scanner is positioned within a pre-determined range of the RFID tag 25210 that allows for the RFID scanner to be able to receive the emitted signal 25215 transmitted by the RFID tag 25210. Depending on the application, the RFID scanner can be positioned on a surgical instrument, on the contents of the packaging, or remotely located on a console, such as a remote surgical system in communication with the surgical instrument. Additionally, the controller can be located in any suitable location, such as, for example, the surgical instrument or on a remote console.

In various embodiments, an RFID system comprising an RFID tag mounted to the staple cartridge 25100 can be used. Further to the above, the RFID tag comprises an internal power source positioned within the staple cartridge 25100. Suitable locations for the RFID tag include, for example, on a sled of the staple cartridge, on a sidewall of the staple cartridge, or on a retainer of a staple cartridge assembly. An insulator, similar to the insulator 25220, is attached to the packaging 25000 and, when the packaging 25000 is opened, the RFID tag on the staple cartridge 25100 is activated. The insulator is attached to, or otherwise associated with, the first layer 25010 and/or the second layer 25020 of the packaging 25000. When the packaging is in a sealed configuration, the insulator 25220 is attached to, or otherwise connected to, the RFID tag in the staple cartridge 25100 and holds open the circuit between the power source and the RFID tag. The interface between the insulator 25220 and the RFID tag prevents the power source from activating the RFID tag, and the RFID tag is unable to emit a signal. When a clinician breaks the seal of the packaging 25000 by peeling away the first layer 25010, for example, the insulator 25220 is disconnected, or otherwise disassociated, from the RFID tag and the circuit between the power source and the RFID tag is closed. At such point, the RFID tag is energized and begins to emit a signal.

In various instances, the RFID system 25200 further comprises a transponder. The transponder is configured to receive a first signal from an RFID scanner. In various instances, the first signal from the RFID scanner energizes the transponder to a degree sufficient for the transponder to communicate with the RFID tag. In various instances, the transponder is energized prior to receiving the first signal from the RFID scanner. In any event, the transponder is configured to automatically transmit a second signal to the RFID tag upon hearing, or otherwise receiving, the first signal from the RFID scanner. The power source of the RFID tag energizes the RFID tag upon receiving the second signal from the transponder, and the RFID tag is able to respond to the RFID scanner's first signal by transmitting a third signal to the RFID scanner. The transponder preserves the battery life of the RFID tag 25210 until, for example, the RFID tag 25210 is within range of the RFID scanner.

As described in greater detail herein, it is valuable for a clinician to be able to verify the compatibility of a staple cartridge for use with a particular surgical instrument and/or for use during a particular surgical procedure. For various reasons, it can be also be meaningful for a clinician to be able to ensure that the surgical staple cartridge has not been previously used and/or tampered with. The clinician may also want to confirm, for example, that the surgical staple cartridge is not contaminated, a staple retaining member has not been removed, and/or that a firing member, such as a sled positioned in the cartridge body.

Figure 81:
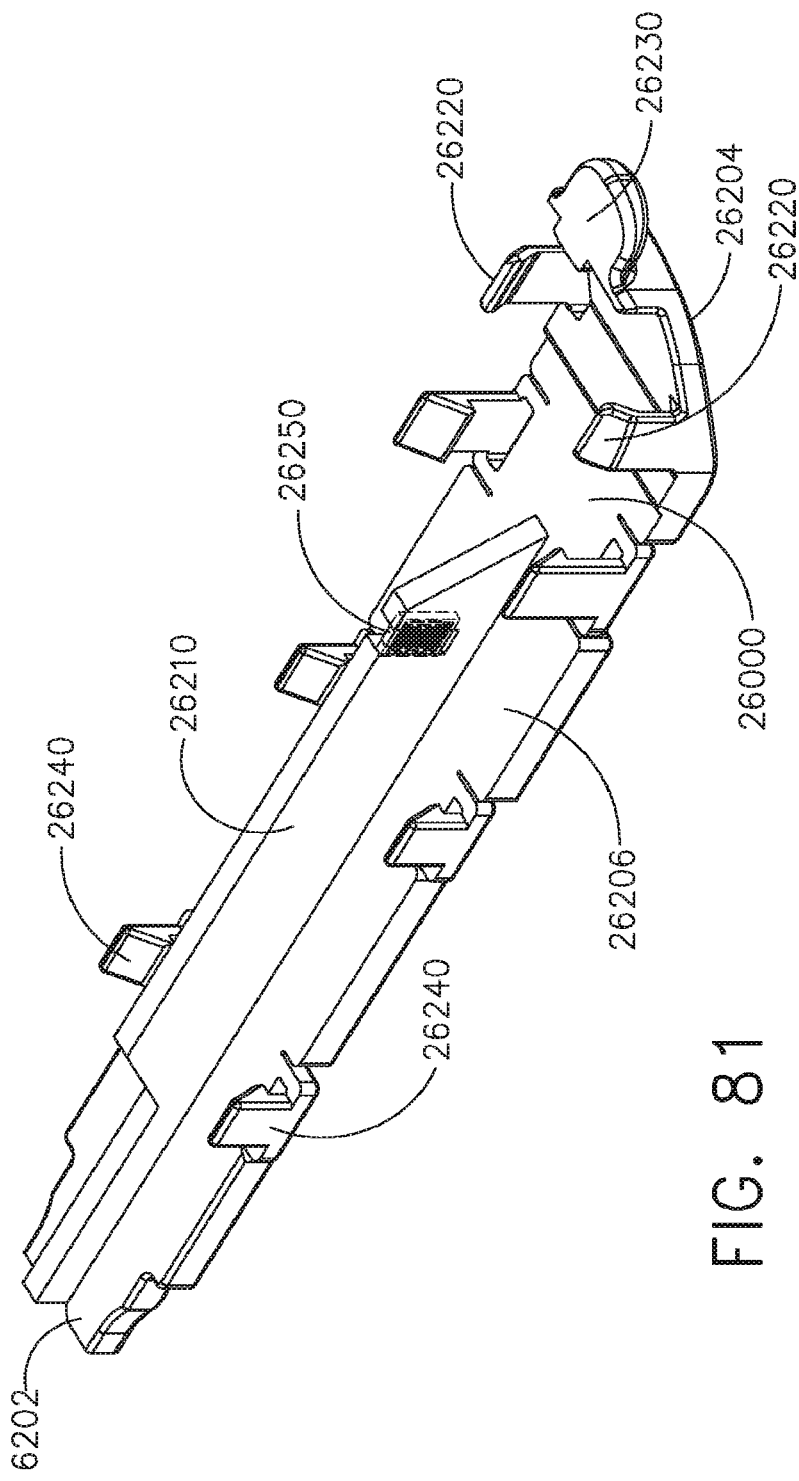
FIG. 81 is a perspective view of a retainer for use with a surgical staple cartridge, wherein the retainer comprises an integrated RFID tag.
Figure 82:
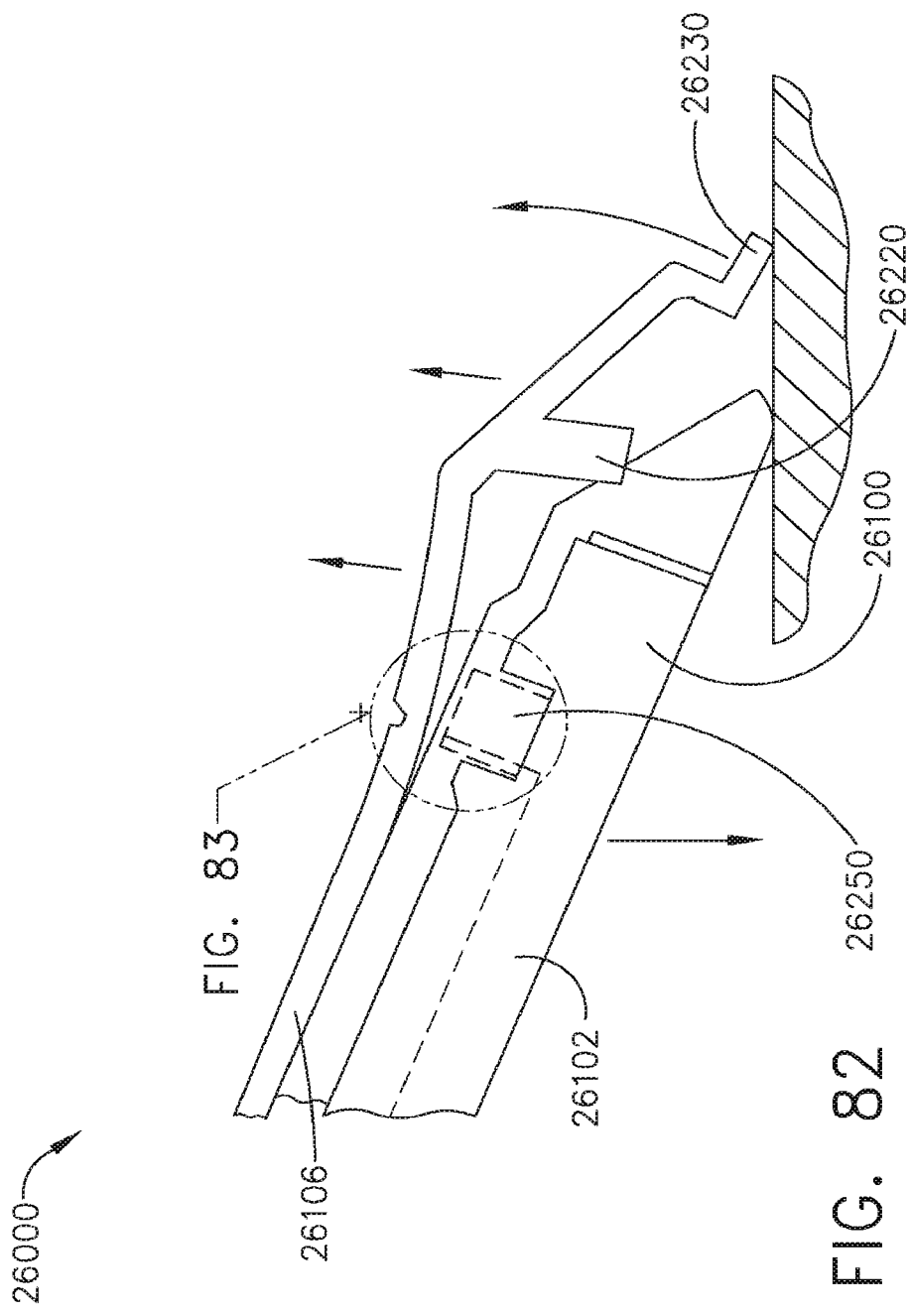
FIG. 82 is a perspective view of the retainer of FIG. 81 being removed from a surgical staple cartridge.
Figure 83:
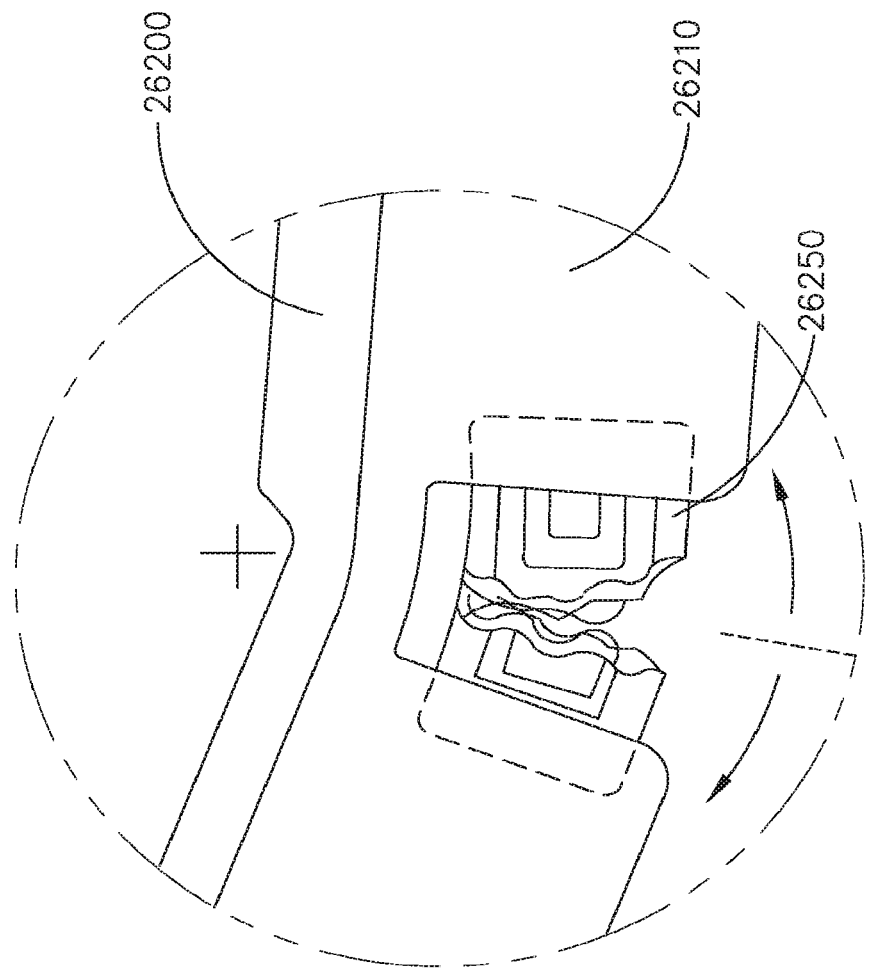
FIG. 83 is a detailed view of the RFID tag of FIGS. 81 and 82 as the retainer is removed from the surgical staple cartridge.

FIGS. 81-83 illustrate a staple cartridge assembly 26000. The staple cartridge assembly 26000 comprises a staple cartridge 26100 and a staple retaining member, or retainer, 26200 attached to the staple cartridge 26100. The retainer 26200 is positioned alongside the staple cartridge 26100 to, among other things, facilitate the attachment of the staple cartridge 26100 to a surgical instrument and/or to retain the staples within their respective staple cavities in the staple cartridge 26100. The retainer 26200 comprises a longitudinal projection 26210 configured to be received by an elongate slot defined in the staple cartridge 26100. The longitudinal projection 26210 projects from a bottom surface 26206 of the retainer 26200 and extends from a proximal end 26202 of the retainer 26200 toward a distal end 26204 of the retainer 26200. The retainer 26200 further comprises a proximal set of exterior projections 26240 and a distal set of exterior projections 26220. The exterior projections 26220, 26240 are configured to wrap around a portion of a sidewall 26102 of the staple cartridge 26100. The longitudinal projection 26210 and the exterior projections 26220, 26240 serve to, for example, hold the retainer 26200 to the staple cartridge 26100. The retainer 26200 comprises a thumb projection 26230 extending from the distal end 26204 to facilitate, for example, the removal of the retainer 26200 from the staple cartridge 26100.

When the retainer 26200 is attached to the staple cartridge 26100, the bottom surface 26206 of the retainer 26200 is positioned alongside a deck surface 26106 of the staple cartridge 26100. In various instances, the bottom surface 26206 does not contact the deck surface 26106 of the staple cartridge 26100 until a pushing force is applied to the top of the retainer 25200. In other instances, the bottom surface 20206 is in contact with the deck surface 26106. To remove the retainer 26200 from the staple cartridge 26100, and thus facilitate the attachment of the staple cartridge 26100 to a surgical instrument, a clinician pulls, or lifts, the thumb projection 26230 in a direction away from the staple cartridge 26100. The retainer 26200 is manufactured from a material, such as plastic, for example, that provides a degree of flexibility to the retainer 26200. As the thumb projection 26230 is being lifted away from the staple cartridge 26100, the exterior projections 26220, 26240 provide opposing forces in an effort to maintain the connection between the retainer 26200 and the staple cartridge 26100. In order to remove the retainer 26200, the clinician must exert a force on the thumb projection 26230 that is strong enough to overcome the opposing retention forces produced by the exterior projections 26220, 26240. As the thumb projection 26230 is pulled away from the staple cartridge 26100, the retainer 26200 begins to flex and/or bend, such bending of the retainer 26200 can be used to deactivate a RFID tag, as described below.

The retainer 26200 further comprises an RFID tag 26250. The RFID tag 26250 comprises a chip, such as a microchip, for example, that stores information about the staple cartridge assembly 26000. As shown in FIGS. 81-83, the RFID tag 26250 is molded into the retainer 26200. However, the RFID tag 26250 can be embedded within, mounted to, and/or attached to the retainer 26200 by any suitable method. In the depicted embodiment, the RFID tag 26250 is molded into a distal portion of the longitudinal projection 26210. The RFID tag 26250 is positioned within the retainer 26200 at a structurally weak location. The structurally weak location can be any portion of the retainer 26200 that bends and/or flexes in response to the upward pulling of the thumb projection 26230 and/or removal of the retainer 26200 from the staple cartridge 26100. The RFID tag 26250 is affixed to the retainer 26200 in a manner and a location that facilitates physical destruction of the RFID tag 26250 during the retainer removal process. A first end 26252 of the RF ID tag 26250 is attached to a first portion 26212 of the retainer 26200, and a second end 26254 of the RFID tag 26250 is attached to a second portion 26214 of the retainer 26200. As the retainer 26200 begins to bend in response to upward pulling on the thumb projection 26230, the first portion 26212 of the retainer 26200 and the second portion 26214 of the retainer flex apart from one another. The first end 26252 of the RFID tag 26250 is pulled by the first portion 26212 of the retainer 26200, and the second end 26254 of the RFID tag 26250 is pulled in an opposite direction by the second portion 26214 of the retainer 26200. As a result of the stretching and/or flexing, the RFID tag 26250 is pulled apart and/or otherwise destroyed. The RFID tag 26250 is frangible, brittle, and/or fragile and is not configured to stretch significantly. It is envisioned that the RFID tag 26250 can be positioned at any suitable location on the retainer 26200 that experiences sufficient bending and flexing during the removal process of the retainer 26200 from the staple cartridge 26100 to cause destruction of the RFID tag 26250. The RFID tag 26250 can be affixed to the retainer 26200 in any suitable manner that renders the RFID tag 26250 inoperable during and/or after the removal of the retainer 26200 from the staple cartridge 26100. In various embodiments, the RFID tag 26250 can disassociate, or become detached, from the retainer 26200 during the removal process.

In various instances, breaking a component of a surgical system is undesirable. However, the destruction of the RFID tag 26250 in the retainer 26200 prevents a clinician from reusing the retainer 26200 with incompatible, or otherwise inappropriate, staple cartridges. Prior to enabling at least one operating parameter of a surgical instrument, a controller of the surgical instrument must receive a signal from the RFID tag 26250 on the retainer 26200. Such a signal indicates to the controller that the retainer 26200 remains connected to the staple cartridge 26100. In various instances, the signal can also indicate that the staple cartridge 26100 is compatible or incompatible with the surgical instrument. Without receiving the signal and/or receiving an incompatible signal, various functions of the surgical instrument are unavailable. In various instances, and as described below, the RFID tag 26250 in the retainer 26200 must lose the ability to send and/or transmit signals with the RFID scanner. The RFID tag 26250 can lose the ability to communicate through physical destruction and/or positioning of the RFID tag 26250 outside of the range of the RFID scanner. In any event, the inability for the RFID tag 26250 to communicate with the RFID scanner indicates to the controller of the surgical instrument that the retainer 26200 is no longer connected to the staple cartridge 26100. The physical destruction of the RFID tag 26250 on the retainer 26200 ensures that a clinician is unable to reuse the retainer 26200 on an incompatible staple cartridge. In various instances, the staple cartridge 26100 comprises an RFID tag that is in the communication range of the RFID scanner. When the controller receives information detected from the staple cartridge RFID tag but not the retainer RFID tag 26250, the controller is configured to recognize that the staple cartridge 26100 remains attached to the surgical instrument, but the retainer 26200 was removed.

The RFID tag 26250 in the retainer 26200 provides a lockout for the surgical instrument. The surgical instrument will not perform a staple firing stroke if the information stored on the RFID tag 26250 is not received by a controller of the surgical instrument. In various instances, the surgical instrument will not perform a staple firing stroke when the RFID tag 26250 is still in communication with the RFID scanner. Such a lockout prevents the surgical instrument from performing a staple firing stroke when the staple cartridge 26100 has been inappropriately seated in the surgical instrument with the retainer 26200 still attached.

In various instances, the staple cartridge 26100 and the retainer 26200 are assembled into the staple cartridge assembly 26000 by a manufacturer. In such circumstances, the retainer 26200 is removed from the staple cartridge 26100 only when the staple cartridge 26100 has been inserted for use with a surgical instrument, the staple cartridge assembly 26000 has been tampered with, and/or there was a manufacturing defect inhibiting proper attachment. Disassociation and/or physical destruction of the RFID tag 26250 prevents, for example, placement of a retainer 26200 on a used and/or otherwise inappropriate staple cartridge 26100.

As mentioned in greater detail herein, a surgical instrument can comprise an RFID scanner configured to communicate with nearby RFID tags. The RFID scanner comprises a scanner antenna configured to transmit radio signals. The radio signals activate RFID tags that are positioned within a pre-determined range of the RFID scanner. The RFID scanner then receives one or more response signals that are "bounced back" from the RFID tag. In various instances, the one or more response signals comprise the same signal as the interrogation signal. In various instances, the one or more response signals comprise a modified signal from the interrogation signal. In various instances, the RFID scanner comprises reading and writing capabilities. Software on the RFID scanner is then able to pass the collected information from the RFID tag to a controller for further interpretation. The controller can be positioned in the surgical instrument, the remote console, or in any suitable location. The RFID scanner and/or the controller can comprise a stored set of information that corresponds to surgical stapling assemblies that are compatible with a particular surgical instrument and/or for use during a particular surgical procedure.

More specifically, the surgical system comprises an RFID scanner configured to interact with the RFID tag 26250 molded into the retainer 26200. The RFID scanner can be present in various locations. For example, the RFID scanner can be located in the staple cartridge 26100. In various instances, the RFID scanner can be located in a jaw of an end effector of a surgical instrument, in an alternative location within the surgical system, and/or any other suitable location that would allow for communication between the RFID tag 26250 and the RFID scanner when the retainer 26200 is appropriately attached to the staple cartridge 26100. The RFID scanner and/or the RFID tag 26250 are powered such that the signal(s) they emit can only be detected within a limited radius. The RFID scanner and the RFID tag 26250 are close enough to be in communication when the retainer 26200 is attached to the staple cartridge 26100, but are not close enough to communicate when the retainer 26200 is removed from the staple cartridge 26100. That said, as the retainer 26200 is removed from the staple cartridge 26100, the RFID tag 26250 is rendered inoperable through, for example, physical destruction or disassociation. When the RFID tag 26250 is inoperable, the signals, such as interrogation signals, sent by the RFID scanner go unanswered.

If a used retainer having a destroyed RFID tag 26250 is attached to another staple cartridge, the RFID scanner and the destroyed RFID tag 26250 will be unable to communicate. In such instances, the staple cartridge verification system of the surgical instrument will be unable to permit the surgical instrument to perform a staple firing stroke. If the RFID scanner receives a response to the interrogation signal that is not found within a stored set of compatible stapling assemblies, the controller of the surgical instrument is programmed to communicate an error to the clinician. Likewise, if the RFID scanner does not receive a response to the interrogation signal, the controller of the surgical instrument is programmed to communicate an error to the clinician. In various instances, the detection of an error by the controller can render the surgical instrument inoperable for use with that particular staple cartridge. In various instances, a detected error can prevent the surgical instrument from performing a staple firing stroke and/or tissue cutting stroke. In various instances, the surgical instrument further comprises a manual override that can be activated to allow a clinician to override any system lockout and utilize operational functions of the surgical instrument in an emergency. As discussed above, the controller is configured to alert the clinician that an error has been detected. Such an alert can be communicated through various forms of feedback, including, for example, haptic, acoustic, and/or visual feedback. In at least one instance, the feedback comprises audio feedback, and the surgical instrument can comprise a speaker which emits a sound, such as a beep, for example, when an error is detected. In certain instances, the feedback comprises visual feedback and the surgical instrument can comprise a light emitting diode (LED), for example, which flashes when an error is detected. In various instances, the feedback comprises haptic feedback and the surgical instrument can comprise an electric motor comprising an eccentric element which vibrates when an error is detected. The alert can be specific or generic. For example, the alert can specifically state that the RFID tag 26250 on the retainer 26200 is unable to be detected, or the alert can specifically state that the RFID tag 26250 comprises information representative of an incompatible and/or defective staple cartridge assembly 26000.

Figure 84:
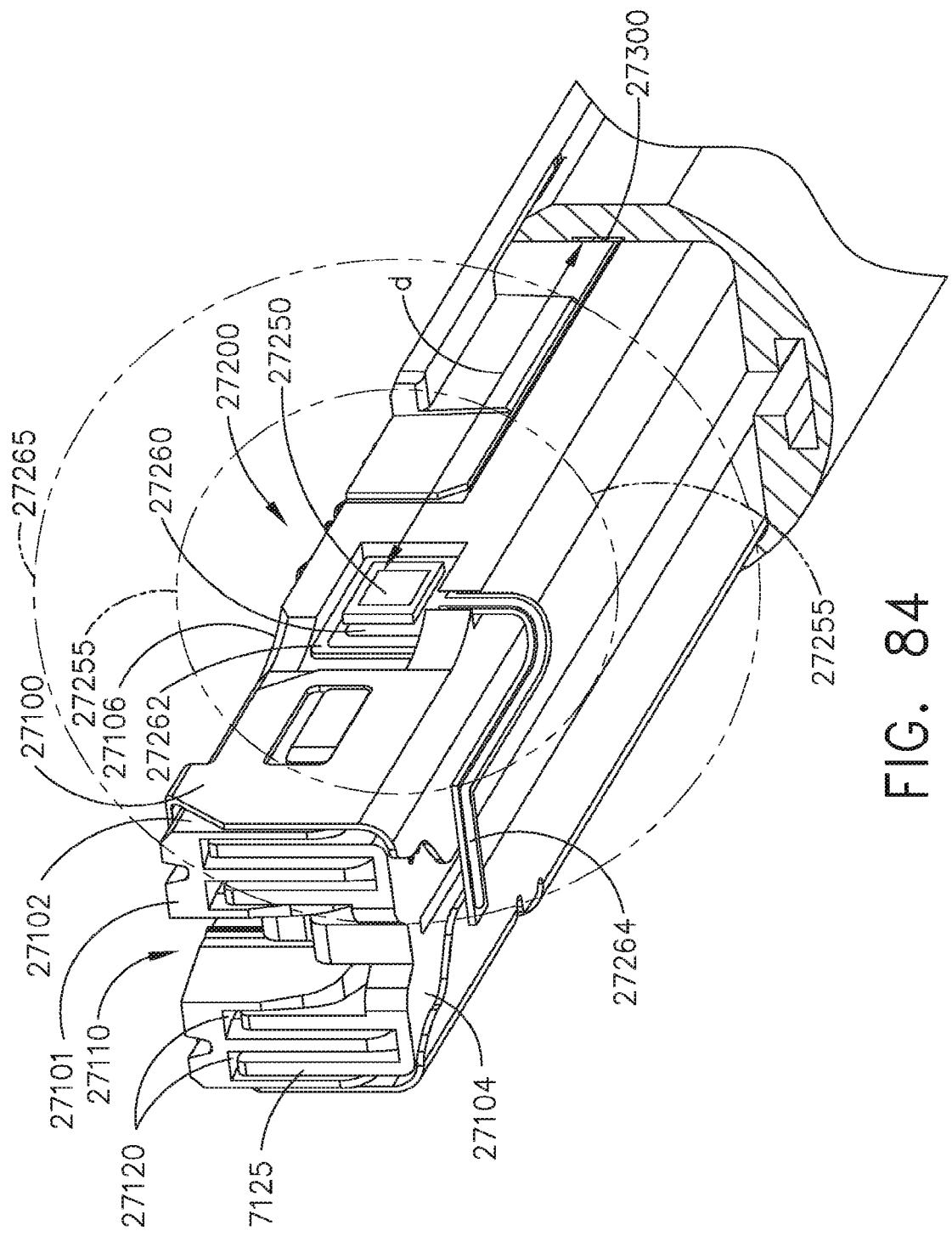
FIG. 84 is a partial perspective view of a surgical staple cartridge comprising an RFID system comprising an extended antenna, wherein a portion of the extended antenna traverses a cutting path of a tissue cutting member.

FIG. 84 illustrates a staple cartridge assembly 27000. The staple cartridge assembly comprises a staple cartridge 27100. The staple cartridge 27100 comprises a staple cartridge body including a base 27104, a deck surface 27106, and sidewalls 27102 extending between the base 27104 and the deck surface 27106. An elongate slot 27110 is defined in the staple cartridge 27100 and extends from a proximal end 27101 toward a distal end of the staple cartridge 27100. The elongate slot 27100 is sized to facilitate a firing and/or cutting member to pass there through, such as a sled 27125, during a staple firing stroke. Channels 27120 are defined within the staple cartridge 27100 that extend from the proximal end 27101 toward the distal end of the staple cartridge 27100. Each channel 27120 is configured to receive a ramp of a sled 27125. The staple cartridge 27100 further comprises longitudinal rows of staple cavities defined in the cartridge body and staples removably stored in the staple cavities. The staples are ejected from the staple cartridge 27100 by the sled 27125 during the staple firing stroke.

The staple cartridge assembly 27000 further comprises an RFID system 27200. The RFID system 27200 comprises an RFID tag 27250 mounted to the staple cartridge assembly 27000 and an RFID scanner 27300 mounted to the surgical instrument. The RFID tag 27250 comprises a chip, such as a microchip, for example, that stores information about the staple cartridge assembly 27000. In various instances, the chip comprises a basic identification number of the staple cartridge 27100. In various instances, the chip comprises additional information such as, for example, manufacturing data, shipping data, and/or compatibility data. The RFID tag 27250 further comprises a radio antenna configured to receive an interrogation signal from and send a response signal to the RFID scanner 27300. The RFID scanner 27300 is configured to communicate with the RFID tag 27250 when the staple cartridge 27100 is seated in the surgical instrument. The RFID scanner 27300 comprises a scanner antenna configured to transmit and receive radio signals, for example. That said, the RFID system 27200 can use any suitable frequency. As electromagnetic waves behave differently at the various frequencies, the desired frequency is selected based on the particular application. In various instances, the RFID system 27200 can utilize low frequencies, high frequencies, and/or ultra-high frequencies. The radio signals activate RFID tags that are positioned within a pre-determined range of the RFID scanner 27300. The RFID scanner 27300 then receives one or more response signals that are "bounced back" from the RFID tag. In various instances, the one or more response signals comprise the same signal as the interrogation signal. In various instances, the one or more response signals comprise a modified signal from the interrogation signal. In various instances, the RFID scanner 27300 comprises reading and writing capabilities. Software on the RFID scanner 27300 is then able to pass the collected information from the RFID tag to a controller for further interpretation. The controller can be positioned in the surgical instrument, on a remote console, or in any suitable location. The RFID scanner and/or the controller can comprise a stored set of information that corresponds to surgical stapling assemblies that are compatible with a particular surgical instrument and/or a particular surgical procedure.

As discussed above, the RFID scanner 27300 in the surgical instrument is configured to interact with the RFID tag 27250 positioned on the staple cartridge 27100. As shown in FIG. 84, the RFID tag 27250 is affixed to one of the sidewalls 27102 of the staple cartridge 27100 and the RFID scanner 27300 is mounted within the surgical instrument. As described above, the RFID tag 27250 comprises a radio antenna 27252 and a chip 27254. In the depicted embodiment, the radio antenna 27252 and the chip 27254 are positioned within the RFID tag 27250. In various instances, the radio antenna 27252 is positioned on an exterior surface of the RFID tag 27250. The RFID tag 27250 is positioned a distance "D" away from the RFID scanner 27300 when the staple cartridge 27100 is seated in the surgical instrument. Notably, the distance "D" can be approximately ¼ of the length of the staple cartridge 27100, ⅓ of the length of the staple cartridge 27100, or ½ of the length of the staple cartridge 27100, for example. In the depicted embodiment, the communication range 27255 of the RFID tag's radio antenna and the RFID scanner's antenna spans approximately 1 centimeter (cm), for example. The distance "D" is greater than 1 cm, and thus, is outside of the range of communication 27255 between the RFID scanner 27300 and the radio antenna 27252 of the RFID tag 27250. As such, the RFID tag 27250 is unable to receive interrogation signals and respond to interrogation signals from the RFID scanner 27300 absent more.

In order to facilitate communication with the RFID scanner 27300, the RFID tag system 27200 depicted in FIG. 84 further comprises an extended antenna 27260 in communication with the RFID tag 27250. The extended antenna 27260 serves to, for example, broaden the range of communication of the RFID tag 27250 as compared to the radio antenna 27252. The extended antenna 27260 extends along, and is attached to, the sidewall 27102 and across a portion of the base 27104 of the staple cartridge 27100. At least a portion of the extended antenna 27260 traverses the elongate slot 27110. In the depicted embodiment, the communication range 27265 of the extended antenna 27260 spans approximately 2 centimeters (cm), for example. As previously discussed, the RFID scanner 27300 is positioned at a distance "D" from the RFID tag 27250. While the distance "D" is greater than 1 cm, the distance "D" is less than 2 cm, and thus, is within the range of communication 27265 by way of the extended antenna 27260 and the RFID scanner antenna. With the extended antenna 27260, the RFID tag 27250 is able to receive interrogation signals and respond to interrogation signals from the RFID scanner 27300. Without the extended antenna 27260, however, the RFID tag 27250 could not communicate with the RFID scanner 27300. The RFID tag 27250 and the extended antenna 27260 can be attached to the staple cartridge 27100 in any suitable manner, including, for example, mounted on, embedded within, and/or affixed to the staple cartridge 27100. Furthermore, the RFID tag 27250 can be positioned at any suitable location on the staple cartridge 27100, such as on the base 27104 and/or the deck surface 27106, for example.

As previously discussed, at least a portion of the extended antenna 27260 traverses the elongate slot 27110 of the staple cartridge 27100. During a staple firing stroke, a tissue cutting and/or staple firing member is configured to longitudinally translate through the elongate slot 27110 during the staple firing stroke and, in the process, transect, or otherwise destroy, the extended antenna 27260. The portion of the extended antenna 27260 that traverses the elongate slot 27110 is positioned at a location proximal to the proximal-most staple cavities. As such, the extended antenna 27260 is only functional prior to the commencement of a staple firing stroke. Any distal movement of a tissue cutting and/or staple firing member that results in the firing of staples renders the extended antenna 27260 inoperable. The extended antenna 27260 can be rendered inoperable in any suitable manner. For example, the extended antenna 27260 can be cut, and thus, physically destroyed, by the tissue cutting member. In various instances, the extended antenna 27260 can disassociate from the RFID tag 27250 and/or the staple cartridge 27100 in response to forces exerted by the tissue cutting and staple firing member. Notably, the staple firing stroke does not damage the radio antenna 27252 of the RFID tag 27250. However, the range of the radio antenna 27252 is insufficient to facilitate communication between the RFID tag 27250 and the RFID scanner 27300. As such, disassociation of the extended antenna 27260 can alter the communication range 27265 of the RFID tag 27250 and remove the ability for the RFID tag 27250 to communicate with the RFID scanner 27300.

Destroying the extended antenna 27260 in this manner does not negatively impact the operation of the surgical instrument. Stated another way, the extended antenna 27260 is not destroyed until after the staple cartridge 271000 has been authenticated. As such, the staple firing stroke can be performed after the extended antenna 27260 has been destroyed. That said, once the extended antenna 27260 has been destroyed and the staple cartridge 27100 has been removed from the surgical instrument, reseating the staple cartridge 27100 in the surgical instrument will not re-authenticate the staple cartridge 27100 as the RFID scanner can no longer communicated with the RFID tag 27250. Such an arrangement serves as a spent cartridge lockout, among other things.

As discussed above, in instances where the extended antenna 27260 is inoperable, the RFID scanner 27300 does not receive a response to its interrogation signal. When the RFID scanner 27300 does not receive a response to the interrogation signal, the controller of the surgical instrument is programmed to recognize an error. In instances where the RFID scanner 27300 receives a response to its interrogation signal that is unable to be recognized and/or does not signify a compatible staple cartridge assembly 27000, the controller of the surgical instrument is also programmed to recognize an error. In various instances, the detection of error by the controller can render the surgical instrument inoperable for use with the staple cartridge assembly 27000. In various instances, a detected error can prevent the surgical instrument from performing a staple firing stroke and/or tissue cutting stroke when the staple cartridge assembly 27000 is attached to the surgical instrument. A manual override can be activated to allow a clinician to override any system lockout and utilize operational functions of the surgical instrument in an emergency. In various instances, the controller is configured to alert the clinician that an error has been detected. Such an alert can be communicated through various forms of feedback, including, for example, haptic, acoustic, and/or visual feedback. The alert can be specific or generic. For example, the alert can specifically state that the RFID tag 27250 is unable to be detected, or the alert can specifically state that the RFID tag 27250 comprises information representative of an incompatible and/or defective staple cartridge assembly 27000.

The portion of the extended antenna 27260 that traverses the elongate slot 27110 can be located at any suitable position along the elongate slot 27110. For example, the extended antenna 27260 can traverse the elongate slot 27110 at a location in line with or slightly proximal to the distal-most staple cavities. In such an embodiment, as the tissue cutting and staple firing stroke is completed, the extended antenna 27260 is rendered inoperable. When the RFID scanner 27300 is unable to communicate with the RFID tag 27250 in this scenario, the clinician would be able to, for example, confirm that an entire staple firing stroke was completed. Furthermore, the RFID tag 27250 can be positioned at any suitable location on the staple cartridge 27100, such as, for example, on the base 27104 and/or the deck surface 27106 of the staple cartridge 27100.

In various instances, the extended antenna 27260 comprises a first antenna that is configured to traverse the elongate slot 27110 of the staple cartridge 27100 and a second antenna that does not traverse the elongate slot 27110 of the staple cartridge 27100. In other words, the second antenna is not transected by the firing member during the staple firing stroke. When the first antenna is transected by the firing member, the communication range of the RFID tag 27250 is diminished. However, the communication range of the RFID tag 27250 can be bolstered using the first antenna that was not transected by the firing member during the staple firing stroke.

Figure 85:
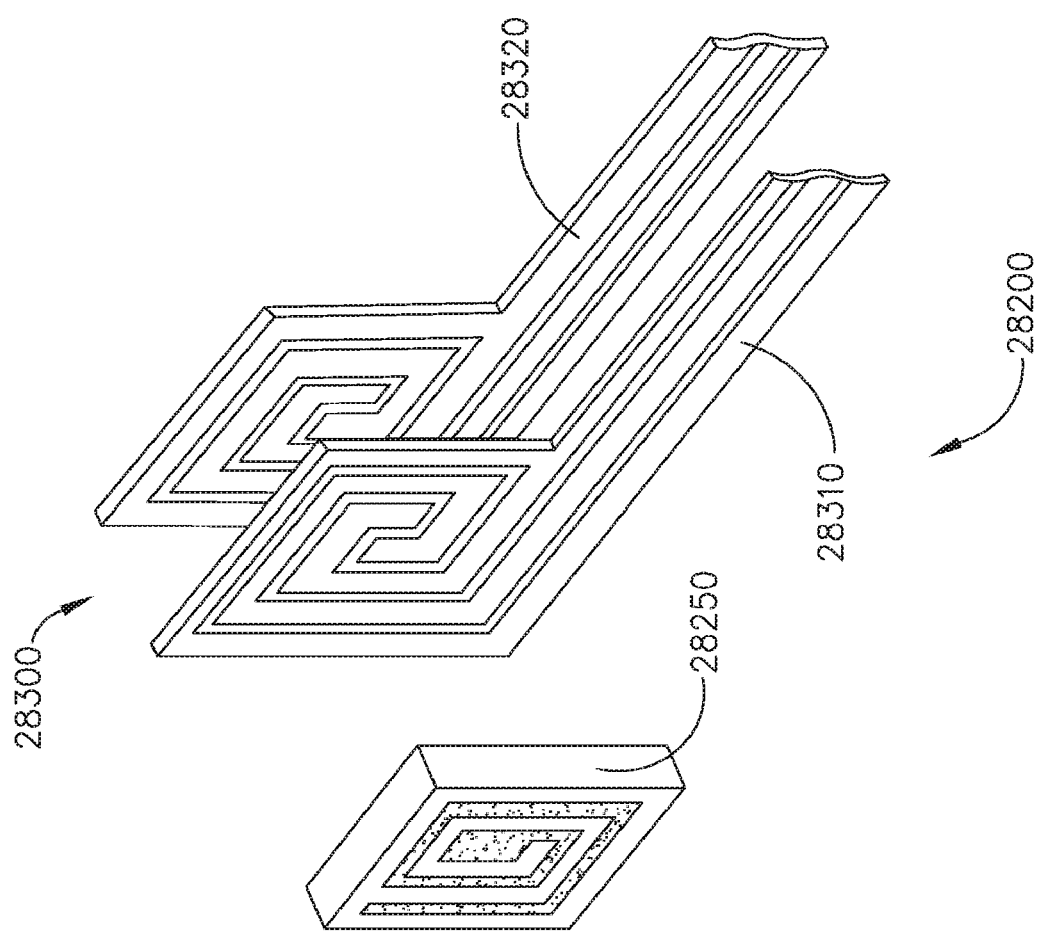
FIG. 85 is an RFID system comprising an RFID tag, a first RFID scanner integrated into a first flex circuit layer, and a second RFID scanner integrated into a second flex circuit layer.

FIG. 85 depicts an exemplary RFID system 28200 that can be incorporated into a surgical instrument, such as the surgical instrument 400 discussed herein, for example. The RFID system 28200 can be integrated into, for example, a staple cartridge, an end effector jaw, and/or any other suitable location within the surgical instrument. The RFID system 28200 comprises an RFID tag 28250 and an RFID scanner system 28300. The structure and functionality of the RFID tag 28250 is similar to the RFID tags discussed herein, such as the RFID tags 26250, 27250, for example. The RFID scanner system 28300 comprises a first RFID scanner 28310 and a second RFID scanner 28320. The functionality of the RFID scanners 28310, 28320 is similar to other RFID scanners discussed herein, such as the RFID scanner 27300, for example.

The RFID tag 28250 comprises a chip, such as a microchip, for example, that stores information about a replaceable component within the surgical system. In various instances, the chip comprises an identification number of a staple cartridge. In various instances, the chip comprises additional information such as, for example, the manufacturing data, shipping data, and/or other compatibility data of the staple cartridge. The RFID tag 28250 further comprises a radio antenna configured to receive an interrogation signal from one and/or both of the RFID scanners 28310, 28320.

Each RFID scanner 28310, 28320 comprises a scanner antenna configured to transmit radio signals. The radio signals activate the RFID tag 28250 that is positioned within a pre-determined range of the RFID scanner 28310. The RFID scanner 28310, then receives one or more response signals that are "bounced back" from the RFID tag 28250. In various instances, the one or more response signals comprise the same signal as the interrogation signal. In various instances, the one or more response signals comprise a modified signal from the interrogation signal. The second RFID scanner 28320 is also configured to transmit a signal to the RFID tag 28250.

In various instances, the RFID scanner 28310 comprises reading and writing capabilities. Software on the RFID scanner 28310 is then able to pass the collected information from the RFID tag 28250 to a controller for further interpretation. The controller can be positioned in the surgical instrument, on a remote console, or in any suitable location. The second RFID scanner 28320 could also be used in this way.

The RFID scanner system 28300 comprises a flex circuit, wherein the flex circuit comprises a first layer and a second layer. The first layer functions as a first RFID scanner 28310, and the second layer functions as a second RFID scanner 28320. The RFID scanners 28310, 28320 further comprise an RF amplifier which determines the power of the signal to be transmitted by the RFID scanners 28310, 28320 and amplifies the interrogation signal to the desired power level.

When energized, the first layer 28310 is configured to transmit a signal 2815 with approximately 1 watt of power, or less. When energized, the second layer 28320 is configured to send a signal 28325 with more than 1 watt of power. In fact, the amplifier is in communication with the controller of the surgical instrument and, as described in greater detail below, the signal of the second RFID scanner 28320 can be transmitted with power well in excess of 1 watt.

Figure 86:
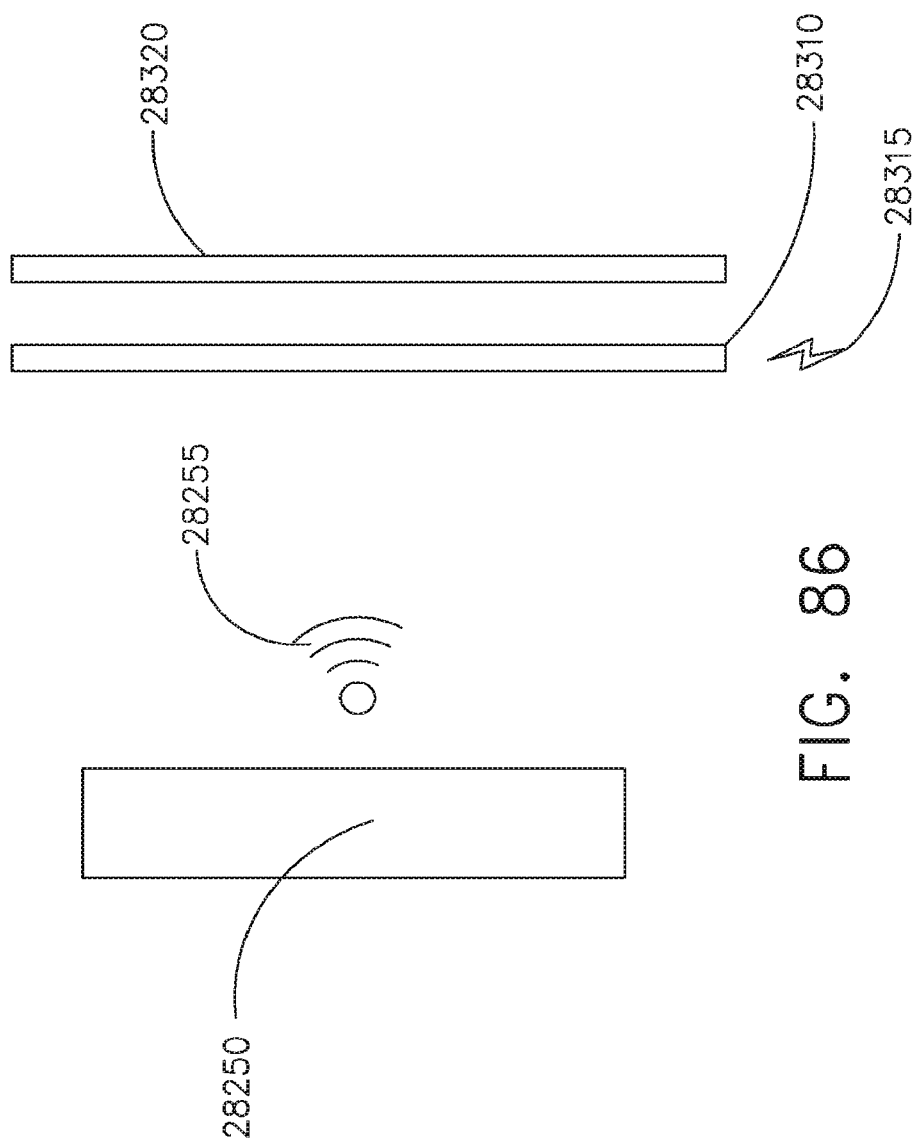
FIG. 86 is a representation of the communication pathways of the RFID system of FIG. 85 prior to a staple firing stroke.

Prior to a staple firing stroke, the first RFID scanner 28310 is energized. As shown in FIG. 86, the first RFID scanner 28310 sends an interrogation signal 28315 to the RFID tag 28250. The RFID tag 28250 receives the energy, or interrogation signal 28315, using the radio antenna of the RFID tag 28250. The received energy travels through the tag's antenna, and a portion of the received energy is used to activate the chip and prepare for transmission of data based on commands received from the first RFID scanner 28310. The activation of the chip allows the chip to modulate the received energy with the information stored in the RFID tag 28250 and "reflect" the remaining energy back in the form of a response signal 28255. The chip transmits a response signal 28255 that is the same as and/or different than the interrogation signal back to the RFID scanner 28310. The response signal 28255 is received by the first RFID scanner's antenna in order for the first RFID scanner 28310 to recover the information stored on the RFID tag 28250.

Figure 87:
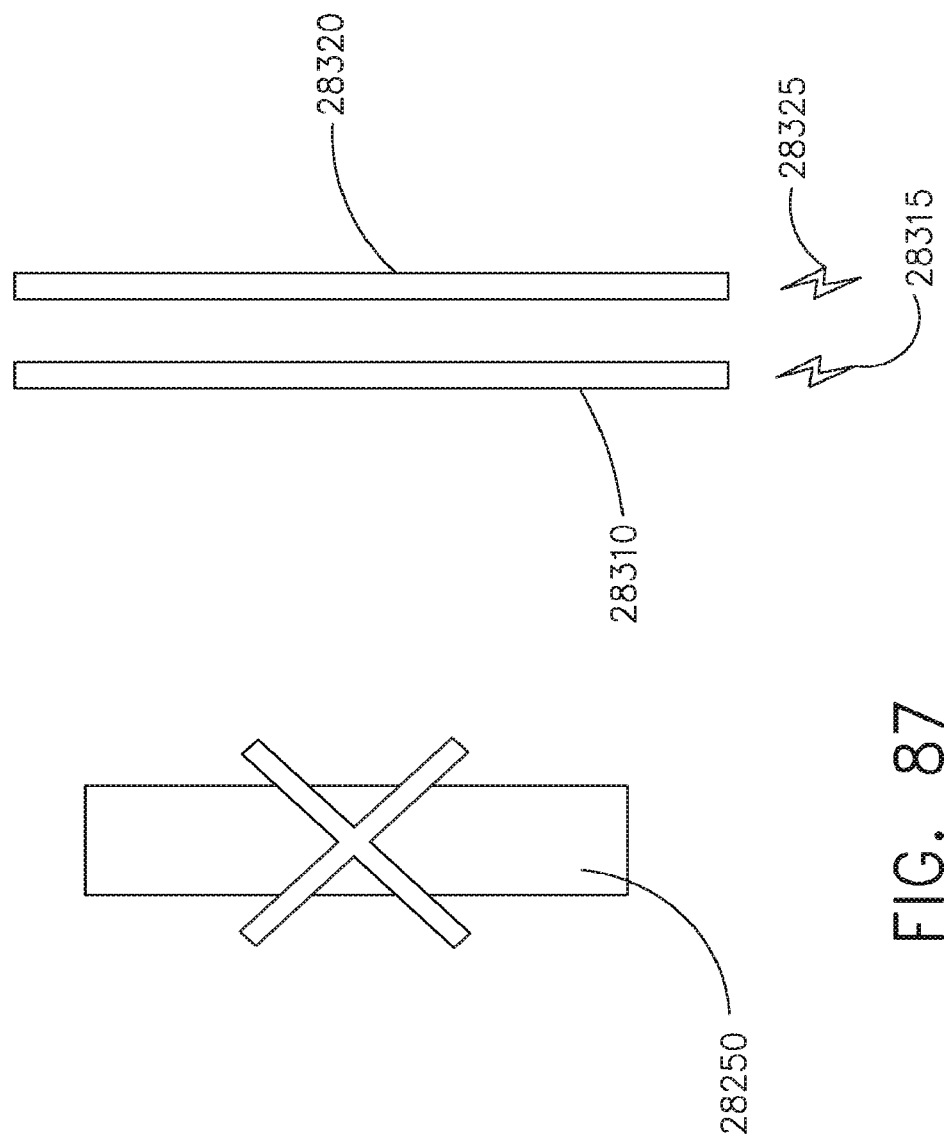
FIG. 87 is a representation of the communication pathways of the RFID system of FIG. 85 during and after a staple firing stroke.

After the commencement of the staple firing stroke, the second RFID scanner 28320 is energized in addition to and/or in lieu of the first RFID scanner 28310. As shown in FIG. 87, both the first RFID scanner 28310 and the second RFID scanner 28320 send interrogation signals 28315, 28325 to the RFID tag 28250 at the same time. The RFID tag 28250 receives the energy from both interrogation signals 28315, 28325 using the radio antenna of the RFID tag 28250. The received energy totals approximately 2 watts of power, for example, and exceeds the operating power threshold of the RFID tag 28250 of 1 watt, for example. The RFID tag 28250 is rendered inoperable when it receives the interrogation signals 28315, 28325 from both the first RFID scanner 28310 and the second RFID scanner 28320. In various instances, the RFID tag 28250 overheats due to the operating power threshold being exceeded. The increase in heat can, for example, burn a fuse within the RFID tag, melt a portion of the RFID tag, and/or otherwise render the RFID tag 28250 inoperable.

Destroying the RFID tag 28250 in this manner does not negatively effect the operation of the surgical instrument. Stated another way, the destruction of the RFID tag 28250 does not occur until after the staple cartridge has been authenticated by the surgical instrument. Instead, once the staple cartridge has been authenticated, the surgical instrument can be used to perform the staple firing stroke, among other functions. After the staple firing stroke and/or after the staple cartridge is removed from the surgical instrument, the staple cartridge cannot be re-authenticated by the surgical instrument and, thus, the staple cartridge cannot be reused. This system serves as a spent cartridge lockout, among other things.

In any event, the RFID tag 28250 is unable to receive signals from an RFID scanner and/or transmit signals to an RFID scanner in the inoperable configuration. When the first RFID scanner 28310 does not receive a response to its interrogation signals 28315, the controller of the surgical instrument is configured to communicate an error to the clinician. In instances where the first RFID scanner 28310 receives a response to its interrogation signal 28315 that is unable to be recognized and/or does not represent a compatible staple cartridge assembly, the controller of the surgical instrument is also programmed to communicate an error to the clinician. In various instances, the communication of a detected error from the controller can render the surgical instrument inoperable when the staple cartridge assembly is attached. In various instances, a detected error can prevent the surgical instrument from performing a staple firing stroke and/or tissue cutting stroke while the staple cartridge assembly is attached. A manual override can be activated to allow a clinician to override any system lockout and utilize operational functions of the surgical instrument in an emergency. In various instances, the controller is configured to alert the clinician that an error has been detected. Such an alert can be communicated through various forms of feedback, including, for example, haptic, acoustic, and/or visual feedback. The alert can be specific or generic. For example, the alert can specifically state that the RFID tag 28250 is unable to be detected, or the alert can specifically state that the RFID tag 28250 comprises information representative of an incompatible and/or defective staple cartridge assembly.

As discussed above, the first RFID scanner 28310 can be used to communicate with the RFID tag 28250 and the combined operation of the first RFID scanner 28310 and the second RFID scanner 28320 can be used to destroy the RFID tag 28250. Alternatively, the first RFID scanner 28310 can be used to communicate with the RFID tag 28250 and the second RFID scanner 28320 can be used to destroy the RFID tag 28250. In this embodiment, the first RFID scanner 28310 uses a power below a threshold and the second RFID scanner 28320 uses a power above the threshold. Also, alternatively, a second RFID scanner may not be used as both the communication and destruction functions can be performed by a single scanner. In at least one such instance, the signal amplifier is used to transmit signals below a power threshold to communicate and signals above the power threshold to destroy.

Figure 88:
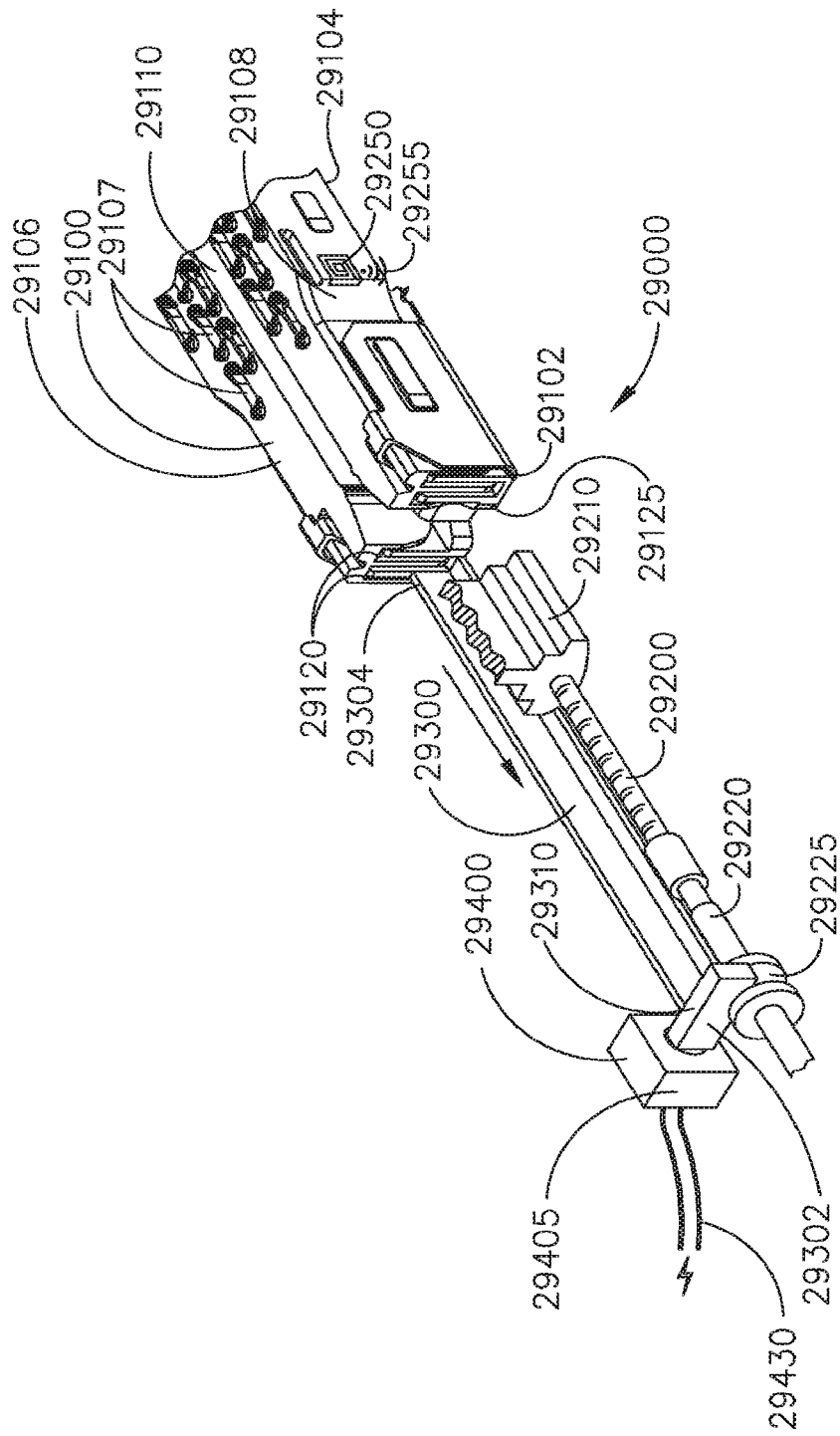
FIG. 88 is a partial perspective view of a staple firing lockout system in an unlocked configuration.
Figure 88A:
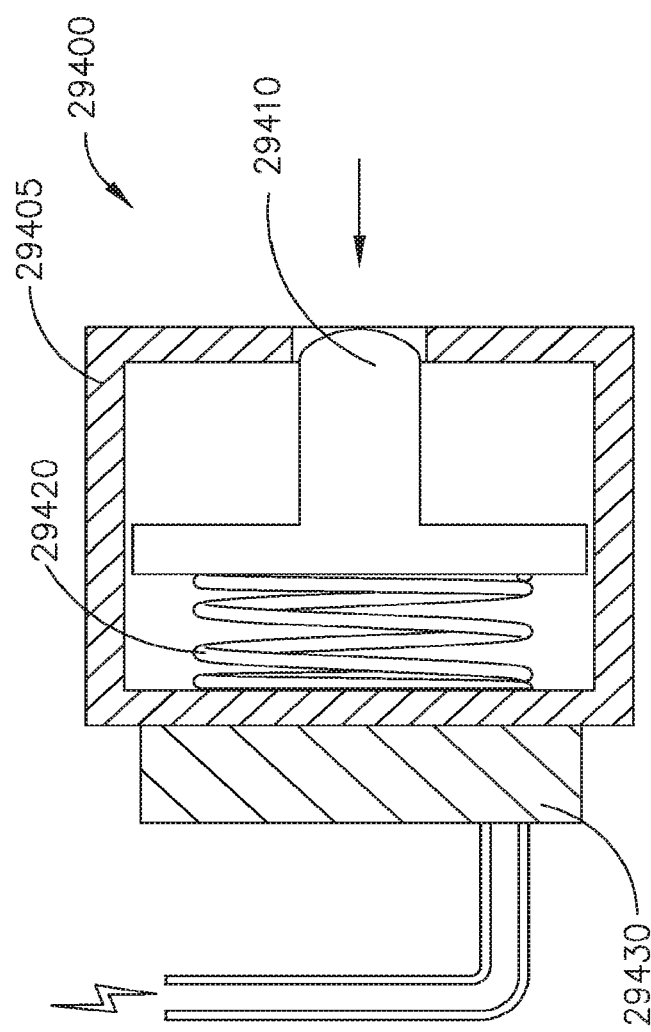
FIG. 88A is a perspective view of a blocking bolt assembly of the staple firing lockout system of FIG. 88 in an unlocked configuration.
Figure 89:
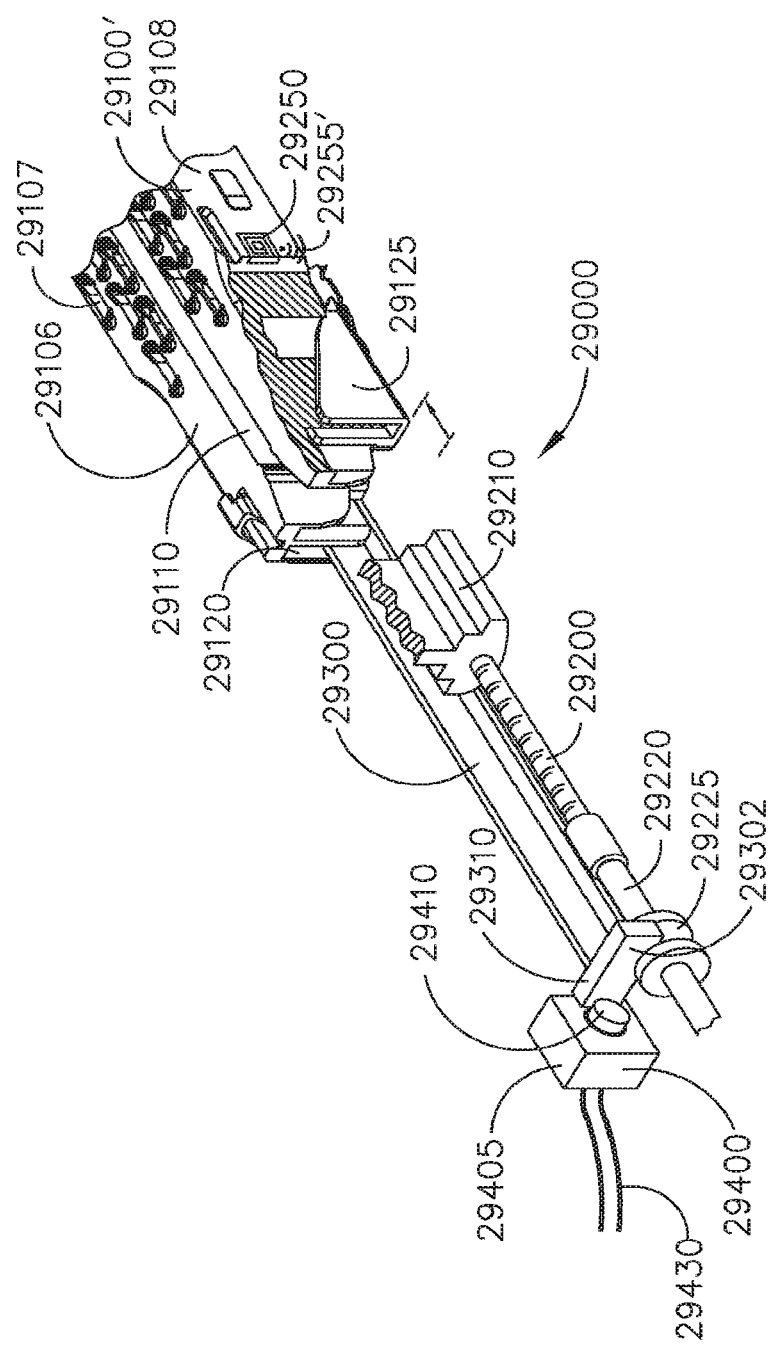
FIG. 89 is a partial perspective view of the staple firing lockout system of FIG. 88 in a locked configuration.
Figure 89A:
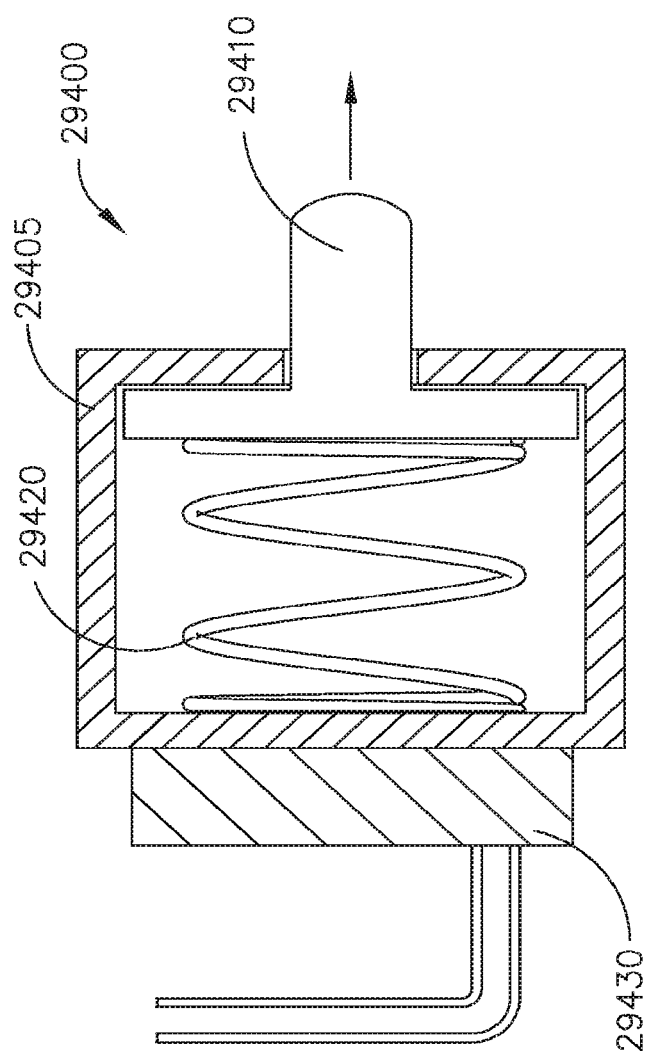
FIG. 89A is a perspective view of the blocking bolt assembly of FIG. 88A in the locked configuration.

FIGS. 88-89A illustrate a cartridge lockout system 29000. The cartridge lockout system 29000 is configured to prevent a surgical instrument from performing a staple firing stroke when an incompatible and/or spent staple cartridge is detected. When an unspent, compatible staple cartridge is detected, the controller of the surgical instrument permits the staple firing stroke to be performed. One such compatible staple cartridge includes staple cartridge 29100, for example.

The staple cartridge 29100 comprises a cartridge body including a cartridge deck 29106, a base 29104, and sidewalls 29108 extending between the cartridge deck 29106 and the base 29104. A plurality of staple cavities 29107 are defined in the cartridge body. The staple cavities 29107 are arranged in longitudinal rows, and a staple is removably supported within each staple cavity 29107. The staple cartridge 29100 further comprises a proximal end 29102 and a distal end. An elongate slot 29110 extends from the proximal end 29102 toward the distal end and is configured to receive a firing member 29210 during a staple firing stroke. The staple cartridge 29100 further comprises a wedge sled 29125 and channels 29120 defined within the cartridge body. The wedge sled 29125 is configured to drive staples out of the cartridge body and toward an anvil during the staple firing stroke. The channels 29120 are configured to receive ramps of the wedge sled 29125 as the wedge sled 29125 is translated through the staple cartridge 29100 during the staple firing stroke. Detents are formed on the inside of the channels 29120 to, among other things, interface with the ramps of the wedge sled 29125 and to control the lateral position of the wedge sled 29125 within the channels 29120. In at least one instance, ribs can be used to releasably hold the wedge sled 29125 in a proximal, unfired position.

The staple cartridge 29100 further comprises an RFID tag 29250. The RFID tag 29250 comprises a chip, such as a microchip, for example, that stores information about the staple cartridge 29100. In various instances, the chip comprises a basic identification number. In various instances, the chip comprises additional information such as, for example, manufacturing data, shipping data, and/or compatibility data. The RFID tag 26250 further comprises a radio antenna configured to receive an interrogation signal from an RFID scanner. As shown in FIGS. 88 and 89, the RFID tag 29250 is affixed to one of the sidewalls 29108 of the staple cartridge 29100. However, it is envisioned that the RFID tag 29250 can be embedded within the staple cartridge 29100 and/or attached to the staple cartridge 29100 in any suitable manner and/or in any suitable location.

The surgical system further comprises an RFID scanner. The RFID scanner comprises a scanner antenna configured to transmit radio signals. The radio signals activate RFID tags that are positioned within a pre-determined transmission range of the RFID scanner. The RFID scanner then receives one or more response signals 29255 that are "bounced back" from the RFID tag. In various instances, the one or more response signals comprise the same signal as the interrogation signal. In various instances, the one or more response signals comprise a modified signal from the interrogation signal. The RFID scanner can be positioned in various locations, such as, for example, the staple cartridge 29100, the end effector of the surgical instrument, and/or a console remotely positioned with respect to the surgical instrument. In other words, the RFID scanner can be positioned in any suitable location that allows the RFID scanner to communicate with the RFID tag 29250 as the staple cartridge 29100 is being seated into and/or once the staple cartridge 29100 is seated in the end effector of the surgical instrument. In various instances, the RFID scanner comprises reading and writing capabilities. Software on the RFID scanner is able to pass the collected information 29255 from the RFID tag 29250 to a controller for further interpretation. The controller can be positioned in the surgical instrument or in any suitable location. The RFID scanner and/or the controller can comprise a stored set of information that corresponds to staple cartridges that are compatible with the particular surgical instrument and/or for use during a particular surgical procedure.

Based on the collected information 29255 from the RFID tag 29250, the controller can maintain, activate, and/or deactivate a cartridge lockout assembly, such as the cartridge lockout assembly 29000, for example. The cartridge lockout assembly 29000 comprises a lockout bar 29300. The lockout bar 29300 comprises a proximal end 29302 and a distal end 29304. The distal end 29304 of the lockout bar 29300 is configured to interface with the wedge sled 29125 as the staple cartridge 29100 is being seated in the jaw of the end effector. The lockout bar 29300 is sized to fit within one of the channels 29120 formed in the cartridge body. The proximal end 29302 of the lockout bar 29300 comprises a lateral projection, or flange, 29310. The proximal end 29302 of the lockout bar 29300 is engaged with a firing bar 29200 of the staple firing drive such that the lockout bar 29300 and the firing bar 29200 move together. The firing bar 29200 comprises a groove 29225 which receives the lateral projection 29310 of the lockout bar 29300.

The cartridge lockout assembly 29000 further comprises a blocking bolt assembly 29400. In the depicted embodiment, the blocking bolt assembly 29400 comprises a solenoid. The blocking bolt assembly 29400 comprises a locking bolt 29410, a resilient member 29420, and an inductive coil 29430. In the embodiment depicted in FIGS. 88-89A, the resilient member 29420 is a spring, although any resilient member can be used. The blocking bolt assembly 29400 is configurable in an unlocked configuration and a locked configuration. The locking bolt 29410 and the resilient member 29420 are positioned in a housing 29405 of the blocking bolt assembly 29400. The resilient member 29240 biases the locking bolt 29410 into its locked configuration. In the locked configuration, a portion of the locking bolt 29410 extends outside of the housing 29405. In the unlocked configuration, the locking bolt 29410 is entirely positioned within the housing 29405.

The blocking bolt assembly 29400 is placed in the unlocked configuration by the controller when a compatible staple cartridge 29100 has been detected by the controller. A compatible staple cartridge 29100 is detected when the RFID tag 29250 emits a signal 29255 that corresponds to a stored set of information within the RFID scanner, and/or the controller, and/or when the clinician overrides the controller. In such instances, the controller is configured to activate the inductive coil 29430 of the blocking bolt assembly 29400. The controller applies a voltage source to the coil 29430 to active the coil 29430. Activating the inductive coil 29430 generates a magnetic field that pulls the locking bolt 29410 into the housing 29405. To this end, the locking bolt 29410 is comprised of iron, nickel, and/or any suitable magnetic material. That said, the resilient member 29420 is compressed by the movement of the locking bolt 29410 and, as such, the resilient member 29240 opposes the movement of the locking bolt 29410. In any event, the locking bolt 29410 is retracted a sufficient amount to be out of the path of the lockout bar 29300. At such point, the staple firing stroke can be performed. If the staple cartridge 29100 is removed from the surgical instrument, the controller will deactivate the inductive coil 29430 thereby allowing the resilient member 29240 to re-extend the locking bolt 29410.

When a staple cartridge 29100 is being seated into the jaw of the end effector, further to the above, the distal end 29304 of the lockout bar 29300 comes into contact with the sled 29125 of the staple cartridge 29100. If the locking bolt 29410 has been retracted, the proximal end 29302 of the lockout bar 29300 is pushed proximally by the sled 29125 of the staple cartridge 29100 as the clinician attempts to seat the staple cartridge 29100 within the jaw. In such instances, the lockout bar 29300 is configured to freely translate in the proximal direction. The lack of resistance against the proximal movement of the lockout bar 29300 allows the lockout bar 29300 to move without displacing the wedge sled 29125 in the staple cartridge 29100. In other words, the retention forces acting on the wedge sled 29125 by the detents within the channels 29120 are sufficient enough to maintain the wedge sled 29125 in its current position while pushing the lockout bar 29300 when the staple cartridge 29100 is seated in the surgical instrument.

As discussed above, the blocking bolt assembly 29400 is in the locked configuration when an incompatible staple cartridge 29100' has been detected. As illustrated in FIG. 89, an incompatible staple cartridge 29100' is detected when the RFID tag 29250 emits a signal 29255' that does not correspond to a stored set of information within the RFID scanner and/or the controller. In various instances, a staple cartridge 29100' is deemed incompatible by the controller of the surgical instrument when the RFID scanner is unable to detect a signal from a RFID tag. When the emitted signal 29255', or lack of signal, is indicative of an incompatible staple cartridge 29100', the inductive coil 29430 of the blocking bolt assembly 29400 is not activated by the controller. Without activating the inductive coil 29430, the biasing member 29420 holds a portion of the locking bolt 29410 extends outside of the housing 29405. When a staple cartridge 29100' is being seated into the jaw of the end effector and the locking bolt 29410 is extended, the distal end 29304 of the lockout bar 29300 comes into contact with the sled 29125 of the staple cartridge 29100'. The lockout bar 29300 is prevented from translating in the proximal direction, as the locking bolt 29410 is in its path. In such instances, the resistance provided by the locking bolt 29410 against the lockout bar 29300 exceeds the retention forces provided by the detents in the channel 29120 holding the wedge sled 29125 in place. As such, the wedge sled 29125 is displaced distally from its unfired position when the staple cartridge 29100' is seated and the locking bolt 29410 is not retracted. The distal movement of the wedge sled 29125 from its unfired position spends the staple cartridge 29100', even though no staples have been fired from the staple cartridge 29100'. The firing lockout systems disclosed in U.S. Pat. No. 7,143,923, entitled SURGICAL STAPLING INSTRUMENT HAVING A FIRING LOCKOUT FOR AN UNCLOSED ANVIL, which issued on Dec. 5, 2006; U.S. Pat. No. 7,044,352, SURGICAL STAPLING INSTRUMENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOSING AND FIRING SYSTEMS, which issued on Feb. 21, 2006; U.S. Pat. No. 6,988,649, SURGICAL STAPLING INSTRUMENT HAVING A SPENT CARTRIDGE LOCKOUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, the disclosures of which are incorporated herein in their entireties, would mechanically prevent the staple firing stroke from being performed in such instances.

Figure 90:
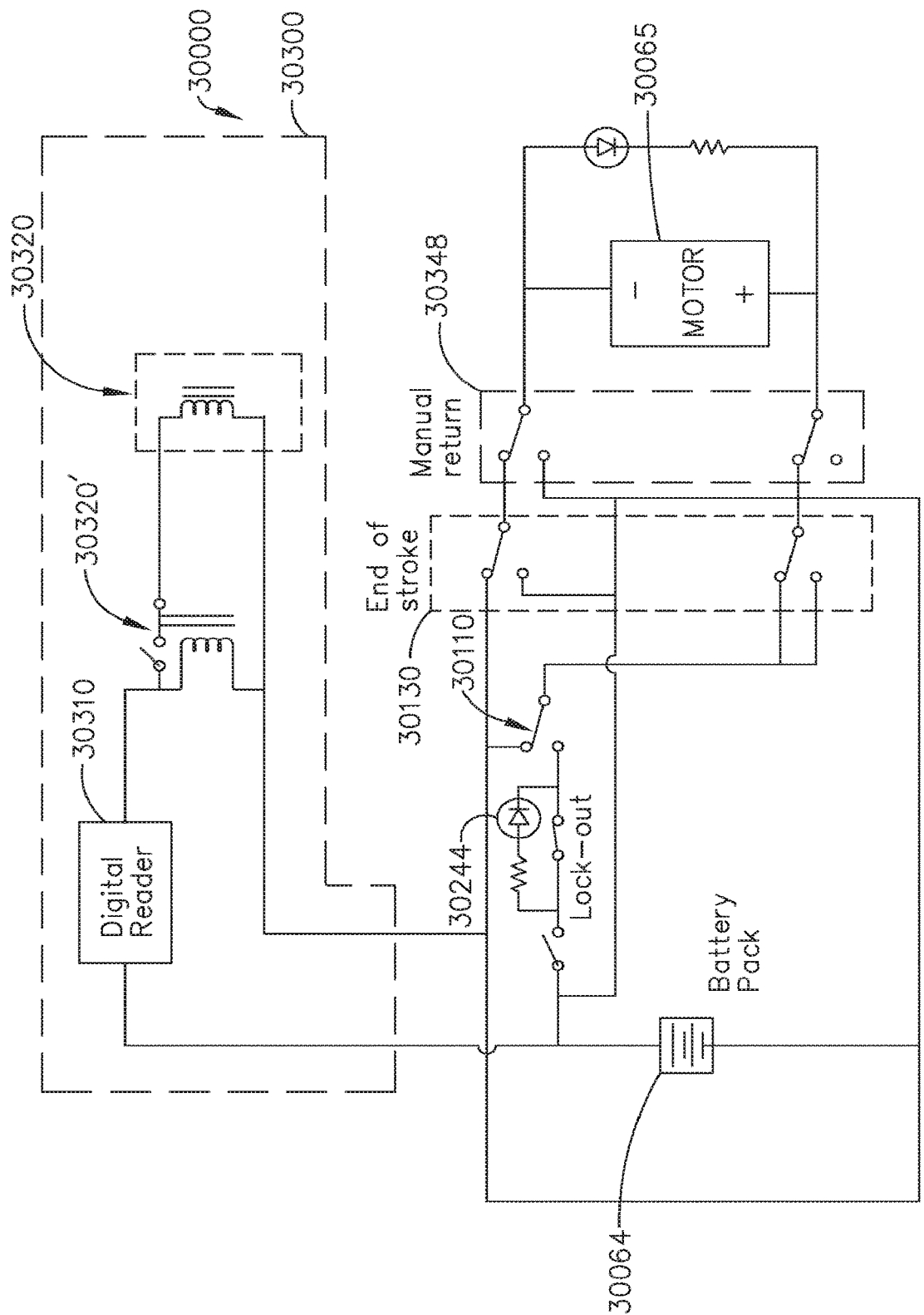
FIG. 90 is a motor control circuit diagram of a surgical instrument comprising the cartridge lockout assembly of FIGS. 88-89A.

FIG. 90 depicts a motor control circuit 30000 for use in controlling the cartridge lockout assembly 29000. Various details of the motor control circuit 30000 are described in greater detail in U.S. Patent Application Publication No. 2010/007647, entitled MOTOR-DRIVEN SURGICAL CUTTING INSTRUMENT, issued as U.S. Pat. No. 8,210,411 on Jul. 3, 2012, the disclosure of which is incorporated by reference in its entirety. A battery, or other suitable power source, 30064 powers an electric motor 30065. When a clinician initially pulls in a firing trigger of the surgical instrument, a run motor (or fire) switch 30110 is closed. When the run motor switch 30110 is closed, a safety switch is closed, and a lockout switch is opened, current flows through the safety switch, through a lockout indicator 30244, and to the motor 30065. When the end of the staple firing stroke is reached, an end-of-stroke or direction switch 30130 is switched, reversing the direction of the motor 30065. The circuit 30000 may also comprise a manual return switch 30348. The clinician may manually flip this switch 30348 if the firing member, such as the firing member 29210, has only been partially fired. Switching the manual return switch 30348 causes the motor 30065 to reverse rotate, causing the firing member to return to its original or home position.

The motor control circuit 30000 further comprises a cartridge lockout switch 30300. When a controller 30310 determines, through received signals from an RFID tag, such as RFID tag 29250, that a compatible staple cartridge is being seated in the end effector, an inductive coil 30320 is energized. The energizing of the inductive coil 30320 closes the cartridge lockout switch 30300 and allows the compatible staple cartridge to be seated within the end effector without displacement of a wedge sled of the staple cartridge. When a controller 30310 determines, through received signals from an RFID tag, such as RFID tag 29250, that an incompatible staple cartridge is being seated in the end effector, the inductive coil 30320' is not energized. The inactive inductive coil 30320' allows the cartridge lockout switch 30300 to remain open. A cartridge lockout, such as the cartridge lockout 29000, then causes distal displacement of the wedge sled within the incompatible surgical cartridge. The surgical instrument is then unable to perform a staple firing stroke while the incompatible surgical cartridge is attached.

Various surgical instruments are comprised of replaceable components that are required to be replaced prior to the start of and/or during a surgical procedure. For example, a surgical stapling instrument, such as the surgical stapling instrument 400, comprises a replaceable staple cartridge. A clinician may desire and/or need to replace the staple cartridge for various reasons such as, for example, the type of surgical procedure being performed, the thickness of the tissue being treated during the surgical procedure, and/or the state of the staple cartridge. The state of the staple cartridge corresponds to, for example, whether or not the staple cartridge is spent, i.e., whether one or more of the staples from within the staple cartridge was ejected during a staple firing stroke.

Figure 91:
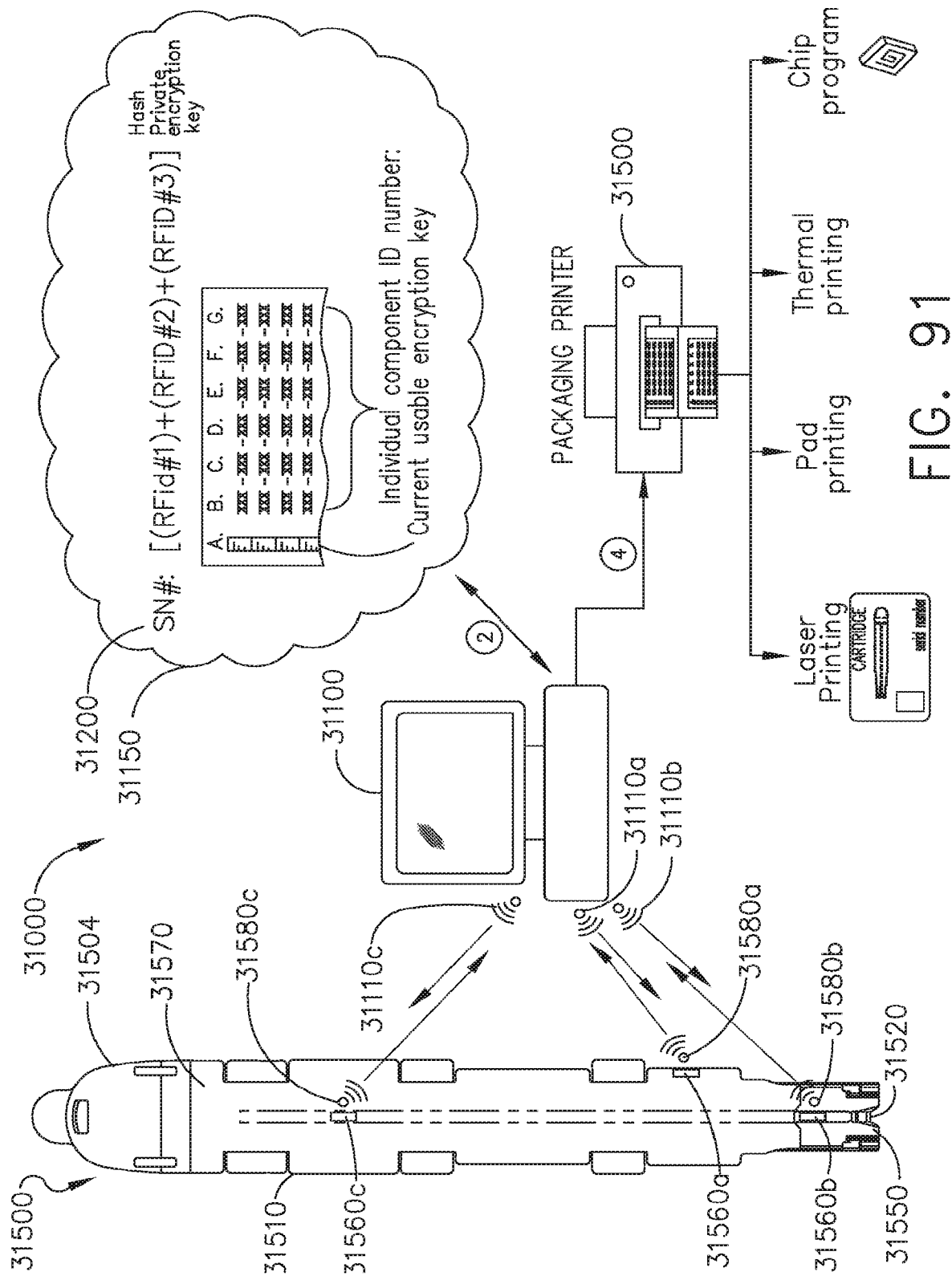
FIG. 91 is a schematic representation of a manufacturing process configured to use an encryption protocol to facilitate the assembly and packaging of a staple cartridge.

As described in greater detail herein, various identification systems, such as RFID tags, QR codes, and/or bar codes, for example, can be positioned throughout a surgical system. For example, and as shown in FIG. 91, a first RFID tag 31560*a* is located on a cartridge body 31510 of a staple cartridge 31500, a second RFID tag 31560*b* is located on a wedge sled 31550 of the staple cartridge 31500, and a third RFID tag 31560*c* is located on a retainer 31570 of the staple cartridge 31500. Each RFID tag comprises a chip storing information relating to, among other things, a state of the staple cartridge assembly, staple cartridge identification, and/or compatibility of the staple cartridge assembly with a specific surgical instrument. To ensure patient safety and the proper assembly of the components within the surgical system, among other things, the information stored on each chip is encrypted. Encryption of the information on the chips provides that only authorized parties can access the stored information and those who are not authorized cannot. In other words, if the information stored on the chips is unable to be decrypted, the surgical system will be unable to be assembled with the incompatible assembled components and/or one or more operating parameters of the surgical system will be unavailable and/or modified when the incompatible assembled components are attached. An encryption key is stored within a controller and/or an external storage medium of the surgical system to decrypt the information collected from the RFID tags by one or more RFID scanners. In various instances, all of the RFID tags comprise encrypted information. In other instances, only one of the RFID tags comprises encrypted information, such as, for example, the RFID tag located on the staple cartridge. However, it is envisioned that any suitable combination of RFID tags can comprise chips with encrypted information.

In various instances one or more of the encryption keys are stored in a memory on the surgical instrument, however any suitable storage location is envisioned.

Data stored on the RFID tags of a staple cartridge can be encrypted during the manufacturing process of the staple cartridge using an encryption protocol. The information can be encrypted to, for example, prevent the use of staple cartridges that were duplicated without authorization and/or with inferior components, among other things. Such unauthorized duplicates of the staple cartridge may not be manufactured with the same specifications and/or dimensions as the compatible staple cartridge. If an incompatible staple cartridge is used with the surgical instrument, the incompatible staple cartridge may not perform a surgical function(s) in the same manner as the compatible staple cartridge, thereby exposing a patient to an increased risk when the incompatible staple cartridge is used with the surgical instrument.

During the manufacturing process, an RFID scanner transmits a first interrogation signal to interrogate the first RFID tag 31560*a* of the staple cartridge 31500. The first RFID tag 31560*a* transmits a first signal 31580*a* in response to the first interrogation signal. The first response signal 31580*a* comprises unencrypted, or unsecured, data relating to the staple cartridge 31500. Such data can include, for example, manufacturing data and/or cartridge identification data. An RFID scanner transmits a second interrogation signal and a third interrogation signal to interrogate the second RFID tag 31560*b* and the third RFID tag 31560*c*, respectively. The second RFID tag 31560*b* transmits a second signal 31580*b* in response to the second interrogation signal and the third RFID tag 31560*c* transmits a third signal 31580*c* in response to the third interrogation signal. The second response signal 31580*b* and the third response signal 31580*c* comprise unencrypted, or unsecured, data relating to the wedge sled 31550 and the retainer 31570, respectively. Such data can include, for example, manufacturing data and/or identification data.

The RFID scanner transmits the response signals 31580*a*, 31580*b*, 31580*c* to a manufacturing controller 31100. The manufacturing controller 31100 accesses a cloud storage medium 31150 to, for example, encrypt the received data. The cloud storage medium 31150 comprises an encryption protocol configured to encrypt the data contained in the response signals 31580*a*, 31580*b*, 31580*c*. Using an encryption protocol, the cloud storage medium 31150 creates an encrypted serial number reflecting the various components of the staple cartridge 31500 having the RFID tags. For example, the unsecured data stored on the first RFID tag 31560*a* is encrypted with a first value 31202. The unsecured data stored on the second RFID tag 31560*b* is encrypted with a second value 31204, and the unsecured data stored on the third RFID tag 31560*c* is encrypted with a third value 31206. The first value 31202, the second value 31204, and the third value 31026 are combined to form a unique serial number 31200 reflective of an identity of the staple cartridge 31500. Such an encryption process is conducted on each manufactured staple cartridge. See also FIG. 63.

After the cloud storage medium 31150 completes the encryption protocol, the manufacturing controller 31100 rewrites the RFID tags 31560*a*, 31560*b*, 31560*c* with the encrypted data. The manufacturing controller 31100 directs the RFID scanner to send a first rewrite signal 31110*a* to the first RFID tag 31560*a*. The first rewrite signal 31110*a* serves to delete the unsecured data stored on the first RFID tag 31560*a* and replace the unsecured data with the new, secured data 31202. The RFID scanner transmits a second rewrite signal 31110*b* to the second RFID tag 31560*b* and a third rewrite signal 31110*c* to the third RFID tag 31560*c*. The second rewrite signal 31110*b* serves to delete the unsecured data stored on the second RFID tag 31560*b* and replace the unsecured data with the new, secured data 31204. The third rewrite signal 31110*c* serves to delete the unsecured data stored on the third RFID tag 31560*c* and replace the unsecured data with the new, secured data 31206. At this point, the RFID tags 31560*a*, 31560*b*, 31560*c* comprise only encrypted data, and only the cloud storage medium 31150 comprises access to the unsecure, unencrypted data through a decryption protocol. As discussed above, the RFID reader is configured to transmit signals to and receive signals from the RFID tags. In such cases, the RFID reader comprises both reading and writing capabilities.

As the data stored on each staple cartridge 31500 is being encrypted, the cloud storage medium 31150 creates a list 31250 of the unique serial number 31200 of the staple cartridge 31500 along with an associated encryption key. The list 31250 can be updated in real-time and/or can be created after each RFID tag 31560*a*, 31560*b*, 31560*c* is programmed with the encrypted information. The manufacturing controller 31100 is configured to access the list 31250 of unique serial numbers 31200 from the cloud storage medium 31150. During the packaging process, the manufacturing controller 31100 directs a packaging printer 31600 to print the unique serial number 31200 on the packaging for the staple cartridge 31500.

When the staple cartridge 31500 is needed for attachment to the surgical instrument, the clinician is required to scan the packaging of the staple cartridge 31500. A controller of the surgical instrument and/or a remote controlled within the operating room communicates the scanned packaging data to the cloud storage medium 31150. The remote controller, for example, communicates the scanned packaging data to the cloud storage medium 31150 for decryption. The cloud storage medium 31150 performs a decryption protocol on the scanned packaging data and compares the received data to the list 31250 of compatible, or otherwise acceptable, staple cartridges. If the cloud storage medium 31150 recognizes the scanned packaging data as acceptable for use with the surgical instrument, the cloud storage medium 31150 communicates an approval signal to the remote controller. The remote controller communicates the approval signal to the controller on the surgical instrument, and the surgical instrument is capable of performing a staple firing stroke, for example. If the cloud storage medium 31150 is unable to recognize the scanned packaging data, the cloud storage medium 31150 communicates an error to the remote controller. The remote controller communicates the error to the controller on the surgical instrument, and the surgical instrument is prevented from performing a staple firing stroke. In various instances, the surgical instrument comprises an override input that the clinician can activate, but only after the clinician has been adequately warned that the staple cartridge did not pass the authentication protocol.

As previously discussed, the packaging, such as packaging 25000, of a modular component comprises one or more identification systems that relates to the contents of the packaging. The manufacturing controller and the packaging printer 31600 create the identification systems using the encrypted information discussed above. Various techniques can be used to label the packaging. Such techniques include, for example, laser printing, pad printing, thermal printing, and/or chip programming. For example, laser printing can be used to print QR codes and/or bar codes on the product packaging. Chip programming can be used to alter the information stored within an RFID system, such as the RFID system 25200, for example.

Figure 92:
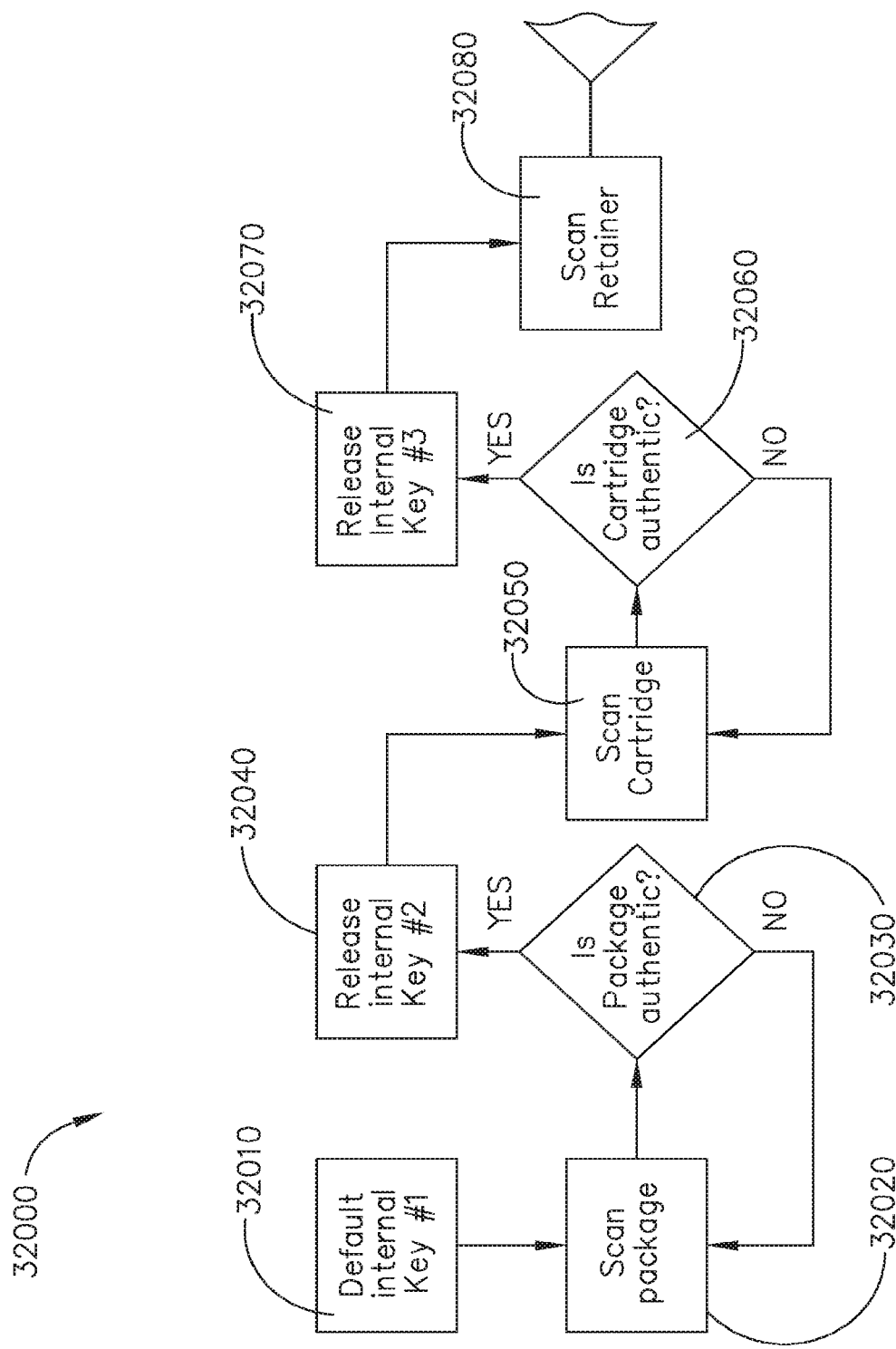
FIG. 92 is a flowchart representative of a decryption protocol for the authentication of a staple cartridge for use with a surgical system.

FIG. 92 illustrates a decryption protocol 32000 operated by the controller of the surgical instrument. The controller uses automated incrementing encryption keys to facilitate the assembly and/or use of a surgical instrument, such as the surgical instrument described above, for example. The surgical instrument controller comprises a memory. The memory stores a default internal key 32010 that allows the controller to decrypt a first RFID tag. The first RFID tag is positioned on a staple cartridge packaging and the first RFID tag comprises a first set of encrypted information. The first set of encrypted information can only be decrypted by the controller using the default internal key 32010. The decryption protocol 32000 releases a second internal key 32040 upon the successful decryption of the first RFID tag. If the controller determines that the packaging is not authentic, if the controller is unable to decrypt the information stored on the first RFID tag and/or if the information stored on the first RFID tag is unable to be recognized, the second internal key 32040 is not released, and the decryption protocol 32000 cannot move forward. The first RFID tag can be rescanned, or a new packaging can be scanned by the RFID scanner 32020. Without continuing to the next authentication step of the decryption protocol 32000, the controller of the surgical instrument prevents the surgical instrument from performing a staple firing stroke.

The staple cartridge comprises a second RFID tag positioned on the cartridge body, and the second RFID tag comprises a second set of encrypted information. The second set of encrypted information can only be decrypted by the controller using the second internal key 32040. The decryption protocol 32000 releases a third internal key 32070 upon the successful decryption of the second RFID tag data. If the controller determines that the staple cartridge is not authentic, if the controller is unable to decrypt the information stored on the second RFID tag and/or if the information stored on the second RFID tag is unable to be recognized, the third internal key 32070 is not released, and the decryption protocol 32000 cannot move forward. The second RFID tag can be rescanned, or a new staple cartridge can be scanned by the RFID scanner 32050. Without continuing to the next authentication step of the decryption protocol 32000, the controller of the surgical instrument prevents the surgical instrument from performing a staple firing stroke.

The staple cartridge previously contained in the packaging as discussed above comprises a passive second RFID tag. The second RFID tag is positioned at any suitable location in the staple cartridge. The clinician can bring the RFID scanner into a range of the second RFID tag, wherein the RFID scanner emits a signal to scan 32050 the second RFID tag of the staple cartridge. In response to the RFID scanner's emitted signal, the second RFID tag is configured to transmit its encrypted information back to the RFID scanner. The software on the RFID scanner is configured to transmit the communicated information to the controller for decryption using the released and/or unlocked internal key 32040. Once the received information is decrypted, the controller is configured to determine if the staple cartridge comprises authentic components that are compatible with the surgical instrument 32060. In other words, the information stored by the second RFID tag allows a clinician to confirm that the packaging did contain an authentic staple cartridge. In various instances, the controller is also configured to determine if the staple cartridge has been tampered with, has been previously used, and/or is a fraudulent form of an otherwise compatible staple cartridge. If the controller determines that the staple cartridge is not authentic, the controller is unable to decrypt the information stored on the second RFID tag and/or the information stored on the second RFID tag is unable to be recognized. The staple cartridge may then be rescanned, or a new staple cartridge can be scanned by the RFID scanner 32050. If the controller determines that the staple cartridge is authentic, the controller releases and/or unlocks a third internal key 32070 for use in the detection of the presence of a retainer on a staple cartridge assembly. Without releasing and/or unlocking the third internal key 32070, the clinician is unable to complete the protocol 32000 and, in various instances, is unable to activate the surgical instrument with the inauthentic component(s), absent an override input as described above.

The staple cartridge comprises a third RFID tag positioned on the retainer, and the third RFID tag comprises a third set of encrypted information. The third set of encrypted information can only be decrypted by the controller using the third internal key 32070. If the encrypted information comprises data representing a compatible staple cartridge, the decryption protocol 32000 releases a fourth internal key and/or the decryption protocol 32000 successfully concludes. If the controller determines that the staple cartridge is not authentic, if the controller is unable to decrypt the information stored on the third RFID tag and/or if the information stored on the third RFID tag is unable to be recognized, the next, or fourth, internal key is not released, and the decryption protocol 32000 cannot move forward. The third RF ID tag can be rescanned, or a new retainer can be scanned by the RFID scanner 32080. Without releasing and/or unlocking the fourth internal key, the controller is unable to complete the protocol 32000 and, in various instances, may be unable to activate the surgical instrument with the inauthentic component(s). In various instances, the retainer is the last modular component that is assessed in the protocol 32000. However, in other instances, additional modular components comprise RFID tags with encrypted information that require authentication prior to use with the surgical system.

It is envisioned that any of the identification systems described herein can be used in place of the active and/or passive RFID tags described in connection with the protocol 32000.

Various aspects of the subject matter described herein are set out in the following examples.

Example Set 1

Example 1. A method for authenticating the compatibility of a staple cartridge with a surgical instrument comprises inserting a staple cartridge into a surgical instrument. The method also comprises transmitting a first signal from a first RFID tag on a first component of the staple cartridge to an RFID reader system and transmitting a second signal from a second RFID tag on a second component of the staple cartridge to the RFID reader system. The method also comprises comparing the first signal and the second signal to a set of stored data for a compatible staple cartridge and unlocking a staple firing system of the surgical instrument if the first signal and the second signal match the set of stored data for a compatible staple cartridge.

Example 2. The method of Example 1, wherein the comparing step comprises comparing the first signal and the second signal to more than one set of stored data for compatible staple cartridges.

Example 3. The method of Examples 1 or 2, wherein the first RFID tag and the second RFID tag comprise active RFID tags.

Example 4. The method of Examples 1-3, further comprising a step of interrogating the first RFID tag with the RFID reader system before the step of transmitting a first signal from the first RFID tag.

Example 5. The method of Examples 1-4, further comprising a step of interrogating the second RFID tag with the RFID reader system before the step of transmitting a second signal from the second RFID tag.

Example 6. The method of Examples 1-5, further comprising the step of operating the staple firing system to perform a staple firing stroke after the unlocking step.

Example 7. The method of Examples 1-6, wherein the first component comprises a cartridge body and the second component comprises a sled movable from a proximal unfired position to a distal fired position during a staple firing stroke.

Example 8. The method of Example 7, wherein the step of transmitting the second signal to the RFID reader system can only occur when the sled is in its proximal unfired position.

Example 9. The method of Examples 1-8, wherein the first component comprises a cartridge body and the second component comprises a cover removably attached to the cartridge body.

Example 10. The method of Example 9, wherein the step of transmitting the second signal to the RFID reader system can only occur when the cover is attached to the cartridge body.

Example 11. A method for authenticating the compatibility of a staple cartridge with a surgical instrument comprises inserting a staple cartridge into a surgical instrument. The method also comprises receiving a first signal from a first RFID tag on a first component of the staple cartridge with an RFID reader system and receiving a second signal from a second RFID tag on a second component of the staple cartridge with the RFID reader system. The method also comprises comparing the first signal and the second signal to stored data for a compatible staple cartridge and locking a staple firing system of the surgical instrument if the first signal and the second signal do not match the stored data for a compatible staple cartridge.

Example 12. The method of Example 11, wherein the comparing step comprises comparing the first signal and the second signal to stored data for more than one compatible staple cartridge.

Example 13. The method of Examples 11 and 12, wherein the first RFID tag and the second RFID tag comprise active RFID tags.

Example 14. The method of Examples 11-13, further comprising a step of interrogating the first RFID tag with the RFID reader system before the step of receiving a first signal from the first RFID tag.

Example 15. The method of Examples 11-14, further comprising a step of interrogating the second RFID tag with the RFID reader system before the step of receiving a second signal from the second RFID tag.

Example 16. The method of Examples 11-15, further comprising the step of operating the staple firing system to perform a staple firing stroke if the locking step does not occur.

Example 17. The method of Examples 11-16, wherein the first component comprises a cartridge body and the second component comprises a sled movable from a proximal unfired position to a distal fired position during a staple firing stroke.

Example 18. The method of Example 17, wherein the step of receiving the second signal with the RFID reader system can only occur when the sled is in its proximal unfired position.

Example 19. The method of Examples 11-18, wherein the first component comprises a cartridge body and the second component comprises a cover removably attached to the cartridge body.

Example 20. The method of Example 19, wherein the step of receiving the second signal with the RFID reader system can only occur when the cover is attached to the cartridge body.

Example Set 2

Example 1. A surgical instrument comprises a firing system configured to perform a firing motion, an end effector, and a RFID reader system. The end effector comprises an anvil, a staple cartridge support, and a staple cartridge positioned in the staple cartridge support. The staple cartridge comprises a cartridge body defining a longitudinal axis, a longitudinal slot defined in the cartridge body, and staple cavities defined in the cartridge body. The staple cartridge also comprises staples removably stored in the staple cavities, a cover releasably attached to the cartridge body, wherein the cover extends over the staple cavities when the cover is attached to the cartridge body. The staple cartridge also comprises a sled movable from a proximal unfired position to a distal fired position during the firing motion, a first RFID tag affixed to the cartridge body at a first longitudinal position, and a second RFID tag affixed to the sled, wherein the proximal unfired position of the sled is at a second longitudinal position which is not at the first longitudinal position. The staple cartridge also comprises a third RFID tag affixed to the cover at a third longitudinal position which is not at the first longitudinal position and the second longitudinal position. The RFID reader system is configured to receive a first signal from the first RFID tag at the first longitudinal position, a second signal from the second RFID tag at the second longitudinal position, and a third signal from the third RFID tag at the third longitudinal position.

Example 2. The stapling instrument of Example 1, wherein the RFID reader system comprises a first RFID reader, a second RFID reader, and a third RFID reader.

Example 3. The stapling instrument of Example 2, wherein the first RFID reader system comprises a first antenna adjacent the first longitudinal position, wherein the second RFID system comprises a second antenna adjacent the second longitudinal position, and wherein the third RFID system comprises a third antenna adjacent the third longitudinal position.

Example 4. The stapling instrument of Examples 1-3, wherein the first RFID tag is configured to emit the first signal a first range, wherein the first antenna positioned in the first range and is configured to receive the first signal, wherein the second RFID tag is configured to emit the second signal a second range, wherein the second antenna is positioned in the second range and configured to receive the second signal, wherein the third RFID tag is configured to emit the third signal a third range, and wherein the third antenna is positioned in the third range and configured to receive the third signal.

Example 5. The stapling instrument of Example 4, wherein the first range does not overlap with the second range and the third range, and wherein the second range does not overlap with the first range and the third range.

Example 6. The stapling instrument of Examples 2-5, wherein the first RFID reader system comprises a first inductive coil sensor adjacent the first longitudinal position, wherein the second RFID system comprises a second inductive coil sensor adjacent the second longitudinal position, and wherein the third RFID system comprises a third inductive coil sensor adjacent the third longitudinal position.

Example 7. The stapling instrument of Example 6, wherein the first RFID tag is configured to emit the first signal a first range, wherein the first inductive coil sensor positioned in the first range and is configured to receive the first signal, wherein the second RFID tag is configured to emit the second signal a second range, wherein the second inductive coil sensor is positioned in the second range and configured to receive the second signal, wherein the third RFID tag is configured to emit the third signal a third range, and wherein the third inductive coil sensor is positioned in the third range and configured to receive the third signal.

Example 8. The stapling instrument of Examples 6 and 7, wherein the first range does not overlap with the second range and the third range, and wherein the second range does not overlap with the first range and the third range.

Example 9. The stapling instrument of Examples 1-8, wherein the first RFID tag comprises an active RFID tag, wherein the second RFID tag comprises an active RFID tag, and wherein the third RFID tag comprises an active RFID tag.

Example 10. The stapling instrument of Examples 1-8, wherein the first RFID tag comprises a passive RFID tag, wherein the second RFID tag comprises a passive RFID tag, and wherein the third RFID tag comprises a passive RFID tag.

Example 11. The stapling instrument of Examples 1-10, wherein the staple cartridge comprises a lateral width, and wherein the first longitudinal location, the second longitudinal location, and the third longitudinal location are not aligned laterally across the lateral width.

Example 12. The stapling instrument of Examples 1-11, further comprising a controller in communication with the RFID reader system and the firing system, wherein the controller is configured to prevent the operation of the firing system if at least one of the first signal, the second signal, and the third signal is not received by the RFID system.

Example 13. The stapling instrument of Examples 1-12, further comprising a controller in communication with the RFID reader system and the firing system, wherein the controller comprises at least one set of data stored in a memory device, wherein the controller is configured to compare data from the first signal, the second signal, and the third signal to a set of data, wherein the controller is configured to disable the firing system if data from at least one of the first signal, the second signal, and the third signal is inconsistent with the set of data.

Example 14. A staple cartridge assembly comprises a cartridge body defining a longitudinal axis, a longitudinal slot defined in the cartridge body, and staple cavities defined in the cartridge body. The staple cartridge assembly also comprises staples removably stored in the staple cavities, a cover releasably attached to the cartridge body, wherein the cover extends over the staple cavities when the cover is attached to the cartridge body. The staple cartridge assembly also comprises a sled movable from a proximal unfired position to a distal fired position during the firing motion, a first RFID tag affixed to the cartridge body at a first longitudinal position, a second RFID tag affixed to the sled, wherein the proximal unfired position of the sled is at a second longitudinal position which is not at the first longitudinal position, and a third RFID tag affixed to the cover at a third longitudinal position which is not at the first longitudinal position and the second longitudinal position.

Example 15. A surgical instrument comprises a firing system configured to perform a firing motion, an end effector, an RFID reader system, and a controller. The end effector comprises an anvil, a staple cartridge support, and a staple cartridge positionable in the staple cartridge support. The staple cartridge comprises a cartridge body comprising a proximal end and a distal end, a longitudinal slot defined in the cartridge body, and staple cavities defined in the cartridge body. The staple cartridge also comprises staples removably stored in the staple cavities and a sled movable from a proximal unfired position to a distal fired position during the firing motion. The staple cartridge also comprises a first RFID tag affixed to the cartridge body at the proximal end and a second RFID tag affixed to the cartridge body at the distal end. The RFID reader system is configured to receive a first signal from the first RFID tag and a second signal from the second RFID tag. The controller is in communication with the RFID reader system and the firing system, wherein the controller is configured to disable the operation of the firing system if the controller receives one of the first signal and the second signal but not the other.

Example 16. The surgical instrument of Example 15, further comprising a feedback system in communication with the controller, wherein the controller is configured to activate the feedback system when the controller disables the operation of the firing system.

Example 17. The surgical instrument of Examples 15 or 16, wherein the controller comprises a set of data stored in a memory device, wherein the controller is configured to compare data from the first signal and the second signal to a set of data, wherein the controller is configured to disable the firing system if data from one of the first signal and the second signal is inconsistent with the set of data.

Example 18. A staple cartridge comprises a cartridge body comprising a proximal end and a distal end. The staple cartridge also comprises a longitudinal slot defined in the cartridge body, staple cavities defined in the cartridge body, and staples removably stored in the staple cavities. The staple cartridge also comprises a sled movable from a proximal unfired position to a distal fired position during the firing motion, a first RFID tag affixed to the cartridge body at the proximal end, and a second RFID tag affixed to the cartridge body at the distal end.

Example Set 3

Example 1. A surgical instrument comprises a staple firing system, an end effector, a first RFID reader, a second RFID reader, and a controller. The end effector comprises an anvil, a staple cartridge channel, and a staple cartridge positioned in the staple cartridge channel. The staple cartridge comprises a cartridge body comprising a longitudinal slot, staple cavities defined in the cartridge body, and staples removably stored in the staple cavities. The staple cartridge also comprises a sled movable between a proximal unfired position and a distal fired position by the staple firing system, a first RFID tag affixed to the cartridge body, and a second RFID tag affixed to the sled. The first RFID reader is configured to detect a first signal from the first RFID tag and the second RFID reader is configured to detect a second signal from the second RFID tag. The controller is in communication with the first RFID reader, the second RFID reader, and the staple firing system, wherein the controller verifies the presence of the staple cartridge in the staple cartridge channel upon receiving the first signal from the first RFID tag, and wherein the controller verifies that the staple cartridge is an unfired staple cartridge upon receiving the second signal from the second RFID tag.

Example 2. The surgical instrument of Example 1, wherein the controller is configured to disable the staple firing system if the controller receives the first signal but not the second signal.

Example 3. The surgical instrument of Examples 1 and 2, wherein the controller is configured to unlock the staple firing system when the controller receives the first signal and the second signal.

Example 4. The surgical instrument of Examples 1-3, wherein the first RFID tag comprises a first operational range and the second RFID tag comprises a second operational range, and wherein the first operational range and the second operational range do not overlap when the sled is in the proximal unfired position.

Example 5. The surgical instrument of Examples 1-4, wherein the first RFID reader comprises a first operational range and the second RFID reader comprises a second operational range, and wherein the first operational range and the second operational range do not overlap.

Example 6. The surgical instrument of Examples 1-5, further comprising a third RFID reader in communication with the controller, and wherein the third RFID reader is configured to detect the second signal from the second RFID tag when the sled is in the distal fired position.

Example 7. The surgical instrument of Example 6, wherein the second RFID reader is unable to detect the second signal when the sled is in the distal fired position, and wherein the third RFID reader is unable to detect the second signal when the sled is in the proximal unfired position.

Example 8. The surgical instrument of Examples 1-7, wherein the controller comprises a set of data stored in a memory device, wherein the controller is configured to compare data from the first signal and the second signal to a set of data, wherein the controller is configured to disable the staple firing system if data from one of the first signal and the second signal is inconsistent with the set of data.

Example 9. The surgical instrument of Examples 1-8, wherein the staple cartridge further comprises a removable cover releasably attached to the cartridge body, wherein the removable cover comprises a third RFID tag affixed thereto, wherein the third RFID tag is configured to emit a third signal, wherein the surgical instrument further comprises a third RFID reader configured to receive the third signal when the removable cover is attached to the cartridge body, and wherein the third RFID reader is unable to receive the third signal when the removable cover is detached from the cartridge body.

Example 10. The surgical instrument of Examples 1-9, wherein the first RFID tag comprises an active RFID tag, and wherein the second RFID tag comprises an active RFID tag.

Example 11. The surgical instrument of Examples 1-9, wherein the first RFID tag comprises a passive RFID tag, and wherein the second RFID tag comprises a passive RFID tag.

Example 12. A surgical instrument comprises a staple firing system, an end effector, a first RFID reader, a second RFID reader, and a controller. The end effector comprises an anvil, a staple cartridge support, and a staple cartridge positioned in the staple cartridge support. The staple cartridge comprises a cartridge body comprising a longitudinal slot, staple cavities defined in the cartridge body, and staples removably stored in the staple cavities. The staple cartridge also comprises a sled movable between a proximal unfired position and a distal fired position by the staple firing system, a first RFID tag mounted to the cartridge body, and a second RFID tag mounted to the sled. The first RFID reader is configured to receive a first signal from the first RFID tag. The second RFID reader is configured to receive a second signal from the second RFID tag. The controller is in communication with the first RFID reader, the second RFID reader, and the staple firing system, wherein the controller verifies the presence of the staple cartridge in the staple cartridge channel upon receiving the first signal from the first RFID tag, and wherein the controller verifies that the staple cartridge is an unfired staple cartridge upon receiving the second signal from the second RFID tag.

Example 13. A surgical instrument comprises a staple firing system, an end effector, a first RFID reader, a second RFID reader, and a controller. The end effector comprises an anvil, a staple cartridge channel, and a staple cartridge positioned in the staple cartridge channel. The staple cartridge comprises a cartridge body comprising a longitudinal slot, staple cavities defined in the cartridge body, and staples removably stored in the staple cavities. The staple cartridge also comprises a removable cover releasably attached to the cartridge body, a sled movable between a proximal unfired position and a distal fired position by the staple firing system, a first RFID tag affixed to the cartridge body, and a second RFID tag affixed to the removable cover. The first RFID reader is configured to detect a first signal from the first RFID tag. The second RFID reader is configured to detect a second signal from the second RFID tag. The controller in communication with the first RFID reader, the second RFID reader, and the staple firing system, wherein the controller verifies the presence of the staple cartridge in the staple cartridge channel upon receiving the first signal from the first RFID tag, and wherein the controller verifies that the staple cartridge is an unspoiled staple cartridge upon receiving the second signal from the second RFID tag.

Example 14. The surgical instrument of Example 13, wherein the controller is configured to disable the staple firing system if the controller receives the first signal but not the second signal.

Example 15. The surgical instrument of Examples 13 and 14, wherein the controller is configured to unlock the staple firing system when the controller receives the first signal and the second signal.

Example 16. The surgical instrument of Examples 13-15, wherein the first RFID tag comprises a first operational range and the second RFID tag comprises a second operational range, and wherein the first operational range and the second operational range do not overlap when the cover is attached to the cartridge body.

Example 17. The surgical instrument of Examples 13-16, wherein the first RFID reader comprises a first operational range and the second RFID reader comprises a second operational range, and wherein the first operational range and the second operational range do not overlap.

Example 18. The surgical instrument of Examples 13-17, wherein the controller comprises a set of data stored in a memory device, wherein the controller is configured to compare data from the first signal and the second signal to a set of data, wherein the controller is configured to disable the staple firing system if data from one of the first signal and the second signal is inconsistent with the set of data.

Example Set 4

Example 1. A surgical instrument comprises an end effector and a RFID reader. The end effector comprises a proximal end, a distal end, and a longitudinal axis extending between the proximal end and the distal end. The end effector also comprises an anvil, a staple cartridge channel, and a staple cartridge positioned in the staple cartridge channel. The staple cartridge comprises a cartridge body comprising a longitudinal slot, a removable cover releasably attached to the cartridge body, and staple cavities defined in the cartridge body. The staple cartridge also comprises staples removably stored in the staple cavities, a sled movable relative to the longitudinal slot during a staple firing stroke, and a RFID tag mounted to the staple cartridge in a tag plane. The RFID reader comprises an induction coil receiver, wherein the induction coil receiver is mounted to a sidewall of the staple cartridge channel in a receiver plane, wherein the receiver plane is substantially parallel to the tag plane, and wherein the receiver plane is substantially parallel to the longitudinal axis.

Example 2. The surgical instrument of Example 1, wherein the RFID tag is mounted to the cartridge body.

Example 3. The surgical instrument of Examples 1 and 2, wherein the cartridge body comprises a first sidewall, a second sidewall, and a deck extending between the first sidewall and the second sidewall, wherein the staple cavities are defined in the deck, and wherein the RFID tag is mounted to the first sidewall.

Example 4. The surgical instrument of Example 3, wherein the RFID tag is mounted to an outer surface of the first sidewall.

Example 5. The surgical instrument of Example 3, wherein the RFID tag is mounted to an inner surface of the first sidewall.

Example 6. The surgical instrument of Example 3, wherein the RFID tag is embedded in the first sidewall.

Example 7. The surgical instrument of Example 6, wherein the RFID tag is integrally-molded into the first sidewall.

Example 8. The surgical instrument of Example 3, wherein the first sidewall comprises a recess defined therein, and wherein the RFID tag is seated in the recess.

Example 9. The surgical instrument of Example 8, wherein the recess defines a recess perimeter, and wherein the RFID tag comprises a tag perimeter that matches the recess perimeter.

Example 10. The surgical instrument of Example 1, wherein the RFID tag is mounted to the sled.

Example 11. The surgical instrument of Example 10, wherein the sled comprises a longitudinal portion positioned in the longitudinal slot, and wherein the RFID tag is affixed to the longitudinal portion.

Example 12. The surgical instrument of Example 11, wherein the RFID tag is integrally-molded into the longitudinal portion.

Example 13. The surgical instrument of Example 10, wherein the longitudinal portion comprises a recess defined therein, and wherein the RFID tag is seated in the recess.

Example 14. The surgical instrument of Example 13, wherein the recess defines a recess perimeter, and wherein the RFID tag comprises a tag perimeter that matches the recess perimeter.

Example 15. The surgical instrument of Example 10, wherein the sidewall comprises a bottom sidewall extending between a first lateral sidewall and a second lateral sidewall.

Example 16. The surgical instrument of Example 10, wherein the sidewall comprises a lateral sidewall extending from a bottom sidewall.

Example 17. The surgical instrument of Example 10, further comprising staple drivers movably positioned within the staple cavities, wherein the sled comprises rails configured to engage the staple drivers to eject the staples from the staple cavities during the staple firing stroke, wherein the RFID tag is mounted to one of the rails.

Example 18. The surgical instrument of Example 1, wherein the RFID tag is affixed to the removable cover.

Example 19. The surgical instrument of Example 18, wherein the removable cover extends over the staple cavities, wherein the removable cover comprises latches releasably engaged with the cartridge body and a longitudinal fin positioned in the longitudinal slot, and wherein the RFID tag is mounted to the longitudinal fin.

Example 20. The surgical instrument of Example 19, wherein the RFID tag is integrally-molded into the longitudinal fin.

Example 21. The surgical instrument of Example 18, wherein the longitudinal fin comprises a recess defined therein, and wherein the RFID tag is seated in the recess.

Example 22. The surgical instrument of Example 21, wherein the recess defines a recess perimeter, and wherein the RFID tag comprises a tag perimeter that matches the recess perimeter.

Example 23. The surgical instrument of Examples 1-22, wherein the RFID tag comprises a base, a microchip mounted to the base, and a chip antenna mounted to the base, wherein the chip antenna is substantially parallel to a receiver antenna of the induction coil receiver.

Example 24. The surgical instrument of Examples 1-23, wherein the chip antenna is circumferential about a chip antenna axis, wherein the receiver antenna is circumferential about a receiver antenna axis, and wherein the chip antenna axis and the receiver antenna axis are collinear.

Example 25. The surgical instrument of Examples 1-23, wherein the chip antenna is circumferential about a chip antenna axis, wherein the receiver antenna is circumferential about a receiver antenna axis, and wherein the chip antenna axis and the receiver antenna axis are orthogonal to the longitudinal axis.

Example 26. A surgical instrument comprises an end effector and a RFID reader. The end effector comprises a staple cartridge support and a staple cartridge positioned in the staple cartridge support. The staple cartridge comprises a cartridge body comprising a longitudinal slot, staple cavities defined in the cartridge body, and staples removably stored in the staple cavities. The staple cartridge also comprises a RFID tag mounted to the staple cartridge, wherein the RFID tag comprises a base and a tag antenna mounted to the base, and wherein the tag antenna is defined in a tag plane. The RFID reader comprises an induction coil receiver, wherein the induction coil receiver is mounted to the staple cartridge support in a receiver plane, wherein the receiver plane is substantially parallel to the tag plane.

Example 27. An end effector of a surgical instrument comprises a staple cartridge support, a staple cartridge, and a RFID reader. The staple cartridge is positioned in the staple cartridge support and comprises a cartridge body comprising a longitudinal slot and staple cavities defined in the cartridge body. The staple cartridge also comprises staples removably stored in the staple cavities and a RFID tag mounted to the staple cartridge, wherein the RFID tag comprises a tag antenna defined in a tag plane. The RFID reader comprises a receiver antenna, wherein the receiver antenna is mounted to the staple cartridge support in a receiver plane, wherein the receiver plane is parallel to the tag plane.

Example Set 5

Example 1. A surgical system comprises a surgical instrument, a replaceable staple cartridge, a retainer, an RFID scanner, a controller. The surgical instrument comprises an elongate shaft and an end effector extending from the elongate shaft, wherein the end effector comprises a first jaw and a second jaw. The replaceable staple cartridge is configured to be seated in the first jaw, wherein the replaceable staple cartridge is stored in a packaging prior to being seated in the first jaw, wherein the packaging comprises a first RFID tag, wherein the first RFID tag comprises a first set of encrypted information, and wherein the replaceable staple cartridge comprises a cartridge body comprising a cartridge deck, staples removably stored in the cartridge body, a sled configured to drive the staples out of the cartridge body during a staple firing stroke, and a second RFID tag comprising a second set of encrypted information. The retainer is releasably attached to the replaceable staple cartridge, wherein the retainer extends over the cartridge deck, and wherein the retainer comprises a third RFID tag comprising a third set of encrypted information. The RFID scanner is configured to receive the first set of encrypted information, the second set of encrypted information, and the third set of encrypted information. The controller is configured to perform a decryption protocol, wherein the controller comprises a first internal key, wherein the controller uses the first internal key to decrypt the first set of encrypted information, wherein the controller releases a second internal key if the first set of encrypted information is recognized by the controller, wherein the controller uses the second internal key to decrypt the second set of encrypted information, wherein the controller releases a third internal key if the second set of encrypted information is recognized by the controller, wherein the controller uses the third internal key to decrypt the third set of encrypted information, and wherein the controller prevents the surgical instrument from performing the staple firing stroke if at least one of the first set of encrypted information, the second set of encrypted information, and the third set of encrypted information is unable to be recognized.

Example 2. The surgical system of Example 1, wherein the controller prevents the surgical instrument from performing the staple firing stroke if the controller is unable to decrypt at least one of the first set of encrypted information, the second set of encrypted information, and the third set of encrypted information.

Example 3. The surgical system of Examples 1 or 2, wherein the RFID scanner is configured to receive the first set of encrypted information in response to a first interrogation signal.

Example 4. The surgical system of Example 3, wherein the controller prevents the surgical instrument from performing the staple firing stroke if the RFID scanner does not receive the first set of encrypted information in response to the first interrogation signal.

Example 5. The surgical system of Examples 3 or 4, wherein the RFID scanner is configured to receive the second set of encrypted information in response to a second interrogation signal.

Example 6. The surgical system of Example 5, wherein the RFID scanner does not transmit the second interrogation signal if the controller is unable to recognize the first set of encrypted information.

Example 7. The surgical system of Examples 5 or 6, wherein the RFID scanner is configured to receive the third set of encrypted information in response to a third interrogation signal.

Example 8. The surgical system of Example 7, wherein the RFID scanner does not transmit the third interrogation signal if the controller is unable to recognize the second set of encrypted information.

Example 9. The surgical system of any one of Examples 1-8, wherein the RFID scanner comprises reading capabilities and writing capabilities.

Example 10. A surgical system comprises a surgical instrument, a replaceable staple cartridge, a retainer releasably attached to the replaceable staple cartridge, a first RFID tag comprising a first set of encrypted information, a second RFID tag comprising a second set of encrypted information, an RFID scanner configured to receive the first set of encrypted information and the second set of encrypted information, and a controller comprising a first internal key. The surgical instrument comprises an elongate shaft and an end effector extending from the elongate shaft, wherein the end effector comprises a first jaw and a second jaw. The replaceable staple cartridge is configured to be seated in the first jaw, wherein the replaceable staple cartridge comprises a cartridge body comprising a cartridge deck, staples removably stored in the cartridge body, and a sled configured to drive the staples out of the cartridge body during a staple firing stroke. The retainer extends over the cartridge deck. The controller uses the first internal key to decrypt the first set of encrypted information, wherein the controller releases a second internal key if the first set of encrypted information is recognized by the controller, wherein the controller uses the second internal key to decrypt the second set of encrypted information, and wherein the controller prevents the surgical instrument from performing an operational function if at least one of the first set of encrypted information and the second set of encrypted information is unable to be recognized.

Example 11. The surgical system of Example 10, wherein the operational function comprises the staple firing stroke.

Example 12. The surgical system of Examples 10 or 11, wherein the controller comprises a memory, wherein a set of compatible information is stored in the memory, wherein the controller prevents the surgical instrument from performing the operational function if at least one of the first set of encrypted information and the second set of encrypted information does not correspond to the set of compatible information.

Example 13. The surgical system of any one of Examples 10-12, wherein the first RFID tag is positioned on the replaceable staple cartridge.

Example 14. The surgical system of any one of Examples 10-13, wherein the second RFID tag is positioned on the retainer.

Example 15. The surgical system of any one of Examples 10-14, wherein the RFID scanner is configured to receive the first set of encrypted information in response to a first interrogation signal.

Example 16. The surgical system of Example 15, wherein the controller prevents the surgical instrument from performing the staple firing stroke if the RFID scanner does not receive the first set of encrypted information in response to the first interrogation signal.

Example 17. The surgical system of Examples 15 or 16, wherein the RFID scanner is configured to receive the second set of encrypted information in response to a second interrogation signal.

Example 18. The surgical system of Example 17, wherein the RFID scanner does not transmit the second interrogation signal if the controller is unable to recognize the first set of encrypted information.

Example 19. The surgical system of any one of Examples 10-18 further comprising a third RFID tag, wherein the replaceable staple cartridge is stored within a packaging prior to being seated in the first jaw, and wherein the third RFID tag is positioned on the packaging.

Example 20. A surgical system comprises a surgical instrument, a replaceable staple cartridge, a retainer releasably attached to the replaceable staple cartridge, an RFID scanner, and a controller comprising a first internal key. The surgical instrument comprises an elongate shaft and an end effector extending from the elongate shaft, wherein the end effector comprises a first jaw and a second jaw. The replaceable staple cartridge is configured to be seated in the first jaw, wherein the replaceable staple cartridge is stored in a packaging prior to being seated in the first jaw, wherein the packaging comprises a first RFID tag, wherein the first RFID tag comprises a first set of encrypted information, and wherein the replaceable staple cartridge comprises a cartridge body comprising a cartridge deck, staples removably stored in the cartridge body, a sled configured to drive the staples out of the cartridge body during a staple firing stroke, and a second RFID tag comprising a second set of encrypted information. The retainer extends over the cartridge deck and comprises a third RFID tag comprising a third set of encrypted information. The RFID scanner is configured to receive the first set of encrypted information, the second set of encrypted information, and the third set of encrypted information. The controller uses the first internal key to decrypt the first set of encrypted information, wherein the controller releases a second internal key if the controller determines that the first set of encrypted information is compatible for use with the surgical system, wherein the controller uses the second internal key to decrypt the second set of encrypted information, wherein the controller releases a third internal key if the controller determines that the second set of encrypted information is compatible for use with the surgical system, wherein the controller uses the third internal key to decrypt the third set of encrypted information, and wherein the surgical instrument is inoperable if at least one of the first set of encrypted information, the second set of encrypted information, and the third set of encrypted information is incompatible for use with the surgical system.

Example Set 6

Example 1. A surgical system comprises a surgical instrument, an RFID scanner, a controller, and a remote storage system. The surgical instrument comprises an end effector, a replaceable staple cartridge, and a retainer. The end effector comprises a first jaw and a second jaw. The replaceable staple cartridge is configured to be seated in the first jaw, wherein the replaceable staple cartridge comprises a cartridge body comprising a cartridge deck, staples removably positioned in the cartridge body, a first RFID tag comprising a first set of information, and a sled comprising a second RFID tag comprising a second set of information, wherein the sled is configured to drive the staples out of the cartridge body during a staple firing stroke. The retainer is removably attached to the replaceable staple cartridge, wherein the retainer is positioned adjacent to the cartridge deck, wherein the retainer comprises a third RFID tag comprising a third set of information, wherein the first set of information, the second set of information, and the third set of information collectively form a unique combination, and wherein the unique combination is representative of the replaceable staple cartridge. The RFID scanner is configured to receive the first set of information, the second set of information, and the third set of information. The controller is in communication with the RFID scanner. The remote storage system comprises a set of compatible combinations, wherein the controller compares the unique combination to the set of compatible combinations to determine if the replaceable staple cartridge is compatible for use with the surgical instrument, and wherein the controller prevents at least one operation of the surgical instrument if the controller determines that the unique combination is not compatible for use with the surgical instrument.

Example 2. The surgical system of Example 1, wherein the set of compatible combinations comprises a list of unique combinations associated with replaceable staple cartridges.

Example 3. The surgical system of Examples 1 or 2, wherein the set of compatible combinations comprises recall information, wherein the controller prevents the at least one operation of the surgical instrument if at least one of the replaceable staple cartridge and the retainer are recalled.

Example 4. The surgical system of any one of Examples 1-3, wherein the at least one operation of the surgical system comprises the staple firing stroke.

Example 5. The surgical system of any one of Examples 1-4, wherein the replaceable staple cartridge is stored in a packaging prior to being seated in the first jaw, and wherein the unique combination is displayed on the packaging in an encrypted form.

Example 6. The surgical system of Example 5, wherein the remote storage system comprises a decryption protocol configured to decrypt the encrypted form of the unique combination.

Example 7. The surgical system of Examples 5 or 6, wherein the encrypted form of the unique combination is printed on the packaging.

Example 8. The surgical system of any one of Examples 1-7, wherein the first RFID tag, the second RFID tag, and the third RFID tag comprise encrypted information.

Example 9. The surgical system of Example 8, wherein the remote storage system comprises a decryption protocol configured to decrypt the encrypted information comprised on the first RFID tag, the second RFID tag, and the third RFID tag.

Example 10. The surgical system of any one of Examples 1-9, wherein the RFID scanner is configured to receive the first set of information in response to a first interrogation signal.

Example 11. The surgical system of any one of Examples 1-10, wherein the controller is positioned on the surgical instrument.

Example 12. The surgical system of any one of Examples 1-10, wherein the controller is positioned remotely with respect to the surgical instrument.

Example 13. A surgical system comprises a surgical instrument, a replaceable staple cartridge, a retainer, a first RFID tag, a second RFID tag, a third RFID tag, an RFID scanner, a controller, and a remote storage system. The replaceable staple cartridge comprises a cartridge body comprising a cartridge deck, staples removably positioned in the cartridge body, and a sled configured to drive the staples out of the cartridge body during a staple firing stroke. The retainer is removably attached to the replaceable staple cartridge, wherein the retainer is positioned adjacent to the cartridge deck. The first RFID tag comprises a first set of information, the second RFID tag comprises a second set of information, and the third RFID tag comprises a third set of information, wherein the first set of information, the second set of information, and the third set of information collectively form a unique combination. The RFID scanner is configured to receive the first set of information, the second set of information, and the third set of information. The controller is in communication with the RFID scanner. The remote storage system comprises a set of compatible combinations, wherein the controller compares the unique combination to the set of compatible combinations to determine if the replaceable staple cartridge is compatible for use with the surgical system, and wherein the controller prevents at least one operation of the surgical system if the controller determines that the replaceable staple cartridge is not compatible for use with the surgical system.

Example 14. The surgical system of Example 13, wherein the set of compatible combinations comprises a list of unique combinations associated with individual replaceable staple cartridges.

Example 15. The surgical system of Examples 13 or 14, wherein the set of compatible combinations comprises recall information, wherein the controller prevents the at least one operation of the surgical instrument if the replaceable staple cartridge is recalled.

Example 16. The surgical system of any one of Examples 13-15, wherein the at least one operation of the surgical system comprises the staple firing stroke.

Example 17. The surgical system of any one of Examples 13-16, wherein the replaceable staple cartridge is stored in a packaging prior to being seated in a first jaw of the surgical instrument, and wherein the unique combination is displayed on the packaging in an encrypted form.

Example 18. The surgical system of any one of Examples 13-17, wherein the first RFID tag, the second RFID tag, and the third RFID tag comprise encrypted information.

Example 19. The surgical system of Example 18, wherein the remote storage system comprises a decryption protocol configured to decrypt the encrypted information comprised on the first RFID tag, the second RFID tag, and the third RFID tag.

Example 20. A surgical system comprises a surgical instrument, a replaceable staple cartridge, an RFID scanner, a controller, and a remote storage system. The replaceable staple cartridge comprises a cartridge body comprising a cartridge deck, staples removably positioned in the cartridge body, a first RFID tag comprising a first set of encrypted information, and a sled comprising a second RFID tag comprising a second set of encrypted information, wherein the sled is configured to drive the staples out of the cartridge body during a staple firing stroke, wherein the first set of encrypted information and the second set of encrypted information collectively form a unique combination, and wherein the unique combination is representative of the replaceable staple cartridge. The RFID scanner is configured to receive the first set of encrypted information and the second set of encrypted information. The controller is in communication with the RFID scanner. The remote storage system comprises a decryption protocol and a set of compatible combinations, wherein the remote storage system decrypts the unique combination and compares the decrypted unique combination to the set of compatible combinations to determine if the replaceable staple cartridge is compatible for use with the surgical instrument, and wherein the controller prevents at least one operation of the surgical instrument if the controller determines that the replaceable staple cartridge is not compatible for use with the surgical instrument.

Example Set 7

Example 1. A surgical stapling instrument comprises an elongate shaft, an end effector, a replaceable staple cartridge, an RFID scanner, a controller, a lockout member, and a solenoid. The end effector comprises a first jaw and a second jaw. The replaceable staple cartridge is configured to be seated in the first jaw, wherein the replaceable staple cartridge comprises a cartridge body comprising a cartridge deck, staples removably stored in the cartridge body, a sled configured to drive the staples out of the cartridge body during a staple firing stroke, wherein the sled comprises a proximal portion, and an RFID tag comprising stored information. The RFID scanner is configured to communicate with the RFID tag as the replaceable staple cartridge is being seated in the first jaw. The lockout member comprises a proximal end and a distal end, wherein the distal end of the lockout member contacts the proximal portion of the sled as the replaceable staple cartridge is seated in the first jaw. The solenoid is configurable in an active configuration and an inactive configuration, wherein the solenoid comprises a housing, a bolt, a resilient member, and an inductive coil, wherein the controller places the solenoid in the active configuration when the controller determines the replaceable staple cartridge is compatible for use with the surgical stapling instrument, wherein the bolt and the resilient member are positioned entirely within the housing when the solenoid is in the active configuration, wherein the controller places the solenoid in the inactive configuration when the RFID scanner receives a signal from the RFID tag indicative that the replaceable staple cartridge is incompatible for use with the surgical stapling instrument, wherein a portion of the bolt extends outside of the housing when the solenoid is in the inactive configuration, wherein the portion of the bolt prevents proximal movement of the lockout member when the solenoid is in the inactive configuration, and wherein the lockout member pushes the sled distally as the replaceable staple cartridge is seated in the first jaw and the solenoid is in the inactive configuration.

Example 2. The surgical stapling instrument of Example 1, wherein the surgical stapling instrument is unable to perform the stapling firing stroke when the controller determines that the replaceable staple cartridge is incompatible with the surgical stapling instrument.

Example 3. The surgical stapling instrument of Examples 1 or 2, wherein distal movement of the sled caused by the lockout member prevents the surgical stapling instrument from performing the staple firing stroke.

Example 4. The surgical stapling instrument of any one of Examples 1-3, further comprising a firing member configured to translate the sled along a firing path during the staple firing stroke.

Example 5. The surgical stapling instrument of Example 4, wherein the proximal end of the lockout member comprises a lateral projection, wherein a portion of the lateral projection engages the firing member.

Example 6. The surgical stapling instrument of any one of Examples 1-5, wherein channels are defined within the cartridge body, and wherein the distal end of the lockout member is sized to be received within one of the channels.

Example 7. The surgical stapling instrument of any one of Examples 1-6, wherein the solenoid is in the inactive configuration until a compatible staple cartridge is detected by the controller.

Example 8. The surgical stapling instrument of any one of Examples 1-7, wherein the solenoid is in the inactive configuration when the replaceable staple cartridge is not seated in the first jaw.

Example 9. The surgical stapling instrument of any one of Examples 1-8, further comprising an electric motor and a power source, wherein the power source is prevented from supplying power to the electric motor when the solenoid is in the inactive configuration.

Example 10. A surgical instrument comprises an elongate shaft, an end effector, a replaceable staple cartridge, an RFID scanner, a controller, a lockout member, and a blocking bolt system. The end effector comprises a first jaw and a second jaw. The replaceable staple cartridge is configured to be seated in the first jaw, wherein the replaceable staple cartridge comprises a cartridge body comprising a cartridge deck, staples removably stored in the cartridge body, a sled configured to drive the staples out of the cartridge body during a staple firing stroke, wherein the sled comprises a proximal portion, and an RFID tag comprising stored information. The RFID scanner is configured to communicate with the RFID tag as the replaceable staple cartridge is being seated in the first jaw. The lockout member comprises a proximal end and a distal end, wherein the distal end of the lockout member contacts the proximal portion of the sled as the replaceable staple cartridge is seated in the first jaw, wherein the lockout member is configured to translate proximally along a path when the controller determines that the replaceable staple cartridge is compatible for use with the surgical instrument. The blocking bolt system comprises a housing, a bolt, a resilient member, and an inductive coil, wherein the controller places the blocking bolt system in an active configuration when the controller determines that the replaceable staple cartridge is compatible for use with the surgical instrument, wherein the bolt is positioned outside of the path of the lockout member when the blocking bolt system is in the active configuration, wherein the controller places the blocking bolt system in an inactive configuration when the controller determines that the replaceable staple cartridge is incompatible for use with the surgical instrument, wherein the bolt is positioned within the path of the lockout member when the blocking bolt system is in the inactive configuration, wherein the bolt prevents the proximal translation of the lockout member when the blocking bolt system is in the inactive configuration, and wherein the lockout member pushes the sled distally as the replaceable staple cartridge is seated in the first jaw and the blocking bolt system is in the inactive configuration.

Example 11. The surgical instrument of Example 10, wherein the controller determines that the replaceable staple cartridge is incompatible for use with the surgical instrument when the RFID scanner fails to receive a signal from the RFID tag.

Example 12. The surgical instrument of Example 10, wherein the controller determines that the replaceable staple cartridge is incompatible for use with the surgical instrument when the RFID scanner receives a signal from the RFID tag comprising data representative of an incompatible staple cartridge.

Example 13. The surgical instrument of Example 12, wherein the incompatible staple cartridge comprises a spent staple cartridge.

Example 14. The surgical instrument of any one of Examples 10-13, wherein the surgical instrument is unable to perform the stapling firing stroke when the controller determines that the replaceable staple cartridge is incompatible with the stapling instrument.

Example 15. The surgical instrument of any one of Examples 10-14, wherein distal movement of the sled caused by the lockout member prevents the surgical instrument from performing the staple firing stroke.

Example 16. The surgical instrument of any one of Examples 10-15, further comprising a firing member configured to translate the sled along a firing path during the staple firing stroke, wherein the proximal end of the lockout member comprises a lateral projection, and wherein a portion of the lateral projection engages the firing member.

Example 17. The surgical instrument of any one of Examples 10-16, wherein channels are defined within the cartridge body, and wherein the distal end of the lockout member is sized to be received within one of the channels.

Example 18. The surgical instrument of any one of Examples 10 or 12-17, wherein the RFID scanner transmits an interrogation signal to the RFID tag, and wherein the blocking bolt system is in the inactive configuration when the RFID scanner fails to receive a response signal to the interrogation signal.

Example 19. The surgical instrument of any one of Examples 10-18, further comprising an electric motor and a power source, wherein the power source is prevented from supplying power to the electric motor when the blocking bolt system is in the inactive configuration.

Example 20. A replaceable staple cartridge for use with a surgical instrument, wherein the replaceable staple cartridge comprises a cartridge body comprising a cartridge deck, staples removably positioned within the cartridge body, a sled configured to drive the staples out of the cartridge body during a staple firing stroke, and an RFID tag comprising stored information, wherein the RFID tag is in communication with an RFID scanner of the surgical instrument as the replaceable staple cartridge is being attached to the surgical instrument, wherein the sled is advanced distally within the replaceable staple cartridge when a controller of the surgical instrument determines that the replaceable staple cartridge is incompatible for use with the surgical instrument, and wherein the controller prevents the surgical instrument from performing the staple firing stroke when the determined incompatible staple cartridge is attached to the surgical instrument.

Example Set 8

Example 1. A surgical system comprises a surgical instrument comprising an end effector, a replaceable staple cartridge, an RFID tag, an RFID scanner, and a controller. The end effector comprises a first jaw and a second jaw. The replaceable staple cartridge is configured to be seated in the first jaw, wherein the replaceable staple cartridge comprises a proximal end, a distal end, a cartridge body comprising a cartridge deck, an elongate slot extending from the proximal end toward the distal end, staples removably stored in the cartridge body, and a sled configured to translate along the elongate slot and drive the staples out of the cartridge body during a staple firing stroke. The RFID tag comprises stored information, wherein the RFID tag is inoperable after a predefined action of the surgical instrument. The RFID scanner is configured to transmit a first signal to the RFID tag, wherein the RFID scanner is configured to receive a second signal from the RFID tag in response to the first signal. The controller prevents at least one operation of the surgical instrument when the RFID scanner does not receive the second signal from the RFID tag in response to the first signal.

Example 2. The surgical system of Example 1, wherein the at least one operation of the surgical instrument comprises the staple firing stroke.

Example 3. The surgical system of Examples 1 or 2, wherein the predefined action of the surgical instrument comprises commencement of the staple firing stroke.

Example 4. The surgical system of Examples 1 or 2, wherein the predefined action of the surgical instrument comprises distal movement of the sled.

Example 5. The surgical system of any one of Examples 1-4, wherein the controller prevents the at least one operation of the surgical instrument when the controller determines that the stored information of the second signal corresponds to an incompatible replaceable staple cartridge.

Example 6. The surgical system of any one of Examples 1-5, wherein the RFID tag comprises a portion that traverses the elongate slot, wherein the sled transects the portion during the staple firing stroke, and wherein the RFID tag is unable to communicate with the RFID scanner after the portion is transected.

Example 7. The surgical system of any one of Examples 1-6, wherein the RFID scanner is configured to transmit a third signal to the RFID tag, wherein the third signal is transmitted at a power level that exceeds a threshold power level of the RFID tag, and wherein the third signal renders the RFID tag inoperable.

Example 8. The surgical system of Example 7, wherein at least a portion of the RFID tag melts in response to the third signal.

Example 9. The surgical system of any one of Examples 1-8, further comprising a retainer releasably attached to the replaceable staple cartridge, wherein the retainer extends along the cartridge deck, wherein the RFID tag is positioned on the retainer, and wherein the RFID tag is rendered inoperable as the retainer is removed from the replaceable staple cartridge.

Example 10. The surgical system of Example 9, wherein the RFID tag is physically destroyed as the retainer is removed from the replaceable staple cartridge.

Example 11. A replaceable staple cartridge for use with a surgical instrument, wherein the replaceable staple cartridge comprises a proximal end, a distal end, a cartridge body comprising a cartridge deck, an elongate slot extending from the proximal end toward the distal end, staples removably stored in the cartridge body, a sled configured to translate along the elongate slot and drive the staples out of the cartridge body during a staple firing stroke, an RFID tag comprising stored information relevant to the replaceable staple cartridge, wherein the RFID tag is rendered inoperable after a predefined action of the surgical instrument, and an RFID scanner in communication with a controller of the surgical instrument, wherein the RFID scanner transmits a first signal to the RFID tag, wherein the RFID scanner is configured to receive a second signal from the RFID tag in response to the first signal, wherein the controller prevents at least one operation of the surgical instrument when the RFID tag is inoperable.

Example 12. The replaceable staple cartridge of Example 11, wherein the RFID tag comprises a first antenna comprising a first communication range, wherein the RFID scanner is positioned outside the first communication range.

Example 13. The replaceable staple cartridge of Example 12, further comprising a second antenna comprising a second communication range, wherein the second antenna is in communication with the RFID tag, and wherein the RFID scanner is positioned within the second communication range.

Example 14. The replaceable staple cartridge of Example 13, wherein a portion of the second antenna traverses a proximal portion of the elongate slot, wherein the sled destroys the portion of the second antenna as the sled translates distally through the elongate slot, and wherein the RFID tag is unable to communicate with the RFID scanner after the portion of the second antenna is destroyed.

Example 15. The replaceable staple cartridge of any one of Examples 11-14, further comprising a retainer, wherein the retainer is replaceably attached to the cartridge body, wherein the retainer extends along the cartridge deck, and wherein the RFID tag is rendered inoperable as the retainer is removed from the replaceable staple cartridge.

Example 16. The replaceable staple cartridge of any one of Examples 11-15, wherein the at least one operation of the surgical instrument comprises the staple firing stroke.

Example 17. The replaceable staple cartridge of any one of Examples 11-16, wherein the predefined action of the surgical instrument comprises commencement of the staple firing stroke.

Example 18. The replaceable staple cartridge of any one of Examples 11-16, wherein the predefined action of the surgical instrument comprises distal movement of the sled.

Example 19. The replaceable staple cartridge of any one of Examples 11-18, wherein the controller of the surgical instrument prevents the at least one operation of the surgical instrument when the controller determines that the stored information of the second signal corresponds to an incompatible replaceable staple cartridge.

Example 20. A surgical system comprises a surgical instrument, a replaceable staple cartridge, an RFID tag, an RFID scanner, and a controller. The surgical instrument comprises an end effector, wherein the end effector comprises a first jaw and a second jaw. The replaceable staple cartridge is configured to be seated in the first jaw, wherein the replaceable staple cartridge comprises a proximal end, a distal end, a cartridge body comprising a cartridge deck, an elongate slot extending from the proximal end toward the distal end, staples removably stored in the cartridge body, and a sled configured to translate along the elongate slot and drive the staples out of the cartridge body during a staple firing stroke. The RFID tag is inoperable after a predefined action of the surgical instrument. The RFID scanner is configured to transmit a first signal to the RFID tag, wherein the RFID scanner is configured to receive a second signal from the RFID tag in response to the first signal. The controller prevents at least one operation of the surgical instrument when the controller determines that the second signal comprises information corresponding to an incompatible replaceable staple cartridge.

Example Set 9

Example 1. A replaceable staple cartridge for use with a surgical instrument, wherein the replaceable staple cartridge is stored in a packaging prior to being attached to the surgical instrument, wherein the packaging comprises a first layer, a second layer, and an RFID system. The first layer and the second layer form a seal around the replaceable staple cartridge. The RFID system comprises an RFID tag and an insulator.

The RFID tag is attached to the first layer, wherein the RFID tag comprises an integrated battery, a tag antenna, and an RFID chip comprising stored information. The insulator is attached to the second layer, wherein the insulator electrically decouples the integrated battery from the RFID chip, wherein the insulator is configured to detach from the integrated battery when the seal is broken between the first layer and the second layer, and wherein the RFID tag becomes active and transmits the stored information to an RFID scanner of the surgical instrument when the insulator is detached from the integrated battery.

Example 2. The replaceable staple cartridge of Example 1, wherein a controller of the surgical instrument compares the transmitted stored information from the RFID tag to a set of compatible information, and wherein the controller prevents the surgical instrument from performing at least one function if the transmitted stored information is not found in the set of compatible information.

Example 3. The replaceable staple cartridge of Example 2, wherein the at least one function of the surgical instrument comprises a staple firing stroke.

Example 4. The replaceable staple cartridge of Example 1, wherein a controller of the surgical instrument prevents the surgical instrument from performing at least one function if the controller does not recognize the transmitted stored information from the RFID tag.

Example 5. The replaceable staple cartridge of Example 4, wherein the at least one function of the surgical instrument comprises a staple firing stroke.

Example 6. The replaceable staple cartridge of any one of Examples 1-5, wherein the RFID tag is configured to continuously transmit the stored information when the insulator is detached from the integrated battery.

Example 7. The replaceable staple cartridge of any one of Examples 1-6, wherein the RFID tag comprises encrypted information.

Example 8. The replaceable staple cartridge of any one of Examples 1-7, wherein the RFID tag is positioned within an ionizing radiation proof barrier, and wherein the RFID tag is gamma sterilization resistant.

Example 9. The replaceable staple cartridge of any one of Examples 1-8, wherein the stored information of the RFID chip comprises an expiration date, and
wherein a controller of the surgical instrument prevents the surgical instrument from performing at least one function if the controller determines that the replaceable staple cartridge is expired.

Example 10. A replaceable staple cartridge for use with a surgical instrument, wherein the replaceable staple cartridge is stored in a packaging prior to being attached to the surgical instrument, wherein the packaging comprises a first layer, a second layer, an RFID tag, and an insulator. The replaceable staple cartridge is positioned in between the first layer and the second layer. The RFID tag comprises a battery, a tag antenna, and an RFID chip comprising stored information. The insulator electrically decouples the battery from the RFID chip when the first layer is pulled apart from the second layer, and wherein the RFID tag becomes active and transmits the stored information to an RFID scanner of the surgical instrument when the insulator is decoupled from the battery.

Example 11. The replaceable staple cartridge of Example 10, wherein a controller of the surgical instrument compares the transmitted stored information from the RFID tag to a set of compatible information, and wherein the controller prevents the surgical instrument from performing at least one function if the transmitted stored information is not found in the set of compatible information.

Example 12. The replaceable staple cartridge of Example 11, wherein the at least one function of the surgical instrument comprises a staple firing stroke.

Example 13. The replaceable staple cartridge of Example 10, wherein a controller of the surgical instrument prevents the surgical instrument from performing at least one function if the controller does not recognize the transmitted stored information from the RFID tag.

Example 14. The replaceable staple cartridge of Example 13, wherein the at least one function of the surgical instrument comprises a staple firing stroke.

Example 15. The replaceable staple cartridge of any one of Examples 10-14, wherein the RFID tag is configured to continuously transmit the stored information when the insulator is detached from the battery.

Example 16. The replaceable staple cartridge of any one of Examples 10-15, wherein the RFID tag comprises encrypted information.

Example 17. The replaceable staple cartridge of any one of Examples 10-16, wherein the RFID tag is positioned within an ionizing radiation proof barrier, and wherein the RFID tag is gamma sterilization resistant.

Example 18. The replaceable staple cartridge of any one of Examples 10-17, wherein the stored information of the RFID chip comprises an expiration date, and wherein a controller of the surgical instrument prevents the surgical instrument from performing at least one function if the controller determines that the replaceable staple cartridge is expired.

Example 19. A replaceable staple cartridge for use with a surgical instrument, wherein the replaceable staple cartridge is stored in a packaging prior to being attached to the surgical instrument, wherein the packaging comprises a first layer, a second layer, an RFID tag, and an insulator. The first layer and the second layer form a seal around the replaceable staple cartridge. The RFID tag is attached to the replaceable staple cartridge, wherein the RFID tag comprises an integrated power source, a tag antenna, and an RFID chip comprising stored information. The insulator is attached to the second layer of the packaging, wherein the insulator electrically decouples the integrated power source from the RFID chip, wherein the insulator is configured to detach from the integrated power source when the first layer is removed from the second layer, and wherein the RFID tag becomes active and transmits the stored information to an RFID scanner of the surgical instrument when the insulator is detached from the integrated power source.

Example 20. The replaceable staple cartridge of Example 19, wherein a controller of the surgical instrument compares the transmitted stored information from the RFID tag to a set of compatible information, and wherein the controller prevents the surgical instrument from performing at least one function if the transmitted information is not found in the set of compatible information.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail and is incorporated by reference herein in its entirety.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Various embodiments described herein are described in the context of linear end effectors and/or linear fastener cartridges. Such embodiments, and the teachings thereof, can be applied to non-linear end effectors and/or non-linear fastener cartridges, such as, for example, circular and/or contoured end effectors. For example, various end effectors, including non-linear end effectors, are disclosed in U.S. patent application Ser. No. 13/036,647, filed Feb. 28, 2011, entitled SURGICAL STAPLING INSTRUMENT, now U.S. Patent Application Publication No. 2011/0226837, now U.S. Pat. No. 8,561,870, which is hereby incorporated by reference in its entirety. Additionally, U.S. patent application Ser. No. 12/893,461, filed Sep. 29, 2012, entitled STAPLE CARTRIDGE, now U.S. Patent Application Publication No. 2012/0074198, issued as U.S. Pat. No. 8,733,613 on May 27, 2014, is hereby incorporated by reference in its entirety. U.S. patent application Ser. No. 12/031,873, filed Feb. 15, 2008, entitled END EFFECTORS FOR A SURGICAL CUTTING AND STAPLING INSTRUMENT, now U.S. Pat. No. 7,980,443, is also hereby incorporated by reference in its entirety. U.S. Pat. No. 8,393,514, entitled SELECTIVELY ORIENTABLE IMPLANTABLE FASTENER CARTRIDGE, which issued on Mar. 12, 2013, is also hereby incorporated by reference in its entirety.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A staple cartridge configured for use with a surgical instrument, the staple cartridge comprising:
    (a) a cartridge body comprising:
        (i) a proximal end,
        (ii) a distal end,
        (iii) a first lateral side disposed between the proximal and distal ends, and
        (iv) a second lateral side disposed between the proximal and distal ends and opposite to the first lateral side; and
    (b) a flex circuit positioned on the cartridge body, wherein the flex circuit is configured to provide feedback to a controller and alter the operation of the surgical instrument, the flex circuit comprising:
        (i) a first RFID chip,
        (ii) a first RFID power coil or antenna in communication with the first RFID chip and configured to provide power to the first RFID chip, wherein the first RFID power coil or antenna has a first transmission range, and
        (iii) a first RFID receiving antenna in communication with the first RFID chip and configured to receive data from the first RFID chip and transmit the data to the controller, wherein the first RFID receiving antenna has a second transmission range that does not overlap with the first transmission range.

2. The staple cartridge of claim 1, wherein the first and second lateral sides are separated by a maximum width, wherein the first RFID power coil or antenna and the first RFID receiving antenna are separated at least by the maximum width.

3. The staple cartridge of claim 1, wherein the first RFID power coil or antenna and the first RFID receiving antenna are separated by at least double the maximum width.

4. The staple cartridge of claim 1, wherein the first RFID power coil or antenna and the first RFID receiving antenna are separated by at least triple the maximum width.

5. The staple cartridge of claim 1, wherein the first RFID power coil or antenna includes an inductive coil.

6. The staple cartridge of claim 1, wherein the first RFID power coil or antenna is positioned on the first lateral side, wherein the first RFID receiving antenna is positioned on the second lateral side.

7. The staple cartridge of claim 1, the flex circuit further comprising:
(a) a second RFID chip,
(b) a second RFID power coil or antenna configured to provide power to the second RFID chip, wherein the first RFID power coil or antenna has a third transmission range, and
(c) a second RFID receiving antenna configured to receive data from the second RFID chip and transmit the data to the controller, wherein the second RFID receiving antenna has a fourth transmission range that does not overlap with the first, second, or the third transmission ranges.

8. The staple cartridge of claim 7, wherein the first RFID power coil or antenna is positioned on the first lateral side, wherein the second RFID power coil or antenna is positioned on the second lateral side.

9. The staple cartridge of claim 1, further comprising a channel defined between the proximal end, the distal end, the first lateral side, and the second lateral side, wherein the first RFID power coil or antenna and the first RFID receiving antenna are not longitudinally aligned in the channel.

10. The staple cartridge of claim 1, wherein the first RFID power coil or antenna and the first RFID receiving antenna are spaced both laterally between the first and second lateral sides and longitudinally between the proximal and distal ends.

11. The staple cartridge of claim 1, further comprising the controller positioned within the surgical instrument.

12. The staple cartridge of claim 1, further comprising a single smart control system that includes the controller, wherein the flex circuit is configured to coordinate power and data to the single smart control system.

13. The staple cartridge of claim 1, further comprising a wall defined between the proximal and distal ends and the first and second lateral sides, wherein the wall comprises an elongate slot that separates the first RFID power coil or antenna from the second RFID power coil or antenna.

14. The staple cartridge of claim 13, further comprising:
(a) staples removably stored in the cartridge body, and
(b) a sled configured to translate along the elongate slot and drive the staples out of the cartridge body during a staple firing stroke.

15. The staple cartridge of claim 1, further comprising a wall defined between the proximal and distal ends and the first and second lateral sides, wherein the first RFID power coil or antenna and the first RFID receiving antenna are not laterally on the wall or the first and second lateral sides.

16. A staple cartridge configured for use with a surgical instrument, the staple cartridge comprising:
(a) a cartridge body comprising:
(i) a proximal end,
(ii) a distal end,
(iii) a first lateral side disposed between the proximal and distal ends, and
(iv) a second lateral side disposed between the proximal and distal ends and opposite to the first lateral side; and
(b) a flex circuit positioned on the cartridge body and configured to provide feedback to a controller to alter the operation of the surgical instrument, the flex circuit comprising:
(i) first and second RFID chips,
(ii) a first RFID power coil or antenna configured to provide power to the first RFID chip, wherein the first RFID power coil or antenna has a first transmission range,
(iii) a first RFID receiving antenna configured to receive data from the first RFID chip and transmit the data to the controller,
(iv) a second RFID power coil or antenna configured to provide power to the second RFID chip, wherein the first RFID power coil or antenna has a third transmission range, and
(v) a second RFID receiving antenna configured to receive data from the second RFID chip and transmit the data to the controller, wherein the second RFID receiving antenna has a fourth transmission range that does not overlap with the first, second, or the third transmission ranges.

17. The staple cartridge of claim 16, wherein the first and second lateral sides are separated by a maximum width, wherein the first RFID power coil or antenna and the first RFID receiving antenna are separated at least by the maximum width.

18. The staple cartridge of claim 17, wherein the first RFID power coil or antenna and the first RFID receiving antenna are separated by at least double the maximum width.

19. A staple cartridge configured for use with a surgical instrument, the staple cartridge comprising:
(a) a cartridge body comprising:
(i) a proximal end,
(ii) a distal end,
(iii) a first lateral side disposed between the proximal and distal ends, and
(iv) a second lateral side disposed opposite to the first lateral side; and
(b) a flex circuit positioned on the cartridge body and configured to alter the operation of the surgical instrument, the flex circuit comprising:
(i) a plurality of RFID chips,
(ii) a plurality of RFID power coils or antennae each having a first transmission range, and
(iii) a plurality of RFID receiving antennae each having a second transmission range, wherein the second transmission range does not overlap with the first transmission range.

20. The staple cartridge of claim 19, wherein the cartridge body further comprises a channel defined between the proximal end, the distal end, the first lateral side, and the second lateral side, wherein the plurality of RFID chips, the plurality of RFID power coils or antennas, and the plurality of RFID receiving antennae are positioned within the channel.

* * * * *